US007026484B2

(12) United States Patent
Zhi et al.

(10) Patent No.: US 7,026,484 B2
(45) Date of Patent: Apr. 11, 2006

(54) TRICYCLIC ANDROGEN RECEPTOR MODULATOR COMPOUNDS AND METHODS

(75) Inventors: Lin Zhi, San Diego, CA (US); Cornelis Arjan Van Oeveren, San Diego, CA (US); Jyun-Hung Chen, San Diego, CA (US); Robert I. Higuchi, Solana Beach, CA (US)

(73) Assignee: Ligand Pharmaceuticals Incorporated, San Diego, CA (US)

( * ) Notice: Subject to any disclaimer, the term of this patent is extended or adjusted under 35 U.S.C. 154(b) by 0 days.

(21) Appl. No.: 10/080,926

(22) Filed: Feb. 22, 2002

(65) Prior Publication Data

US 2002/0183346 A1 Dec. 5, 2002

Related U.S. Application Data

(60) Provisional application No. 60/271,189, filed on Feb. 23, 2001.

(51) Int. Cl.
*C07D 455/04* (2006.01)
*C07D 221/18* (2006.01)
*C07D 471/00* (2006.01)
*A61K 31/44* (2006.01)

(52) U.S. Cl. .......................... 546/80; 546/84; 546/89; 546/62; 546/70; 514/291; 514/292; 514/285

(58) Field of Classification Search ................ 546/80, 546/84, 89, 62, 70; 514/291, 292, 285
See application file for complete search history.

(56) References Cited

U.S. PATENT DOCUMENTS

| | | | | |
|---|---|---|---|---|
| 3,919,238 | A | 11/1975 | Spencer et al. | 260/288 |
| 4,460,475 | A | 7/1984 | Hayatsu et al. | 210/674 |
| 4,623,638 | A | 11/1986 | Hayatsu et al. | 502/401 |
| 4,777,052 | A | 10/1988 | Weisburger et al. | 426/92 |
| 4,981,784 | A | 1/1991 | Evans et al. | 435/6 |
| 5,011,697 | A | 4/1991 | Jones et al. | 426/92 |
| 5,071,773 | A | 12/1991 | Evans et al. | 436/501 |
| 5,179,202 | A | 1/1993 | Gross | 536/120 |
| 5,576,324 | A * | 11/1996 | Kyotani et al. | 514/291 |
| 5,696,130 | A | 12/1997 | Jones et al. | |
| 6,017,924 | A | 1/2000 | Edwards et al. | 514/292 |
| 6,030,967 | A | 2/2000 | Marui et al. | 514/215 |
| 6,180,794 | B1 | 1/2001 | Edwards et al. | 546/152 |
| 6,340,704 | B1 | 1/2002 | Marui et al. | 514/463 |
| 2002/0183314 | A1 | 12/2002 | Higuchi et al. | 514/224.5 |

FOREIGN PATENT DOCUMENTS

| | | | |
|---|---|---|---|
| DE | 24 27 409 A1 | | 1/1975 |
| EP | 0 638 571 A1 | | 4/1993 |
| JP | 50-25595 | | 3/1975 |
| SU | 241441 | * | 4/1969 |
| SU | 548608 | * | 2/1977 |
| WO | WO 96/19458 A2 | | 6/1996 |
| WO | WO 97/49709 | | 12/1997 |
| WO | WO 00/12502 | * | 3/2000 |
| WO | 02/066475 | | 8/2002 |
| WO | 02/068427 | | 9/2002 |

OTHER PUBLICATIONS

Chapman NB et al. Journal of the Chemical Society (Section) C: Organic (1970), 17:2334-9.*
Yudin LG et al. Khimiya Geterotsikicheskikh Soedinenii (1979), 10:1381-5.*
Gryanznov AP. Izvestiya Timiryazevskoi Sel'skokhozyaistvennoi Akademii (1988), 3: 185-90.*
Yoshikawa T. Yakugaku Zasshi (1961), 81:1317-22.*
Ferlin MG et al. Bioorganic & Medicinal Chemistry (2000), 8(6): 1415-1422.*
Yamashkin et al. Chemistry.of Heterocyclic Compounds (New York)(Translation of Khimiya Geterotsiklicheskikh Soedinenii)(1999), vol. Date 1998, 34(9), 1050-1065.*
El-Desoky et al. Zeitschrift fuer Naturforschung, B: Chemical Sciences (1998), 53(10), 1216-1222.*
Majumdar et al. Journal of Chemical Research, Synopses (1997), (9), 310-311.*
Yamashkin et al. Khimiya Geterotsikicheskikh Soedinenii (1983), (4), 493-7.*
Akhvlediani et al. Zhurnal Organicheskoi Khimii (1981), 17(7), 1542-6.*
Bush, et al., "Sample-distance Partial Least Squares: PLS optimized for many variables, with application to CoMFA," *J. Comput.-Aided Mol. Des.*, 7:587-619 (1993).
McIlroy, et al., "Effects of Proteinase Inhibitors on Adenylate Cyclase," *Biochem. J.*, 188:423-435 (1980).
Ohta, "Juvenile Hormone Antagonists," *Kagaku to Seibutsu*, 17(2):92-94 (1979).

(Continued)

*Primary Examiner*—D. Margaret Seaman
(74) *Attorney, Agent, or Firm*—Fish & Richardson P.C.; Stephanie Seidman

(57) ABSTRACT

This invention relates to non-steroidal tricyclic compounds that are modulators of androgen receptors and to methods for making and using such compounds.

61 Claims, No Drawings

OTHER PUBLICATIONS

Saksena, et al., "Androgenic, antiandrogenic, and anabolic activity of azasteroids on immature castrated rats," Abstract of *Indian J. Med. Res., Database CA 'Online'*, 58(4):513-518 (1970).

Sperry, et al., "Farnesol oxidation in insects: evidence that the biosynthesis of insect juvenile hormone is mediated by a specific alcohol oxidase," *Insect Biochem. Mol. Biol.*, 31(2):171-178 (2001).

Evans, R., "The Steroid and Thyroid Hormone Receptor Superfamily," *Science*, 240:889-895 (1988).

Hamann, L., et al., "Synthesis and Biological Activity of a Novel Series of Nonsteroidal, Peripherally Selective Androgen Receptor Antagonists Derived from 1,2-Dihydropyridono[5,6-g] quinolines," *J. Med. Chem.*, 41: 623-639 (1998).

Edwards, J., et al., "New Nonsteroidal Androgen Receptor Modulators Based on 4-(Trifluoromethyl)-2(1*H*)-Pyrrolidino[3,2-g]Quinolinone," *Bioorganic & Medicinal Chemistry Letters*, 8:745-750 (1999).

Edwards, J., et al., "Nonsteroidal Androgen Receptor Agonists Based on 4-(Trifluoromethyl)-2*H*-Pyrano[3,2-g] Quinolin-2-One," *Bioorganic & Medicinal Chemistry Letters*, 9:1003-1008 (1999).

Higuchi, R., et al., "4-Alkyl- and 3,4-Dialkyl-1,2,3,4-Tetrahydro-8-Pyridono[5,6-g]Quinolines: Potent, Nonsteroidal Androgen Receptor Agonists," *Bioorganic & Medicinal Chemistry Letters*, 9:1335-1340 (1999).

Jones, G., *Comprehensive Heterocyclic Chemistry*, Katrizky, A. R.; Rees, C.W., eds. Pergamon, New York, 1984, vol. 2, Chap. 2.08, pp 421-426.

Fujisaki, S., et al., "Halogenation using N-Halogenocompounds. I. Effect of Amines on *ortho*-Bromination of Phenols with NBS," *Bull. Chem. Soc. Jpn.*, 66:1576-1579 (1993).

Wagaw, S., et al., "Palladium-Catalyzed Coupling of Optically Active Amines with Aryl Bromides," *J.Am. Chem. Soc.*, 119:8451-8458 (1997).

Berger et al., "Interaction of glucocorticoid analogues with the human glucocorticoid receptor," J. Steroid Biochemistry and Molecular Biology 41(3-8): 733-738 (1992).

Bolognese et al., "Photochemistry of Ommochrome Pigments," J. Heterocyclic Chem. 25: 1243-1246 (1988).

Bolognese et al., "Oxidation of 3-Hydroxykynurenine. A Reexamination," J. Heterocyclic Chem. 25: 1247-1250 (1988).

Bolognese et al., "Photochemistry of Ommochromes and Related Compounds," J. Heterocyclic Chem. 25: 979-983 (1988).

Boyer, M., "The management of prostrate cancer," Aust. Prescr. 19:22-24 (1996) http://www.australianprescriber.com/magazines/vol19no1/ap19-1-11.htm(accessed on Jan. 28, 2005.

Castillo, P. and J.C. Rodriguez-Ubis, "A high-yield method for the methylenation of o-dihdroxyaromatic compounds: synthesis of methylenedioxycoumarins," Synthesis pp. 839-840 (1986).

Chemical Abstracts vol. 54, No. 8821, (1960) Mustafa et al., "Photochemical reaction in sunlight. Experiments with benzo [k]quinoline-5,6-quinone, monoamine and monoxmine derivatives in sunlight and in dark," J. A. Chem. Soc. 81:3409-3413 (1959).

Chemical Abstracts vol. 83, No. 179036, p. 577 (1975) JP 50-25595 published Mar. 18, 1975, entitled "9-Halothiazoloquinolines".

Claman et al., "SOGC clinical practice guidelines. Hirsutism: evaluation and treatment," J Obstet Gynaecol Can. 24(1):62-7 (2002).

Debenedetti et al., "Isopurasol, a coumarin from *Pterocaulon virgatum*, " Phytochemistry 51: 701-703 (1999).

Ishii et al., "Formation of Hydroxanthommatin-Derived Radical in the Oxidation of 3-Hydroxykynurenine," Archives of Biochemistry and Biophysics 294(2): 616-622 (1992).

Kalinin et al., "Directed *ortho* Metalation—Cross Coupling Links. Carbamoyl Rendition of the Baker-Venkatarman Rearrangement. Reiospecific Route to Substituted 4-Hydroxycoumarins," Tetrahedron Letters 39: 4995-4998 (1998).

Kawamori et al., "Effects of heterocyclic amines with mammary gland carcinogenic potential on estrogenic response of uterus in ovariectomized rats," Cancer Letters 162: 31-37 (2001).

Lancelot et al., "Pyrido[2,3-h]pyrrolo[1,2-α]quinoxalines," Chem. Pharm. Bull. 31: 3160-3167 (1983) [Article in French, English abstract on first page of article].

LaMontagne et al., "Antimalarials. 13.5-Alkoxy Analogues of 4-Methylprimaquine," J. Med. Chem. 25: 964-968 (1982).

Simenthal et al., "Transcriptional Activation and Nuclear Targeting Signals of the Human Androgen Receptor," The Journal of Biological Chemistry 266(1): 510-518 (1991).

Singh et al., "Androgen receptor antagonists (antiandrogens): structure-activity relationships," Curr. Med. Chem. 7(2): 211-247 (2000).

Willard et al. , "Potential Diuretic-β-Adrenergic Blocking Agents: Synthesis of 3-[2-[1,1-Dimethylethyl)amino]-1-hydroxyethyl]-1,4-dioxino[2,3-g]quinolines," J. Org. Chem. 46: 3846-3852 (1981).

Certified English translation of Japanese Patent Application No. JP 50-25595 entitled "Production method for 9-halogeno thiozolo quinoline materials." .

* cited by examiner

TRICYCLIC ANDROGEN RECEPTOR MODULATOR COMPOUNDS AND METHODS

RELATED APPLICATION

The present application claims the benefit of priority to U.S. Provisional Application No. 60/271,189, filed on Feb. 23, 2001 which is incorporated by reference in its entirety.

FIELD OF THE INVENTION

This invention relates to non-steroidal compounds that are modulators (i.e. agonists, partial agonists and antagonists) of androgen receptors and to methods for making and using such compounds.

BACKGROUND OF THE INVENTION

Intracellular receptors (IRs) form a class of structurally-related genetic regulators scientists have named "ligand dependent transcription factors" (R. M. Evans, *Science,* 240:889, 1988). Sex steroid hormone receptors are a recognized subset of the IRs, including androgen receptor (AR), progesterone receptor (PR) and estrogen receptor (ER). Regulation of a gene by such factors requires both the receptor itself and a corresponding ligand, which has the ability to selectively bind to the receptor in a way that affects gene transcription.

The natural hormones for sex steroid receptors have been known for a long time, such as testosterone for AR and progesterone for PR. A compound that binds to a receptor and mimics the effect of the native hormone is referred to as an "agonist", while a compound that inhibits the effect of the native hormone is called an "antagonist." The term "modulators" refers to compounds that are agonists, partial agonists or antagonists.

Synthetic female sex hormones have been widely used in oral contraception, hormone replacement therapy and the treatment of hormone-dependent disorders. The development of new generations of selective estrogen receptor modulators (SERMs) significantly improved women's health. On the other hand, similar hormone therapy for men has not been fully explored due to lack of availability of selective, orally administered, safe agents.

A group of hydroquinoline derivatives was recently described as AR modulators (e.g., U.S. Pat. No. 5,696,130). This group of AR modulators was developed by using cell-based high-throughput assays, termed cotransfection assays.

The entire disclosures of the publications and references referred to herein are incorporated by reference herein and are not admitted to be prior art.

SUMMARY OF THE INVENTION

The present invention is directed to tricyclic androgen receptor modulator compounds. This invention is also directed to pharmaceutical compositions containing such compounds as well as methods of using such compounds and pharmaceutical compositions for modulating processes mediated by androgen receptor (AR). More particularly, the invention relates to nonsteroidal compounds and compositions that may be high affinity, high specificity agonists, partial agonists (i.e., partial activators and/or tissue-specific activators) or antagonists for androgen receptor. Also provided are methods of making such compounds and pharmaceutical compositions, as well as intermediates used in their synthesis.

The present invention provides a novel class of AR modulator compounds of the formula:

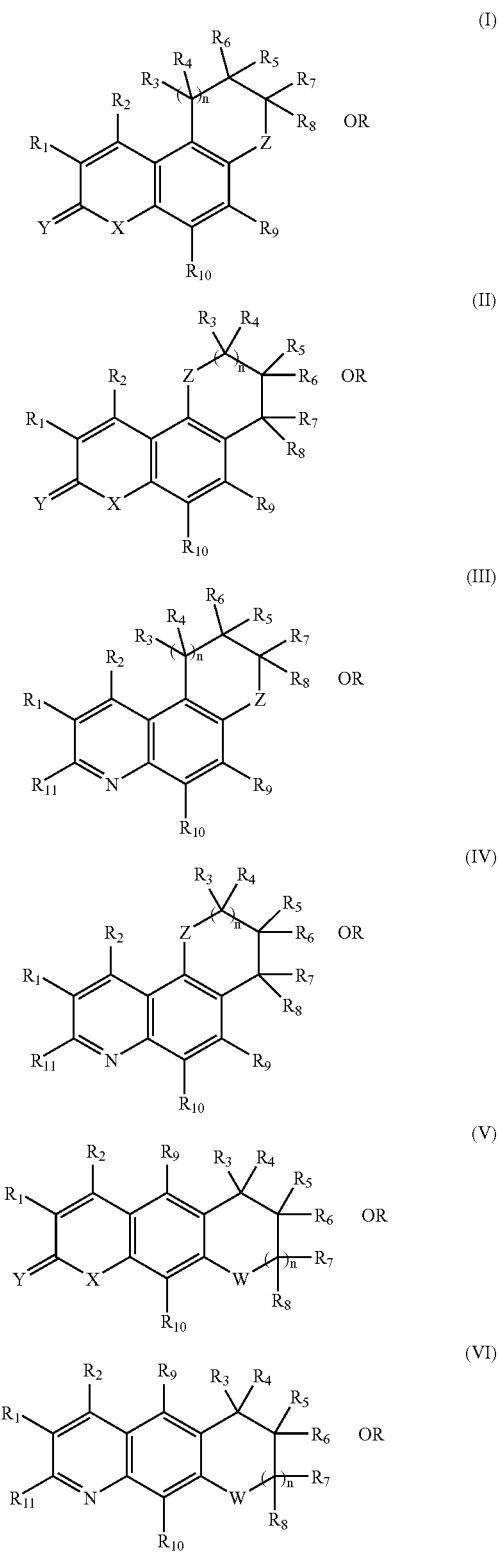

-continued

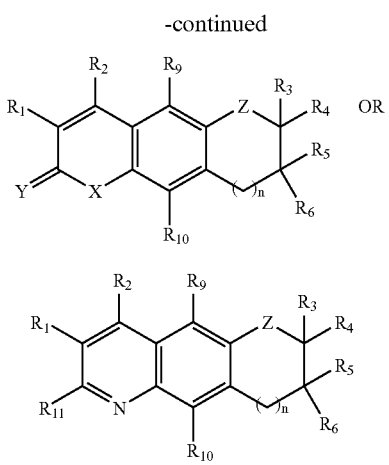

(VII)

(VIII)

wherein:

$R^1$ is selected from the group of hydrogen, F, Cl, Br, I, $NO_2$, $OR^2$, $SR^{12}$, $SOR^{12}$, $SO_2R^{12}$, $NR^{12}R^{13}$, $C_1$–$C_8$ alkyl, $C_1$–$C_8$ haloalkyl and $C_1$–$C_8$ heteroalkyl, wherein the alkyl, haloalkyl and heteroalkyl groups may be optionally substituted;

$R^2$ is selected from the group of hydrogen, F, Cl, Br, I, $CH_3$, $CF_3$, $CHF_2$, $CH_2F$, $CF_2Cl$, CN, $CF_2OR^{12}$, $CH_2OR^{12}$, $OR^{12}$, $SR^{12}$, $SOR^{12}$, $SO_2R^{12}$, $NR^{12}R^{13}$, $C_1$–$C_8$ alkyl, $C_1$–$C_8$ haloalkyl, $C_1$–$C_8$ heteroalkyl, $C_2$–$C_8$ alkenyl and $C_2$–$C_8$ alkynyl, wherein the alkyl, haloalkyl, heteroalkyl, alkenyl and alkynyl groups may be optionally substituted;

$R^3$ through $R^8$ each independently is selected from the group of hydrogen, F, Cl, Br, I, $OR^{12}$, $NR^{12}R^{13}$, $SR^{12}$, $SOR^{12}$, $SO_2R^{12}$, $C_1$–$C_8$ alkyl, $C_1$–$C_8$ haloalkyl, $C_1$–$C_8$ heteroalkyl, $C_2$–$C_8$ alkynyl, $C_2$–$C_8$ alkenyl, aryl, heteroaryl and arylalkyl, wherein the alkyl, haloalkyl, heteroalkyl, alkynyl, alkenyl, aryl, heteroaryl and arylalkyl groups may be optionally substituted; or $R^3$ and $R^5$ taken together form a bond; or $R^5$ and $R^7$ taken together form a bond; or $R^4$ and $R^6$ taken together form a three- to eight-membered saturated or unsaturated carbocyclic or heterocyclic ring, wherein the carbocyclic or heterocyclic ring may optionally substituted; or $R^6$ and $R^8$ taken together form a three- to eight-membered saturated or unsaturated carbocyclic or heterocyclic ring, wherein the carbocyclic or heterocyclic ring may optionally substituted;

$R^9$ and $R^{10}$ each independently is selected from the group of hydrogen, F, Cl, Br, I, CN, $OR^{12}$, $NR^{12}R^{13}$, $C_m(R^{12})_{2m}OR^{13}$, $SR^{12}$, $SOR^{12}$, $SO_2R^{12}$, $NR^{12}C(O)R^{13}$, $C_1$–$C_8$ alkyl, $C_1$–$C_8$ haloalkyl, $C_1$–$C_8$ heteroalkyl and arylalkyl, wherein the alkyl, haloalkyl, heteroalkyl and arylalkyl groups may be optionally substituted;

$R^{11}$ is selected from the group of hydrogen, F, Br, Cl, I, CN, $C_1$–$C_8$ alkyl, $C_1$–$C_8$ haloalkyl, $C_1$–$C_8$ heteroalkyl, $OR^{14}$, $NR^{14}R^{13}$, $SR^{14}$, $CH_2R^{14}$, $C(O)R^{14}$, $CO_2R^{14}$, $C(O)NR^{14}R^{13}$, $SOR^{14}$ and $SO_2R^{14}$, wherein the alkyl, haloalkyl and heteroalkyl groups may be optionally substituted;

$R^{12}$ and $R^{13}$ each independently is selected from the group of hydrogen, $C_1$–$C_8$ alkyl, $C_1$–$C_8$ haloalkyl, $C_1$–$C_8$ heteroalkyl, $C_2$–$C_8$ alkenyl, $C_2$–$C_8$ alkynyl, heteroaryl and aryl, wherein the alkyl, haloalkyl, heteroalkyl, alkenyl, alkynyl, heteroaryl and aryl groups may be optionally substituted;

$R^{14}$ is selected from the group of hydrogen, $C_1$–$C_8$ alkyl, $C_1$–$C_8$ haloalkyl, $C_1$–$C_8$ heteroalkyl, aryl, heteroaryl, $C(O)R^{15}$, $CO_2R^{15}$ and $C(O)NR^{15}R^{16}$, wherein the alkyl, haloalkyl, heteroalkyl, aryl and heteroaryl groups may be optionally substituted;

$R^{15}$ and $R^{16}$ each independently is selected from the group of hydrogen, $C_1$–$C_8$ alkyl, $C_1$–$C_8$ haloalkyl, $C_1$–$C_8$ heteroalkyl, wherein the alkyl, haloalkyl and heteroalkyl groups may be optionally substituted;

W is O or S;

X is selected from the group of O, S and $N\{R^{14}\}$;

Y is selected from the group of O, S, $N\{R^{12}\}$, $N\{OR^{12}\}$ and $CR^{12}R^{13}$;

Z is selected from the group of O, S and $N\{R^{12}\}$;

n is 0, 1 or 2;

m is 0, 1, or 2;

and pharmaceutically acceptable salts thereof.

DETAILED DESCRIPTION OF THE INVENTION

In accordance with the present invention and as used herein, the following terms are defined with the following meanings, unless explicitly stated otherwise.

The term "alkyl," alone or in combination, refers to an optionally substituted straight-chain or branched-chain alkyl radical having from 1 to about 12 carbon atoms. The term also includes substituted straight-chain or branched-chain alkyl radicals having from 1 to about 6 carbon atoms as well as those having from 1 to about 4 carbon atoms. Examples of alkyl radicals include methyl, ethyl, n-propyl, isopropyl, n-butyl, isobutyl, sec-butyl, tert-butyl, tert-amyl, pentyl, hexyl, heptyl, octyl and the like.

The term "alkenyl," alone or in combination, refers to an optionally substituted straight-chain or branched-chain hydrocarbon radical having one or more carbon-carbon double-bonds and having from 2 to about 18 carbon atoms. The term also includes substituted straight-chain or branched-chain hydrocarbon radicals having one or more carbon-carbon double bonds and having from 2 to about 6 carbon atoms as well as those having from 2 to about 4 carbon atoms. Examples of alkenyl radicals include ethenyl, propenyl, butenyl, 1,4-butadienyl and the like.

The term "alkynyl," alone or in combination, refers to an optionally substituted straight-chain or branched-chain hydrocarbon radical having one or more carbon-carbon triple-bonds and having from 2 to about 12 carbon atoms. The term also includes substituted straight-chain or branched-chain hydrocarbon radicals having one or more carbon-carbon triple bonds and having from 2 to about 6 carbon atoms as well as those having from 2 to about 4 carbon atoms. Examples of alkynyl radicals include ethynyl, propynyl, butynyl and the like.

The term "heteroalkyl" refers to alkyl groups, as described above, in which one or more skeletal atoms are oxygen, nitrogen, sulfur or combinations thereof. The term heteroalkyl also includes alkyl groups in which one 1 to about 6 skeletal atoms are oxygen, nitrogen, sulfur or combinations thereof, as well as those in which 1 to 4 skeletal atoms are oxygen, nitrogen, sulfur or combinations thereof and those in which 1 to 2 skeletal atoms are oxygen, nitrogen, sulfur or combinations thereof.

The term "alkoxy," alone or in combination, refers to an alkyl ether radical, alkyl-O—, wherein the term alkyl is defined as above. Examples of alkoxy radicals include methoxy, ethoxy, n-propoxy, isopropoxy, n-butoxy, iso-butoxy, sec-butoxy, tert-butoxy and the like.

The term "aryloxy," alone or in combination, refers to an aryl ether radical wherein the term aryl is defined as below. Examples of aryloxy radicals include phenoxy, benzyloxy and the like.

The term "alkylthio," alone or in combination, refers to an alkyl thio radical, alkyl-S—, wherein the term alkyl is defined as above.

The term "arylthio," alone or in combination, refers to an aryl thio radical, aryl-S—, wherein the term aryl is defined as below.

The term "oxo" refers to =O.

The term "aryl," alone or in combination, refers to an optionally substituted aromatic ring system. The term aryl includes monocyclic aromatic rings, polyaromatic rings and polycyclic aromatic ring systems containing from six to about twenty carbon atoms. The term aryl also includes monocyclic aromatic rings, polyaromatic rings and polycyclic ring systems containing from 6 to about 12 carbon atoms, as well as those containing from 6 to about 10 carbon atoms. The polyaromatic and polycyclic aromatic rings systems may contain from two to four rings. Examples of aryl groups include, without limitation, phenyl, biphenyl, naphthyl and anthryl ring systems.

The term "heteroaryl" refers to optionally substituted aromatic ring systems containing from about five to about 20 skeletal ring atoms and having one or more heteroatoms such as, for example, oxygen, nitrogen and sulfur. The term heteroaryl also includes optionally substituted aromatic ring systems having from 5 to about 12 skeletal ring atoms, as well as those having from 5 to about 10 skeletal ring atoms. The term heteroaryl may include five- or six-membered heterocyclic rings, polycyclic heteroaromatic ring systems and polyheteroaromatic ring systems where the ring system has two, three or four rings. The terms heterocyclic, polycyclic heteroaromatic and polyheteroaromatic include ring systems containing optionally substituted heteroaromatic rings having more than one heteroatom as described above (e.g., a six membered ring with two nitrogens), including polyheterocyclic ring systems of from two to four rings. The term heteroaryl includes ring systems such as, for example, furanyl, benzofuranyl, chromenyl, pyridyl, pyrrolyl, indolyl, quinolinyl, N-alkyl pyrrolyl, pyridyl-N-oxide, pyrimidoyl, pyrazinyl, imidazolyl, pyrazolyl, oxazolyl, benzothiophenyl, purinyl, indolizinyl, thienyl and the like.

The term "heteroarylalkyl" refers to a $C_1$–$C_4$ alkyl group containing a heteroaryl group, each of which may be optionally substituted.

The term "heteroarylthio" refers to the group —S-heteroaryl.

The term "acyloxy" refers to the ester group —OC(O)—R, where R is hydrogen, alkyl, alkenyl, alkynyl, aryl, or arylalkyl, wherein the alkyl, alkenyl, alkynyl and arylalkyl groups may be optionally substituted.

The term "carboxy esters" refers to —C(O)OR where R is alkyl, aryl or arylalkyl, wherein the alkyl, aryl and arylalkyl groups may be optionally substituted.

The term "carboxamido" refers to

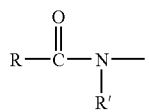

where R and R' each independently is selected from the group of hydrogen, alkyl, aryl and arylalkyl, wherein the alkyl, aryl and arylalkyl groups may be optionally substituted.

The term "cycloalkyl", alone or in combination, refers to a monocyclic, bicyclic or tricyclic alkyl radical wherein each cyclic moiety has from 3 to about 8 carbon atoms. Examples of cycloalkyl radicals include cyclopropyl, cyclobutyl, cyclopentyl, cyclohexyl and the like.

The term "arylalkyl," alone or in combination, refers to an alkyl radical as defined above in which one hydrogen atom is replaced by an aryl radical as defined above, such as, for example, benzyl, 2-phenylethyl and the like.

The terms haloalkyl, haloalkenyl, haloalkynyl and haloalkoxy include alkyl, alkenyl, alkynyl and alkoxy structures, as described above, that are substituted with one or more fluorines, chlorines, bromines or iodines, or with combinations thereof.

The terms cycloalkyl, aryl, arylalkyl, heteroaryl, alkyl, alkynyl, alkenyl, haloalkyl and heteroalkyl include optionally substituted cycloalkyl, aryl, arylalkyl, heteroaryl, alkyl, alkynyl, alkenyl, haloalkyl and heteroalkyl groups.

The term "carbocycle" includes optionally substituted, saturated or unsaturated, three- to eight-membered cyclic structures in which all of the skeletal atoms are carbon.

The term "heterocycle" includes optionally substituted, saturated or unsaturated, three- to eight-membered cyclic structures in which one or more skeletal atoms is oxygen, nitrogen, sulfur, or combinations thereof.

The term "acyl" includes alkyl, aryl, heteroaryl, arylalkyl or heteroarylalkyl substituents attached to a compound via a carbonyl functionality (e.g., —CO-alkyl, —CO-aryl, —CO-arylalkyl or —CO-heteroarylalkyl, etc.).

"Optionally substituted" groups may be substituted or unsubstituted. The substituents of an "optionally substituted" group may include, without limitation, one or more substituents independently selected from the following groups or designated subsets thereof: alkyl, alkenyl, alkynyl, heteroalkyl, haloalkyl, haloalkenyl, haloalkynyl, cycloalkyl, aryl, heteroaryl, arylalkyl, heteroarylalkyl, alkoxy, aryloxy, haloalkoxy, amino, alkylamino, dialkylamino, alkylthio, arylthio, heteroarylthio, oxo, carboxyesters, carboxamido, acyloxy, hydrogen, F, Cl, Br, I, CN, $NO_2$, $NH_2$, $N_3$, $NHCH_3$, $N(CH_3)_2$, SH, $SCH_3$, OH, $OCH_3$, $OCF_3$, $CH_3$, $CF_3$, $C(O)CH_3$, $CO_2CH_3$, $CO_2H$, $C(O)NH_2$, $OR^9$, $SR^9$ and $NR^{10}R^{11}$. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstututed (e.g., —$CH_2CF_3$).

The term "halogen" includes F, Cl, Br and I.

The term "mediate" means affect or influence. Thus, for example, conditions mediated by an androgen receptor are those in which an androgen receptor plays a role. Androgen receptors are known to play a role in conditions including, for example, acne, male-pattern baldness, sexual dysfunction, impotence, wasting diseases, hirsutism, hypogonadism, prostatic hyperplasia, osteoporosis, cancer cachexia, and hormone-dependent cancers.

The term "selective" refers to compounds that display reactivity towards a particular receptor (e.g., an androgen receptor) without displaying substantial cross-reactivity towards another receptor (e.g., glucocorticoid receptor). Thus, for example, selective compounds of the present invention may display reactivity towards androgen receptors without displaying substantial cross-reactivity towards glucocorticoid receptors.

In one embodiment, selective compounds of the present invention display at least 50-fold greater reactivity towards a particular receptor than towards another receptor. In another embodiment, selective compounds of the present invention display at least 100-fold greater reactivity towards a particular receptor than towards another receptor. In yet another embodiment, selective compounds of the present invention display at least 500-fold greater reactivity towards a particular receptor than towards another receptor. In still another embodiment, selective compounds of the present invention display at least 1,000-fold greater reactivity towards a particular receptor than towards another receptor.

Compounds of the present invention may be represented by the formulae:

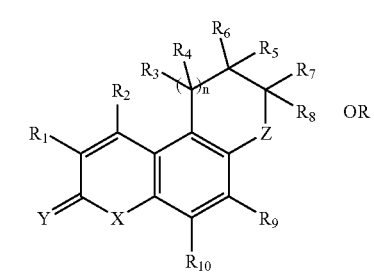

(I)

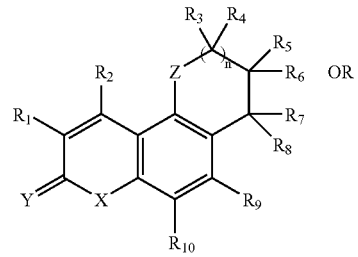

(II)

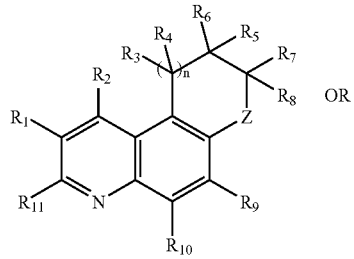

(III)

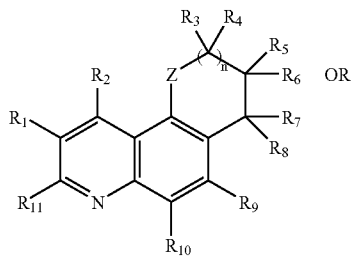

(IV)

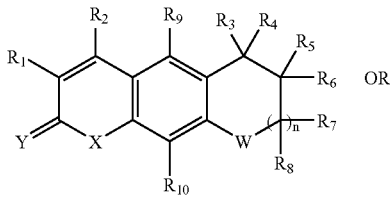

(V)

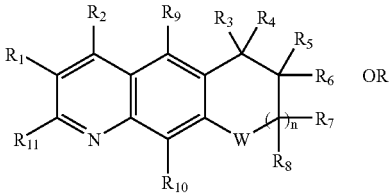

(VI)

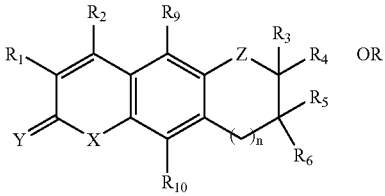

(VII)

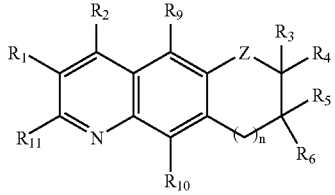

(VIII)

wherein:

$R^1$ is selected from the group of hydrogen, F, Cl, Br, I, $NO_2$, $OR^{12}$, $SR^{12}$, $SOR^{12}$, $SO_2R^{12}$, $NR^{12}R^{13}$, $C_1$–$C_8$ alkyl, $C_1$–$C_8$ haloalkyl and $C_1$–$C_8$ heteroalkyl, wherein the alkyl, haloalkyl and heteroalkyl groups may be optionally substituted;

$R^2$ is selected from the group of hydrogen, F, Cl, Br, I, $CH_3$, $CF_3$, $CHF_2$, $CH_2F$, $CF_2Cl$, CN, $CF_2OR^{12}$, $CH_2OR^{12}$, $OR^{12}$, $SR^{12}$, $SOR^{12}$, $SO_2R^{12}$, $NR^{12}R^{13}$, $C_1$–$C_8$ alkyl, $C_1$–$C_8$ haloalkyl, $C_1$–$C_8$ heteroalkyl, $C_2$–$C_8$ alkenyl and $C_2$–$C_8$ alkynyl, wherein the alkyl, haloalkyl, heteroalkyl, alkenyl and alkynyl groups may be optionally substituted;

$R^3$ through $R^8$ each independently is selected from the group of hydrogen, F, Cl, Br, I, $OR^{12}$, $NR^{12}R^{13}$, $SR^{12}$, $SO_2R^{12}$, $SOR^{12}$, $C_1$–$C_8$ alkyl, $C_1$–$C_8$ haloalkyl, $C_1$–$C_8$ heteroalkyl, $C_2$–$C_8$ alkynyl, $C_2$–$C_8$ alkenyl, aryl, heteroaryl and arylalkyl, wherein the alkyl, haloalkyl, heteroalkyl, alkynyl, alkenyl, aryl, heteroaryl and arylalkyl groups may be optionally substituted; or $R^3$ and $R^5$ taken together form a bond; or $R^5$ and $R^7$ taken together form a bond; or $R^4$ and $R^6$ taken together form a three- to eight-membered saturated or unsaturated carbocyclic or heterocyclic ring, wherein the carbocyclic or heterocyclic ring may optionally substituted; or $R^6$ and $R^8$ taken together form a three- to eight-membered saturated or unsaturated carbocyclic or heterocyclic ring, wherein the carbocyclic or heterocyclic ring may optionally substituted;

$R^9$ and $R^{10}$ each independently is selected from the group of hydrogen, F, Cl, Br, I, CN, $OR^{12}$, $NR^{12}R^{13}$, $C_m(R^{12})_{2m}OR^{13}$, $SR^{12}$, $SOR^{12}$, $SO_2R^{12}$, $NR^{12}C(O)R^{13}$, $C_1$–$C_8$ alkyl, $C_1$–$C_8$ haloalkyl, $C_1$–$C_8$ heteroalkyl and arylalkyl, wherein the alkyl, haloalkyl, heteroalkyl and arylalkyl groups may be optionally substituted;

$R^{11}$ is selected from the group of hydrogen, F, Br, Cl, I, CN, $C_1$–$C_8$ alkyl, $C_1$–$C_8$ haloalkyl, $C_1$–$C_8$ heteroalkyl, $OR^{14}$, $NR^{14}R^{13}$, $SR^{14}$, $CH_2R^{14}$, $C(O)R^{14}$, $CO_2R^{14}$, C(O)

$NR^{14}R^{13}$, $SOR^{14}$ and $SO_2R^{14}$, wherein the alkyl, haloalkyl and heteroalkyl groups may be optionally substituted;

$R^{12}$ and $R^{13}$ each independently is selected from the group of hydrogen, $C_1$–$C_8$ alkyl, $C_1$–$C_8$ haloalkyl, $C_1$–$C_8$ heteroalkyl, $C_2$–$C_8$ alkenyl, $C_2$–$C_8$ alkynyl, heteroaryl and aryl, wherein the alkyl, haloalkyl, heteroalkyl, alkenyl, alkynyl, heteroaryl and aryl groups may be optionally substituted;

$R^{14}$ is selected from the group of hydrogen, $C_1$–$C_8$ alkyl, $C_1$–$C_8$ haloalkyl, $C_1$–$C_8$ heteroalkyl, aryl, heteroaryl, C(O)$R^{15}$, $CO_2R^{15}$ and $C(O)NR^{15}R^{16}$, wherein the alkyl, haloalkyl, heteroalkyl, aryl and heteroaryl groups may be optionally substituted;

$R^{15}$ and $R^{16}$ each independently is selected from the group of hydrogen, $C_1$–$C_8$ alkyl, $C_1$–$C_8$ haloalkyl, $C_1$–$C_8$ heteroalkyl, wherein the alkyl, haloalkyl and heteroalkyl groups may be optionally substituted;

W is O or S;

X is selected from the group of O, S and N{$R^{14}$};

Y is selected from the group of O, S, N{$R^{12}$}, N{$OR^{12}$} and $CR^{12}R^{13}$;

Z is selected from the group of O, S and N{$R^{12}$};

n is 0, 1 or 2;

m is 0, 1, or 2;

and pharmaceutically acceptable salts thereof.

In one aspect, the present the invention provides compounds represented by formula I through VIII. In another aspect, the present invention provides a pharmaceutical composition comprising an effective amount of an AR modulating compound of formula I through VIII shown above, wherein $R^1$ through $R^{16}$, m, n, W, X, Y, and Z are as described above.

In another aspect, the present invention provides a method of modulating processes mediated by ARs by administering to a patient a pharmaceutically effective amount of a compound of formula I through VIII shown above, wherein $R^1$ through $R^{16}$, m, n, W, X, Y, and Z are as described above. In one aspect, the modulation is activation, while in another aspect, the modulation is inhibition. In each case, the method involves administering to a patient a pharmaceutically effective amount of a compound of formula I through VIII shown above, wherein $R^1$ through $R^{16}$, m, n, W, X, Y, and Z are as described above.

With regard to the foregoing variables, the inventors contemplate any combination of the Markush groups as set forth above and as described in the following table.

TABLE A

Table of Markush Groups by Variable

| | Markush Group A | Markush Group B | Markush Group C | Markush Group D |
|---|---|---|---|---|
| $R^1$ | hydrogen, F, Cl, Br, I, $C_1$–$C_6$ alkyl, $C_1$–$C_6$ haloalkyl and $C_1$–$C_6$ heteroalkyl, wherein the alkyl, haloalkyl and heteroalkyl groups may be optionally substituted | hydrogen, F, Cl, $C_1$–$C_4$ alkyl, $C_1$–$C_4$ haloalkyl and $C_1$–$C_4$ heteroalkyl, wherein the alkyl, haloalkyl and heteroalkyl groups may be optionally substituted | hydrogen, F and optionally substituted $C_1$–$C_2$ alkyl | hydrogen and F |
| $R^2$ | hydrogen, F, Cl, Br, $CF_3$, $CF_2Cl$, $CF_2H$, $CFH_2$, $C_1$–$C_6$ alkyl, $C_1$–$C_6$ haloalkyl and $C_1$–$C_6$ heteroalkyl, wherein the alkyl, haloalkyl and heteroalkyl groups may be optionally substituted $CF_2OR^{12}$, $CH_2OR^{12}$, $OR^{12}$, $SR^{12}$, $SOR^{12}$, $SO_2R^{12}$ and $NR^{12}R^{13}$ | hydrogen, F, Cl, Br, $CF_3$, $CF_2Cl$, $CF_2H$, $CFH_2$, $C_1$–$C_4$ alkyl, $C_1$–$C_4$ haloalkyl, $C_1$–$C_4$ heteroalkyl, $C_2$–$C_4$ alkenyl and $C_2$–$C_4$ alkynyl, wherein the alkyl, haloalkyl, heteroalkyl, alkenyl and alkynyl groups may be optionally substituted | hydrogen, F, Cl, $C_1$–$C_4$ alkyl, $C_1$–$C_4$ haloalkyl and $C_1$–$C_4$ heteroalkyl, wherein the alkyl, haloalkyl and heteroalkyl groups may be optionally substituted | hydrogen, F, Cl, $CF_3$, $CF_2Cl$, $CF_2H$, $CFH_2$ and optionally substituted $C_1$–$C_4$ alkyl |
| $R^3$ | hydrogen, $C_1$–$C_6$ alkyl, $C_1$–$C_6$ haloalkyl and $C_1$–$C_6$ heteroalkyl, wherein the alkyl, haloalkyl and heteroalkyl groups may be optionally substituted $R^3$ and $R^5$ taken together form a bond | hydrogen, $C_1$–$C_4$ alkyl, $C_1$–$C_4$ haloalkyl and $C_1$–$C_4$ heteroalkyl, wherein the alkyl, haloalkyl and heteroalkyl groups may be optionally substituted | hydrogen and optionally substituted $C_1$–$C_4$ alkyl | hydrogen |
| $R^4$ | hydrogen, $C_1$–$C_6$ alkyl, $C_1$–$C_6$ haloalkyl and $C_1$–$C_6$ heteroalkyl, wherein the alkyl, haloalkyl and | hydrogen, $C_1$–$C_6$ alkyl, $C_1$–$C_6$ haloalkyl and $C_1$–$C_6$ heteroalkyl, wherein the alkyl, haloalkyl and | hydrogen, $C_1$–$C_4$ alkyl, $C_1$–$C_4$ haloalkyl and $C_1$–$C_4$ heteroalkyl, wherein the alkyl, haloalkyl and | hydrogen and $C_1$–$C_4$ alkyl |

TABLE A-continued

Table of Markush Groups by Variable

| | Markush Group A | Markush Group B | Markush Group C | Markush Group D |
|---|---|---|---|---|
| | heteroalkyl groups may be optionally substituted $R^4$ and $R^6$ taken together form a four to six membered saturated or unsaturated carbocyclic or heterocyclic ring, wherein the carbocyclic or heterocyclic ring may be optionally substituted | heteroalkyl groups may be optionally substituted | heteroalkyl groups may be optionally substituted | |
| $R^5$ | hydrogen, $C_1$–$C_6$ alkyl, $C_1$–$C_6$ haloalkyl and $C_1$–$C_6$ heteroalkyl, wherein the alkyl, haloalkyl and heteroalkyl groups may be optionally substituted $R^5$ and $R^7$ taken together form a bond $R^3$ and $R^5$ taken together form a bond | hydrogen, $C_1$–$C_4$ alkyl, $C_1$–$C_4$ haloalkyl and $C_1$–$C_4$ heteroalkyl, wherein the alkyl, haloalkyl and heteroalkyl groups may be optionally substituted $R^5$ and $R^7$ taken together form a bond | hydrogen, $C_1$–$C_4$ alkyl, $C_1$–$C_4$ haloalkyl and $C_1$–$C_4$ heteroalkyl, wherein the alkyl, haloalkyl and heteroalkyl groups may be optionally substituted | hydrogen and $C_1$–$C_4$ alkyl |
| $R^6$ | hydrogen, $C_1$–$C_6$ alkyl, $C_1$–$C_6$ haloalkyl, $C_1$–$C_6$ heteroalkyl, heteroaryl and aryl, wherein the alkyl, haloalkyl, heteroalkyl, heteroaryl and aryl groups may be optionally substituted $R^4$ and $R^6$ taken together form a four to six membered saturated or unsaturated carbocyclic or heterocyclic ring, wherein the carbocyclic or heterocyclic ring may be optionally substituted $R^6$ and $R^8$ taken together form a three to eight membered saturated or unsaturated carbocyclic or heterocyclic ring, wherein the carbocyclic or heterocyclic ring may optionally substituted | hydrogen, $C_1$–$C_4$ alkyl, $C_1$–$C_4$ haloalkyl, $C_1$–$C_4$ heteroalkyl, heteroaryl and aryl, wherein the alkyl, haloalkyl, heteroalkyl, heteroaryl and aryl groups may be optionally substituted $R^6$ and $R^8$ taken together form a four to six membered saturated or unsaturated carbocyclic or heterocyclic ring, wherein the carbocyclic or heterocyclic ring may optionally substituted | hydrogen, $C_1$–$C_6$ alkyl, $C_1$–$C_6$ haloalkyl and $C_1$–$C_6$ heteroalkyl, wherein the alkyl, haloalkyl and heteroalkyl groups may be optionally substituted $R^6$ and $R^8$ taken together form a four to six membered saturated or unsaturated carbocyclic or heterocyclic ring, wherein the carbocyclic or heterocyclic ring may optionally substituted | hydrogen, $C_1$–$C_4$ alkyl, $C_1$–$C_4$ haloalkyl and $C_1$–$C_4$ heteroalkyl, wherein the alkyl, haloalkyl and heteroalkyl groups may be optionally substituted |
| $R^7$ | hydrogen, $C_1$–$C_6$ alkyl, $C_1$–$C_6$ haloalkyl and $C_1$–$C_6$ heteroalkyl, wherein the alkyl, | hydrogen, $C_1$–$C_4$ alkyl, $C_1$–$C_4$ haloalkyl and $C_1$–$C_4$ heteroalkyl, wherein the alkyl, | hydrogen, $C_1$–$C_4$ alkyl, $C_1$–$C_4$ haloalkyl and $C_1$–$C_4$ heteroalkyl, wherein the alkyl, | hydrogen and $C_1$–$C_4$ alkyl |

TABLE A-continued

Table of Markush Groups by Variable

| | Markush Group A | Markush Group B | Markush Group C | Markush Group D |
|---|---|---|---|---|
| | haloalkyl and heteroalkyl groups may be optionally substituted $R^5$ and $R^7$ taken together form a bond | haloalkyl and heteroalkyl groups may be optionally substituted $R^5$ and $R^7$ taken together form a bond | haloalkyl and heteroalkyl groups may be optionally substituted | |
| $R^8$ | hydrogen, $C_1$–$C_6$ alkyl, $C_1$–$C_6$ haloalkyl, $C_1$–$C_6$ heteroalkyl, heteroaryl and aryl, wherein the alkyl, haloalkyl, heteroalkyl, heteroaryl and aryl groups may be optionally substituted | hydrogen, $C_1$–$C_4$ alkyl, $C_1$–$C_4$ haloalkyl, $C_1$–$C_4$ heteroalkyl, heteroaryl and aryl, wherein the alkyl, haloalkyl, heteroalkyl, heteroaryl and aryl groups may be optionally substituted | hydrogen, $C_1$–$C_6$ alkyl, $C_1$–$C_6$ haloalkyl and $C_1$–$C_6$ heteroalkyl, wherein the alkyl, haloalkyl, heteroalkyl groups may be optionally substituted | hydrogen, methyl, and ethyl |
| | $R^6$ and $R^8$ taken together form a three- to eight-membered saturated or unsaturated carbocyclic or heterocyclic ring, wherein the carbocyclic or heterocyclic ring may be optionally substituted | $R^6$ and $R^8$ taken together form a four- to six-membered saturated or unsaturated carbocyclic or heterocyclic ring, wherein the carbocyclic or heterocyclic ring may be optionally substituted | $R^6$ and $R^8$ taken together form a four- to six-membered saturated or unsaturated carbocyclic or heterocyclic ring, wherein the carbocyclic or heterocyclic ring may be optionally substituted | $R^6$ and $R^8$ taken together form a four- to six-membered carbocyclic or heterocyclic ring, wherein the carbocyclic or heterocyclic ring may optionally substituted |
| $R^9$ | hydrogen, F, Cl, Br, $C_1$–$C_6$ alkyl, $C_1$–$C_6$ haloalkyl and $C_1$–$C_6$ heteroalkyl, wherein the alkyl, haloalkyl and heteroalkyl groups may be optionally substituted | hydrogen, F, Cl, $C_1$–$C_4$ alkyl, $C_1$–$C_4$ haloalkyl and $C_1$–$C_4$ heteroalkyl, wherein the alkyl, haloalkyl and heteroalkyl groups may be optionally substituted | hydrogen, F and $CH_3$ | hydrogen |
| $R^{10}$ | hydrogen, F, Cl, Br, $C_1$–$C_6$ alkyl, $C_1$–$C_6$ haloalkyl and $C_1$–$C_6$ heteroalkyl, wherein the alkyl, haloalkyl and heteroalkyl groups may be optionally substituted | hydrogen, F, Cl, $C_1$–$C_4$ alkyl, $C_1$–$C_4$ haloalkyl and $C_1$–$C_4$ heteroalkyl, wherein the alkyl, haloalkyl and heteroalkyl groups may be optionally substituted | hydrogen, F and $CH_3$ | hydrogen |
| $R^{11}$ | hydrogen, F, Br, Cl, CN, $C_1$–$C_6$ alkyl, $C_1$–$C_6$ haloalkyl, $C_1$–$C_6$ heteroalkyl, $OR^{14}$, $NR^{14}R^{13}$, $SR^{14}$, $CH_2R^{14}$, $C(O)R^{14}$, $CO_2R^{14}$, $C(O)NR^{14}R^{13}$, $SOR^{14}$ and $SO_2R^{14}$, wherein the alkyl, haloalkyl and heteroalkyl groups may be optionally substituted | hydrogen, F, Cl, $OR^{14}$, $SR^{14}$, $NR^{14}R^{13}$, $CH_2R^{14}$, $C(O)R^{14}$, $CO_2R^{14}$, $C(O)NR^{14}R^{13}$, $SOR^{14}$, $SO_2R^{14}$ and optionally substituted $C_1$–$C_4$ alkyl | hydrogen, F, Cl, $OR^{14}$ and $SR^{14}$ | $OR^{14}$ |
| $R^{12}$ | hydrogen, $C_1$–$C_6$ alkyl, $C_1$–$C_6$ haloalkyl, $C_1$–$C_6$ heteroalkyl, $C_2$–$C_6$ alkenyl, $C_2$–$C_6$ alkynyl, | hydrogen, $C_1$–$C_6$ alkyl, $C_1$–$C_6$ haloalkyl, $C_1$–$C_6$ heteroalkyl, $C_2$–$C_6$ alkenyl and $C_2$–$C_6$ alkynyl, wherein | hydrogen, $C_1$–$C_4$ alkyl, $C_1$–$C_4$ haloalkyl and $C_1$–$C_4$ heteroalkyl, wherein the alkyl, haloalkyl and | hydrogen and $C_1$–$C_4$ alkyl |

TABLE A-continued

Table of Markush Groups by Variable

| | Markush Group A | Markush Group B | Markush Group C | Markush Group D |
|---|---|---|---|---|
| | heteroaryl and aryl, wherein the alkyl, haloalkyl, heteroalkyl, alkenyl, alkynyl, heteroaryl and aryl groups may be optionally substituted | the alkyl, haloalkyl, heteroalkyl, alkenyl, and alkynyl groups may be optionally substituted | heteroalkyl groups may be optionally substituted | |
| $R^{13}$ | hydrogen, $C_1$–$C_6$ alkyl, $C_1$–$C_6$ haloalkyl, $C_1$–$C_6$ heteroalkyl, $C_2$–$C_6$ alkenyl, $C_2$–$C_6$ alkynyl, heteroaryl and aryl, wherein the alkyl, haloalkyl, heteroalkyl, alkenyl, alkynyl, heteroaryl and aryl groups may be optionally substituted | hydrogen, $C_1$–$C_6$ alkyl, $C_1$–$C_6$ haloalkyl, $C_1$–$C_6$ heteroalkyl, $C_2$–$C_6$ alkenyl and $C_2$–$C_6$ alkynyl, wherein the alkyl, haloalkyl, heteroalkyl, alkenyl, and alkynyl groups may be optionally substituted | hydrogen, $C_1$–$C_4$ alkyl, $C_1$–$C_4$ haloalkyl and $C_1$–$C_4$ heteroalkyl, wherein the alkyl, haloalkyl and heteroalkyl groups may be optionally substituted | hydrogen and $C_1$–$C_4$ alkyl |
| $R^{14}$ | hydrogen, $C_1$–$C_6$ alkyl, $C_1$–$C_6$ haloalkyl, $C_1$–$C_6$ heteroalkyl, aryl, heteroaryl, $C(O)R^{15}$, $CO_2R^{15}$ and $C(O)NR^{15}R^{16}$, wherein the alkyl, haloalkyl, heteroalkyl, aryl and heteroaryl groups may be optionally substituted | hydrogen, $C(O)R^{15}$, $C(O)NR^{15}R^{16}$, $C_1$–$C_4$ alkyl, $C_1$–$C_4$ haloalkyl, and $C_1$–$C_4$ heteroalkyl, wherein the alkyl, haloalkyl and heteroalkyl groups may be optionally substituted | hydrogen, optionally substituted $C_1$–$C_2$ alkyl, $C(O)CH_3$ and $C(O)N(CH_3)_2$ | hydrogen and $C_1$–$C_2$ alkyl |
| $R^{15}$ | hydrogen, $C_1$–$C_6$ alkyl, $C_1$–$C_6$ haloalkyl, and $C_1$–$C_6$ heteroalkyl, wherein the alkyl, haloalkyl and heteroalkyl groups may be optionally substituted | hydrogen, $C_1$–$C_4$ alkyl, $C_1$–$C_4$ haloalkyl, and $C_1$–$C_4$ heteroalkyl, wherein the alkyl, haloalkyl and heteroalkyl groups may be optionally substituted | hydrogen, $C_1$–$C_2$ alkyl, $C_1$–$C_2$ haloalkyl, and $C_1$–$C_2$ heteroalkyl, wherein the alkyl, haloalkyl and heteroalkyl groups may be optionally substituted | hydrogen and $C_1$–$C_2$ alkyl |
| $R^{16}$ | hydrogen, $C_1$–$C_6$ alkyl, $C_1$–$C_6$ haloalkyl and $C_1$–$C_6$ heteroalkyl, wherein the alkyl, haloalkyl and heteroalkyl groups may be optionally substituted | hydrogen, $C_1$–$C_4$ alkyl, $C_1$–$C_4$ haloalkyl and $C_1$–$C_4$ heteroalkyl, wherein the alkyl, haloalkyl and heteroalkyl groups may be optionally substituted | hydrogen, $C_1$–$C_2$ alkyl, $C_1$–$C_2$ haloalkyl and $C_1$–$C_2$ heteroalkyl, wherein the alkyl, haloalkyl and heteroalkyl groups may be optionally substituted | hydrogen and $C_1$–$C_2$ alkyl |
| W | O and S | O | S | |
| X | O and N{$R^{14}$} | N{$R^{14}$} | O | NH |
| Y | O and S | O | S | |
| Z | O and N{$R^{12}$} | N{$R^{12}$} | O | |
| n | 0 and 1 | 0 | 1 | |
| m | 0 and 1 | 0 | 1 | |

The compounds of the present invention may be synthesized as pharmaceutically acceptable salts for incorporation into various pharmaceutical compositions. As used herein, pharmaceutically acceptable salts include, but are not limited to, hydrochloric, hydrobromic, hydroiodic, hydrofluoric, sulfuric, citric, maleic, acetic, lactic, nicotinic, succinic, oxalic, phosphoric, malonic, salicylic, phenylacetic, stearic, pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino and tris(hydroxymethyl)aminomethane and the like and suitable combination of any two or more thereof. Additional pharmaceutically acceptable salts are known to those skilled in the art.

AR agonist, partial agonist and antagonist compounds of the present invention may be useful in the treatment of conditions including, but not limited to, hypogonadism, frailty, wasting diseases, cachexia, osteoporosis, hirsutism, acne, male-pattern baldness, prostatic hyperplasia, various hormone-dependent disorders and cancers, including, without limitation, prostate and breast cancer. The compounds of the present invention may also prove useful in male hormone replacement therapy, female androgen replacement therapy, stimulation of hematopoiesis, and as anabolic agents and libido stimulants.

It is understood by those skilled in the art that although the compounds of the present invention may be typically employed as selective agonists, partial agonists or antagonists, there may be instances where a compound with a mixed steroid receptor profile is desirable.

Furthermore, it is understood by those skilled in the art that the compounds of the present invention, as well as pharmaceutical compositions and formulations containing these compounds, can be used in a wide variety of combination therapies to treat the conditions and diseases described above. Thus, the compounds of the present invention can be used in combination with other hormones and other therapies, including, without limitation, chemotherapeutic agents such as cytostatic and cytotoxic agents, immunological modifiers such as interferons, interleukins, growth hormones and other cytokines, hormone therapies, surgery and radiation therapy.

Representative AR modulator compounds (i.e., agonists, partial agonists and antagonists) according to the present invention include:

5,6,7,8-Tetrahydro-7,7-dimethyl-4-trifluoromethylpyridino[3,2-f]quinolin-2(1H)-one (Compound 104);
5,6,7,8-Tetrahydro-7,7-diethyl-4-trifluoromethylpyridino[3,2-f]quinolin-2(1H)-one (Compound 105);
7,8-Dihydro-7,7-dimethyl-4-trifluoromethylpyridino[3,2-f]quinolin-2(1H)-one (Compound 106);
5,6,7,8-Tetrahydro-7,7,8-trimethyl-4-trifluoromethylpyridino[3,2-f]quinolin-2(1H)-one (Compound 107);
8-Ethyl-5,6,7,8-tetrahydro-7,7-dimethyl-4-trifluoromethylpyridino[3,2-f]quinolin-2(1H)-one (Compound 108);
5,6,7,8-Tetrahydro-7,7-dimethyl-4-trifluoromethyl-8-propylpyridino[3,2-f]quinolin-2(1H)-one (Compound 109);
8-(2,2,2-Trifluoroethyl)-5,6,7,8-tetrahydro-7,7-dimethyl-4-trifluoromethyl-pyridino[3,2-f]quinolin-2(1H)-one (Compound 110);
6-Hydrazino-4-trifluoromethylquinolin-2(1H)-one (Compound 111);
6-Methyl-4-trifluoromethyl-7H-pyrrolo[3,2-f]quinolin-2(1H)-one (Compound 112);
5-Isopropyl-6-methyl-4-trifluoromethyl-7H-pyrrolo[3,2-f]quinolin-2(1H)-one (Compound 113);
5-Allyl-6-methyl-4-trifluoromethyl-7H-pyrrolo[3,2-f]quinolin-2(1H)-one (Compound 114);
5-(4-Methoxyphenyl)-6-methyl-4-trifluoromethyl-7H-pyrrolo[3,2-f]quinolin-2(1H)-one (Compound 115);
5-(3-Trifluoromethylphenyl)-6-methyl-4-trifluoromethyl-7H-pyrrolo[3,2-f]quinolin-2(1H)-one (Compound 116);
4-Trifluoromethyl-5,6,7,8-tetrahydrocyclopentano[g]pyrrolo[3,2-f]quinolin-2(1H)-one (Compound 117);
4-Trifluoromethyl-5,6,7,8,9,10-hexahydrocycloheptano[g]pyrrolo[3,2-f]quinolin-2(1H)-one (Compound 118);
(±)-4c,5,6,7,7a(cis),8-Hexahydro-8-trifluoroethyl-4-trifluoromethylcyclopentano-[g]pyrrolo[3,2-f]quinolin-2(1H)-one (Compound 119);
(±)-6,6a,7,8,9,9a(cis)-Hexahydro-6-trifluoroethyl-4-trifluoromethylcyclopentano-[i]pyrrolo[2,3-g]quinolin-2(1H)-one (Compound 120);
(±)-4c,5,6,7,7a(cis),8-Hexahydro-8-ethyl-4-trifluoromethylcyclopentano-[g]pyrrolo[3,2-f]quinolin-2(1H)-one (Compound 121);
(±)-6,6a,7,8,9,9a(cis)-Hexahydro-6-ethyl-4-trifluoromethylcyclopentano-[i]pyrrolo[2,3-g]quinolin-2(1H)-one (Compound 122);
(±)-5,6-Dihydro-5,6-cis-dimethyl-7-trifluoroethyl-4-trifluoromethyl-7H-pyrrolo[3,2-f]quinolin-2(1H)-one (Compound 123);
(±)-7,8-Dihydro-7,8-cis-dimethyl-6-trifluoroethyl-4-trifluoromethyl-6H-pyrrolo[2,3-g]quinolin-2(1H)-one (Compound 124);
(±)-4c,5,6,7,7a(cis),8-Hexahydro-8-propyl-4-trifluoromethylcyclopentano-[g]pyrrolo-[3,2-f]quinolin-2(1H)-one (Compound 125);
(±)-4c,5,6,7,7a(cis),8-Hexahydro-8-(3-furanylmethyl)-4-trifluoromethyl-cyclopentano[g]pyrrolo[3,2-f]quinolin-2(1H)-one (Compound 126);
(±)-4c,5,6,7,7a(cis),8-Hexahydro-8-(3-thiophenemethyl)-4-trifluoromethyl-cyclopentano[g]pyrrolo[3,2-f]quinolin-2(1H)-one (Compound 127);
(±)-4c,5,6,7,7a(cis),8-Hexahydro-8-(2-methylpropyl)-4-trifluoromethyl-cyclopentano[g]pyrrolo[3,2-f]quinolin-2(1H)-one (Compound 128);
(±)-4c,5,6,7,7a(cis),8-Hexahydro-8-(2,2,2-chlorodifluoroethyl)-4-trifluoromethylcyclopentano[g]pyrrolo[3,2-f]quinolin-2(1H)-one (Compound 129);
(±)-4c,5,6,7,7a(cis),8-Hexahydro-8-cyclopropylmethyl-4-trifluoromethyl-cyclopentano[g]pyrrolo[3,2-f]quinolin-2(1H)-one (Compound 130);
(±)-4c,5,6,7,7a(cis),8-Hexahydro-8-(2,2-dimethoxyethyl)-4-trifluoromethyl-cyclopentano[g]pyrrolo[3,2-f]quinolin-2(1H)-one (Compound 131);
(±)-4c,5,6,7,8,8a(cis)-Hexahydro-9-(2,2,2-trifluoroethyl)-4-trifluoromethyl-9H-cyclohexano[g]pyrrolo[3,2-f]quinolin-2(1H)-one (Compound 132);
(±)-4c,5,6,7,8,9,9a(cis),10-Octahydro-10-(2,2,2-trifluoroethyl)-4-trifluoromethyl-cycloheptano[g]pyrrolo[3,2-f]quinolin-2(1H)-one (Compound 133);
(±)-5,6-cis-Dihydro-6-ethyl-5-methyl-7-(2,2,2-trifluoroethyl)-4-trifluoromethyl-7H-pyrrolo[3,2-f]quinolin-2(1H)-one (Compound 134);
(±)-5,6-cis-Dihydro-5-butyl-6-methyl-7-(2,2,2-trifluoroethyl)-4-trifluoromethyl-7H-pyrrolo[3,2-f]quinolin-2(1H)-one (Compound 135);
(±)-5,6-cis-Dihydro-5-(4-nitrophenyl)-6-methyl-7-(2,2,2-trifluoroethyl)-4-trifluoromethyl-7H-pyrrolo[3,2-f]quinolin-2(1H)-one (Compound 136);
(±)-5,6-cis-Dihydro-5-(4-dimethylaminophenyl)-6-methyl-7-(2,2,2-trifluoroethyl)-4-trifluoromethyl-7H-pyrrolo[3,2-f]quinolin-2(1H)-one (Compound 137);
(±)-5,6-cis-Dihydro-5-(4-methoxyphenyl)-6-methyl-7-(2,2,2-trifluoroethyl)-4-trifluoromethyl-7H-pyrrolo[3,2-f]quinolin-2(1H)-one (Compound 138);
(±)-5,6-cis-Dihydro-5-(3-trifluoromethylphenyl)-6-methyl-7-(2,2,2-trifluoroethyl)-4-trifluoromethyl-7H-pyrrolo[3,2-f]quinolin-2(1H)-one (Compound 139);
(±)-5,6-cis-Dihydro-5-(4-fluorophenyl)-6-methyl-7-(2,2,2-trifluoroethyl)-4-trifluoromethyl-7H-pyrrolo[3,2-f]quinolin-2(1H)-one (Compound 140);
(±)-5,6-Dihydro-5-phenyl-7-(2,2,2-trifluoroethyl)-4-trifluoromethyl-7H-pyrrolo[3,2-f]quinolin-2(1H)-one (Compound 141);
(±)-5,6-cis-Dihydro-5-(4-methoxyphenyl)-6-methyl-4-trifluoromethyl-7H-pyrrolo[3,2-f]quinolin-2(1H)-one (Compound 142);
(±)-5,6-cis-Dihydro-5-(4-methoxyphenyl)-6-methyl-7-(2,2-dimethoxyethyl)-4-trifluoromethyl-7H-pyrrolo[3,2-f]quinolin-2(1H)-one (Compound 143);

(±)-5,6-cis-Dihydro-5-isopropyl-6-methyl-7-(2,2,2-trifluoroethyl)-4-trifluoromethyl-7H-pyrrolo[3,2-f]quinolin-2(1H)-one (Compound 144);

(±)-5,6-Dihydro-5-ethyl-6-methyl-7-(2,2,2-trifluoroethyl)-4-trifluoromethyl-7H-pyrrolo[3,2-f]quinolin-2(1H)-one (Compound 145);

(±)-5,6-Dihydro-5-ethyl-6-propyl-7-(2,2,2-trifluoroethyl)-4-trifluoromethyl-7H-pyrrolo[3,2-f]quinolin-2(1H)-one (Compound 146);

(±)-5,6-Dihydro-5-(2-ethoxycarbonylethyl)-6-methyl-7-(2,2,2-trifluoroethyl)-4-trifluoromethyl-7H-pyrrolo[3,2-f]quinolin-2(1H)-one (Compound 147);

6-Ethyl-5-methyl-7H-pyrrolo[3,2-f]quinolin-2(1H)-one (Compound 148);

(±)-5,6-cis-Dihydro-5-methyl-6-ethyl-7-(2,2,2-trifluoroethyl)-7H-pyrrolo[3,2-f]quinolin-2(1H)-one (Compound 149);

5,6-Dimethyl-7-(2,2,2-trifluoroethyl)-4-trifluoromethyl-7H-pyrrolo[3,2-f]quinolin-2(1H)-one (Compound 150);

6-Ethyl-5-methyl-7-(2,2,2-trifluoroethyl)-7H-pyrrolo[3,2-f]quinolin-2(1H)-one (Compound 151);

6-Methyl-7-(2,2,2-trifluoroethyl)-4-trifluoromethyl-7H-pyrrolo[3,2-f]quinolin-2(1H)-one (Compound 152);

6-Ethyl-5-methyl-7-(2,2,2-trifluoroethyl)-4-trifluoromethyl-7H-pyrrolo[3,2-f]quinolin-2(1H)-one (Compound 153);

5-Ethyl-6-methyl-7-(2,2,2-trifluoroethyl)-4-trifluoromethyl-7H-pyrrolo[3,2-f]quinolin-2(1H)-one (Compound 154);

5-Ethyl-6-propyl-7-(2,2,2-trifluoroethyl)-4-trifluoromethyl-7H-pyrrolo[3,2-f]quinolin-2(1H)-one (Compound 155);

5,6,7,8-Tetrahydro-8-trifluoroethyl-4-trifluoromethylcyclopentano[g]pyrrolo[3,2-f]quinolin-2(1H)-one (Compound 156);

8-Trifluoroethyl-4-trifluoromethyl-6,8-dihydrocyclopentano[g]pyrrolo[3,2-f]quinolin-2(1H)-one (Compound 157);

9-Trifluoroethyl-4-trifluoromethyl-9H-benzo[g]pyrrolo[3,2-f]quinolin-2(1H)-one (Compound 158);

6-Trifluoroethyl-4-trifluoromethyl-6,7,8,9-tetrahydrocyclopetano[i]pyrrolo[2,3-g]quinolin-2(1H)-one (Compound 159);

5-(3-Trifluoromethylphenyl)-6-methyl-7-(2,2,2-trifluoroethyl)-4-trifluoromethyl-7H-pyrrolo[3,2-f]quinolin-2(1H)-one (Compound 160);

5-(4-Fluorophenyl)-6-methyl-7-(2,2,2-trifluoroethyl)-4-trifluoromethyl-7H-pyrrolo[3,2-f]quinolin-2(1H)-one (Compound 161);

5-(2-Ethoxycarbonylethyl)-6-methyl-7-(2,2,2-trifluoroethyl)-4-trifluoromethyl-7H-pyrrolo[3,2-f]quinolin-2(1H)-one (Compound 162);

7-Ethyl-8-methyl-6-(2,2,2-trifluoroethyl)-4-trifluoromethyl-6H-pyrrolo[2,3-g]quinolin-2(1H)-one (Compound 163);

5-Hydroxymethyl-6-ethyl-7-(2,2,2-trifluoroethyl)-4-trifluoromethyl-7H-pyrrolo[3,2-f]quinolin-2(1H)-one (Compound 164);

5-Methyl-6-(1-hydroxyethyl)-7-(2,2,2-trifluoroethyl)-4-trifluoromethyl-7H-pyrrolo[3,2-f]quinolin-2(1H)-one (Compound 165);

5-Methyl-6-acetyl-7-(2,2,2-trifluoroethyl)-4-trifluoromethyl-7H-pyrrolo[3,2-f]quinolin-2(1H)-one (Compound 166);

5-Formyl-6-methyl-7-(2,2,2-trifluoroethyl)-4-trifluoromethyl-7H-pyrrolo[3,2-f]quinolin-2(1H)-one (Compound 167);

5-Acetyloxymethyl-6-ethyl-7-(2,2,2-trifluoroethyl)-4-trifluoromethyl-7H-pyrrolo[3,2-f]quinolin-2(1H)-one (Compound 168);

2-Acetyloxy-5-hydroxymethyl-6-ethyl-7-(2,2,2-trifluoroethyl)-4-trifluoromethyl-7H-pyrrolo[3,2-f]quinoline (Compound 169);

6-Ethyl-7-(2,2,2-trifluoroethyl)-4-trifluoromethyl-7H-pyrrolo[3,2-f]quinolin-2(1H)-one (Compound 170);

5-Ethoxymethyl-6-ethyl-7-(2,2,2-trifluoroethyl)-4-trifluoromethyl-7H-pyrrolo[3,2-f]quinolin-2(1H)-one (Compound 171);

6-(1-Methoxyethyl)-5-methyl-7-(2,2,2-trifluoroethyl)-4-trifluoromethyl-7H-pyrrolo[3,2-f]quinolin-2(1H)-one (Compound 172);

7-Allyl-6-methyl-4-trifluoromethyl-5H-pyrrolo[2,3-f]quinolin-2(1H)-one (Compound 173);

6-Ethyl-7-methyl-4-trifluoromethyl-5H-pyrrolo[2,3-f]quinolin-2(1H)-one (Compound 175);

7-(3-Trifluoromethylphenyl)-6-methyl-4-trifluoromethyl-5H-pyrrolo[2,3-f]quinolin-2(1H)-one (Compound 176);

7-(2-Hydroxyethyl)-6-methyl-4-trifluoromethyl-5H-pyrrolo[2,3-f]quinolin-2(1H)-one (Compound 177);

(+)-4c,5,6,7,7a(cis),8-Hexahydro-8-trifluoroethyl-4-trifluoromethylcyclopentano-[g]pyrrolo[3,2-f]quinolin-2(1H)-one (Compound 178);

(−)-4c,5,6,7,7a(cis),8-Hexahydro-8-trifluoroethyl-4-trifluoromethylcyclopentano-[g]pyrrolo[3,2-f]quinolin-2(1H)-one (Compound 179);

4-Trifluoromethyl-6,7-dihydro-7,7,9-trimethyl-pyrido[2,3-g]quinolin-2(1H)-one (Compound 180);

8-(2,2,2-Trifluoroethyl)-5,6,7,8-tetrahydro-5,7,7-trimethylpyrido[3,2-f]quinolin-2(1H)-one (Compound 182);

4,5,7-Tri(trifluoromethyl)pyrido[3,2-f]quinolin-2(1H)-one (Compound 185);

5,7-Bis(trifluoromethyl)pyrido[3,2-f]quinolin-2(1H)-one (Compound 186);

4-Trifluoromethyl-7-methyl-6,7,8,9-tetrahydropyrido[2,3-g]quinolin-2(1H)-one (Compound 187);

4-Trifluoromethyl-7,8-dihydro-6H-pyrrolo[2,3-g]quinolin-2(1H)-one (Compound 190);

4-Trifluoromethyl-5,6,7,8-tetrahydropyrido[2,3-g]quinolin-2(1H)-one (Compound 192);

4-Trifluoromethyl-7-methyl-6-propyl-6,7,8,9-tetrahydropyrido[2,3-g]quinolin-2(1H)-one (Compound 194);

4-Trifluoromethyl-7-methyl-6-cyclopropylmethyl-6,7,8,9-tetrahydropyrido[2,3-g]quinolin-2(1H)-one (Compound 195);

4-Trifluoromethyl-7-methyl-6-ethyl-6,7,8,9-tetrahydropyrido[2,3-g]quinolin-2(1H)-one (Compound 196);

4-Trifluoromethyl-7-methyl-6-(2,2,2-trifluoroethyl)-6,7,8,9-tetrahydropyrido[2,3-g]quinolin-2(1H)-one (Compound 197);

4-Trifluoromethyl-6-(2,2,2-trifluoroethyl)-6,7,8,9-tetrahydropyrido[2,3-g]quinolin-2(1H)-one (Compound 198);

4-Trifluoromethyl-6-propyl-6,7,8,9-tetrahydropyrido[2,3-g]quinolin-2(1H)-one (Compound 199);

4-Trifluoromethyl-6-ethyl-6,7,8,9-tetrahydropyrido[2,3-g]quinolin-2(1H)-one (Compound 200);

4-Trifluoromethyl-6-cyclopropylmethyl-6,7,8,9-tetrahydropyrido[2,3-g]quinolin-2(1H)-one (Compound 201);

6,7-Dihydro-8,8-dimethyl-4-(trifluoromethyl)-8H-pyrano[3,2-g]quinolin-2(1H)-one (Compound 202);

6,7-Dihydro-8,8,10-trimethyl-4-(trifluoromethyl)-8H-pyrano[3,2-g]quinolin-2(1H)-one (Compound 206);

(±)-6,7-Dihydro-6-ethyl-4-methyl-8H-pyrano[3,2-g]quinolin-2(1H)-one (Compound 210);

(±)-7,8-Dihydro-8-ethyl-4-methyl-6H-pyrano[2,3-f]quinolin-2(1H)-one (Compound 215);

(±)-6,7-Dihydro-6-ethyl-4-trifluoromethyl-8H-pyrano[3,2-g]quinolin-2(1H)-one (Compound 216);

(−)-6,7-Dihydro-6-ethyl-4-trifluoromethyl-8H-pyrano[3,2-g]quinolin-2(1H)-one (Compound 217);

(+)-6,7-Dihydro-6-ethyl-4-trifluoromethyl-8H-pyrano[3,2-g]quinolin-2(1H)-one (Compound 218);
(±)-6,7-Dihydro-6-ethyl-3-fluoro-4-trifluoromethyl-8H-pyrano[3,2-g]quinolin-2(1H)-one (Compound 219);
(±)-6,7-Dihydro-6-ethyl-4-trifluoromethyl-1-methyl-8H-pyrano[3,2-g]quinolin-2(1H)-one (Compound 220);
(±)-6,7-Dihydro-6-ethyl-3-fluoro-4-trifluoromethyl-1-methyl-8H-pyrano[3,2-g]quinolin-2(1H)-one (Compound 221);
(±)-6,7-Dihydro-6-ethyl-2,4-bis(trifluoromethyl)-8H-pyrano[3,2-g]quinoline (Compound 222);
6,8,8-Trimethyl-4-trifluoromethyl-8H-pyrano[3,2-g]coumarin (Compound 223);
6-Ethyl-8,8-dimethyl-4-trifluoromethyl-8H-pyrano[3,2-g]coumarin (Compound 227);
(±)-5,6-Dihydro-6-hydroxymethyl-4-trifluoromethylpyrrolo[3,2-f]quinolin-2(1H)-one (Compound 228);
(±)-5,6-Dihydro-7-ethyl-6-hydroxymethyl-4-trifluoromethylpyrrolo[3,2-f]quinolin-2(1H)-one (Compound 229);
7,8-Dihydro-6-(2,2,2-trifluoroethyl)-4-trifluoromethylpyrrolo[2,3-g]quinolin-2(1H)-one (Compound 230);
6-(2,2,2-Trifluoroethyl)-4-trifluoromethylpyrrolo[2,3-g]quinolin-2(1H)-one (Compound 231);
8-Chloro-6-(2,2,2-trifluoroethyl)-4-trifluoromethylpyrrolo[2,3-g]quinolin-2(1H)-one (Compound 232);
5-Methyl-7-(2,2,2-trifluoroethyl)-4-trifluoromethylpyrrolo[3,2-f]quinolin-2(1H)-one (Compound 233);
6-Formyl-5-methyl-7-(2,2,2-trifluoroethyl)-4-trifluoromethyl-7H-pyrrolo[3,2-f]quinolin-2(1H)-one (Compound 234);
5,6-Dimethyl-7-(2,2-difluorovinyl)-4-trifluoromethyl-7H-pyrrolo[3,2-f]quinolin-2(1H)-one (Compound 235).

Within such group, representative compounds include:
8-Ethyl-5,6,7,8-tetrahydro-7,7-dimethyl-4-trifluoromethylpyridino[3,2-f]quinolin-2(1H)-one (Compound 108);
5,6,7,8-Tetrahydro-7,7-dimethyl-4-trifluoromethyl-8-propylpyridino[3,2-f]quinolin-2(1H)-one (Compound 109);
8-(2,2,2-Trifluoroethyl)-5,6,7,8-tetrahydro-7,7-dimethyl-4-trifluoromethyl-pyridino[3,2-f]quinolin-2(1H)-one (Compound 110);
(±)-4c,5,6,7,7a(cis),8-Hexahydro-8-trifluoroethyl-4-trifluoromethylcyclopentano-[g]pyrrolo[3,2-f]quinolin-2(1H)-one (Compound 119);
(±)-6,6a,7,8,9,9a(cis)-Hexahydro-6-trifluoroethyl-4-trifluoromethylcyclopentano-[i]pyrrolo[2,3-g]quinolin-2(1H)-one (Compound 120);
(±)-4c,5,6,7,7a(cis),8-Hexahydro-8-ethyl-4-trifluoromethylcyclopentano-[g]pyrrolo[3,2-f]quinolin-2(1H)-one (Compound 121);
(±)-5,6-Dihydro-5,6-cis-dimethyl-7-trifluoroethyl-4-trifluoromethyl-7H-pyrrolo[3,2-f]quinolin-2(1H)-one (Compound 123);
(±)-7,8-Dihydro-7,8-cis-dimethyl-6-trifluoroethyl-4-trifluoromethyl-6H-pyrrolo[2,3-g]quinolin-2(1H)-one (Compound 124);
(±)-4c,5,6,7,7a(cis),8-Hexahydro-8-propyl-4-trifluoromethylcyclopentano-[g]pyrrolo-[3,2-f]quinolin-2(1H)-one (Compound 125);
(±)-4c,5,6,7,7a(cis),8-Hexahydro-8-(2,2,2-chlorodifluoroethyl)-4-trifluoromethylcyclopentano[g]pyrrolo[3,2-f]quinolin-2(1H)-one (Compound 129);
(±)-4c,5,6,7,7a(cis),8-Hexahydro-8-cyclopropylmethyl-4-trifluoromethyl-cyclopentano[g]pyrrolo[3,2-f]quinolin-2(1H)-one (Compound 130);
(±)-4c,5,6,7,8,8a(cis)-Hexahydro-9-(2,2,2-trifluoroethyl)-4-trifluoromethyl-9H-cyclohexano[g]pyrrolo[3,2-f]quinolin-2(1H)-one (Compound 132);
(±)-5,6-cis-Dihydro-6-ethyl-5-methyl-7-(2,2,2-trifluoroethyl)-4-trifluoromethyl-7H-pyrrolo[3,2-f]quinolin-2(1H)-one (Compound 134);
(±)-5,6-cis-Dihydro-5-butyl-6-methyl-7-(2,2,2-trifluoroethyl)-4-trifluoromethyl-7H-pyrrolo[3,2-f]quinolin-2(1H)-one (Compound 135);
(±)-5,6-Dihydro-5-ethyl-6-methyl-7-(2,2,2-trifluoroethyl)-4-trifluoromethyl-7H-pyrrolo[3,2-f]quinolin-2(1H)-one (Compound 145);
(±)-5,6-Dihydro-5-ethyl-6-propyl-7-(2,2,2-trifluoroethyl)-4-trifluoromethyl-7H-pyrrolo[3,2-f]quinolin-2(1H)-one (Compound 146);
(±)-5,6-cis-Dihydro-5-methyl-6-ethyl-7-(2,2,2-trifluoroethyl)-7H-pyrrolo[3,2-f]quinolin-2(1H)-one (Compound 149);
5,6-Dimethyl-7-(2,2,2-trifluoroethyl)-4-trifluoromethyl-7H-pyrrolo[3,2-f]quinolin-2(1H)-one (Compound 150);
6-Methyl-7-(2,2,2-trifluoroethyl)-4-trifluoromethyl-7H-pyrrolo[3,2-f]quinolin-2(1H)-one (Compound 152);
6-Ethyl-5-methyl-7-(2,2,2-trifluoroethyl)-4-trifluoromethyl-7H-pyrrolo[3,2-f]quinolin-2(1H)-one (Compound 153);
5-Ethyl-6-methyl-7-(2,2,2-trifluoroethyl)-4-trifluoromethyl-7H-pyrrolo[3,2-f]quinolin-2(1H)-one (Compound 154);
5,6,7,8-Tetrahydro-8-trifluoroethyl-4-trifluoromethylcyclopentano[g]pyrrolo[3,2-f]quinolin-2(1H)-one (Compound 156);
6-Trifluoroethyl-4-trifluoromethyl-6,7,8,9-tetrahydrocyclopetano[i]pyrrolo[2,3-g]quinolin-2(1H)-one (Compound 159);
7-Ethyl-8-methyl-6-(2,2,2-trifluoroethyl)-4-trifluoromethyl-6H-pyrrolo[2,3-g]quinolin-2(1H)-one (Compound 163);
6-Ethyl-7-(2,2,2-trifluoroethyl)-4-trifluoromethyl-7H-pyrrolo[3,2-f]quinolin-2(1H)-one (Compound 170);
(+)-4c,5,6,7,7a(cis),8-Hexahydro-8-trifluoroethyl-4-trifluoromethylcyclopentano-[g]pyrrolo[3,2-f]quinolin-2(1H)-one (Compound 178);
(−)-4c,5,6,7,7a(cis),8-Hexahydro-8-trifluoroethyl-4-trifluoromethylcyclopentano-[g]pyrrolo[3,2-f]quinolin-2(1H)-one (Compound 179);
8-(2,2,2-Trifluoroethyl)-5,6,7,8-tetrahydro-5,7,7-trimethylpyrido[3,2-f]quinolin-2(1H)-one (Compound 182);
4-Trifluoromethyl-7-methyl-6-(2,2,2-trifluoroethyl)-6,7,8,9-tetrahydropyrido[2,3-g]quinolin-2(1H)-one (Compound 197);
6,7-Dihydro-8,8-dimethyl-4-(trifluoromethyl)-8H-pyrano[3,2-g]quinolin-2(1H)-one (Compound 202);
(−)-6,7-Dihydro-6-ethyl-4-trifluoromethyl-8H-pyrano[3,2-g]quinolin-2(1H)-one (Compound 217); and
(+)-6,7-Dihydro-6-ethyl-4-trifluoromethyl-8H-pyrano[3,2-g]quinolin-2(1H)-one (Compound 218).

The sequences of steps for several general schemes to synthesize the compounds of the present invention are shown below. In each of the Schemes the R groups (e.g., $R_1$, $R_2$, etc.) correspond to the specific substitution patterns noted in the Examples. However, it will be understood by those skilled in the art that other functionalities disclosed herein at the indicated positions of compounds of formulas I through VIII are also potential substituents for the analogous positions on the structures within the Schemes.

Scheme I

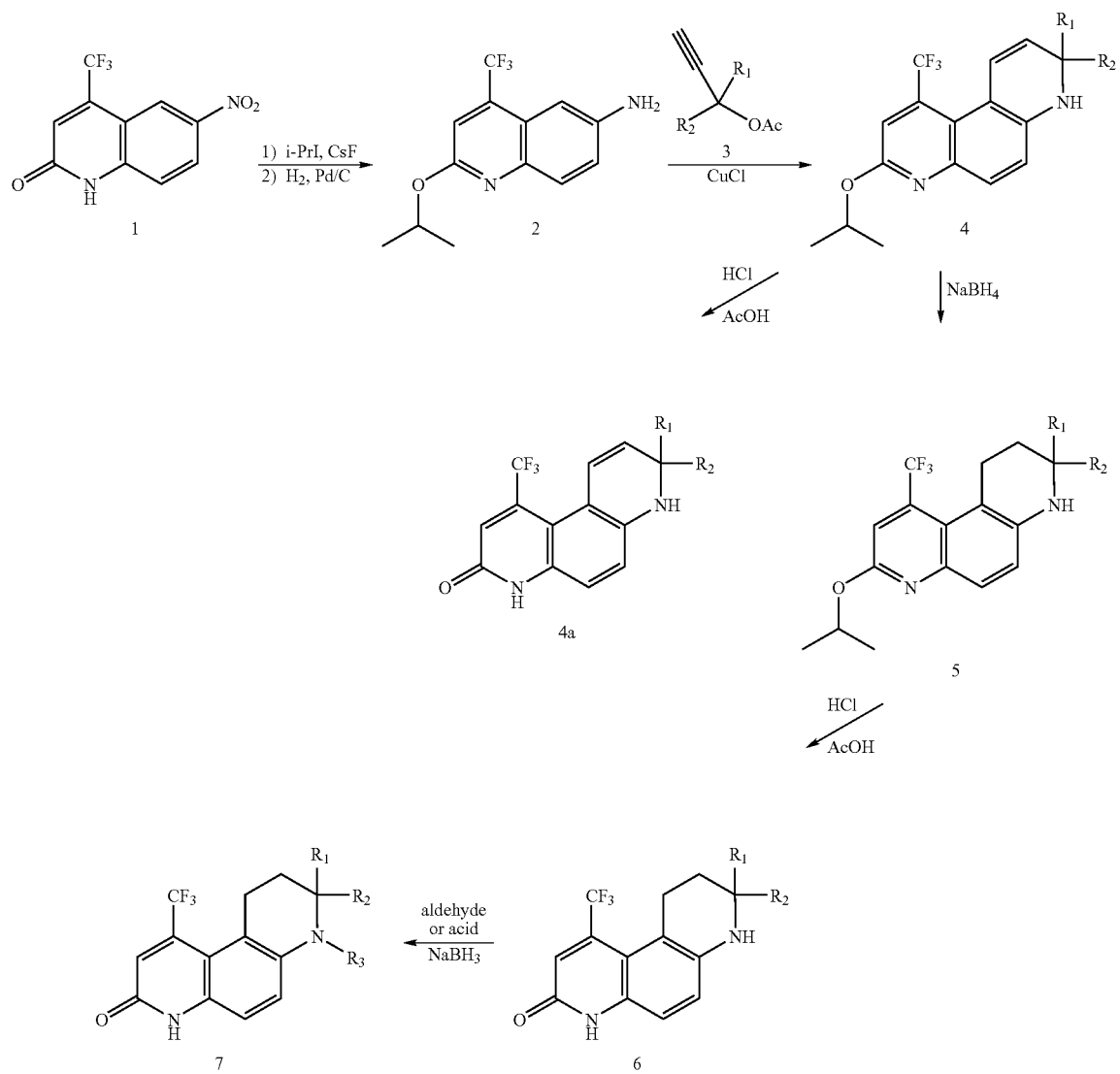

Scheme I describes the synthesis of the tricyclic quinolinones of structure 7. Treatment of 6-nitro-2-quinolinone (structure 1) with alkyl halide such as 2-iodopropane in the presence of CsF followed by a palladium catalyzed hydrogenation provide aminoquinoline of structure 2. Copper catalyzed coupling reaction of structure 2 and propargyl acetate such as structure 3 followed by a copper catalyzed cyclization regioselectively afford tricyclic quinoline derivatives of structure 4. Reduction of dihydroquinolines of structure 4 with NaBH$_4$ gives tetrahydroquinolines of structure 5. Acid catalyzed hydrolysis of structure 5 provides quinolinones of structure 6. Selective alkylation at 8-position with an aldehyde or acid in the presence of a reducing agent such as NaBH$_4$ afford compounds of structure 7.

Scheme II

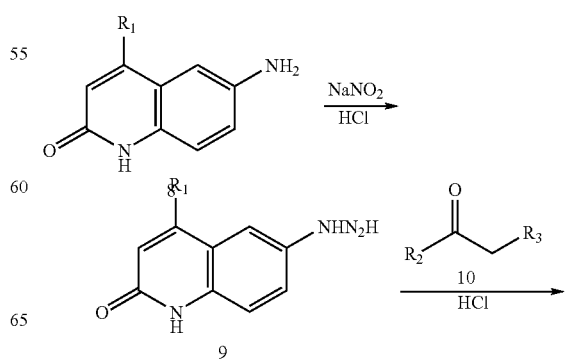

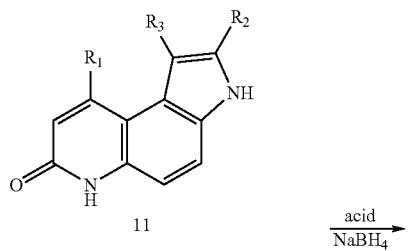
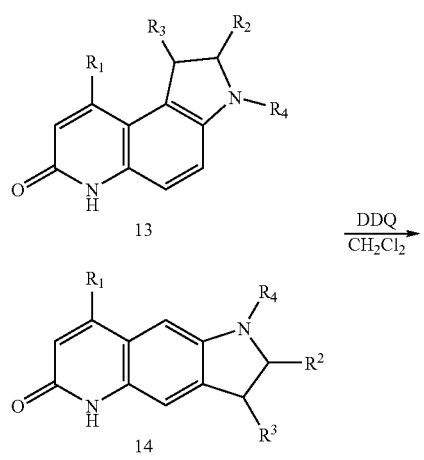
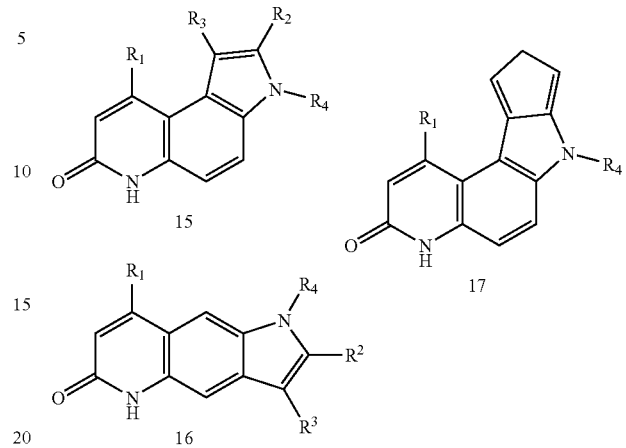

Scheme II describes the synthesis of angular and linear indole/indoline analogues of structures 13–17. Treatment of 6-amino-2-quinolinones of structure 8 with $NaNO_2$ in strongly acidic conditions such as concentrated HCl generates hydrazines of structure 9. Reaction of compound of structure 9 with a ketone such as structure 10 in acidic conditions affords a mixture of pyrroloquinolinones of structures 11 and 12, which can be separated by chromatography. Reductive alkylation of the indole nitrogen atom in structure 11 or 12 with an acid or aldehyde in the presence of a reducing agent such as $NaBH_4$ results in the formation of the reduced and alkylated products of structure 13 or 14. Oxidation of structure 13 or 14 provides analogues of structure 15, 16 or 17.

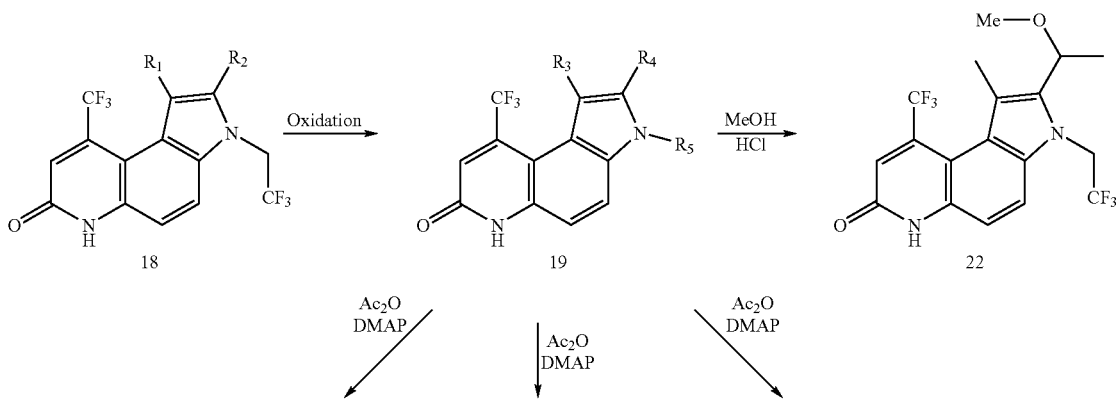

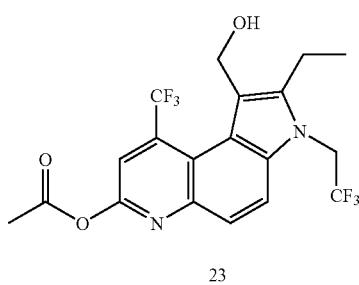
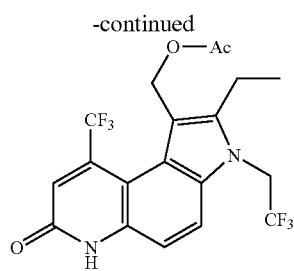
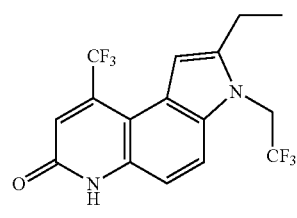

Scheme III describes side chain manipulation of compounds of structure 18. Treatment of compounds of structure 18 with an oxidating reagent such as DDQ or MnO₂ affords products of structure 19. Acylation of compounds of structure 19 with acetyl anhydride in the presence of DMAP generates compounds of structures 20 and 23. Compounds of structure 21 is a by-product of the acylation reaction. Treatment of compounds of structure 19 with HCl in methanol gives the ether products of structure 22.

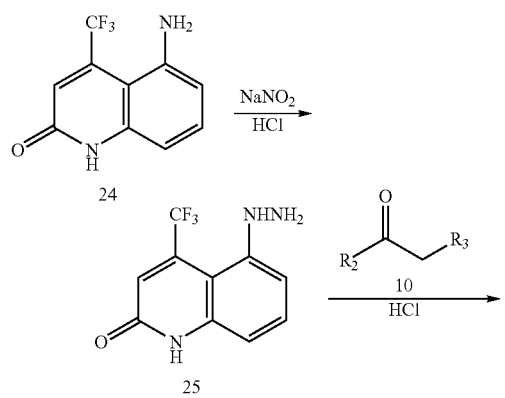

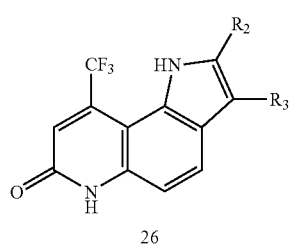

Scheme IV describes the preparation of tricyclic compounds of structure 26 by Fischer indole synthesis. Treatment of the 5-aminoquinolinone of structure 24 with NaNO₂ in acidic conditions provides the hydrazine intermediates of structure 25. Condensation of the hydrazine (structure 25) and a ketone of structure 10 followed by acid catalyzed cyclization afford compounds of structure 26.

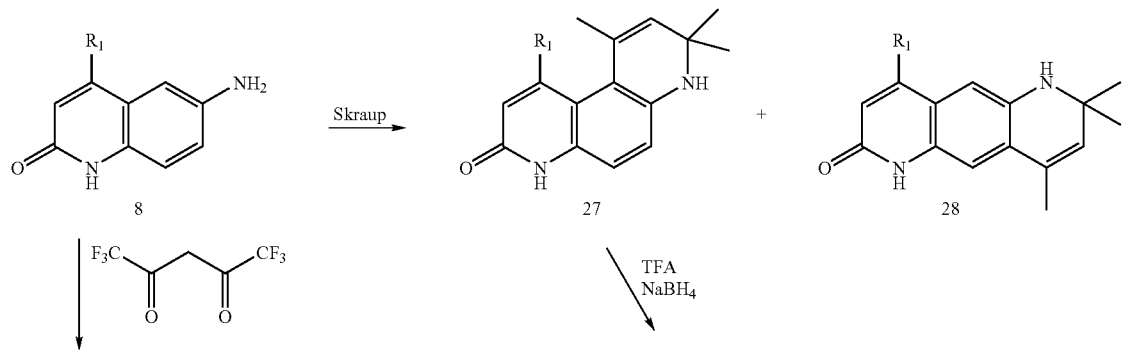

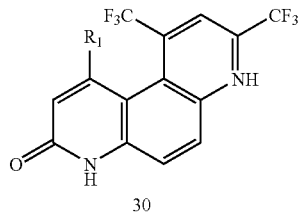

30

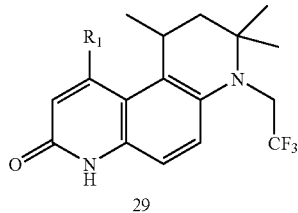

29

Scheme V describes the preparation of tricyclic analogues from 6-aminoquinolinones of structure 8. Skraup reaction of an aminoquinoline of structure 8 in acetone at high temperature affords compounds of structures 27 or 28 that depends on the substituent $R_1$. Treatment of compounds of structure 27 under a reductive alkylation condition such as NaBH$_4$ in TFA provides compounds of structure 29. Condensation of the aminoquinolines of structure 8 with 1,1,1,5,5,5-hexafluoro-2,4-pentadione affords compounds of structure 30.

Scheme VI describes the synthesis of the tricyclic compounds of structures 34 and 34a. Nitration of a tetrahydroquinoline of structure 31 provides compounds of structure 32. Palladium catalyzed hydrogenation of compounds of structure 32 followed by the Knorr reaction afford the mixture compounds of structures 33 and 33a. Selective alkylation of compounds of structures 33 and 33a gives compounds of structures 34 and 34a.

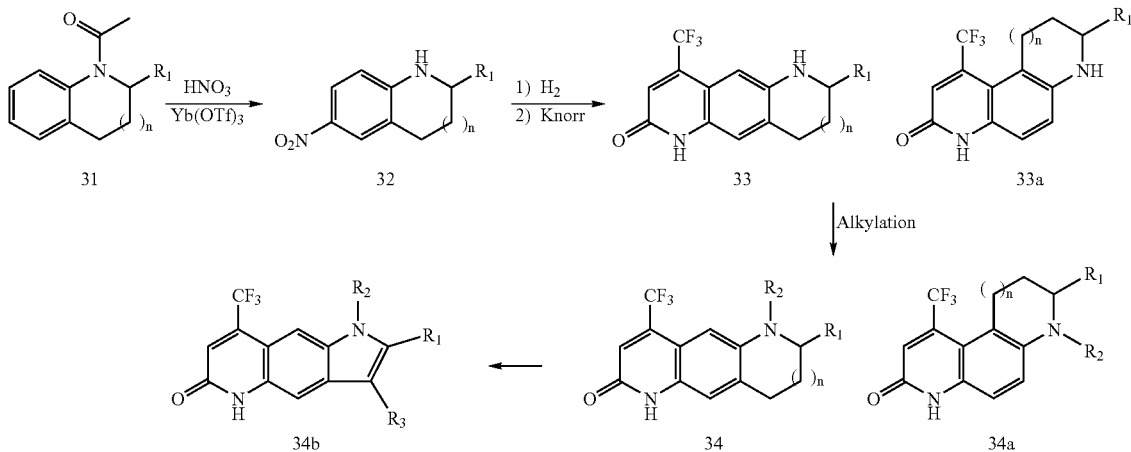

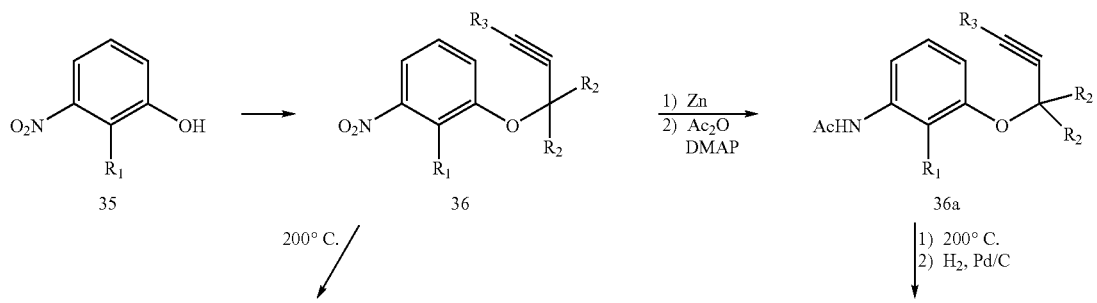

-continued

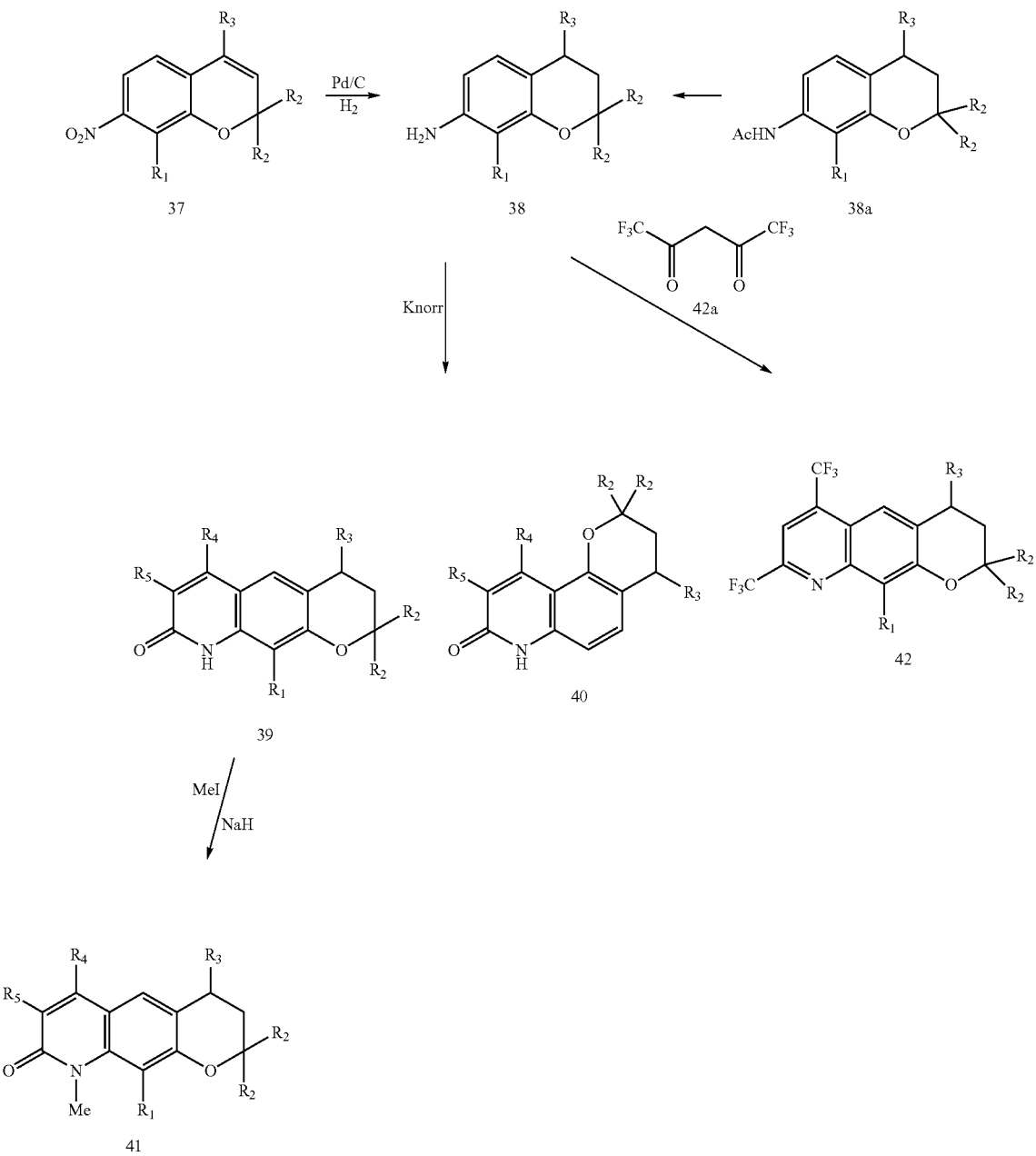

Scheme VII describes the synthesis of the tricyclic pyranoquinolines of structures 39 and 41. Alkylation of 3-nitrophenols of structure 35 gives compounds of structure 36. Thermal cyclization of the propargyl ethers of structure 36 affords the chromenes of structure 37. Reduction of the nitro group by hydrogenation provides the aminochromans of structure 38. An alternate route starts with reduction of the nitro group in compounds of structure 36 with zinc powder followed by acylation to give the compound of structure 36a. Cyclization at high temperature, followed by palladium catalyzed hydrogenation, provides the chroman of structure 38a. Hydrolysis of the acetyl group affords aminochroman of structure 38. Treatment of compounds of structure 38 with a ketoester such as ethyl 4,4,4-trifluoro-3-ketobutyrate under Knorr condition gives compounds of structures 39 and 40. In the case when the diketone of structure 42a is used, a quinoline of structure 42 is the product. Methylation of compounds of structure 39 with iodomethane and sodium hydride affords compounds of structure 41.

Scheme VIII

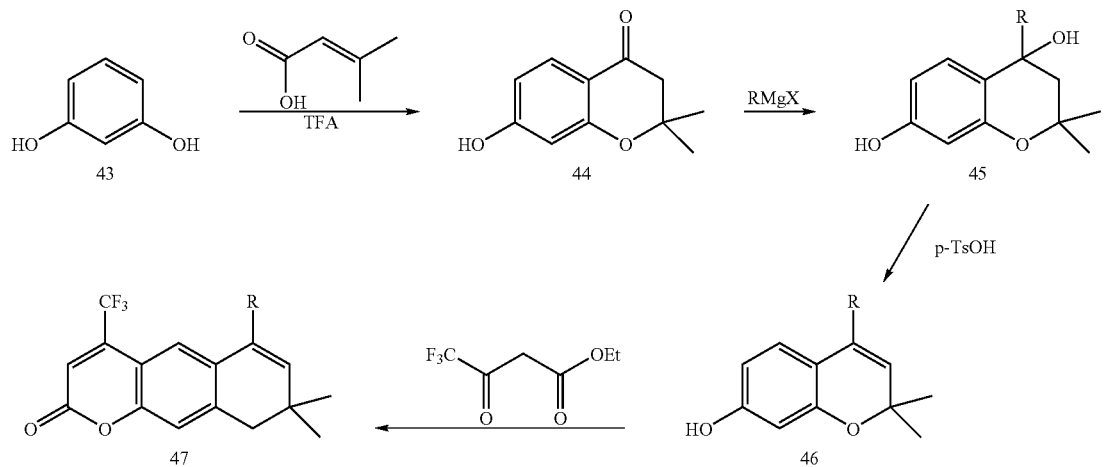

Scheme VIII describes the synthesis of the tricyclic coumarins of structure 47. Annulation to form compounds of structure 44 is accomplished by heating 1,3-resorcinol and 3,3-dimethylacrylic acid in TFA. Grignard addition to chromenones of structure 44 affords compounds of structure 45, which is dehydrated under acidic condition to give chromenes of structure 46. Treatment of the hydroxy-chromenes of structure 46 with a ketoester such as ethyl 4,4,4-trifluoroacetoacetate in the presence of $POCl_3$ affords compounds of structure 47.

mixtures of said compounds, including isotopically-labeled and radio-labeled compounds. Such isomers can be isolated by standard resolution techniques, including fractional crystallization and chiral column chromatography.

As noted above, the androgen receptor modulator compounds of the present invention can be combined in a mixture with a pharmaceutically acceptable carrier to provide pharmaceutical compositions useful for treating the biological conditions or disorders noted herein in mammalian and particularly in human patients. The particular carrier Scheme IX

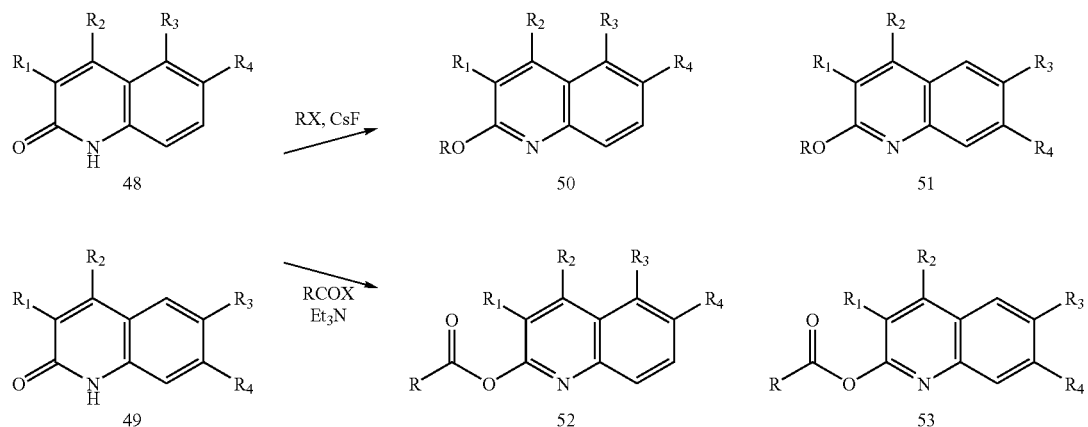

Scheme IX describes the general procedure to convert the 2-quinolinone derivatives to the typical 2-substituted quinoline derivatives. Treatment of compounds of structures 48 and 49 with a haloalkyl in the presence of a catalyst such as CsF produces the corresponding 2-alkoxy quinoline compounds of structures 50 and 51. Treatment of compounds of structures 48 and 49 with an acyl halide in the presence of a base, such as triethylamine, affords the 2-acyloxy quinolines of structures 52 and 53.

The compounds of the present invention also include racemates, stereoisomers, optically pure enantiomers and employed in these pharmaceutical compositions may take a wide variety of forms depending upon the type of administration desired. Suitable administration routes include enteral (e.g., oral), topical, suppository and parenteral (e.g., intravenous, intramuscular and subcutaneous).

In preparing the compositions in oral liquid dosage forms (e.g., suspensions, elixirs and solutions), typical pharmaceutical media, such as water, glycols, oils, alcohols, flavoring agents, preservatives, coloring agents and the like can be employed. Similarly, when preparing oral solid dosage forms (e.g., powders, tablets and capsules), carriers such as starches, sugars, diluents, granulating agents, lubricants, binders, disintegrating agents and the like may be employed. Due to their ease of administration, tablets and capsules represent a desirable oral dosage form for the pharmaceutical compositions of the present invention.

For parenteral administration, the carrier typically will include sterile water, although other ingredients that aid in solubility or serve as preservatives, may also be included. Furthermore, injectable suspensions may also be prepared, in which case appropriate liquid carriers, suspending agents and the like may be employed.

For topical administration, the compounds of the present invention may be formulated using bland, moisturizing bases, such as ointments or creams. Examples of suitable ointment bases are petrolatum, petrolatum plus volatile silicones, lanolin and water in oil emulsions such as Eucerin™, available from Beiersdorf (Cincinnati, Ohio). Examples of suitable cream bases are Nivea™ Cream, available from Beiersdorf (Cincinnati, Ohio), cold cream (USP), Purpose Cream™, available from Johnson & Johnson (New Brunswick, N.J.), hydrophilic ointment (USP) and Lubriderm™, available from Warner-Lambert (Morris Plains, N.J.).

The pharmaceutical compositions and compounds of the present invention generally will be administered in the form of a dosage unit (e.g., tablet, capsule, etc.). The compounds of the present invention generally are administered in a daily dosage of from about 1 µg/kg of body weight to about 500 mg/kg of body weight. Typically, the compounds of the present invention are administered in a daily dosage of from about 10 µg/kg to about 250 mg/kg of body weight. Most often, the compounds of the present invention are administered in a daily dosage of from about 20 µg/kg to about 100 mg/kg body weight. As recognized by those skilled in the art, the particular quantity of pharmaceutical composition according to the present invention administered to a patient will depend upon a number of factors, including, without limitation, the biological activity desired, the condition of the patient and the patient's tolerance for the drug.

The compounds of this invention also have utility when labeled (e.g., radio-labeled, isotopically-labeled and the like) as ligands for use in assays to determine the presence of AR in a cell background or extract. They are particularly useful due to their ability to selectively activate androgen receptors and can therefore be used to determine the presence of such receptors in the presence of other steroid receptors or related intracellular receptors.

These invention methods comprise contacting the cell or cell extract with the compounds of the present invention which have been labeled and testing the contacted cell or cell extract to determine the presence of AR. Testing can be accomplished via testing for activation of androgen receptor(s) (e.g., via elevated presence of the product of androgen mediated process(es)), via separation of the bound compound/receptor combination and the like, which techniques are known to those of skill in the art.

Due to the selective specificity of the compounds of this invention for steroid receptors, these compounds can be used to purify samples of steroid receptors in vitro. Such purification can be carried out by mixing samples containing steroid receptors with one or more of the compounds of the present invention so that the compounds bind to the receptors of choice and then isolating the bound ligand/receptor combination by separation techniques which are known to those of skill in the art. These techniques include column separation, filtration, centrifugation, tagging and physical separation and antibody complexing, among others.

The compounds and pharmaceutical compositions of the present invention can be used in the treatment of the diseases and conditions described herein. In this regard, the compounds and compositions of the present invention may prove particularly useful as modulators of male sex steroid-dependent diseases and conditions such as the treatment of hypogonadism, sexual dysfunction, acne, male-pattern baldness, wasting diseases, hirsutism, prostatic hyperplasia, osteoporosis, impotence, cancer cachexia, various hormone-dependent cancers, including, without limitation, prostate and breast cancer. The compounds of the present invention may also prove useful in male hormone replacement therapy, stimulation of hematopoiesis, male contraception and as anabolic agents.

The compounds of the present invention may be extremely potent activators of AR, displaying 50% maximal activation of AR (e.g., activation of AR, determined by measurement of luciferase production levels compared to levels achieved by dihydrotestosterone (DHT)) at a concentration of less than 100 nM (Cotransfection assay concentration), at a concentration of less than 50 nM, at a concentration of less than 20 nM, or even at a concentration of 10 nM or less. (See, for example, Biological Examples.)

Alternatively, the compounds of the present invention may be extremely potent inhibitors of AR, displaying 50% maximal inhibition of AR (e.g., inhibition of AR, determined by measurement of luciferase production levels compared to levels achieved by dihydrotestosterone (DHT)) at a concentration of less than 100 nM (Cotransfection assay concentration), at a concentration of less than 50 nM, at a concentration of less than 20 nM, or even at a concentration of 10 nM or less. (See, for example, Biological Examples.)

In one embodiment, the selective compounds of the present invention generally do not display undesired cross-reactivity with other steroid receptors, as is seen with the compound mifepristone (RU486; Roussel Uclaf), a known PR antagonist that displays an undesirable cross reactivity on GR and AR, thereby limiting its use in long-term, chronic administration.

The invention will be further illustrated by reference to the following non-limiting Examples.

EXAMPLE 1

7,8-Dihydro-7,7-dimethyl-2-isopropoxy-4-trifluoromethyl-8H-pyridino[3,2-f]quinoline (Compound 101, Structure 4 of Scheme I, where $R_1=R_2=$methyl)

6-Amino-2-isopropoxy-4-trifluoromethylquinoline (Compound 102, Structure 2 of Scheme 1):

In a 250-mL r.b. flask, a solution of 4-trifluoromethyl-6-nitroquinolinone (structure 1 of Scheme I) (3.78 g, 14.6 mmol) in DMF (75 mL) was treated with CsF (12.41 g, 73 mmol, 5.0 equiv.) and 2-iodopropane (11.09 g, 73 mmol, 5.0 equiv). The reaction mixture was stirred at room temperature (rt) for 18 h. The reaction mixture was quenched with $H_2O$ (100 mL) and extracted with EtOAc (3×200 mL). The combined EtOAc extracts were washed with saturated aqueous $NH_4Cl$ solution (300 mL), $H_2O$ (300 mL) and brine (300 mL). Dried ($MgSO_4$), filtered and concentrated in vacuo. The residue was purified by flash column chromatography ($SiO_2$, 5×20 cm, 2% EtOAc in hexane as eluent) to afford 3.94 g (90%) of the 2-isopropoxyquinoline as a white solid. $R_f$ 0.81 (SiO$_2$, 10% EtOAc-hexane). $^1$H NMR (400 MHz, CDCl$_3$) 8.93 (s, 1H), 8.47 (dd, 1H, J=9.2, 2.5) 7.98 (d, 1H, J=9.2), 7.32 (s, 1H), 5.62 (septet, 1H, J=6.2), 1.45 (d, 1H, J=6.2).

In a 100-mL r.b. flask, a solution of 2-isopropoxy-4-trifluoromethyl-6-nitroquinolinone (1.0 g, 3.3 mmol) in a 3:1 ratio of CH$_2$Cl$_2$/MeOH (40 mL) was treated with 10% Pd/C (168 mg, 16 wt. % equiv). The resulting mixture was stirred under H$_2$ (1 atm) at rt for 18 h. The reaction mixture was filtered through a pad of celite and the celite cake was rinsed with MeOH (100 mL). The filtrate was concentrated in vacuo to give 0.85 g (95%) of compound 102 as colorless oil that was used immediately in the next reaction without further purification. $R_f$ 0.27 (SiO$_2$, 10% EtOAc-hexane). $^1$H NMR (400 MHz, CDCl$_3$) 7.70 (d, 1H, J=9.6) 7.13 (m, 3H), 5.49 (septet, 1H, J=6.2), 3.89 (s, 2H), 1.39 (d, 1H, J=6.2).

7,8-Dihydro-7,7-dimethyl-2-isopropoxy-4-trifluoromethyl-8H-pyridino[3,2-f]quinoline (Compound 101, Structure 4 of Scheme I, where R$_1$=R$_2$=methyl).

In a 250-mL r.b. flask, a solution of compound 102 (4.55 g, 16.8 mmol) in THF (150 mL) was treated with Cu(I)Cl (0.167 g, 0.168 mmol, 10 mol %) and 2-acetoxy-2-methyl-3-butyne (structure 3 of Scheme I, where R$_1$=R$_2$=methyl) (3.19 g, 25.3 mmol, 1.5 equiv). The reaction mixture was heated to reflux for 18 h. After cooling to rt, the reaction mixture was filtered through a pad of celite and the celite cake was rinsed with EtOAc (300 mL). The filtrate was washed with saturated aqueous NH$_4$Cl solution (150 mL), H$_2$O (150 mL) and brine (150 mL). Dried (MgSO$_4$), filtered and concentrated in vacuo. The residue was purified by flash column chromatography (SiO$_2$, 5×20 cm, 5% EtOAc in hexane as eluent) to afford 4.85 g (86%) of compound 101 as a yellow-greenish solid. $R_f$ 0.53 (SiO$_2$, 10% EtOAc-hexane). $^1$H NMR (400 MHz, CDCl$_3$) 7.57 (d, 1H, J=8.9), 7.19 (s, 1H), 6.95 (d, 1H, J=8.9), 6.91 (d, 1H, J=10), 5.50–5.43 (m, 2H), 4.06 (s, 1H), 1.38 (d, 6H, J=6.2), 1.33 (s, 6H).

EXAMPLE 2

5,6,7,8-Tetrahydro-7,7-dimethyl-2-isopropoxy-4-trifluoromethylpyridino[3,2-f]quinoline (Compound 103, Structure 5 of Scheme I, where R$_1$=R$_2$=methyl)

In a 250-mL r.b. flask, a solution of compound 101 (3.64 g, 10.8 mmol) in TFA (50 mL) was treated with NaBH$_4$ caplets (4.5 g, 119 mmol, 11 equiv). The reaction mixture was stirred at rt for 20 h. The reaction mixture was poured onto 200 mL of ice-water, neutralized with NaHCO$_3$ powder to pH 7 and extracted with EtOAc (3×250 mL). The combined extracts were washed with brine (2×200 mL), dried (MgSO$_4$), filtered and concentrated in vacuo. The residue was purified by flash column chromatography (SiO$_2$, 5×20 cm, 5% EtOAc in hexane as eluent) to afford 3.38 g (92%) of compound 103 as a yellow solid. $R_f$ 0.50 (SiO$_2$, 10% EtOAc-hexane). $^1$H NMR (400 MHz, CDCl$_3$) 7.56 (d, 1H, J=8.8), 7.24 (s, 1H), 6.89 (d, 1H, J=8.8), 5.46 (septet, 1H, J=6.2), 3.85 (s, 1H), 3.07 (t, 2H, J=6.5), 1.68 (t, 2H, J=6.5), 1.38 (d, 6H, J=6.2), 1.26 (s, 6H).

EXAMPLE 3

5,6,7,8-Tetrahydro-7,7-dimethyl-4-trifluoromethylpyridino[3,2-f]quinolin-2(1H)-one (Compound 104, Structure 6 of Scheme I, where R$_1$=R$_2$=methyl)

In a 250-mL r.b. flask, a solution of compound 103 (3.97 g, 11.7 mmol) in AcOH (50 mL) was treated with conc. HCl (50 mL). The reaction mixture was heated to 95° C. and stirred for 4 h. After cooling to rt, the reaction mixture was poured onto ice-water, neutralized with NaHCO$_3$ powder to pH 7 and extracted with EtOAc (3×500 mL). The combined extracts were washed with H$_2$O (500 mL) and brine (500 mL), dried (MgSO$_4$), filtered and concentrated in vacuo. The residue was purified by recrystallizing from EtOAc/hexane to afford 3.42 g (98%) of compound 104 as a yellow-orange solid. $^1$H NMR (400 MHz, CDCl$_3$) 10.35 (br. s, 1H), 7.27 (d, 1H, J=8.6), 7.25 (s, 1H), 6.82 (d, 1H, J=8.6), 3.80 (s, 1H), 3.03 (t, 2H, J=6.5), 1.67 (t, 2H, J=6.5), 1.24 (s, 6H).

EXAMPLE 4

5,6,7,8-Tetrahydro-7,7-diethyl-4-trifluoromethylpyridino[3,2-f]quinolin-2(1H)-one (Compound 105, Structure 6 of Scheme I, where R$_1$=R$_2$=ethyl)

This compound was prepared in a similar fashion as described in Examples 1, 2 and 3 from compound 102 and 2',2'-diethylpropargyl acetate (structure 3 of Scheme I, where R$_1$=R$_2$=ethyl). Spectral data for compound 105: $^1$H NMR (400 MHz, CDCl$_3$) 7.22 (s, 1H), 7.14 (d, J=8.7, 1H), 6.83 (d, J=8.7, 1H), 3.78 (bs, 1H), 2.98 (t, J=6.5, 2H), 1.67 (t, J=6.5, 2H), 1.49 (q, J=7.4, 6H), 0.89 (t, J=7.4, 4H).

EXAMPLE 5

7,8-Dihydro-7,7-dimethyl-4-trifluoromethylpyridino[3,2-f]quinolin-2(1H)-one (Compound 106, Structure 4a of Scheme I, where R$_1$=R$_1$=hydrogen)

This compound was prepared in a similar fashion as that described in Example 3 from compound 101. Spectral data for compound 106: $^1$H NMR (500 MHz, acetone-d$_6$) 11.0 (bs, 1H), 7.24 (d, J=8.8, 1H), 7.05 (d, J=8.8, 1H), 6.98 (s, 1H), 6.78 (d, J=10.3, 1H), 5.62 (bs, 1H), 5.558 (dd, J=9.8, 1.9, 1H), 1.30 (s, 6H).

EXAMPLE 6

5,6,7,8-Tetrahydro-7,7,8-trimethyl-4-trifluoromethylpyridino[3,2-f]quinolin-2(1H)-one (Compound 107, Structure 7 of Scheme I, where R$_1$=R$_2$=R$_3$=methyl)

In a 25-mL r.b. flask, a solution of compound 104 (structure 6 of Scheme I, where R$_1$=R$_2$=methyl, 41 mg, 0.15 mmol) in MeOH (5 mL) was treated with formaldehyde (5 mL, 37 wt. % solution in water), AcOH (2 mL) and NaCNBH$_3$ (excess). The reaction mixture was stirred at rt for 24 h. The reaction mixture was poured onto ice-water (50 mL), neutralized with NaHCO$_3$ powder to pH 7 and extracted with EtOAc (3×50 mL). The combined extracts were washed with H$_2$O (50 mL) and brine (50 mL), dried (MgSO$_4$), filtered and concentrated in vacuo. The residue was purified by flash column chromatography (SiO$_2$, 1×20 cm, 50% EtOAc in hexane as eluent) to afford 32 mg (75%)

of 107 as an orange solid: $R_f$ 0.40 (SiO$_2$, 2:1=EtOAc:hexane); $^1$H NMR (400 MHz, CDCl$_3$) 11.45 (br. s, 1H), 7.23 (d, 1H, J=9.1), 7.22 (s, 1H), 7.05 (d, 1H, J=9.1), 2.97 (t, 2H, J=6.2), 2.88 (s, 3H), 1.71 (t, 2H, J=6.2), 1.27 (s, 6H).

EXAMPLE 7

8-Ethyl-5,6,7,8-tetrahydro-7,7-dimethyl-4-trifluoromethylpyridino[3,2-f]quinolin-2(1H)-one (Compound 108, Structure 7 of Scheme I, where $R_1$=$R_2$=methyl, $R_3$=ethyl)

In a 25-mL r.b. flask, a solution of compound 104 (structure 6 of Scheme I, where $R_1$=$R_2$=methyl) (35.3 mg, 0.119 mmol) in MeOH (5 mL) was treated with acetaldehyde (2 mL), AcOH (2 mL) and NaCNBH$_3$ (excess). The reaction mixture was stirred at rt for 24 h. The reaction mixture was poured onto ice-water (50 mL), neutralized with NaHCO$_3$ powder to pH 7 and extracted with EtOAc (3×50 mL). The combined extracts were washed with H$_2$O (50 mL) and brine (50 mL), dried (MgSO$_4$), filtered and concentrated in vacuo. The residue was purified by flash column chromatography (SiO$_2$, 1×20 cm, 50% EtOAc in hexane as eluent) to afford 19.1 mg (50%) of compound 108 as an orange solid: $R_f$ 0.51 (SiO$_2$,2:1=EtOAc:hexane); $^1$H NMR (400 MHz, CDCl$_3$) 11.42 (br. s, 1H), 7.23 (d, 1H, J=9.2), 7.21 (s, 1H), 7.05 (d, 1H, J=9.2), 3.38 (q, 2H, J=7.0), 2.97 (t, 2H, J=6.2), 1.71 (t, 2H, J=6.2), 1.27 (s, 6H), 1.17 (t, 3H, J=7.0).

EXAMPLE 8

5,6,7,8-Tetrahydro-7,7-dimethyl-4-trifluoromethyl-8-propylpyridino[3,2-f]quinolin-2(1H)-one (Compound 109, Structure 7 of Scheme I, where $R_1$=$R_2$=methyl, $R_3$=propyl)

In a 25-mL r.b. flask, a solution of compound 104 (structure 6 of Scheme I, where $R_1$=$R_2$=methyl) (34 mg, 0.115 mmol) in MeOH (5 mL) was treated with propionaldehyde (2 mL), AcOH (2 mL) and NaCNBH$_3$ (excess). The reaction mixture was stirred at rt for 24 h. The reaction mixture was poured onto ice-water (50 mL), neutralized with NaHCO$_3$ powder to pH 7 and extracted with EtOAc (3×50 mL). The combined extracts were washed with H$_2$O (50 mL) and brine (50 mL), dried (MgSO$_4$), filtered and concentrated in vacuo. The residue was purified by flash column chromatography (SiO$_2$, 1×20 cm, 50% EtOAc in hexane as eluent) to afford 13.2 mg (34%) of compound 109 as an orange solid: $R_f$ 0.51 (SiO$_2$, 2:1=EtOAc:hexane); $^1$H NMR (400 MHz, CDCl$_3$) 10.89 (br. s, 1H), 7.28 (d, 1H, J=9.0), 7.21 (s, 1H), 7.01 (d, 1H, J=9.0), 3.20 (t, 2H, J=7.7), 2.96 (t, 2H, J=6.1), 1.70 (t, 2H, J=6.1), 1.60–1.50 (m, 2H), 1.25 (s, 6H), 0.92 (t, 3H, J=7.3).

EXAMPLE 9

8-(2,2,2-Trifluoroethyl)-5,6,7,8-tetrahydro-7,7-dimethyl-4-trifluoromethyl-pyridino[3,2-f]quinolin-2 (1H)-one (Compound 110, Structure 7 of Scheme I, where $R_1$=$R_2$=methyl, $R_3$=2,2,2-trifluoroethyl)

In a 100-mL r.b. flask, a solution of compound 104 (structure 6 of Scheme I, where $R_1$=$R_2$=methyl) (0.59 g, 2.0 mmol) in TFA (15 mL) was treated with NaBH$_4$ (6.0 g). The reaction mixture was heated to 95° C. and stirred for 6 h. The reaction mixture was diluted with EtOAc (50 mL) and poured onto ice-water (50 mL), neutralized with NaHCO$_3$ powder to pH 7 and extracted with EtOAc (2×100 mL). The combined extracts were washed with H$_2$O (150 mL) and brine (150 mL), dried (MgSO$_4$), filtered and concentrated in vacuo. The residue was purified by flash column chromatography (SiO$_2$, 3×20 cm, 50% EtOAc in hexane as eluent) to afford 0.62 g (81%) of compound 110 as a yellow solid: $R_f$ 0.56 (SiO$_2$, 2:1=EtOAc:hexane); $^1$H NMR (400 MHz, Acetone-d$_6$) 11.0 (s, 1H), 7.43 (d, 1H, J=9.2), 7.35 (d, 1H, J=9.2), 7.05 (s, 1H), 4.22 (q, 2H, J=9.0), 2.98 (t, 2H, J=6.1), 1.77 (t, 2H, J=6.1), 1.31 (s, 6H).

EXAMPLE 10

6-Hydrazino-4-trifluoromethylquinolin-2(1H)-one (Compound 111, Structure 9 of Scheme II, where $R_1$=trifluoromethyl)

In a 250 mL r.b. flask a suspension of 6-amino-4-trifluoromethylquinolin-2(1H)-one (structure 8 of Scheme II, where $R_1$=trifluoromethyl) (2.28 g, 10 mmol) in 10 mL conc. HCl was cooled to −1° C. and a solution of NaNO$_2$ (0.40 g, 12 mmol) in water (5 mL) was added dropwise in 20 min. The dark yellow suspension was stirred at −1° C. for 1 h and then a solution of SnCl$_2$.2H$_2$O (5.2 g, 15 mmol) in conc. HCl (10 mL) was added dropwise in 10 min. The light yellow suspension of the hydrazine was stirred at −1° C. for 2 h and then used directly or kept in a refrigerator at −1° C. until it was used (the crude compound can be stored for at least one month without decomposition).

EXAMPLE 11

6-Methyl-4-trifluoromethyl-7H-pyrrolo[3,2-f]quinolin-2(1H)-one (Compound 112, Structure 11 of Scheme II, where $R_3$=H $R_2$=methyl, $R_1$=trifluoromethyl)

To the crude suspension of compound 111 (~0.4 M) in aqueous HCl was added a solution of acetone (structure 10 of Scheme II, 2–5 eq.) in an equal volume of EtOH and the mixture was heated in a sealed tube at 130° C. for 2 h. Then the mixture was diluted with an equal volume of water while still hot and allowed to cool to rt. The precipitate was filtered and washed with water to give compound 112 as a yellow solid: $^1$H NMR (500 MHz, acetone-d$_6$) 11.1 (bs, 1 H), 10.6 (bs, 1 H), 7.69 (d, J=8.8, 1 H), 7.25 (d, J=8.8, 1 H), 6.94 (s, 1 H), 6.64 (s, 1 H), 2.51 (s, 3 H).

EXAMPLE 12

5-Isopropyl-6-methyl-4-trifluoromethyl-7H-pyrrolo[3,2-f]quinolin-2(1H)-one (Compound 113, Structure 11 of Scheme II, where $R_3$=isopropyl, $R_2$=methyl, $R_1$=trifluoromethyl)

To the crude suspension of compound 111 (structure 9 of Scheme II, where $R_1$=trifluoromethyl) (~0.4 M) in aqueous HCl was added a solution of a ketone (structure 10 of Scheme II) (2–5 eq.) in an equal volume of EtOH and the mixture was refluxed for 2 h. Then the mixture was diluted with an equal volume of water while still hot and allowed to cool to rt. The precipitate was filtered and washed with water to give the indole as a mixture of regioisomers. The ratio of angular and linear isomers was determined by $^1$H NMR. The mixture of regioisomers could be separated by chromatography (Silica gel, hex/EtOAc 1:1 to 0:1 gradient). Spectra data for compound 113: $^1$H NMR (500 MHz, DMSO-d$_6$)

12.2 (bs, 1H), 11.3 (bs, 1H), 7.52 (d, J=8.8, 1H), 7.03 (d, J=8.8, 1H), 6.87 (s, 1H), 3.30–3.24 (m, 1H), 6.64 (s, 1H), 2.48 (s, 3H), 1.22 (d, J=6.8, 6H).

EXAMPLE 13

5-Allyl-6-methyl-4-trifluoromethyl-7H-pyrrolo[3,2-f]quinolin-2(1H)-one (Compound 114, Structure 11 of Scheme II, where $R_3$=allyl, $R_2$=methyl, $R_1$=trifluoromethyl)

This compound was prepared in a similar fashion as that described in Example 12 from compound 111 (structure 9 of Scheme II, where $R_1$=trifluoromethyl) and 5-hexen-2-one (structure 10 of Scheme II) as a yellow solid: $^1$H NMR (500 MHz, DMSO-$d_6$) 12.3 (bs, 1H), 11.5 (bs, 1H), 7.59 (d, J=8.8, 1H), 7.10 (d, J=8.8, 1H), 6.89 (s, 1H), 5.82–5.76 (m, 1H), 4.85 (dd, J=10.8, 2.0, 1H), 4.76 (dd, J=17.1, 2.0, 1H), 3.50 (d, J=5.9, 2H), 2.33 (s, 3H).

EXAMPLE 14

5-(4-Methoxyphenyl)-6-methyl-4-trifluoromethyl-7H-pyrrolo[3,2-f]quinolin-2(1H1)-one (Compound 115, Structure 11 of Scheme II, where $R_3$=4-methoxyphenyl, $R_2$=methyl, $R_1$=trifluoromethyl)

This compound was prepared in a similar fashion as that described in Example 12 from compound 111 (structure 9 of Scheme II, where $R_1$=trifluoromethyl) and 1-(4-methoxyphenyl)acetone (structure 10 of Scheme II) as a yellow solid: $^1$H NMR (500 MHz, DMSO-$d_6$) 12.3 (bs, 1 H), 11.7 (bs, 1 H), 7.64 (d, J=8.8, 1 H), 7.14 (d, J=8.8, 1 H), 7.06 (d, J=8.8, 2 H), 6.91 (d, J=8.8, 2 H), 6.68 (s, 1 H), 3.77 (s, 3 H), 2.22 (s, 3 H).

EXAMPLE 15

5-(3-Trifluoromethylphenyl)-6-methyl-4-trifluoromethyl-7H-pyrrolo[3,2-f]quinolin-2(1H)-one (Compound 116, Structure 11 of Scheme II, where $R_3$=3-trifluoromethylphenyl, $R_2$=methyl, $R_1$=trifluoromethyl)

This compound was prepared in a similar fashion as that described in Example 12 from compound 111 (structure 9 of Scheme II, where $R_1$=trifluoromethyl) and 1-(3-trifluoromethylphenyl)acetone (structure 10 of Scheme II) as a yellow solid: $^1$H NMR (500 MHz, DMSO-$d_6$) 12.4 (bs, 1H), 11.9 (bs, 1H), 7.69 (d, J=8.8, 1H), 7.62–7.59 (m, 2H), 7.53 (bd, J=4.9, 1H), 7.41 (s, 1H), 7.21 (d, J=8.8, 2H), 6.73 (s, 1 H), 2.27 (s, 3H).

EXAMPLE 16

4-Trifluoromethyl-5,6,7,8-tetrahydrocyclopentano[g]pyrrolo[3,2-f]quinolin-2(1H)-one (Compound 117, Structure 11 of Scheme II, where $R_3$, $R_2$=—$CH_2CH_2CH_2$—, $R_1$=trifluoromethyl This compound was prepared in a similar fashion as that described in Example 12 from compound 111 (structure 9 of Scheme II, where $R_1$=trifluoromethyl) and cyclopentanone (structure 10 of Scheme II) as a yellow solid: $^1$H NMR (500 MHz, DMSO-$d_6$) 11.6 (bs, 1H), 10.5 (bs, 1H), 7.73 (d, J=8.8, 1H), 7.26 (d, J=8.8, 1H), 6.92 (s, 1H), 3.05–3.02 (m, 2H), 2.91–2.88 (m, 2H), 2.47–2.43 (m, 2H).

EXAMPLE 17

4-Trifluoromethyl-5,6,7,8,9,10-hexahydrocycloheptano[g]pyrrolo[3,2-f]quinolin-2(1H)-one (Compound 118, Structure 11 of Scheme II, where $R_3$, $R_2$=—$(CH_2)_5$—, $R_1$=trifluoromethyl)

This compound was prepared in a similar fashion as that described in Example 12 from compound 111 (structure 9 of Scheme II, where $R_1$=trifluoromethyl) and cycloheptanone (structure 10 of Scheme II) as a yellow solid: $^1$H NMR (500 MHz, DMSO-$d_6$) 11.4 (bs, 1H), 10.5 (bs, 1H), 7.63 (d, J=8.3, 1H), 7.17 (d, J=8.3, 1 H), 6.91 (s, 1H), 2.98–2.94 (m, 2 H), 2.91–2.87 (m, 2 H), 1.92–1.86 (m, 2H). 1.81–1.75 (m, 2H), 1.69–1.63 (m, 2H).

EXAMPLE 18

(±)-4c,5,6,7,7a(cis),8-Hexahydro-8-(2,2,2-trifluoroethyl)-4-trifluoromethylcyclopentano-[g]pyrrolo[3,2-f]quinolin-2(1H)-one (Compound 119, Structure 13 of Scheme II, where $R_3$, $R_2$=—$(CH_2)_3$—, $R_1$=trifluoromethyl, $R_4$=2,2,2-trifluoroethyl)

To a solution of compound 117 (structure 11 of Scheme II, where $R_3$, $R_2$=—$(CH_2)_3$—, 1.30 g, 4.45 mmol) in TFA (40 mL) in a 250 mL r.b. flask was added a pellet (~0.75 g, 22 mmol) of $NaBH_4$. Two more pellets of $NaBH_4$ were added with 30 min intervals and the mixture was stirred at rt for 16 h until the starting material was consumed. Water was carefully added (~150 mL) and the yellow precipitate was filtered and washed with water. The yellow solid was purified by column chromatography (Silica gel, hex:EtOAc, 7:3) to give compound 119 (1.27 g, 76%) as a yellow solid: $^1$H NMR (500 MHz, $CDCl_3$) 12.3 (bs, 1H), 7.28 (d, J=8.8, 1H), 7.19 (s, 1H), 6.87 (d, J=8.8, 1H), 4.30 (d, J=4.9, 2H), 4.06–4.02 (m, 2H), 3.74–3.58 (m, 2H), 2.15–2.13 (m, 2H), 1.77–1.66 (m, 3H), 1.58–1.53 (m, 1H).

EXAMPLE 19

(±)-6,6a,7,8,9,9a(cis)-Hexahydro-6-(2,2,2-trifluoroethyl)-4-trifluoromethylcyclopentano-[i]pyrrolo[2,3-g]quinolin-2(1H)-one (Compound 120, Structure 14 of Scheme II, where $R_3$, $R_2$=—$(CH_2)_3$—, $R_1$=trifluoromethyl, $R_4$=2,2,2-trifluoroethyl)

This compound was isolated as a regioisomer of compound 119 (structure 13 of Scheme II, where $R_3$, $R_2$=—$(CH_2)_3$—, $R_1$=trifluoromethyl, $R_4$=trifluoroethyl) in the same reaction process as a yellow solid: $^1$H NMR (500 MHz, $CDCl_3$) 12.4 (bs, 1H), 7.18 (s, 1H), 7.03 (s, 1H), 6.64 (s, 1H), 4.35 (dd, J=6.3, 6.3, 1H), 3.89–3.85 (m, 1H), 3.76 (q, $J_{H-F}$=9.3, 1H), 2.14–2.06 (m, 1H), 1.98–1.92 (m, 1H), 1.888–1.82 (m, 1H), 1.79–1.70 (m, 2H), 1.59–1.53 (m, 1H).

EXAMPLE 20

(±)-4c,5,6,7,7a(cis),8-Hexahydro-8-ethyl-4-trifluoromethylcyclopentano-[g]pyrrolo[3,2-f]quinolin-2(1H)-one (Compound 121, Structure 13 of Scheme II, where $R_3$, $R_2$=—$(CH_2)_3$—, $R_1$=trifluoromethyl, $R_4$=ethyl)

This compound was prepared in a similar fashion as that described in Example 18 from Compound 117 (structure 11 of Scheme II, where $R_3$, $R_2$=—$(CH_2)_3$—) and acetic acid.

¹H NMR (500 MHz, CDCl₃) 12.0 (bs, 1H), 7.21 (d, J=8.3, 1H), 7.19 (s, 1H), 6.87 (d, J=8.8, 1H), 4.30 (d, J=4.9, 2H), 4.06–4.02 (m, 2H), 3.74–3.58 (m, 2H), 2.15–2.13 (m, 2H), 1.77–1.66 (m, 3H), 1.58–1.53 (m, 1H).

EXAMPLE 21

(±)-6,6a,7,8,9,9a(cis)-Hexahydro-6-ethyl-4-trifluoromethylcyclopentano-[i]pyrrolo[2,3-g]quinolin-2(1H)-one (Compound 122, Structure 14 of Scheme II, where $R_3$, $R_2$=—$(CH_2)_3$—, $R_1$=trifluoromethyl, $R_4$=ethyl)

This compound was isolated as a regioisomer of compound 121 (Structure 13 of Scheme II, where $R_3$, $R_2$=—$(CH_2)_3$—, $R_1$=trifluoromethyl, $R_4$=ethyl) in the same reaction described in Example 20 as a yellow solid: ¹H NMR (500 MHz, CDCl₃) 11.9 (bs, 1H), 7.08 (s, 1H), 6.99 (s, 1 H), 6.41 (d, J=2.0, 1 H), 4.30–4.27 (m, 1H), 3.79–3.75 (m, 1H), 3.34 (dq, J=7.3, 7.3, 1H), 3.21 (dq, J=7.3, 7.3, 1H), 2.08–2.01 (m, 1H), 1.89–1.86 (m, 1H), 1.82–1.79 (m, 1H), 1.72–1.65 (m, 2 H), 1.58–1.52 (m, 1H), 1.18 (t, J=7.3, 3H).

EXAMPLE 22

(±)-5,6-Dihydro-5,6-cis-dimethyl-7-(2,2,2-trifluoroethyl)-4-trifluoromethyl-7H-pyrrolo[3.2-f]quinolin-2(1H)-one (Compound 123, Structure 13 of Scheme II, where $R_3$=$R_2$=methyl, $R_1$=trifluoromethyl, $R_4$=2,2,2-trifluoroethyl)

This compound was prepared in a similar fashion as that described in Examples 12 and 18 from Compound 111 (Structure 9 of Scheme II, where $R_1$=trifluoromethyl) and 2-butanone. ¹H NMR (500 MHz, CDCl₃) 12.3 (bs, 1H), 7.32 (d, J=8.8, 1H), 7.21 (s, 1H), 6.95 (d, J=8.8, 1H), 3.75–3.53 (m, 4H), 1.38 (d, J=6.8, 3H), 0.98 (d, J=6.8, 3H).

EXAMPLE 23

(±)-7,8-Dihydro-7,8-cis-dimethyl-6-(2,2,2-trifluoroethyl)-4-trifluoromethyl-6H-pyrrolo[2,3-g]quinolin-2(1H)-one (Compound 124, Structure 14 of Scheme II, where $R_3$=$R_2$=methyl, $R_1$=trifluoromethyl, $R_4$=2,2,2-trifluoroethyl)

This compound was isolated as a regioisomer of compound 123 (Structure 13 of Scheme II, where $R_3$=$R_2$=methyl, $R_1$=trifluoromethyl, $R_4$=trifluoroethyl) in the same reaction described in Example 22 as a yellow solid: ¹H NMR (500 MHz, CDCl₃) 12.1 (bs, 1H), 7.13 (d, J=1.5, 1H), 7.04 (s, 1H), 6.76 (s, 1H), 3.75–3.60 (m, 2H), 3.33 (dq, J=6.3, 5.9, 1H), 2.95 (dq, J=7.3, 5.9, 1H), 1.41 (d, J=7.3, 3H), 1.39 (d, J=6.3, 3H).

EXAMPLE 24

(±)-4c,5,6,7,7a(cis),8-Hexahydro-8-propyl-4-trifluoromethylcyclopentano-[g]pyrrolo-[3,2-f]quinolin-2(1H)-one (Compound 125, Structure 13 of Scheme II, where $R_3$, $R_2$=—$(CH_2)_3$,—$R_1$=trifluoromethyl, $R_4$=propyl)

This compound was prepared in a similar fashion as that described in Example 18 from Compound 117 (structure 11 of Scheme II, where $R_3$, $R_2$=—$(CH_2)_3$—) and propionic acid. ¹H NMR (500 MHz, CDCl₃) 10.4 (bs, 1H), 7.31 (dd, J=8.8, 1.8, 1H), 7.20 (s, 1H), 6.78 (d, J=8.8, 1H), 4.28–4.26 (m, 1H), 3.96–3.95 (m, 1H), 3.14–3.05 (m, 2H), 2.06–2.03 (m, 2H), 1.72–1.51 (m, 6H), 0.95 (t, J=7.3, 3H).

EXAMPLE 25

(±)-4c,5,6,7,7a(cis),8-Hexahydro-8-(3-furanylmethyl)-4-trifluoromethyl-cyclopentano[g]pyrrolo[3,2-f]quinolin-2(1H)-one (Compound 126, Structure 13 of Scheme II, where $R_3$, $R_2$=—$(CH_2)_3$—, $R_1$=trifluoromethyl, $R_4$=3-furanylmethyl)

This compound was prepared in a similar fashion as that described in Example 18 from Compound 117 (structure 11 of Scheme II, where $R_3$, $R_2$=—$(CH_2)_3$—) and 3-furoic acid. ¹H NMR (500 MHz, CDCl₃) 12.2 (bs, 1H), 7.36–7.35 (m, 1H), 7.29 (s, 1H), 7.22 (d, J=8.8, 1H), 7.16 (s, 1 H), 6.82 (d, J=8.3, 1H), 6.26 (d, J=1.0, 1H), 4.27–4.22 (m, 2H), 4.08 (d, J=16.1, 1H), 3.97–3.91 (m, 1H), 2.12–2.08 (m, 1H), 2.03–2.01 (m, 1H), 1.72–1.70 (m, 3H), 1.60–1.58 (m, 1H).

EXAMPLE 26

(±)-4c,5,6,7,7a(cis),8-Hexahydro-8-(3-thiophenemethyl)-4-trifluoromethyl-cyclopentano[g]pyrrolo[3,2-f]quinolin-2(1H)-one (Compound 127, Structure 13 of Scheme II, where $R_3$, $R_2$=—$(CH_2)_3$—, $R_1$=trifluoromethyl, $R_4$=3-thiophenemethyl)

This compound was prepared in a similar fashion as that described in Example 18 from Compound 117 (structure 11 of Scheme II, where $R_3$, $R_2$=—$(CH_2)_3$—) and 3-thiophenecarboxylic acid. ¹H NMR (500 MHz, CDCl₃) 10.9 (bs, 1H), 7.29 (dd, J=5.4, 2.9, 1H), 7.13 (s, 1H), 7.07 (d, J=8.3, 1H), 7.06 (s, 1H), 6.96 (dd, J=5.4, 1.5, 1H), 7.12–7.04 (m, 1H), 6.72 (d, J=8.3, 1H), 4.38 (d, J=16.1, 1H), 4.26 (d, J=16.1, 1H), 4.27–4.25 (m, 1H), 3.98–3.94 (m, 1H), 2.16–2.07 (m, 1H), 2.04–2.22 (m, 1H), 1.78–1.68 (m, 3H), 1.60–1.54 (m, 1H).

EXAMPLE 27

(±)-4c,5,6,7,7a(cis),8-Hexahydro-8-(2-methylpropyl)-4-trifluoromethyl-cyclopentano[g]pyrrolo[3,2-f]quinolin-2(1H)-one (Compound 128, Structure 13 of Scheme II, where $R_3$, $R_2$=—$(CH_2)_3$—, $R_1$=trifluoromethyl, $R_4$=2-methylpropyl)

This compound was prepared in a similar fashion as that described in Example 18 from Compound 117 (structure 11 of Scheme II, where $R_3$, $R_2$=—$(CH_2)_3$—) and isobutyric acid. ¹H NMR (500 MHz, CDCl₃) 12.2 (bs, 1H), 7.20 (d, J=8.8, 1H), 7.15 (s, 1H), 6.74 (d, J=8.8, 1H), 4.22–4.19 (m, 1H), 3.98–3.93 (m, 1H), 2.93 (dd, J=14.3, 7.3, 1H), 2.81 (dd, J=14.3, 7.9, 1H), 2.14–2.00 (m, 3H), 1.72–1.63 (m, 3H), 1.56–1.52 (m, 1 H), 0.97 (d, J=6.7, 3H), 0.92 (d, J=6.7, 3H).

EXAMPLE 28

(±)-4c,5,6,7,7a(cis),8-Hexahydro-8-(2,2,2-chlorodifluoroethyl)-4-trifluoromethylcyclopentano[g]pyrrolo[3,2-f]quinolin-2(1H)-one (Compound 129, Structure 13 of Scheme II, where $R_3$, $R_2$=—$(CH_2)_3$—, $R_1$=trifluoromethyl, $R_4$=2,2,2-chlorodifluoroethyl)

This compound was prepared in a similar fashion as that described in Example 18 from Compound 117 (structure 11 of Scheme II, where $R_3$, $R_2$=—$(CH_2)_3$—) and chlorodifluoroacetic acid. ¹H NMR (500 MHz, CDCl₃) 12.3 (bs, 1H), 7.38 (d, J=8.8, 1 H), 7.29 (s, 1H), 7.00 (d, J=8.8, 1H), 4.46–4.44 (m, 1H), 4.09–4.05 (m, 1H), 3.94–3.81 (m, 2H), 2.21–2.12 (m, 2H), 1.81–1.74 (m, 2H), 1.69–1.63 (m, 1H), 1.56–1.52 (m, 1 H).

EXAMPLE 29

(±)-4c,5,6,7,7a(cis),8-Hexahydro-8-cyclopropylmethyl-4-trifluoromethyl-cyclopentano[g]pyrrolo[3,2-f]quinolin-2(1H)-one (Compound 130, Structure 13 of Scheme II, where $R_3$, $R_2$=—$(CH_2)_3$—, $R_1$=trifluoromethyl, $R_4$=cyclopropylmethyl)

This compound was prepared in a similar fashion as that described in Example 18 from Compound 117 (structure 11 of Scheme II, where $R_3$, $R_2$=—$(CH_2)_3$—) and cyclopropanecarboxylic acid. $^1$H NMR (500 MHz, CDCl$_3$) 12.4 (bs, 1H), 7.25 (d, J=8.8, 1H), 7.16 (s, 1H), 6.84 (d, J=8.8, 1H), 4.41–4.38 (m, 1H), 3.97–3.92 (m, 1 H), 3.18 (dd, J=14.9, 5.5, 1H), 2.90 (dd, J=14.9, 7.3, 1H), 2.14–2.04 (m, 2H), 1.78–1.66 (m, 3H), 1.55–1.49 (m, 1H), 0.97–0.92 (m, 1H), 0.61–0.55 (m, 1H), 0.53–0.47 (m, 1H), 0.28–0.22 (m, 1H), 0.19–0.14 (m, 1H).

EXAMPLE 30

(±)-4c,5,6,7,7a(cis),8-Hexahydro-8-(2,2-dimethoxyethyl)-4-trifluoromethyl-cyclopentano[g]pyrrolo[3,2-f]quinolin-2(1H)-one (Compound 131, Structure 13 of Scheme II, where $R_3$, $R_2$=—$(CH_2)_3$—, $R_1$=trifluoromethyl, $R_4$=2,2-dimethoxyethyl)

This compound was prepared in a similar fashion as that described in Example 18 from Compound 117 (structure 11 of Scheme II, where $R_3$, $R_2$=—$(CH_2)_3$—) and dimethoxyacetaldehyde. $^1$H NMR (500 MHz, CDCl$_3$) 11.1 (bs, 1H), 7.14 (s, 1H), 7.12 (d, J=8.8, 1H), 6.91 (d, J=8.8, 1H), 4.43 (dd, J=5.9, 4.4, 1H), 4.31–4.30 (m, 1H), 3.94–3.93 (m, 1H), 3.41 (s, 6H), 3.30 (dd, J=15.1, 5.9, 1H), 3.21 (dd, J=15.1, 4.4, 1H), 2.12–2.09 (m, 2H), 1.72–1.55 (m, 4H).

EXAMPLE 31

(±)-4c,5,6,7,8,8a(cis)-Hexahydro-9-(2,2,2-trifluoroethyl)-4-trifluoromethyl-9H-cyclohexano[g]pyrrolo[3,2-f]quinolin-2(1H)-one (Compound 132, Structure 13 of Scheme II, where $R_3$, $R_2$=—$(CH_2)_4$—, $R_1$=trifluoromethyl, $R_4$=2,2,2-trifluoroethyl)

This compound was prepared in a similar fashion as that described in Examples 12 and 18 from Compound 111 (structure 9 of Scheme II, where $R_1$=trifluoromethyl) and cyclohexanone. $^1$H NMR (500 MHz, CDCl$_3$) 12.1 (bs, 1H), 7.29 (d, J=8.8, 1H), 7.19 (s, 1H), 7.02 (d, J=8.8, 1H), 3.70–3.60 (m, 2H), 3.56 (m, 1H), 3.41–3.38 (m, 1H), 2.14 (d, J=14.6, 1H), 1.75–1.67 (m, 3H), 1.61–1.56 (m, 2H), 1.31–1.25 (m, 1H), 1.05–0.98 (m, 1H).

EXAMPLE 32

(±)-4c,5,6,7,8,9,9a(cis),10-Octahydro-10-(2,2,2-trifluoroethyl)-4-trifluoromethyl-cycloheptano[g]pyrrolo[3,2-f]quinolin-2(1H)-one (Compound 133, Structure 13 of Scheme II, where $R_3$, $R_2$=—$(CH_2)_5$—,$R_1$=trifluoromethyl, $R_4$=2,2,2-trifluoroethyl)

This compound was prepared in a similar fashion as that described in Example 18 from Compound 118 (structure 11 of Scheme II, where $R_3$, $R_2$=—$(CH_2)_5$—). $^1$H NMR (500 MHz, CDCl$_3$) 12.0 (bs, 1H), 7.32 (d, J=8.8, 1H), 7.25 (s, 1H), 6.98 (d, J=8.8, 1H), 3.96–3.91 (m, 1H), 3.73–3.62 (m, 3H), 2.36–2.26 (m, 2H), 1.93–1.86 (m, 3H), 1.78–1.69 (m, 2H), 1.48–1.36 (m, 3H).

EXAMPLE 33

(±)-5,6-cis-Dihydro-6-ethyl-5-methyl-7-(2,2,2-trifluoroethyl)-4-trifluoromethyl-7H-pyrrolo[3,2-f]quinolin-2(1H)-one (Compound 134, Structure 13 of Scheme II, where $R_3$=methyl, $R_2$=ethyl, $R_1$=trifluoromethyl, $R_4$=2,2,2-trifluoroethyl)

This compound was prepared in a similar fashion as that described in Examples 12 and 18 from Compound 111 (structure 9 of Scheme II, where $R_1$=trifluoromethyl) and 3-pentanone. $^1$H NMR (500 MHz, CDCl$_3$) 11.6 (bs, 1H), 7.26 (d, J=8.3, 1H), 7.15 (s, 1H), 6.74 (d, J=8.3, 1H), 4.25 (dd, J=7.3, 3.4, 1H), 3.96–3.91 (m, 1H), 3.29 (dq, J=7.3, 1H), 3.16 (dq, J=7.3, 7.3, 1H), 1.965–1.85 (m, 2H), 1.08 (t, J=7.3, 3H), 0.98 (d, J=6.3, 3H).

EXAMPLE 34

(±)-5,6-cis-Dihydro-5-butyl-6-methyl-7-(2,2,2-trifluoroethyl)-4-trifluoromethyl-7H-pyrrolo[3,2-f]quinolin-2(1H)-one (Compound 135, Structure 13 of Scheme II, where $R_3$=butyl, $R_2$=methyl, $R_1$=trifluoromethyl, $R_1$=2,2,2-trifluoroethyl)

This compound was prepared in a similar fashion as that described in Examples 12 and 18 from Compound 111 (structure 9 of Scheme II, where $R_1$=trifluoromethyl) and 2-heptanone. $^1$H NMR (500 MHz, CDCl$_3$) 12.1 (bs, 1H), 7.29 (d, J=8.8, 1H), 7.20 (s, 1H), 6.94 (d, J=8.8, 1H), 3.76–3.68 (m, 1H), 3.67–3.57 (m, 2H), 3.47–3.43 (m, 1H), 1.74–1.66 (m, 1H), 1.44 (d, J=6.8, 3H), 1.36–1.29 (m, 1H), 1.28–1.20 (m, 1H), 1.20–1.12 (m, 3H), 0.81 (t, J=7.3, 3 H).

EXAMPLE 35

(±)-5,6-cis-Dihydro-5-(4-nitrophenyl)-6-methyl-7-(2,2,2-trifluoroethyl)-4-trifluoromethyl-7H-pyrrolo[3,2-f]quinolin-2(1H)-one (Compound 136, Structure 13 of Scheme II, where $R_3$=4-nitrophenyl, $R_2$=methyl, $R_1$=trifluoromethyl, $R_1$=2,2,2-trifluoroethyl)

This compound was prepared in a similar fashion as that described in Examples 12 and 18 from Compound 111 (Structure 9 of Scheme II, where $R_1$=trifluoromethyl) and 4-nitrophenylacetone. $^1$H NMR (500 MHz, CDCl$_3$) 12.1 (bs, 1H), 8.05 (d, J=8.3, 2H), 7.47 (d, J=8.8, 1H), 7.13 (d, J=8.8, 1H), 7.13 (s, 1H), 6.90 (bs, 2H), 4.79 (d, J=7.3, 1H), 4.11 (dq, J=7.3, 6.3, 1H), 3.78–3.61 (m, 2H), 0.96 (d, J=6.3, 3H).

EXAMPLE 36

(±)-5,6-cis-Dihydro-5-(4-dimethylaminophenyl)-6-methyl-7-(2,2,2-trifluoroethyl)-4-trifluoromethyl-7H-pyrrolo[3,2-f]quinolin-2(1H)-one (Compound 137, Structure 13 of Scheme II, where $R_3$=4-dimethylaminophenyl, $R_2$=methyl, $R_1$=trifluoromethyl, $R_4$=2,2,2-trifluoroethyl)

This compound was prepared in a similar fashion as that described in Examples 12 and 18 from Compound 111

(Structure 9 of Scheme II, where $R_1$=trifluoromethyl) and 4-dimethylaminophenylacetone. $^1$H NMR (500 MHz, CDCl$_3$) 12.3 (bs, 1H), 7.40 (d, J=8.8, 1H), 7.09 (s, 1H), 7.06 (d, J=8.8, 1H), 6.56–6.52 (m, 4H), 4.59 (d, J=7.3, 1H), 3.96 (dq, J=7.3, 6.3, 1H), 3.77–3.67 (m, 1H), 3.67–3.57 (m, 1H), 2.86 (s, 6H), 0.95 (d, J=6.3, 3H).

EXAMPLE 37

(±)-5,6-cis-Dihydro-5-(4-methoxyphenyl)-6-methyl-7-(2,2,2-trifluoroethyl)-4-trifluoromethyl-7H-pyrrolo[3,2-f]quinolin-2(1H)-one (Compound 138, Structure 13 of Scheme II, where $R_3$=4-methoxyphenyl, $R_2$=methyl, $R_1$=trifluoromethyl, $R_4$=2,2,2-trifluoroethyl)

This compound was prepared in a similar fashion as that described in Example 18 from Compound 115 (Structure 11 of Scheme II, where $R_3$=4-methoxyphenyl, $R_2$=methyl, $R_1$=trifluoromethyl). $^1$H NMR (500 MHz, CDCl$_3$) 11.6 (bs, 1H), 7.36 (d, J=8.8, 1H), 7.09 (s, 1H), 7.07 (d, J=8.8, 1H), 6.71 (d, J=8.8, 2H), 6.63 (bs, 2H), 4.63 (d, J=7.3, 1H), 3.99 (dq, J=7.3, 6.3, 1H), 3.74–3.58 (m, 2H), 3.73 (s, 3H), 0.94 (d, J=6.3, 3H).

EXAMPLE 38

(±)-5,6-cis-Dihydro-5-(3-trifluoromethylphenyl)-6-methyl-7-(2,2,2-trifluoroethyl)-4-trifluoromethyl-7H-pyrrolo[3,2-f]quinolin-2(1H)-one (Compound 139, Structure 13 of Scheme II, where $R_3$=3-trifluoromethylphenyl, $R_2$=methyl, $R_1$=trifluoromethyl, $R_4$=2,2,2-trifluoroethyl)

This compound was prepared in a similar fashion as that described in Example 18 from Compound 116 (Structure 11 of Scheme II, where $R_3$=3-trifluoro-methylphenyl, $R_2$=methyl, $R_1$=trifluoromethyl). $^1$H NMR (500 MHz, CDCl$_3$) 12.8 (bs, 1H), 7.51 (d, J=8.8, 1H), 7.43 (d, J=7.8, 1H), 7.30–7.26 (m, 1H), 7.14 (s, 1H), 7.12 (d, J=8.8, 1H), 7.12–7.04 (m, 1H), 6.92–6.78 (bs, 1H), 4.74 (d, J=6.8, 1H), 4.08 (dq, J=6.8, 6.3, 1H), 3.78–3.60 (m, 2H), 0.93 (d, J=6.3, 3H).

EXAMPLE 39

(±)-5,6-cis-Dihydro-5-(4-fluorophenyl)-6-methyl-7-(2,2,2-trifluoroethyl)-4-trifluoromethyl-7H-pyrrolo[3,2-f]quinolin-2(1H)-one (Compound 140, Structure 13 of Scheme II, where $R_3$=4-fluorophenyl, $R_2$=methyl, $R_1$=trifluoromethyl, $R_1$=2,2,2-trifluoroethyl)

This compound was prepared in a similar fashion as that described in Examples 12 and 18 from Compound 111 (Structure 9 of Scheme II, where $R_1$=trifluoromethyl) and 4-fluorophenylacetone. $^1$H NMR (500 MHz, CDCl$_3$) 10.6 (bs, 1H), 7.28 (d, J=8.8, 1H), 7.08 (s, 1H), 7.07 (d, J=8.8, 1H), 6.88–6.85 (m, 2H), 6.68 (bs, 2H), 4.66 (d, J=6.8, 1H), 4.01 (dq, J=6.3, 6.3, 1H), 3.73–3.67 (m, 2H), 3.67–3.60 (m, 1H), 0.94 (d, J=6.3, 3H).

EXAMPLE 40

(±)-5,6-Dihydro-5-phenyl-7-(2,2,2-trifluoroethyl)-4-trifluoromethyl-7H-pyrrolo[3,2-f]quinolin-2(1H)-one (Compound 141, Structure 13 of Scheme II, where $R_3$=phenyl, $R_2$=H, $R_1$=trifluoromethyl, $R_4$=2,2,2-trifluoroethyl)

This compound was prepared in a similar fashion as that described in Examples 12 and 18 from Compound 111 (Structure 9 of Scheme II, where $R_1$=trifluoromethyl) and phenylacetaldehyde. $^1$H NMR (500 MHz, CDCl$_3$) 12.6 (bs, 1H), 7.48 (d, J=8.8, 1H), 7.20–7.14 (m, 3H), 7.14 (s, 1H), 7.05 (d, J=8.8, 1H), 6.76–6.74 (m, 2H), 4.89 (d, J=8.3, 2H), 3.93 (dd, J=8.3, 8.3, 1H), 3.84–3.77 (m, 1H), 3.64–3.56 (m, 1H), 3.55 (d, J=8.8, 1H).

EXAMPLE 41

(±)-5,6-cis-Dihydro-5-(4-methoxyphenyl)-6-methyl-4-trifluoromethyl-7H-pyrrolo[3,2-f]quinolin-2(1H)-one (Compound 142, Structure 13 of Scheme II, where $R_3$=4-methoxyphenyl, $R_2$=methyl, $R_1$=trifluoromethyl, $R_4$=H)

This compound was isolated as a minor product from the same reaction described in Examples 37. $^1$H NMR (500 MHz, CDCl$_3$) 12.0 (bs, 1H), 7.32 (d, J=8.8, 1H), 7.09 (s, 1H), 7.14 (d, J=8.8, 1H), 7.08 (s, 1H), 6.73 (d, J=8.8, 2H), 6.65 (bs, 2H), 4.60 (d, J=7.3, 1H), 4.21 (dq, J=7.3, 6.3, 1H), 3.73 (s, 3H), 1.25 (bs, 1H), 0.92 (d, J=6.3, 3H).

EXAMPLE 42

(±)-5,6-cis-Dihydro-5-(4-methoxyphenyl)-6-methyl-7-(2,2-dimethoxyethyl)-4-trifluoromethyl-7H-pyrrolo[3,2-f]quinolin-2(1H)-one (Compound 143, Structure 13 of Scheme II, where $R_3$=4-methoxyphenyl, $R_2$=methyl, $R_1$=trifluoromethyl, $R_4$=2,2-dimethoxyethyl)

This compound was prepared in a similar fashion as that described in Example 30 from Compound 115 (Structure 11 of Scheme II, where $R_3$=4-methoxyphenyl, $R_2$=methyl, $R_1$=trifluoromethyl). $^1$H NMR (500 MHz, CDCl$_3$) 11.7 (bs, 1H), 7.33 (d, J=8.8, 1H), 7.17 (d, J=8.8, 1H), 7.07 (s, 1H), 6.69 (bd, J=8.8, 2H), 6.63 (bs, 2H), 4.58 (d, J=7.3, 1H), 4.31 (dd, J=5.9, 3.9, 1H), 3.93 (dq, J=7.3, 6.8, 1H), 3.73 (s, 3H), 3.41 (s, 3H), 3.37 (s, 3H), 3.27 (dd, J=15.1, 3.9, 1H), 3.22 (dq, J=15.1, 5.9, 1H), 0.92 (d, J=6.8, 3H).

EXAMPLE 43

(±)-5,6-cis-Dihydro-5-isopropyl-6-methyl-7-(2,2,2-trifluoroethyl)-4-trifluoromethyl-7H-pyrrolo[3,2-f]quinolin-2(1H)-one (Compound 144, Structure 13 of Scheme II, where $R_3$=isopropyl, $R_2$=methyl, $R_1$=trifluoromethyl, $R_4$=2,2,2-trifluoroethyl)

This compound was prepared in a similar fashion as that described in Example 18 from Compound 113 (Structure 11 of Scheme II, where $R_3$=isopropyl, $R_2$=methyl, $R_1$=trifluoromethyl). $^1$H NMR (500 MHz, CDCl$_3$) 11.6 (bs, 1H), 7.25 (d, J=8.3, 1H), 7.17 (s, 1H), 6.93 (d, J=8.3, 1H), 3.80 (dq, J=6.8, 6.8, 1H), 3.69–3.52 (m, 2H), 3.40 (dd, J=6.8, 5.4, 1H), 1.96–1.88(m, 1H), 1.53 (d, J=6.8, 3H), 0.83 (d, J=6.8, 1H), 0.79 (d, J=7.3, 3H).

EXAMPLE 44

(±)-5,6-Dihydro-5-ethyl-6-methyl-7-(2,2,2-trifluoroethyl)-4-trifluoromethyl-7H-pyrrolo[3,2-f]quinolin-2(1H)-one (Compound 145, Structure 13 of Scheme II, where $R_3$=ethyl, $R_2$=methyl, $R_1$=trifluoromethyl, $R_4$=2,2,2-trifluoroethyl)

This compound was prepared in a similar fashion as that described in Examples 12 and 18 from Compound 111 (Structure 9 of Scheme II, where $R_1$=trifluoromethyl) and 2-pentanone. $^1$H NMR (500 MHz, CDCl$_3$) 12.3 (bs, 1H), 7.29 (d, J=8.8, 1H), 7.23 (s, 1H), 6.98 (d, J=8.8, 1H), 3.84–3.78 (m, 1H), 3.71–3.59 (m, 2H), 3.46–3.43 (m, 1H), 1.78–1.70 (m, 2H), 1.47 (d, J=6.8, 3H), 0.86 (t, J=7.3, 3H).

EXAMPLE 45

(±)-5,6-Dihydro-5-ethyl-6-propyl-7-(2,2,2-trifluoroethyl)-4-trifluoromethyl-7H-pyrrolo[3,2-f]quinolin-2(1H)-one (Compound 146, Structure 13 of Scheme II, where $R_3$=ethyl, $R_2$=propyl, $R_1$=trifluoromethyl, $R_4$=2,2,2-trifluoroethyl)

This compound was prepared in a similar fashion as that described in Examples 12 and 18 from Compound 111 (Structure 9 of Scheme II, where $R_1$=trifluoromethyl) and 4-heptanone. $^1$H NMR (500 MHz, CDCl$_3$) 12.1 (bs, 1H), 7.30 (d, J=8.8, 1H), 7.19 (s, 1H), 6.95 (d, J=8.8, 1H), 3.70–3.51 (m, 4H), 1.88–1.53 (m, 4H), 1.47–1.36 (m, 2H), 1.05 (t, J=7.3, 3H), 0.70 (t, J=7.3, 3H).

EXAMPLE 46

(±)-5,6-Dihydro-5-(2-ethoxycarbonylethyl)-6-methyl-7-(2,2,2-trifluoroethyl)-4-trifluoromethyl-7H-pyrrolo[3,2-f]quinolin-2(1H)-one (Compound 147, Structure 13 of Scheme II, where $R_3$=2-ethoxycarbonylethyl, $R_2$=methyl, $R_1$=trifluoromethyl, $R_4$=2,2,2-trifluoroethyl)

This compound was prepared in a similar fashion as that described in Examples 12 and 18. $^1$H NMR (500 MHz, CDCl$_3$) 11.6 (bs, 1H), 7.27 (d, J=8.8, 1H), 7.20 (s, 1H), 6.95 (d, J=8.8, 1H), 4.01 (q, J=7.3, 2H), 3.82–3.76 (m, 1H), 3.70–3.58 (m, 2H), 3.56–3.52 (m, 1H), 2.40–2.32 (m, 1H), 2.15–2.08 (m, 1H), 2.05–1.98 (m, 1H), 1.70–1.62 (m, 1H), 1.46 (d, J=6.4, 3H), 1.18 (t, J=7.3, 3H).

EXAMPLE 47

6-Ethyl-5-methyl-7H-pyrrolo[3,2-f]quinolin-2(1H)-one (Compound 148, Structure 11 of Scheme II, where $R_3$=methyl, $R_2$=ethyl, $R_1$=H)

This compound was prepared in a similar fashion as that described in Example 12 from structure 9 of Scheme II (where $R_1$=H) and 3-pentanone as a yellow solid: $^1$H NMR (500 MHz, DMSO-d$_6$) 11.23 (s, 1H), 8.58 (d, J=9.5, 1H), 7.56 (d, J=8.6, 1H), 7.14 (d, J=8.6, 1H), 6.69 (d, J=9.5, 1H), 2.76 (q, J=7.5, 1H), 2.50 (s, 1H), 2.44 (s, 3H), 1.23 (t, J=7.5, 3H).

EXAMPLE 48

(±)-5,6-cis-Dihydro-5-methyl-6-ethyl-7-(2,2,2-trifluoroethyl)-7H-pyrrolo[3,2-f]quinolin-2(1H)-one (Compound 149, Structure 13 of Scheme II, where $R_3$=methyl, $R_2$=ethyl, $R_1$=H, $R_4$=2,2,2-trifluoroethyl)

This compound was prepared in a similar fashion as that described in Example 18 from Compound 148 (Structure 11 of Scheme II, where $R_3$=methyl, $R_2$=ethyl, $R_1$=H). $^1$H NMR (500 MHz, CDCl$_3$) 11.16 (s, 1H), 7.75 (d, J=9.5, 1H), 6.81 (d, J=8.5, 1H), 6.71 (d, J=9.6, 1H), 3.60–3.45 (m, 3H), 3.44–3.31 (m, 1H), 1.89–1.75 (m, 2H), 1.11 (d, J=6.8, 3H), 1.06 (t, J=7.3, 3H).

EXAMPLE 49

5,6-Dimethyl-7-(2,2,2-trifluoroethyl)-4-trifluoromethyl-7H-pyrrolo[3,2-f]quinolin-2(1H)-one (Compound 150, Structure 15 of Scheme II, where $R_3$=$R_2$=methyl, $R_1$=trifluoromethyl, $R_4$=2,2,2-trifluoroethyl)

To a solution of Compound 123 (Structure 13 of Scheme II, where $R_3$=$R_2$=methyl, $R_1$=trifluoromethyl, $R_4$=2,2,2-trifluoroethyl) (0.35 g, 0.97 mmol) in 30 mL CH$_2$Cl$_2$ was added DDQ (0.35 g, 1.5 mmol, 1.5 eq) in small portions. The resulting green mixture was stirred at rt for about 60 min until almost no more starting material was visible on TLC. Then 5% aq. NaHCO$_3$ (30 mL) was added and the mixture was extracted with EtOAc (3×50 mL) and the combined organic layers were washed with 5% aq. NaHCO$_3$ (30 mL) and brine, dried over MgSO$_4$ and concentrated. Purification by chromatography (Silica gel, hexane:EtOAc 2:1 to 0:1 gradient) afforded Compound 150 (195 mg, 56%) as a slightly yellow solid: $^1$H NMR (500 MHz, CDCl$_3$) 11.4 (bs, 1H), 7.55 (d, J=8.8, 1H), 7.17 (d, J=8.8, 1H), 7.16 (s, 1H), 4.71 (q, $J_{H-F}$=8.3, 2H), 2.43 (s, 3H), 2.33 (s, 3H).

An alternate oxidation method was also used as described as follow:

To a solution of Compound 123 (10 mg, 0.03 mmol) in 10 mL CH$_2$Cl$_2$ was added MnO$_2$ (approx. 0.3 g, 3.5 mmol, 100 eq) in portions until no more starting material was visible on TLC. Then EtOAc (10 mL) was added and the suspension was filtered through a short pad of celite. The solids were rinsed several times with EtOAc and the combined filtrates were concentrated. Purification by chromatography (Silica gel, hexane:EtOAc 2:1 to 0:1 gradient) afforded Compound 150 as a slightly yellow solid.

EXAMPLE 50

6-Ethyl-5-methyl-7-(2,2,2-trifluoroethyl)-7H-pyrrolo[3,2-f]quinolin-2(1H)-one (Compound 151, Structure 15 of Scheme II, where $R_3$=methyl, $R_2$=ethyl, $R_1$=H, $R_4$=2,2,2-trifluoroethyl)

This compound was prepared in a similar fashion as that described in Example 49 from Compound 149 (Structure 13 of Scheme II, where $R_3$=methyl, $R_2$=ethyl, $R_1$=H, $R_4$=2,2,2-trifluoroethyl). $^1$H NMR (500 MHz, CDCl$_3$) 11.20 (s, 1H), 8.54 (d, J=9.7, 1H), 7.46 (d, J=8.6, 1H), 7.16 (d, J=8.7, 1H), 6.77 (d, J=9.7, 1H), 4.69 (q, J=8.4, 2H), 2.83 (q, J=7.6, 2H), 2.56 (s, 3H), 1.23 (t, J=7.6, 3H).

EXAMPLE 51

6-Methyl-7-(2,2,2-trifluoroethyl)-4-trifluoromethyl-7H-pyrrolo[3,2-f]quinolin-2(1H)-one (Compound 152, Structure 15 of Scheme II, where $R_3$=H $R_2$=methyl, $R_1$=trifluoromethyl, $R_4$=2,2,2-trifluoroethyl)

This compound was prepared in a similar fashion as that described in Examples 18 and 49 from Compound 112 (Structure 11 of Scheme II, where $R_3$=H, $R_2$=methyl, $R_1$=trifluoromethyl). $^1$H NMR (500 MHz, CDCl$_3$) 11.1 (bs, 1H), 7.92 (d, J=8.8, 1H), 7.39 (d, J=8.8, 1H), 6.99 (s, 1H), 6.80 (s, 1H), 5.18 (q, $J_{H-F}$=8.8, 1H), 2.58 (s, 3H).

EXAMPLE 52

6-Ethyl-5-methyl-7-(2,2,2-trifluoroethyl)-4-trifluoromethyl-7H-pyrrolo[3,2-f]quinolin-2(1H)-one (Compound 153, Structure 15 of Scheme II, where $R_1$=methyl, $R_2$=ethyl, $R_1$=trifluoromethyl, $R_4$=2,2,2-trifluoroethyl)

This compound was prepared in a similar fashion as that described in Example 49 from Compound 134 (Structure 13 of Scheme II, where $R_3$=methyl, $R_2$=ethyl, $R_1$=trifluoromethyl, $R_4$=2,2,2-trifluoroethyl). $^1$H NMR (500 MHz, CDCl$_3$) 12.2 (bs, 1H), 7.57 (d, J=8.8, 1H), 7.25 (d, J=8.8, 1H), 7.18 (s, 1H), 4.62 (q, $J_{H-F}$=8.3, 2H), 2.45 (q, J=7.8, 2H), 2.34 (d, J=1.9, 3H), 1.24 (t, J=7.8, 3H).

EXAMPLE 53

5-Ethyl-6-methyl-7-(2,2,2-trifluoroethyl)-4-trifluoromethyl-7H-pyrrolo[3,2-f]quinolin-2(1H)-one (Compound 154, Structure 15 of Scheme II, where $R_3$=ethyl, $R_2$=methyl, $R_1$=trifluoromethyl, $R_1$=2,2,2-trifluoroethyl)

This compound was prepared in a similar fashion as that described in Example 49 from Compound 145 (Structure 13 of Scheme II, where $R_3$=ethyl, $R_2$=methyl, $R_1$=trifluoromethyl, $R_4$=2,2,2-trifluoroethyl). $^1$H NMR (500 MHz, CDCl$_3$) 12.6 (bs, 1H), 7.56 (d, J=8.8, 1H), 7.28 (d, J=8.8, 1H), 7.17 (s, 1H), 4.70 (q, $J_{H-F}$=8.3, 2H), 2.89 (q, J=7.3, 2H), 2.46 (s, 3H), 1.01 (t, J=7.3, 3H).

EXAMPLE 54

5-Ethyl-6-propyl-7-(2,2,2-trifluoroethyl)-4-trifluoromethyl-7H-pyrrolo[3,2-f]quinolin-2(1H)-one (Compound 155, Structure 15 of Scheme II, where $R_3$=ethyl, $R_1$=propyl, $R_1$=trifluoromethyl, $R_4$=2,2,2-trifluoroethyl)

This compound was prepared in a similar fashion as that described in Example 49 from Compound 146 (Structure 13 of Scheme II, where $R_3$=ethyl, $R_2$=propyl, $R_1$= trifluoromethyl, $R_4$=2,2,2-trifluoroethyl). $^1$H NMR (500 MHz, CDCl$_3$) 11.7 (bs, 1 H), 7.55 (d, J=8.8, 1H), 7.19 (d, J=8.8, 1H), 7.15 (s, 1H), 4.71 (q, $J_{H-F}$=8.3, 2H), 2.88 (q, J=7.3, 2H), 2.79 (t, J=7.8, 2H), 1.64–1.58 (m, 2H), 1.06 (t, J=7.3, 3H), 0.98 (t, J=7.3, 3H).

EXAMPLE 55

5,6,7,8-Tetrahydro-8-trifluoroethyl-4-trifluoromethylcyclopentano[g]pyrrolo[3,2-f]quinolin-2(1H)-one (Compound 156. Structure 15 of Scheme II, where $R_3$, $R_2$=—(CH$_2$)$_3$—, $R_1$=trifluoromethyl, $R_1$=trifluoroethyl)

This compound was prepared in a similar fashion as that described in Example 49 from Compound 119 (Structure 13 of Scheme II, where $R_3$, $R_2$=—(CH$_2$)$_3$—, $R_1$=trifluoromethyl, $R_4$=trifluoroethyl). $^1$H NMR (500 MHz, CDCl$_3$) 11.3 (bs, 1H), 7.57 (d, J=8.8, 1H), 7.21 (d, J=8.8, 1H), 7.20 (s, 1H), 4.66 (q, $J_{H-F}$=8.3, 2H), 3.16–3.14 (m, 2H), 2.93–2.90 (m, 2H), 2.53–2.49 (m, 2H).

EXAMPLE 56

8-Trifluoroethyl-4-trifluoromethyl-6,8-dihydrocyclopentano[g]pyrrolo[3,2-f]quinolin-2(1H)-one (Compound 157, Structure 17 of Scheme II, where $R_1$=trifluoromethyl, $R_4$=2,2,2-trifluoroethyl)

This compound was isolated as a minor product in the same reaction as that described in Example 55 from Compound 119 (Structure 13 of Scheme II, where $R_3$, $R_2$=—(CH$_2$)$_3$—, $R_1$=trifluoromethyl, $R_4$=trifluoroethyl). $^1$H NMR (500 MHz, CDCl$_3$) 12.2 (bs, 1H), 7.58 (d, J=9.3, 1H), 7.48 (d, J=9.3, 1H), 7.30 (s, 1H), 5.16 (s, 1H), 4.67–4.63 (m, 1H), 4.63 (s, 1H), 4.21–4.16 (m, 1H), 2.77 (d, J=11.2, 1H), 2.65 (d, J=10.7, 1H).

EXAMPLE 57

9-Trifluoroethyl-4-trifluoromethyl-9H-benzo[g]pyrrolo[3,2-f]quinolin-2(1H)-one (Compound 158, Structure 15 of Scheme II, where $R_3$, $R_2$=—(CH=CH)$_2$—, $R_1$=trifluoromethyl, $R_4$=trifluoroethyl)

This compound was prepared in a similar fashion as that described in Example 49 from Compound 132 (Structure 13 of Scheme II, where $R_3$, $R_2$=—(CH$_2$)$_4$—, $R_1$=trifluoromethyl, $R_4$=2,2,2-trifluoroethyl). $^1$H NMR (500 MHz, CDCl$_3$) 11.4 (bs, 1H), 8.39 (d, J=8.8, 1H), 8.19 (d, J=8.8, 1H), 7.82 (d, J=8.3, 1H), 7.76 (d, J=9.3, 1H), 7.57 (t, J=7.3, 1H), 7.34 (t, J=8.3, 1H), 7.21 (s, 1H), 5.46 (q, $J_{H-F}$=8.3, 2H).

EXAMPLE 58

6-Trifluoroethyl-4-trifluoromethyl-6,7,8,9-tetrahydrocyclopetano[i]pyrrolo[2,3-f]quinolin-2(1H)-one (Compound 159, Structure 16 of Scheme II, where $R_3$, $R_2$=—(CH$_2$)$_3$—, $R_1$=trifluoromethyl, $R_4$=trifluoroethyl)

This compound was isolated as a regioisomer of Compound 156 in Example 49. $^1$H NMR (500 MHz, CDCl$_3$) 10.8 (bs, 1H), 7.84 (s, 1H), 7.47 (s, 1H), 6.81 (s, 1H), 5.13 (q, $J_{H-F}$=9.3, 1H), 3.06–3.00 (m, 2H), 2.62–2.56 (m, 2H).

EXAMPLE 59

5-(3-Trifluoromethylphenyl)-6-methyl-7-(2,2,2-trifluoroethyl)-4-trifluoromethyl-7H-pyrrolo[3,2-f]quinolin-2(1H)-one (Compound 160, Structure 15 of Scheme II, where $R_3$=3-trifluoromethylphenyl, $R_2$=methyl, $R_1$=trifluoromethyl, $R_4$=2,2,2-trifluoroethyl)

This compound was prepared in a similar fashion as that described in Example 49 from Compound 139 (Structure 13 of Scheme II, where $R_3$=3-trifluoromethylphenyl, $R_2$=methyl, $R_1$=trifluoromethyl, $R_4$=2,2,2-trifluoroethyl). $^1$H NMR (500 MHz, CDCl$_3$) 12.8 (bs, 1H), 7.65 (d, J=8.8, 1H), 7.60 (d, J=8.3, 1H), 7.53 (dd, J=8.3, 8.3, 1H), 7.46 (s, 1H), 7.45 (d, J=8.3, 1H), 7.39 (d, J=8.8, 1H), 7.00 (s, 1H), 4.78 (q, $J_{H-F}$=8.3, 2H), 2.33 (s, 3H).

EXAMPLE 60

5-(4-Fluorophenyl-6-methyl-7-(2,2,2-trifluoroethyl)-4-trifluoromethyl-7H-pyrrolo[3,2-f]quinolin-2(1H)-one (Compound 161, Structure 15 of Scheme II, where $R_1$=4-fluorophenyl, $R_2$=methyl, $R_1$=trifluoromethyl, $R_4$=2,2,2-trifluoroethyl)

This compound was prepared in a similar fashion as that described in Example 49 from Compound 140 (Structure 13 of Scheme II, where $R_3$=4-fluorophenyl, $R_2$=methyl, $R_1$=trifluoromethyl, $R_4$=2,2,2-trifluoroethyl). $^1$H NMR (500 MHz, CDCl$_3$) 11.1 (bs, 1H), 7.98 (d, J=8.8, 1H), 7.40 (d, J=8.8, 1H), 7.29 (dd, J=8.8, 5.4, 1H), 7.16 (dd, J=8.8, 8.3, 1H), 6.76 (s, 1H), 5.26 (q, $J_{H-F}$=8.8, 2H), 2.38 (s, 3H).

EXAMPLE 61

5-(2-Ethoxycarbonylethyl)-6-methyl-7-(2,2,2-trifluoroethyl)-4-trifluoromethyl-7H-pyrrolo[3,2-f]quinolin-2(1H)-one (Compound 162, Structure 15 of Scheme II, where $R_3$=2-ethoxycarbonylethyl, $R_2$=methyl, $R_1$=trifluoromethyl, $R_4$=2,2,2-trifluoroethyl)

This compound was prepared in a similar fashion as that described in Example 49 from Compound 147 (Structure 13 of Scheme II, where $R_3$=2-ethoxycarbonylethyl, $R_2$=methyl, $R_1$=trifluoromethyl, $R_4$=2,2,2-trifluoroethyl). $^1$H NMR (500 MHz, CDCl$_3$) 11.7 (bs, 1H), 7.55 (d, J=8.3, 1H), 7.21 (d, J=8.8, 1H), 7.17 (s, 1H), 4.71 (q, $J_{H-F}$=7.8, 2H), 3.94 (q, J=7.3, 2H), 3.24 (t, J=7.3, 2H), 2.49 (s, 3H), 2.38 (t, J=7.3, 3H), 1.07 (t, J=7.3, 3H).

EXAMPLE 62

7-Ethyl-8-methyl-6-(2,2,2-trifluoroethyl)-4-trifluoromethyl-6H-pyrrolo[2,3-g]quinolin-2(1H)-one (Compound 163, Structure 16 of Scheme II, where $R_3$=ethyl, $R_2$=methyl, $R_1$=trifluoromethyl, $R_4$=2,2,2-trifluoroethyl)

This compound was a regioisomer of Compound 153 and prepared in a similar fashion as that described in Example 52. $^1$H NMR (500 MHz, CDCl$_3$) 9.4 (bs, 1H), 7.68 (s, 1H), 7.25 (s, 1H), 6.99 (s, 1H), 4.69 (q, $J_{H-F}$=8.3, 2H), 2.85 (q, J=7.8, 2H), 2.30 (s, 3H), 1.25 (t, J=7.8, 3H).

EXAMPLE 63

5-Hydroxymethyl-6-ethyl-7-(2,2,2-trifluoroethyl)-4-trifluoromethyl-7H-pyrrolo[3,2-f]quinolin-2(1H)-one (Compound 164, Structure 19 of Scheme III, where $R_3$=hydroxymethyl, $R_4$=ethyl, $R_5$=2,2,2-trifluoroethyl)

This compound was prepared by the general oxidation procedure described in Example 49 from Compound 153 (Structure 18 of Scheme III, where $R_2$=ethyl). $^1$H NMR (500 MHz, CDCl$_3$) 12.4 (bs, 1H), 7.84 (d, J=8.8, 1H), 7.24 (d, J=8.8, 1H), 7.02 (s, 1H), 5.10 (q, $J_{H-F}$=8.8, 2H), 4.92 (s, 2H), 4.85 (bs, 1H), 3.00 (q, J=7.3, 2H), 1.29 (t, J=7.3, 3H).

EXAMPLE 64

5-Methyl-6-(1-hydroxyethyl)-7-(2,2,2-trifluoroethyl)-4-trifluoromethyl-7H-pyrrolo[3,2-f]quinolin-2(1H)-one (Compound 165, Structure 19 of Scheme III, where $R_3$=methyl, $R_4$=1-hydroxyethyl, $R_5$=2,2,2-trifluoroethyl)

This compound was prepared by the general oxidation procedure described in Example 49 from Compound 153 (Structure 18 of Scheme III, where $R_2$=ethyl). $^1$H NMR (500 MHz, CDCl$_3$) 11.2 (bs, 1H), 7.89 (d, J=8.8, 1H), 7.33 (d, J=8.8, 1H), 6.96 (s, 1H), 5.63–5.54 (m, 1H), 5.49–5.44 (m, 1H), 5.37–5.28 (m, 1H), 4.81–4.77 (m, 1H), 2.37 (d, J=2.4, 3H), 1.62 (d, J=6.8, 3H).

EXAMPLE 65

5-Methyl-6-acetyl-7-(2,2,2-trifluoroethyl)-4-trifluoromethyl-7H-pyrrolo[3,2-f]quinolin-2(1H)-one (Compound 166, Structure 19 of Scheme III, where $R_3$=methyl, $R_1$=acetyl, $R_5$=2,2,2-trifluoroethyl)

This compound was isolated as an over oxidized product in Example 64. $^1$H NMR (500 MHz, CDCl$_3$) 10.5 (bs, 1H), 7.64 (d, J=8.8, 1H), 7.31 (s, 1H), 7.20 (d, J=8.8, 1H), 5.39 (q, $J_{H-F}$=7.8, 2H), 2.72 (s, 3H), 2.64 (s, 3H).

EXAMPLE 66

5-Formyl-6-methyl-7-(2,2,2-trifluoroethyl)-4-trifluoromethyl-7H-pyrrolo[3,2-f]quinolin-2(1H)-one (Compound 167, Structure 19 of Scheme III, where $R_3$=formyl, $R_4$=methyl, $R_5$=2,2,2-trifluoroethyl)

This compound was prepared by the general oxidation procedure described in Example 49 from Compound 150 (Structure 18 of Scheme III, where $R_1$=$R_2$=methyl). $^1$H NMR (500 MHz, CDCl$_3$) 11.9 (bs, 1H), 10.16 (d, J=1.5, 1H), 8.04 (d, J=8.8, 1H), 7.49 (d, J=8.8, 1H), 7.00 (s, 1H), 5.37 (q, $J_{H-F}$=8.8, 2H), 2.85 (s, 3H).

EXAMPLE 67

5-Acetyloxymethyl-6-ethyl-7-(2,2,2-trifluoroethyl)-4-trifluoromethyl-7H-pyrrolo[3,2-f]quinolin-2(1H)-one (Compound 168, Structure 20 of Scheme III)

In a 50 mL r.b. flask, a solution of 30 mg (0.08 mmol) of Compound 164 (Structure 19 of Scheme III, where $R_3$=hydroxymethyl, $R_4$=ethyl, $R_5$=2,2,2-trifluoroethyl) in 10 mL THF was treated with triethylamine (0.5 mL, 3.5 mmol, 40 eq) followed by acetic anhydride (0.2 mL, 2 mmol, 25 eq) and DMAP (1 mg, 0.008 mmol, 0.1 eq). The mixture was stirred at rt for 2 h and then 30 mL 2N HCl and 20 mL EtOAc added and vigorously stirred for 1 h. The layers were separated and the water layer was extracted with EtOAc (20 mL). The combined organic layers were washed with 20 mL portions of 2N HCl, water, 2N NaOH and brine and dried over $MgSO_4$. Concentration followed by purification by flash chromatography (hexane: EtOAc 5:1 to 0:1 gradient) afforded Compound 168. $^1$H NMR (500 MHz, $CDCl_3$) 11.1 (bs, 1H), 7.54 (d, J=8.8, 1H), 7.25 (d, J=8.8, 1H), 7.13 (s, 1H), 4.73 (q, $J_{H-F}$=8.3, 2H), 4.68 (s, 2H), 3.26 (s, 3H), 2.92 (q, J=7.3, 2H), 1.27 (t, J=7.3, 3H).

EXAMPLE 68

2-Acetyloxy-5-hydroxymethyl-6-ethyl-7-(2,2,2-trifluoroethyl)-4-trifluoromethyl-7H-pyrrolo[3,2-f]quinoline (Compound 169, Structure 23 of Scheme III)

This compound was prepared by treatment of Compound 164 (Structure 19 of Scheme III, where $R_3$=hydroxymethyl, $R_4$=ethyl, $R_5$=2,2,2-trifluoroethyl) with acetic anhydride in Example 67. $^1$H NMR (500 MHz, $CDCl_3$) 7.79 (s, 2 H), 7.57 (s, 1H), 4.98 (s, 2H), 4.82 (q, $J_{H-F}$=8.3, 2H), 3.03 (q, J=7.8, 2H), 2.43 (s, 3H), 1.33 (t, J=7.8, 3H).

EXAMPLE 69

6-Ethyl-7-(2,2,2-trifluoroethyl)-4-trifluoromethyl-7H-pyrrolo[3,2-f]quinolin-2(1H)-one (Compound 170, Structure 21 of Scheme III)

This compound was isolated as a by-product in the treatment of Compound 164 (Structure 19 of Scheme III, where $R_3$=hydroxymethyl, $R_4$=ethyl, $R_5$=2,2,2-trifluoroethyl) with acetic anhydride in Example 67. $^1$H NMR (500 MHz, $CDCl_3$) 11.2 (bs, 1H), 7.94 (d, J=8.8, 1H), 7.39 (d, J=8.8, 1H), 7.00 (s, 1H), 6.82 (d, J=2.0, 1H), 5.19 (q, $J_{H-F}$=8.8, 2H), 2.94 (q, J=7.3, 2H), 1.42 (t, J=7.3, 3H).

EXAMPLE 70

5-Ethoxymethyl-6-ethyl-7-(2,2,2-trifluoroethyl)-4-trifluoromethyl-7H-pyrrolo[3,2-f]quinolin-2(1H)-one (Compound 171, Structure 20 of Scheme III)

This compound was isolated as a by-product in the treatment of Compound 164 (Structure 19 of Scheme III, where $R_3$=hydroxymethyl, $R_4$=ethyl, $R_5$=2,2,2-trifluoroethyl) with acetic anhydride in Example 67. $^1$H NMR (500 MHz, $CDCl_3$) 11.3 (bs, 1H), 7.92 (d, J=8.8, 1H), 7.34 (d, J=8.8, 1H), 6.95 (s, 1H), 5.22 (q, $J_{H-F}$=8.8, 2H), 4.72 (s, 2H), 3.37 (q, J=6.8, 2H), 3.00 (q, J=7.3, 2H), 1.29 (t, J=7.3, 3H), 1.07 (t, J=6.8, 3H).

EXAMPLE 71

6-(1-Methoxyethyl)-5-methyl-7-(2,2,2-trifluoroethyl)-4-trifluoromethyl-7H-pyrrolo[3,2-f]quinolin-2(1H)-one (Compound 172, Structure 22 of Scheme III)

In a 50 mL r.b. flask, a solution of 5 mg (0.01 mmol) of Compound 165 (Structure 19 of Scheme III, where $R_3$=methyl, $R_4$=1-hydroxyethyl, $R_5$=2,2,2-trifluoroethyl) in 5 mL MeOH was treated with aqueous 2.5 N HCl (2 mL, 5 mmol). The mixture was stirred at rt for 20 h and then 30 mL water was added and the water layer was extracted with EtOAc (2×30 mL). The combined organic layers were washed with brine and dried over $MgSO_4$. Concentration followed by purification by flash chromatography (hexane: EtOAc 2:1 to 1:1 gradient) afforded 4.2 mg of Compound 172 as a slightly yellow solid. $^1$H NMR (500 MHz, $CDCl_3$) 13.2 (bs, 1H), 7.64 (d, J=8.8, 1H), 7.39 (d, J=8.8, 1H), 7.20 (s, 1H), 5.27–5.20 (m, 1H), 4.69–4.85 (m, 2H), 3.25 (s, 3H), 2.37 (d, J=1.8, 3H), 1.63 (d, J=7.0, 3H).

EXAMPLE 72

7-Allyl-6-methyl-4-trifluoromethyl-5H-pyrrolo[2,3-f]quinolin-2(1H)-one (Compound 173, Structure 26 of Scheme IV, where $R_2$=methyl, $R_3$=allyl)

In a 250 mL r.b. flask a suspension of 5-amino-4-trifluoromethylquinolin-2-one (Structure 24 of Scheme IV) (42 mg, 0.18 mmol) in 4 mL conc. HCl was cooled to −1° C. and a solution of $NaNO_2$ (20 mg, 0.6 mmol) in water (0.5 mL) was added dropwise in 1 min. The dark brown suspension was stirred at −1° C. for 1 h and then a solution of $SnCl_2 \cdot 2H_2O$ (0.20 g, 0.6 mmol) in conc. HCl (1 mL) was added dropwise in 1 min. The light yellow suspension of Compound 174 (Structure 25 of Scheme IV) was stirred at −1° C. for 30 min and then kept in a refrigerator at −1° C. for 3 days. To the crude suspension of the hydrazine was added a solution of 5-hexen-2-one (0.1 mL, 0.9 mmol, 5 eq) in 5 mL of EtOH and the mixture was refluxed for 3 h. Then the mixture was diluted with 30 mL of water and extracted with EtOAc (2×30 mL) and the combined organic layers were washed with brine, dried over $MgSO_4$ and concentrated. Purification by chromatography (Silica gel, hex: EtOAc 3:1) afforded Compound 173 as a yellow solid. $^1$H NMR (500 MHz, $CDCl_3$) 11.1 (bs, 1H), 9.3 (bs, 1H), 7.80 (d, J=8.3, 1H), 7.26 (d, J=8.3, 1H), 6.95 (s, 1H), 6.02–5.95 (m, 1H), 5.05 (dd, J=17.1, 2.0, 1H), 4.97 (dd, J=9.8, 2.0, 1H), 3.50 (d, J=6.3, 1H), 2.46 (s, 3H).

EXAMPLE 73

6-Ethyl-7-methyl-4-trifluoromethyl-5H-pyrrolo[2,3-f]quinolin-2(1H)-one (Compound 175, Structure 26 of Scheme IV, where $R_2$=ethyl, $R_3$=methyl)

This compound was prepared in a similar fashion as that described in Example 72 from Compound 174 (Structure 25 of Scheme IV) and 3-pentanone. $^1$H NMR (500 MHz, $CDCl_3$) 11.2 (bs, 1H), 9.1 (bs, 1H), 7.79 (d, J=8.3, 1H), 7.27 (d, J=8.8, 1H), 6.96 (s, 1H), 2.87 (q, J=7.8, 2H), 2.27 (s, 1H), 1.27 (t, J=7.8, 3H).

EXAMPLE 74

7-(3-Trifluoromethylphenyl)-6-methyl-4-trifluoromethyl-5H-pyrrolo[2,3-f]quinolin-2(1H)-one (Compound 176, Structure 26 of Scheme IV, where $R_2$=methyl, $R_3$=3-trifluoromethylphenyl)

This compound was prepared in a similar fashion as that described in Example 72 from Compound 174 (Structure 25 of Scheme IV) and 3-trifluorophenylacetone. $^1$H NMR (500 MHz, $CDCl_3$) 12.9 (bs, 1H), 8.9 (bs, 1H), 7.90 (d, J=8.8, 1H), 7.71 (s, 1H), 7.64 (s, 3H), 7.30 (d, J=8.8, 1H), 7.29 (s, 1H), 2.59 (s, 3H).

EXAMPLE 75

7-(2-Hydroxyethyl)-6-methyl-4-trifluoromethyl-5H-pyrrolo[2,3-f]quinolin-2(1H)-one (Compound 177, Structure 26 of Scheme IV, where $R_2$=methyl. $R_3$=2-hydroxyethyl This compound was prepared in a similar fashion as that described in Example 72 from Compound 174 (Structure 25 of Scheme IV) and 5-hydroxy-2-pentanone. $^1$H NMR (500 MHz, CDCl$_3$) 11.3 (bs, 1H), 9.4 (bs, 1H), 7.89 (d, J=8.5, 1H), 7.29 (d, J=8.5, 1H), 6.97 (d, J=0.6, 1H), 3.78 (t, J=7.3, 2H), 3.23 (t, J=7.3, 2H), 2.51 (s, 3H).

EXAMPLE 76

(+)-4c,5,6,7,7a(cis),8-Hexahydro-8-trifluoroethyl-4-trifluoromethylcyclopentano-[g]pyrrolo[3,2-f]quinolin-2(1H)-one (Compound 178, Structure 13 of Scheme II, where $R_3$, $R_2$=—(CH$_2$)$_3$—, $R_1$=trifluoromethyl, $R_4$=trifluoroethyl) and (−)-4c,5,6,7,7a(cis),8-Hexahydro-8-trifluoroethyl-4-trifluoromethylcyclopentano-[g]pyrrolo[3,2-f]quinolin-2(1H)-one (Compound 179, Structure 13 of Scheme II, where $R_3$, $R_2$=—(CH$_2$)$_3$—, $R_1$=trifluoromethyl, $R_4$=trifluoroethyl)

Compounds 178 and 179 were enantiomers of Compound 119 and separated by chiral HPLC.

EXAMPLE 77

4-Trifluoromethyl-6,7-dihydro-7,7,9-trimethyl-pyrido[2,3-g]quinolin-2(1H)-one (Compound 180, Structure 28 of Scheme V, where $R_1$=trifluoromethyl)

A mixture of Compound 181 (Structure 8 of Scheme V, where $R_1$=trifluoromethyl), iodine and acetone in a sealed tube was heated at 135° C. overnight and the mixture was concentrated. Chromatography of the crude mixture afforded Compound 180 as a yellow solid. $^1$H NMR (500 MHz, CDCl$_3$) 7.21 (s, 1H), 6.83 (m, 1H), 6.77 (s, 1H), 5.68 (s, 1H), 5.46 (bs, 1H), 2.02 (s, 3H) and 1.31 (s, 6H).

EXAMPLE 78

8-(2,2,2-Trifluoroethyl)-5,6,7,8-tetrahydro-5,7,7-trimethylpyrido[3,2-f]quinolin-2(1H)-one (Compound 182, Structure 29 of Scheme V, where $R_1$=H)

A mixture of Compound 183 (Structure 8 of Scheme V, where $R_1$=H), iodine and acetone in a sealed tube was heated at 135° C. overnight and the mixture was concentrated. Chromatography of the crude mixture afforded Compound 184 (Structure 27 of Scheme V, where $R_1$=H) as a yellow solid.

Compound 184 was treated with TFA and NaBH$_4$ in a similar fashion as that described in Example 18 to afford Compound 182 as a yellow solid. $^1$H NMR (400 MHz, CDCl$_3$) 11.29 (s, 1H), 7.96 (d, J=9.9, 1H), 7.15 (d, J=9.1, 1H), 7.06 (d, J=9.1, 1H), 6.69 (d, J=9.8, 1H), 3.84 (q, J=8.7, 2H), 3.41–3.47 (m, 1H), 2.08 (dd, J=13.6, 7.3, 1H), 1.88 (dd, J=13.6, 7.3, 1H), 1.39 (s, 3H), 1.35 (d, J=6.7, 3H), 1.08 (s, 3H).

EXAMPLE 79

4,5,7-Tri(trifluoromethyl)pyrido[3,2-f]quinolin-2(1H)-one (Compound 185, Structure 30 of Scheme V, where $R_1$=trifluoromethyl)

A mixture of Compound 181 and 1,1,1,5,5,5-hexafluoro-2,4-pentadiene was heated to 170° C. for 2 h and was poured into ice-water. The crude mixture was extracted with EtOAc and the combined organic phase was concentrated. Chromatography provided Compound 185 as a white solid. $^1$H NMR (400 MHz, acetone-d$_6$) 11.15 (s, 1H), 8.25 (s, 1H), 8.04 (d, J=9.0, 1H), 7.58 (d, J=9.0, 1H), 6.99 (s, 1H).

EXAMPLE 80

5,7-Bis(trifluoromethyl)pyrido[3,2-f]quinolin-2(1H)-one (Compound 186, Structure 30 of Scheme V, where $R_1$=H)

This compound was prepared in a similar fashion as that described in Example 79 from Compound 183 (Structure 8 of Scheme V, where $R_1$=H) as a white solid. $^1$H NMR (400 MHz, CDCl$_3$) 12.49 (s, 1H), 8.60 (d, J=9.9, 1H), 8.28 (d, J=9.4, 1H), 8.19 (s, 1H), 7.99 (d, J=9.4, 1H), 6.79 (d, J=9.9, 1H).

EXAMPLE 81

4-Trifluoromethyl-7-methyl-6,7,8,9-tetrahydropyrido[2,3-g]quinolin-2(1H)-one (Compound 187, Structure 33 of Scheme VI, where $R_1$=methyl, n=1)

Preparation of 1-acetyl-2-methyl-6-nitrotetrahydroquinoline (Compound 188, Structure 32 of Scheme VI, where $R_1$=methyl, n=1)

In a 100-mL r.b. flask, a solution of Compound 189 (Structure 31 of Scheme VI, where $R_1$=methyl, n=1) (1.56 g, 8.2 mmol) in 1,2-dichloroethane (15 mL) was treated with Yb(OTf)$_3$ (0.622 g, 1.0 mmol, 12 mol %) and fuming nitric acid (2.0 mL, 47.0 mmol, 5.7 equiv). The reaction mixture was stirred at rt for 16 h. The reaction mixture was diluted with CH$_2$Cl$_2$ (50 mL), washed with H$_2$O (50 mL) and brine (50 mL). Dried (MgSO$_4$), filtered and concentrated in vacuo. The residue was purified by flash column chromatography (SiO$_2$, 4×20 cm, 25% EtOAc/hexane as eluent) to afford 1.22 g (63%) of Compound 188 as white solid. R$_f$ 0.45 (SiO$_2$.50% EtOAc/hexane). $^1$H NMR (400 MHz, CDCl$_3$) 8.10–8.00 (m, 2H), 7.44 (d, 1H, J=8.5), 4.76 (sixtet, 1H, J=6.6), 2.85–2.79 (m, 1H), 2.74–2.68 (m, 1H), 2.38–2.30 (m, 1H), 2.24 (s, 3H), 1.58–1.54 (m, 1H), 1.18 (d, 3H, J=6.6).

4-Trifluoromethyl-7-methyl-6,7,8,9-tetrahydropyrido[2,3-g]quinolin-2(1H)-one (Compound 187, Structure 33 of Scheme VI, where $R_1$=methyl, n=1)

In a 100-mL r.b. flask, a solution of Compound 188 (1.22 g, 5.2 mmol) in a 1:1 mixture of CH$_2$Cl$_2$/EtOH (30 mL) was treated with 10% Pd/C (140 mg, 11 wt % equiv). The reaction mixture was stirred under hydrogen (1 atm) at rt for 18 h. The reaction mixture was filtered through a pad of celite and rinsed with CH$_2$Cl$_2$ (100 mL). The filtrate was concentrated to give 1.02 g (96%) of the corresponding amine which was used immediately in the next reaction without further purification.

In a 100-mL r.b. flask, a solution of the amine (1.02 g, 5.0 mmol) in a 95:5 mixture of toluene/water (30 mL) was heated to reflux for 16 h. After cooling to rt, the reaction mixture was dried (MgSO$_4$), filtered and concentrated in vacuo. The residue was then dissolved in 20 mL conc. H$_2$SO$_4$ and heated to 95° C. for 4 h. The reaction mixture was cooled to rt and poured onto 200 mL of ice-water, neutralized with 6N NaOH to pH 7 and extracted with EtOAc (3×250 mL). The combined extracts were washed with brine (2×200 mL), dried (MgSO$_4$), filtered and concentrated in vacuo. The residue was purified by flash column chromatography (SiO$_2$, 3×20 cm, 50–70% EtOAc in hexane gradient eluent) to afford 0.21 g (15%) of Compound 187 as a yellow solid. R$_f$ 0.30 (SiO$_2$, 2:1=EtOAc:hexane). $^1$H NMR (400 MHz, CDCl$_3$) 11.70 (s, 1H), 7.11 (s, 1H), 7.00 (s, 1H), 6.80 (s, 1H), 4.02 (br, s, 1H), 3.48–3.43 (m, 1H), 2.95–2.91 (m, 2H), 2.01–1.96 (m, 1H), 1.25 (d, 3H, J=6.1), 0.89–0.85 (m, 1H).

EXAMPLE 82

4-Trifluoromethyl-7,8-dihydro-6H-pyrrolo[2,3-g]quinolin-2(1H)-one (Compound 190, Structure 33 of Scheme VI, where R$_1$=H, n=0)

This compound was prepared in a similar fashion as that described in Example 81 from Compound 191 (Structure 31 of Scheme VI, where R$_1$=H, n=0). $^1$H NMR (acetone-d$_6$) 7.28 (s, 1H), 6.82 (s, 2H), 5.25 (bs, 1H), 3.60 (t, J=8.2, 2H), 3.12 (t, J=8.2, 2H).

EXAMPLE 83

4-Trifluoromethyl-5,6,7,8-tetrahydropyrido[2,3-g]quinolin-2(1H)-one (Compound 192, Structure 33 of Scheme VI, where R$_1$=H, n=1)

This compound was prepared in a similar fashion as that described in Example 81 from Compound 193 (Structure 31 of Scheme VI, where R$_1$=H, n=1). $^1$H NMR (400 MHz, CDCl$_3$) 11.18 (s, 1H), 7.09 (s, 1H), 7.00 (s, 1H), 6.80 (s, 1H), 4.08 (s, 1H), 3.35 (t, 2H, J=5.4), 2.91 (t, 2H, J=6.4), 1.97 (m, 2H).

EXAMPLE 84

4-Trifluoromethyl-7-methyl-6-propyl-6,7,8,9-tetrahydropyrido[2,3-g]quinolin-2(1H)-one (Compound 194, Structure 34 of Scheme VI, where R$_1$=methyl, R$_2$=propyl, n=1)

In a 25-mL r.b. flask, a solution of Compound 187 (Structure 33 of Scheme VI, where R$_1$=methyl, n=1) (12.2 mg, 0.043 mmol) in MeOH (5 mL) was treated with propionaldehyde (2 mL), AcOH (2 mL) and NaCNBH$_3$. The reaction mixture was stirred at rt for 18 h. The reaction mixture was poured onto ice-water (50 mL), neutralized with NaHCO$_3$ to pH 7 and extracted with EtOAc (3×50 mL). The combined extracts were washed with H$_2$O (50 mL) and brine (50 mL), dried (MgSO$_4$), filtered and concentrated in vacuo. The residue was purified by flash column chromatography (SiO$_2$, 50% EtOAc/hexane as eluent) to afford 5.0 mg (34%) of Compound 194 as a yellow solid. R$_f$ 0.51 (SiO$_2$, 2:1=EtOAc:hexane). $^1$H NMR (400 MHz, CDCl$_3$) 11.45 (br. s, 1H), 7.09 (s, 1H), 7.00 (s, 1H), 6.75 (s, 1H), 3.55 (m, 1H), 3.35–3.29 (m, 1H), 3.21–3.12 (m, 1H), 2.95–2.80 (m, 2H), 2.00–1.78 (m, 2H), 1.72–1.60 (m, 2H), 1.17 (d, 3H, J=6.5), 0.97 (t, 3H, J=7.3), 0.89–0.85 (m, 1H).

EXAMPLE 85

4-Trifluoromethyl-7-methyl-6-cyclopropylmethyl-6,7,8,9-tetrahydropyrido[2,3-g]quinolin-2(1H)-one (Compound 195, Structure 34 of Scheme VI, where R$_1$=methyl, R$_2$=cyclopropylmethyl, n=1)

This compound was prepared in a similar fashion as that described in Example 84 from Compound 187 (Structure 33 of Scheme VI, where R$_1$=methyl, n=1) and cyclopropanecarboxaldehyde. $^1$H NMR (400 MHz, CDCl$_3$) 10.91 (br. s, 1H), 7.14 (s, 1H), 7.01 (s, 1H), 6.94 (s, 1H), 3.65 (m, 1H), 3.35 (dd, 1H, J=15.0, 5.5), 3.09 (dd, 1H, J=15.0, 6.2), 2.97–2.82 (m, 2H), 2.00–1.94 (m, 1H), 1.84–1.79 (m, 1H), 1.17 (d, 3H, J=6.5), 0.88–0.85 (m, 1H), 0.58 (m, 2H), 0.28 (dd, 2H, J=10.3, 5.0).

EXAMPLE 86

4-Trifluoromethyl-7-methyl-6-ethyl-6,7,8,9-tetrahydropyrido[2,3-g]quinolin-2(1H)-one (Compound 196, Structure 34 of Scheme VI, where R$_1$=methyl, R$_2$=ethyl, n=1)

This compound was prepared in a similar fashion as that described in Example 84 from Compound 187 (Structure 33 of Scheme VI, where R$_1$=methyl, n=1) and acetaldehyde. $^1$H NMR (400 MHz, CDCl$_3$) 11.19 (br. s, 1H), 7.11 (s, 1H), 7.00 (s, 1H), 6.80 (s, 1H), 3.55 (m, 1H), 3.47–3.32 (m, 2H), 2.93–2.80 (m, 2H), 1.93–1.79 (m, 2H), 1.22 (t, 3H, J=7.0), 1.18 (d, 3H, J=6.4).

EXAMPLE 87

4-Trifluoromethyl-7-methyl-6-(2,2,2-trifluoroethyl)-6,7,8,9-tetrahydropyrido[2,3-g]quinolin-2(1H)-one (Compound 197, Structure 34 of Scheme VI, where R$_1$=methyl, R$_2$=2,2,2-trifluoroethyl, n=1)

This compound was prepared in a similar fashion as that described in Example 84 from Compound 187 (Structure 33 of Scheme VI, where R$_1$=methyl, n=1) and trifluoroacetaldehyde ethyl hemiacetal. $^1$H NMR (400 MHz, CDCl$_3$) 11.08 (br. s, 1H), 7.06 (s, 1H), 7.00 (s, 1H), 6.99 (s, 1H), 3.99 (m, 1H), 3.81 (m, 1H), 3.67 (m, 1H), 3.10–2.95 (m, 1H), 2.92–2.82 (m, 1H), 2.07–1.97 (m, 1H), 1.93–1.80 (m, 1H), 1.19 (d, 3H, J=6.5).

EXAMPLE 88

4-Trifluoromethyl-6-(2,2,2-trifluoroethyl)-6,7,8,9-tetrahydropyrido[2,3-g]quinolin-2(1H)-one (Compound 198, Structure 34 of Scheme VI, where R$_1$=H, R$_2$=2,2,2-trifluoroethyl, n=1)

This compound was prepared in a similar fashion as that described in Example 84 from Compound 192 (Structure 33 of Scheme VI, where R$_1$=H, n=1) and trifluoroacetaldehyde ethyl hemiacetal. $^1$H NMR (400 MHz, CDCl$_3$) 11.32 (br. s, 1H), 7.11 (s, 1H), 7.02 (s, 1H), 6.99 (s, 1H), 3.88 (q, 2H, J=8.9), 3.47 (t, 2H, J=5.6), 2.93 (t, 2H, J=6.3), 2.03 (m, 2H).

EXAMPLE 89

4-Trifluoromethyl-6-propyl-6,7,8,9-tetrahydropyrido[2,3-g]quinolin-2(1H)-one (Compound 199, Structure 34 of Scheme VI, where $R_1$=H, $R_2$=propyl, n=1)

This compound was prepared in a similar fashion as that described in Example 84 from Compound 192 (Structure 33 of Scheme VI, where $R_1$=H, n=1) and propionaldehyde. $^1$H NMR (400 MHz, CDCl$_3$) 11.23 (br. s, 1H), 7.07 (s, 1H), 6.99 (s, 1H), 6.78 (s, 1H), 3.34 (t, 2H, J=5.6), 3.26 (t, 2H, J=7.4), 2.88 (t, 2H, J=6.3), 1.97 (m, 2H), 1.65 (m, 2H), 0.97 (t, 3H, J=7.4).

EXAMPLE 90

4-Trifluoromethyl-6-ethyl-6,7,8,9-tetrahydropyrido[2,3-g]quinolin-2(1H)-one (Compound 200, Structure 34 of Scheme VI, where $R_1$=H, $R_2$=ethyl, n=1)

This compound was prepared in a similar fashion as that described in Example 84 from Compound 192 (Structure 33 of Scheme VI, where $R_1$=H, n=1) and acetaldehyde. $^1$H NMR (400 MHz, CDCl$_3$) 11.23 (br. s, 1H), 7.07 (s, 1H), 7.00 (s, 1H), 6.82 (s, 1H), 3.39 (q, 2H, J=7.1), 3.31 (t, 2H, J=5.6), 2.88 (t, 2H, J=6.4), 1.98 (m, 2H), 1.18 (t, 3H, J=7.1).

EXAMPLE 91

4-Trifluoromethyl-6-cyclopropylmethyl-6,7,8,9-tetrahydropyrido[2,3-g]quinolin-2(1H)-one (Compound 201, Structure 34 of Scheme VI, where $R_1$=H, $R_2$=cyclopropylmethyl, n=1)

This compound was prepared in a similar fashion as that described in Example 84 from Compound 192 (Structure 33 of Scheme VI, where $R_1$=H, n=1) and cyclopropanecarboxaldehyde. $^1$H NMR (400 MHz, CDCl$_3$) 11.44 (br. s, 1H), 7.06 (s, 1H), 7.00 (s, 1H), 6.92 (s, 1H), 3.40 (t, 2H, J=5.6), 3.21 (d, 2H, J=6.2), 2.90 (t, 2H, J=6.3), 1.99 (m, 2H), 1.07 (m, 1H), 0.58 (m, 2H), 0.27 (m, 2H).

EXAMPLE 92

6,7-Dihydro-8,8-dimethyl-4-(trifluoromethyl)-8H-pyrano[3,2-g]quinolin-2(1H)-one (Compound 202, Structure 39 of Scheme VII, where $R_1$=$R_3$=$R_5$=H, $R_2$=methyl, $R_4$=trifluoromethyl)

General Method A: Substitution of a propargyl alcohol with a phenol. To a solution of the propargyl alcohol (1.16 equiv) and DBU (1,8-diazabicyclo[5.4.0]undec-7-ene, 1.3 equiv) in CH$_3$CN (0.5 mL/mmol) stirred at −5° C. was added trifluoroacetic anhydride (1.16 equiv) and the flask was stirred for 40 min. In a second flask, to a mixture of the phenol (1.0 equiv) and CuCl (0.01 equiv) in CH$_3$CN (0.8 mL/mmol) was added DBU (1.5 equiv) at 0° C. This solution was added via cannula to the first flask. The mixture was stirred at 0° C. for 4 h, then allowed to warm to rt. The mixture was partitioned between EtOAc (10 mL/mmol) and water (5 mL/mmol) and the aqueous layer was extracted with EtOAc. The combined organic layers were washed sequentially with 1 N NaHSO$_4$ (5 mL/mmol), NaHCO$_3$ (5 mL/mmol) and brine (5 mL/mmol), dried over MgSO$_4$, filtered and concentrated. Flash chromatography affords the desired product as an oil.

1-Nitro-3-(1,1-dimethylprop-2-ynloxy)benzene (Compound 203, Structure 36 of Scheme VII, where $R_1$=$R_3$=H, $R_2$=methyl).

This compound was prepared by the above General Method A from 2-methyl-3-butyn-2-ol (0.976 g, 11.6 mmol) and 3-nitrophenol (1.39 g, 10.0 mmol) in 40% yield (0.76 g) after flash chromatography (hexanes:EtOAc 9:1). $^1$H NMR (400 MHz, CDCl$_3$) 8.11 (t, J=2.2, 1H), 7.86–7.96 (m, 1H), 7.48–7.55 (m, 1H), 7.43 (t, J=8.1, 1H), 2.66 (s, 1H), 1.70 (s, 6H).

General Method B: Thermal cyclization of a propargyl phenyl ether to a 2H-chromene. A solution of the propargyl phenyl ether was heated in N,N-diethylaniline (1–2 M) at 195° C. or reflux for 12–30 h, whereupon the dark brown solution was partitioned between EtOAc (10 mL/mmol) and 1N NaHSO$_4$ (5 mL/mmol). The aqueous layer was extracted with EtOAc (10 mL/mmol) and the combined organic layers were washed sequentially with 1N NaHSO$_4$ (10 mL/mmol) and brine (10 mL/mmol), dried over MgSO$_4$, filtered and concentrated. Flash chromatography (EtOAc:hexanes) afforded the desired product.

2,2-Dimethyl-7-nitro-2H-chromene (Compound 204, Structure 37 of Scheme VII, where $R_1$=$R_3$=H, $R_2$=methyl).

This compound was prepared by the above General Method B from Compound 203 (0.703 g, 3.71 mmol) in 1.9 mL N,N-diethylaniline heated at 195° C. for 14 h in 18% yield (130 mg) after flash chromatography (hexanes:EtOAc 9:1). $^1$H NMR (400 MHz, CDCl$_3$) 7.71 (dd, J=8.3, 2.2, 1H), 7.61 (d, J=2.1, 1H), 7.07 (d, J=8.3, 1H), 6.37 (d, J=9.9, 1H), 5.82 (d, J=9.9, 1H), 1.47 (s, 6H).

7-Amino-2,2-dimethyl-2H-chroman (Compound 205, Structure 38 of Scheme VII, where $R_1$=$R_3$=H, $R_2$=methyl).

A suspension of Compound 204 (124 mg, 0.655 mmol) and 10% Pd—C (6.2 mg, 5 wt %) in 1.3 mL EtOAc and 1.3 mL EtOH was stirred under an atmosphere of hydrogen for 16 h, whereupon the mixture was filtered through Celite and concentrated. Flash chromatography (hexanes:EtOAc 3:1) afforded 112 mg (97%) of Compound 205. $^1$H NMR (400 MHz, CDCl$_3$) δ 6.83 (d, J=8.0, 1H), 6.21 (dd, J=8.0, 2.3, 1H), 6.14 (d, J=2.2, 1H), 3.50 (v. broad s, 2H), 2.66 (t, J=6.7, 2H), 1.76 (t, J=6.7, 2H), 1.31 (s, 3H).

6,7-Dihydro-8,8-dimethyl-4-(trifluoromethyl)-8H-pyrano[3,2-g]quinolin-2(1H)-one (Compound 202, Structure 39 of Scheme VII, where $R_1$=$R_3$=$R_5$=H, $R_2$=methyl, $R_4$=trifluoromethyl).

A solution of Compound 205 (9 mg, 0.050 mmol) and 4,4,4-trifluoroacetoacetate (57 mg, 0.30 mmol) was heated at 190° C. in a sealed tube for 20 h, whereupon the mixture was cooled and precipitated with hexanes. Flash chromatography (CH$_2$Cl$_2$:MeOH 92:8) afforded 4 mg of a brown solid. Final purification by HPLC (ODS semi-prep column, MeOH:water 7:3, 3 mL/min) afforded 1.1 mg (7%) of Compound 205, a white film. $^1$H NMR (400 MHz, acetone-d$_6$) 10.9 (broad s, 1H), 7.50 (s, 1H), 6.84 (s, 1H), 6.69 (s, 1H), 2.93 (t, J=6.8, 2H), 1.91 (t, J=6.8, 2H), 1.38 (s, 6H).

EXAMPLE 93

6,7-Dihydro-8,8,10-trimethyl-4-(trifluoromethyl)-8H-pyrano[3,2-g]quinolin-2(1H)-one (Compound 206, Structure 39 of Scheme VII, where $R_1$=$R_2$=methyl, $R_3$=$R_5$=H, $R_4$=trifluoromethyl)

1-Nitro-2-methyl-3-(1,1-dimethylprop-2-ynloxy)benzene (Compound 207, Structure 36 of Scheme VII, where $R_1$=$R_2$=methyl, $R_3$=H)

This compound was prepared by General Method A (EXAMPLE 92) from 2-methyl-3-butyn-2-ol (0.976 g, 11.6 mmol) and 2-methyl-3-nitrophenol (1.53 g, 10.0 mmol) in 61% (1.34 g) yield after flash chromatography (hexanes: EtOAc 11:1). $^1$H NMR (400 MHz, CDCl$_3$) 7.72 (d, J=7.9, 1H), 7.49 (d, J=7.8, 1H), 7.22 (t, J=8.0, 1H), 2.60 (s, 1H), 2.36 (s, 3H), 1.69 (s, 6H).

2,2,8-Trimethyl-7-nitro-2H-chromene (Compound 208, Structure 37 of Scheme VII, where R$_1$=R$_2$=methyl, R$_3$=H).

This compound was prepared by General Method B (EXAMPLE 92) from Compound 207 (0.415 g, 1.89 mmol) in 2 mL N,N-diethylaniline heated at 190° C. for 16 h in 59% yield (59%) after flash chromatography (hexanes:EtOAc 9:1). $^1$H NMR (400 MHz, CDCl$_3$) 7.39 (d, J=8.2, 1H), 6.91 (d, J=8.2, 1H), 6.33 (d, J=9.8, 1H), 5.78 (d, J=9.8, 1H), 2.36 (s, 3H), 1.46 (s, 6H).

7-Amino-2,2,8-trimethyl-2H-chroman (Compound 209, Structure 38 of Scheme VII, where R$_1$=R$_2$=methyl, R$_3$=H).

A suspension of Compound 208 (241 mg, 1.10 mmol) and 10% Pd—C (12 mg, 5 wt %) in 2.2 mL EtOAc and 2.2 mL EtOH was stirred under an atmosphere of hydrogen for 4 h, whereupon the mixture was filtered through Celite and concentrated. Flash chromatography (hexanes:EtOAc 3:1) afforded 210 mg (100%) of Compound 209. $^1$H NMR (400 MHz, CDCl$_3$) 6.72 (d, J=8.0, 1H), 6.24 (d, J=8.0, 1H), 3.48 (broad s, 2H), 2.68 (t, J=6.8, 2H), 2.01 (s, 3H), 1.74 (t, J=6.8, 2H), 1.31 (s, 6H).

6,7-Dihydro-8,8,10-trimethyl-4-(trifluoromethyl)-8H-pyrano[3,2-g]quinolin-2(1H)-one (Compound 206, Structure 39 of Scheme VII, where R$_1$=R$_2$=methyl, R$_3$=R$_5$=H, R$_4$=trifluoromethyl).

A solution of Compound 209 (39 mg, 0.21 mmol) and 4,4,4-trifluoroacetoacetate (195 mg, 1.03 mmol) in 0.5 mL diphenyl ether was heated at 190° C. in a sealed tube for 44 h, whereupon the mixture was cooled and precipitated with hexanes and filtered. Flash chromatography (CH$_2$Cl$_2$:ether) afforded 6.5 mg (10%) of Compound 209 as a white solid. $^1$H NMR (400 MHz, CDCl$_3$) 9.07 (broad s, 1H), 7.40 (s, 1H), 6.82 (s, 1H), 2.89 (t, J=6.7, 2H), 2.26 (s, 3H), 1.86 (t, J=6.7, 2H), 1.39 (s, 6H).

EXAMPLE 94

(±)-6,7-Dihydro-6-ethyl-4-methyl-8H-pyrano[3,2-g] quinolin-2(1H)-one (Compound 210, Structure 39 of Scheme VII, where R$_1$=R$_2$=R$_5$=H, R$_3$=ethyl, R$_4$=methyl)

1-Nitro-3-(pent-2-ynyloxy)benzene (Compound 211, Structure 36 of Scheme VII, where R$_1$=R$_2$=H, R$_3$=ethyl).

To a solution of 3-nitrophenol (7.5 g, 54 mmol) and K$_2$CO$_3$ (10.4 g, 75.6 mmol) in 27 mL DMF was added 2-pentynylmethanesulfonate (10.5 g, 65 mmol) and the mixture was stirred at rt for 18 h, whereupon the mixture was partitioned in ether:water (200 mL:200 mL). The aqueous layer was extracted with ether (2×100 mL) and the combined organic layers were washed sequentially with water (3×100 mL) and brine (50 mL), dried over MgSO$_4$, filtered and concentrated to afford 11.1 g (ca. 100%) of Compound 211 as a light brown oil. $^1$H NMR (400 MHz, CDCl$_3$) 7.80–7.90 (m, 2H), 7.40–7.50 (m, 1H), 7.27–7.35 (m, 1H), 4.76 (t, J=2.1, 2H), 2.18–2.28 (m, 2H), 1.13 (t, J=7.4, 3H).

1-Acetamido-3-(pent-2-ynyloxy)benzene (Compound 212, Structure 36a of Scheme VII, where R$_3$=ethyl, R$_1$=R$_2$=H).

A suspension of Compound 211 (15.1 g, 73.5 mmol), Zn dust (325 mesh, 19.2 g, 294 mmol) and calcium chloride dihydrate (21.6 g, 147 mmol) in 300 mL 95% ethanol/water was heated at reflux for 20 h, whereupon the reaction mixture was filtered while hot through Celite and rinsed with 300 mL hot ethanol. The filtrate was concentrated to brown paste, which was partitioned between EtOAc (200 mL), water (200 mL) and 0.1 M HCl (25 mL). The aqueous layer was extracted with EtOAc (2×100 mL) and the combined organic layers were washed sequentially with water (100 mL) and brine (100 mL), dried over MgSO$_4$, filtered and concentrated to 12.6 g of a brown oil. This material was dissolved in 28 mL pyridine, cooled to 0° C., then DMAP (433 mg, 3.54 mmol) and acetic anhydride (8.68 g, 85.1 mmol) was added. After 20 min, the mixture was allowed to warm to rt and the mixture was stirred for 6 h. The reaction was quenched by the addition of 1 mL MeOH and the reaction mixture was partitioned between EtOAc (200 mL) and water (200 mL). The aqueous layer was extracted with EtOAc (2×100 mL) and the combined organic layers were washed sequentially with 2N NaHSO$_4$ (3×100 mL), water (100 mL), NaHCO$_3$ (100 mL) and brine (100 mL), dried over MgSO$_4$, filtered and concentrated. Flash chromatography (EtOAc:hexanes 3:2) afforded 9.6 g (62%) of Compound 212. $^1$H NMR (400 MHz, CDCl$_3$) 7.42 (broad s, 1H), 7.24 (broad s, 1H), 7.20 (t, J=8.1, 1H), 7.06 (broad d, J=8.1, 1H), 6.73 (dd, J=8.1, 1.8, 1H), 4.64 (t, J=2.0, 2H), 2.18–2.28 (m, 2H), 2.16 (s, 3H), 1.25 (t, J=7.4, 3H).

7-Acetamido-4-ethyl-2H-chromane (Compound 213, Structure 38a of Scheme VII, where R$_3$=ethyl, R$_1$=R$_2$=H).

A solution of Compound 212 (1.52 g, 7.00 mmol) in 3.5 mL N,N-diethylaniline was heated at reflux for 30 h, whereupon the brown solution was partitioned between EtOAc (60 mL) and 1N NaHSO$_4$ (30 mL). The aqueous layer was extracted with EtOAc (2×30 mL) and the combined organic layers were washed sequentially with NaHSO$_4$ (2×15 mL) brine (30 mL), dried over MgSO$_4$, filtered and concentrated. Flash chromatography (EtOAc:hexanes 1:1) afforded 0.44 g (29%) of Compound 213 as a light amber oil. This was carried on directly by treatment with 10% Pd—C (21 mg, 5 wt %) in 4.7 mL EtOAc and 4.7 mL EtOH and was stirred in 1 atm H$_2$ for 6 h, whereupon the mixture was filtered through Celite and concentrated to an oil. Flash chromatography (EtOAc:hexanes 1:1) afforded 0.42 g (100%, or 29% for the two-steps) of Compound 213. $^1$H NMR (400 MHz, CDCl$_3$) δ 6.98–7.10 (m, 3H), 6.92 (s, 1H), 4.08–4.22 (m, 2H), 2.60–2.70 (m, 1H), 2.14 (s, 3H), 2.00–2.10 (m, 1H), 1.75–1.90 (m, 2H), 1.48–1.58 (m, 1H), 0.98 (t, J=7.4, 3H).

7-Amino-4-ethylchroman (Compound 214, Structure 38 of Scheme VII, where R$_1$=R$_2$=H, R$_3$=ethyl).

A solution of Compound 213 (0.42 g, 1.9 mmol) in 3.8 mL 2N HCl was heated at reflux for 16 h, whereupon the solution was partitioned between EtOAc (40 mL) and saturated NaHCO$_3$ (20 mL). The aqueous layer was extracted with EtOAc (2×20 mL) and the combined organic layers were washed with brine (20 mL), dried over MgSO$_4$, filtered and concentrated. Flash chromatography (EtOAc:hexanes 1:1) afforded 0.30 g (90%) of Compound 214. $^1$H NMR (400 MHz, CDCl$_3$) 6.91 (d, J=8.0, 1H), 6.24 (dd, J=8.0, 2.4, 1H), 6.14 (d, J=2.4, 1H), 4.05–4.19 (m, 2H), 3.52 (broad s, 2H), 2.55–2.65 (m, 1H), 1.95–2.05 (m, 1H), 1.70–1.85 (m, 2H), 1.42–1.52 (m, 1H), 0.97 (t, J=7.4, 3H).

(±)-6,7-Dihydro-6-ethyl-4-methyl-8H-pyrano[3,2-g]
quinolin-2(1H)-one (Compound 210, Structure 39 of
Scheme VII, where $R_1=R_2=R_5=H$, $R_3$=ethyl, $R_4$=methyl).

To a solution of Compound 214 (53 mg, 0.30 mmol) and triethylamine (60 mg, 0.60 mmol) in 3 mL $CH_2Cl_2$ was added diketene (50 mg, 0.60 mmol) at 0° C. The solution was allowed to warm to rt and after 2 h was concentrated to an oil. Flash chromatography (EtOAc:hexanes 3:2) afforded 46 mg (59%) of 7-acetoacetamido-4-ethylchroman, an oil. A portion of this material was carried on directly. A solution of 7-acetoacetamido-4-ethylchroman in 0.2 mL PPA (polyphosphoric acid) was heated at 100° C. for 4 h. The mixture was precipitated with water and neutralized with 6N NaOH. The mixture was extracted with EtOAc (3×20 mL) and the combined organic layers were washed with brine, dried over $MgSO_4$, filtered and concentrated. Flash chromatography (EtOAc:$CH_2Cl_2$ 7:3) afforded 5 mg of a solid. Final purification by HPLC (ODS semi-prep column, MeOH:water 7:3, 3 mL/min) afforded 3.4 mg (36%) of Compound 210 as a white solid. $^1$H NMR (400 MHz, $CDCl_3$) 10.5 (broad s, 1H), 7.39 (s, 1H), 6.68 (s, 1H), 6.35 (s, 1H), 4.17–4.30 (m, 2H), 2.72–2.82 (m, 1H), 2.43 (s, 3H), 2.02–2.12 (m, 1H), 1.80–1.92 (m, 2H), 1.55–1.65 (m, 1H), 1.03 (t, J=7.4, 3H).

EXAMPLE 95

(±)-7,8-Dihydro-8-ethyl-4-methyl-6H-pyrano[2,3-f]
quinolin-2(1H)-one (Compound 215, Structure 40
of Scheme VII, where $R_2=R_5=H$, $R_3$=ethyl,
$R_4$=methyl)

This compound was isolated as a by-product from the preparation of Compound 210 described in Example 94. $^1$H NMR (400 MHz, $CDCl_3$) 10.9 (s, 1H), 7.21 (d, J=8.4, 1H), 6.81 (d, J=8.4, 1H), 6.37 (s, 1H), 4.17–4.30 (m, 2H), 2.67–2.77 (m, 1H), 2.65 (d, J=0.9, 3H), 2.00–2.10 (m, 1H), 1.78–1.90 (m, 2H), 1.50–1.60 (m, 1H), 1.00 (t, J=7.3, 3H).

EXAMPLE 96

(±)-6,7-Dihydro-6-ethyl-4-trifluoromethyl-8H-
pyrano[3,2-g]quinolin-2(1H)-one (Compound 216,
Structure 39 of Scheme VII, where $R_1=R_2=R_5=H$,
$R_3$=ethyl, $R_4$=trifluoromethyl)

A solution of Compound 214 (Structure 38 of Scheme VII, where $R_1=R_2=H$, $R_3$=ethyl) (14 mg, 0.079 mmol) and ethyl 4,4,4-trifluoroacetoacetate (17 mg, 0.095 mmol) in 0.8 mL benzene was heated at reflux for 14 h. The solution was concentrated and purified by flash chromatography (hexanes:EtOAc 3:2) to afford 21 mg of an oil. This was treated with PPA and heated at 100° C. for 6 h. The dark brown sludge was partitioned between water (20 mL) and ethyl acetate (20 mL). The aqueous layer was extracted with EtOAc (2×20 mL) and the combined organic layers were washed with brine, dried over $MgSO_4$, filtered and concentrated. Flash chromatography ($CH_2Cl_2$:EtOAc 4:1) afforded 5.7 mg (29%) of a white solid. Final purification by HPLC (ODS semi-prep column, MeOH:water 7:3, 3 mL/min) afforded 3.4 mg (17%) of Compound 216 as a white solid. $^1$H NMR (400 MHz, $CDCl_3$) 11.2 (broad s 1H), 7.54 (s, 1H), 6.86 (s, 1H), 6.77 (s, 1H), 4.22–4.32 (m, 2H), 2.75–2.85 (m, 1H), 2.05–2.15 (m, 1H), 1.80–1.90 (m, 2H), 1.55–1.65 (m, 2H), 1.03 (t, J=7.3, 3H).

EXAMPLE 97

(−)-6,7-Dihydro-6-ethyl-4-trifluoromethyl-8H-
pyrano[3,2-g]quinolin-2(1H)-one (Compound 217,
Structure 39 of Scheme VII, where $R_1=R_2=R_5=H$,
$R_3$=ethyl, $R_4$=trifluoromethyl) and (+)-6,7-Dihydro-
6-ethyl-4-trifluoromethyl-8H-pyrano[3,2-g]quinolin-
2(1H)-one (Compound 218, Structure 39 of
Scheme VII, where $R_1=R_2=R_5=H$, $R_3$=ethyl,
$R_4$=trifluoromethyl)

Compound 216 was separated into its constitutive enantiomers via chiral HPLC on a semi-prep Chiralcel AD column (hexanes:isopropanol 97:3, 5.0 mL/min) to afford Compound 217 and Compound 218. Data for Compound 217: $t_R$ 46.5 min (hexanes:isopropanol 97:3). Data for Compound 218: $t_R$ 58.3 min (hexanes:isopropanol 97:3).

EXAMPLE 98

(±)-6,7-Dihydro-6-ethyl-3-fluoro-4-trifluoromethyl-
8H-pyrano[3,2-g]quinolin-2(1H)-one (Compound
219, Structure 39 of Scheme VII, where $R_1=R_2=H$,
$R_3$=ethyl, $R_4$=trifluoromethyl, $R_5$=F)

A solution of Compound 214 (Structure 38 of Scheme VII, where $R_1=R_2=H$, $R_3$=ethyl) (100 mg, 0.56 mmol) and ethyl 2,4,4,4-tetrafluoro-3,3-dihydroxybutanoate (185 mg, 0.84 mmol) was heated at 130° C. for 20 h. The mixture was passed through a plug of silica gel (EtOAc) and concentrated to a brown oil. This oil was treated with 1.5 mL PPA and heated at 100° C. for 6 h, then precipitated with cold water and neutralized with 6N NaOH. The mixture was extracted with EtOAc (3×25 mL) and the combined organic layers were washed with brine (25 mL), dried over $MgSO_4$, filtered and concentrated. Flash chromatography ($CH_2Cl_2$:EtOAc 4:1) afforded 70 mg (48%) of Compound 219 as a white solid. $^1$HNMR (400 MHz, $CDCl_3$) 11.8 (broad s, 1H), 7.58 (s, 1H), 6.84 (s, 1H), 4.22–4.32 (m, 2H), 2.78–2.88 (m, 1H), 2.05–2.15 (m, 1H), 1.80–1.95 (m, 2H), 1.55–1.68 (m, 1H), 1.03 (t, J=7.4, 3H).

EXAMPLE 99

(±)-6,7-Dihydro-6-ethyl-4-trifluoromethyl-1-methyl-
8H-pyrano[3,2-g]quinolin-2(1H)-one (Compound
220, Structure 41 of Scheme VII, where
$R_1=R_2=R_5=H$, $R_3$=ethyl, $R_4$=trifluoromethyl)

General Method: N-Methylation of a pyridone with sodium hydride and MeI. To a suspension of the pyridone (1 equiv) and NaH (60% mineral oil dispersion, 1.2–2.5 equiv) in THF (0.05 M) was added MeI (1.2–2.5 equiv). The mixture was stirred for 24 h and partitioned between $CH_2Cl_2$ and pH 7 phosphate buffer. The aqueous layer was extracted with $CH_2Cl_2$ and the combined organic layers were washed with brine, dried over $MgSO_4$, filtered and concentrated and purified as indicated.

This compound was prepared according to the General Method described above from Compound 216 (Structure 39 of Scheme VII, where $R_1=R_2=R_5=H$, $R_3$=ethyl, $R_4$=trifluoromethyl) (7.2 mg, 0.024 mmol), NaH (1.0 mg, 0.029) and MeI (2 μL, 0.029 mmol) in 51% yield (3.8 mg) after flash chromatography ($CH_2Cl_2$:MeOH 24:1). $^1$H NMR (400 MHz, $CDCl_3$) δ 7.58 (broad s, 1H), 6.90 (s, 1H), 6.81 (s, 1H), 4.24–4.36 (m, 2H), 3.65 (s, 3H), 2.75–2.85 (m, 1H), 2.07–2.17 (m, 1H), 1.80–1.95 (m, 2H), 1.58–1.68 (m, 1H), 1.04 (t, J=7.4, 3H).

EXAMPLE 100

(±)-6,7-Dihydro-6-ethyl-3-fluoro-4-trifluoromethyl-1-methyl-8H-pyrano[3,2-g]quinolin-2(1H)-one (Compound 221, Structure 41 of Scheme VII, where $R_1=R_2=H$, $R_3$=ethyl, $R_4$=trifluoromethyl, $R_5$=F)

This compound was prepared according to General Method in Example 99 from Compound 219 (Structure 39 of Scheme VII, where $R_1=R_2=H$, $R_3$=ethyl, $R_4$=trifluoromethyl, $R_5$=F) (11 mg, 0.034 mmol), NaH (3.0 mg, 0.085 mmol) and MeI (5.2 µL, 0.085 mmol) in 30% yield (3.4 mg) after purification by flash chromatography (CH$_2$Cl$_2$:MeOH 24:1). $^1$H NMR (400 MHz, CDCl$_3$) 7.61 (s, 1H), 6.80 (s, 1H), 4.22–4.36 (m, 2H), 3.70 (s, 3H), 2.77–2.87 (m, 1H), 2.05–2.15 (m, 1H), 1.80–1.95 (m, 2H), 1.55–1.65 (m, 1H), 1.03 (t, J=7.4, 3H).

EXAMPLE 101

(±)-6,7-Dihydro-6-ethyl-2,4-bis(trifluoromethyl)-8H-pyrano[3,2-g]quinoline (Compound 222, Structure 42 of Scheme VII, where $R_1=R_2=H$, $R_3$=ethyl)

To a solution of Compound 214 (Structure 38 of Scheme VII, where $R_1=R_2=H$, $R_3$=ethyl) (30 mg, 0.17 mmol) and 1,1,1,5,5,5-hexafluoropentan-2,4-dione in 0.8 mL toluene was heated at 60° C. for 18 h, whereupon p-toluensulfonic acid monohydrate (6.4 mg, 0.034 mmol) was added and the solution heated at 60° C. for 6 h. The mixture was concentrated to an oil and purified by flash chromatography (CH$_2$Cl$_2$:hexanes 1:1) to afford 29 mg (49%) of Compound 222 as a yellow oil. $^1$H NMR (400 MHz, CDCl$_3$) 7.94 (s, 1H), 7.79 (s, 1H), 7.65 (s, 1H), 4.32–4.44 (m, 2H), 2.98–3.08 (m, 1H), 2.14–2.24 (m, 1H), 1.88–2.04 (m, 2H), 1.68–1.86 (m, 1H), 1.08 (t, J=7.4, 3H).

EXAMPLE 102

6,8,8-Trimethyl-4-trifluoromethyl-8H-pyrano[3,2-g] coumarin (Compound 223, Structure 47 of Scheme VIII, where R=methyl)

2,2-Dimethyl-7-hydroxy-4-chromanone (Compound 224, Structure 44 of Scheme VIII).

1,3-Resorcinol (Structure 43 of Scheme VIII) (1 g, 9.1 mmol) and 3,3-dimethylacrylic acid (909 mg, 9.1 mmol) were dissolved in trifluoroacetic acid (10 mL) and stirred at 80° C. for 2 h. The reaction was made basic with 20% KOH to pH 7. The mixture was partitioned between EtOAc (50 mL) and water (50 mL). The aqueous was extracted with EtOAc (2×50 mL). The combined organic layers were washed sequentially with water (50 mL) and brine (50 mL), dried over Na$_2$SO$_4$, filtered and concentrated. Flash chromatography (25% EtOAc/hexanes) afforded 1.5 g (87%) of Compound 224. $^1$H NMR (400 MHz, acetone-d$_6$) 9.26 (bs, 1H), 7.66 (d, J=8.7, 1H), 6.51 (dd, J=8.7, 2.1, 1H), 6.33 (d, J=2.1, 1H), 2.64 (s, 2H), 1.42 (s, 6H).

2,2,4-Trimethyl-4,7-dihydroxychroman (Compound 225, Structure 45 of Scheme VIII, where R=methyl).

Compound 224 (250 mg, 1.3 mmol) was dissolved in diethyl ether and cooled to 0° C. Methyl magnesium bromide (3.0M, 2.6 mL, 7.8 mmol) was added slowly via syringe. The reaction was allowed to warm to room temperature. After 2 h the reaction was quenched with water and partitioned between EtOAc (25 mL) and water (25 mL). The aqueous was extracted with EtOAc (2×25 mL). The combined organic layers were washed sequentially with water (25 mL) and brine (25 mL), dried over Na$_2$SO$_4$, filtered and concentrated. Flash chromatography (30% EtOAc/hexanes) afforded 220 mg (81%) of Compound 225. $^1$H NMR (400 MHz, acetone-d$_6$) 8.16 (s, 1H), 7.32 (d, J=8.5, 1H), 6.4 (dd, J=8.5, 2.5, 1H), 6.2 (d, J=2.5, 1H), 3.7 (s, 1H), 2.03(s, 2H), 1.5 (s, 3H), 1.36 (s, 3H), 1.33 (s, 3H).

2,2,4-Trimethyl-7-hydroxy-2H-chromene (Compound 226, Structure 46 of Scheme VIII, where R=methyl).

2,2,4-trimethyl-4,7-dihydroxychroman (225) (220 mg, 1.06 mmol), was dissolved in CH$_2$Cl$_2$ (5 mL) and treated with p-toluene sulfonic acid monohydrate (25 mg, 0.13 mmol). The resulting solution was stirred at rt for 2 h. The reaction was quenched with NaHCO$_3$ (sat.) to pH 7 and the mixture was partitioned between EtOAc (25 mL) and water (25 mL). The aqueous was extracted with EtOAc (2×25 mL). The combined organic layers were washed sequentially with water (25 mL) and brine (25 mL), dried over Na$_2$SO$_4$, filtered and concentrated. Flash chromatography (15% EtOAc/hexanes) afforded 135 mg (67%) of Compound 226. $^1$H NMR (400 MHz, acetone-d$_6$) 8.37 (s, 1H), 7.0 (dd, J=8.4, 2.4, 1H), 6.26 (d, J=2.4, 1H), 5.32 (s, 1H), 1.94 (s, 3H), 1.33 (s, 6H).

6,8,8-Trimethyl-4-trifluoromethyl-8H-pyrano[3,2-g]coumarin (Compound 223, Structure 47 of Scheme VIII, where R=methyl).

Compound 226 (60 mg, 0.31 mmol) and ethyl-4,4,4-trifluoroacetoacetate (116 mg, 0.63 mmol) were dissolved in toluene and treated with POCl$_3$ (97 mg, 0.63 mmol) and stirred at 100° C. for 8 h. The reaction was allowed to cool down to rt. The reaction was quenched slowly with dropwise addition of water and partitioned between EtOAc (25 mL) and water (25 mL). The aqueous was extracted with EtOAc (3×25 mL). The combined organic layers were washed sequentially with water (25 mL) and brine (25 mL), dried over Na$_2$SO$_4$, filtered and concentrated. Flash chromatography (5% EtOAc/hexanes) afforded 40 mg (41%) of Compound 223. $^1$H NMR (400 MHz, acetone-d$_6$) 7.43 (s, 1H), 6.8 (s, 1H), 6.7 (s, 1H), 5.75 (s, 1H), 2.08 (s, 3H), 1.46 (s, 6H).

EXAMPLE 103

6-Ethyl-8,8-dimethyl-4-trifluoromethyl-8H-pyrano [3,2-g]coumarin (Compound 227, Structure 47 of Scheme VIII, where R=ethyl)

4-Ethyl-2,2-dimethyl-7-hydroxy-2H-chromene (Compound 228, Structure 46 of Scheme VIII, where R=ethyl).

Compound 224 (200 mg, 1.04 mmol) was dissolved in diethyl ether and cooled to 0° C. Ethyl magnesium bromide (3.0M, 1.7 mL, 5.2 mmol) was added slowly via syringe. The reaction was allowed to warm to room temperature. After 2 h the reaction was quenched with water and partitioned between EtOAc (25 mL) and water (25 mL). The aqueous was extracted with EtOAc (2×25 mL). The combined organic layers were washed sequentially with water (25 mL) and brine (25 mL), dried over Na$_2$SO$_4$, filtered and concentrated. The crude material was dissolved in CH$_2$Cl$_2$ (5 mL) and treated with p-toluene sulfonic acid monohydrate (25 mg, 0.13 mmol). The resulting solution was stirred at rt for 2 h. The reaction was quenched with NaHCO$_3$ (sat) to pH 7 and the mixture was partitioned between EtOAc (25 mL) and water (25 mL). The aqueous was extracted with EtOAc (2×25 mL). The combined organic layers were washed sequentially with water (25 mL) and brine (25 mL), dried over $Na_2SO_4$, filtered and concentrated. Flash chromatography (15% EtOAc/hexanes) afforded 220 mg (81%) of Compound 228. $^1$H NMR (400 MHz, acetone-$d_6$) 8.4 (bs, 1H), 7.15 (d, J=8.5, 1H), 6.38 (dd, J=8.5, 2.5, 1H), 6.28 (d, J=2.5, 1H), 5.3 (s, 1H), 2.34 (q, J=7.4, 2H), 1.11 (t, J=7.4, 3H).

6-Ethyl-8,8-dimethyl-4-trifluoromethyl-8H-pyrano[3,2-g]coumarin (Compound 227, Structure 47 of Scheme VIII, where R=ethyl).

Compound 228 (60 mg, 0.29 mmol) and ethyl-4,4,4-trifluoroacetoacetate (107 mg, 0.58 mmol) were dissolved in toluene and treated with $POCl_3$ (90 mg, 0.58 mmol) and stirred at 100° C. for 8 h. The reaction was allowed to cool down to rt. The reaction was quenched slowly with dropwise addition of water and partitioned between EtOAc (25 mL) and water (25 mL). The aqueous was extracted with EtOAc (3×25 mL). The combined organic layers were washed sequentially with water (25 mL) and brine (25 mL), dried over $Na_2SO_4$, filtered and concentrated. Flash chromatography (5% EtOAc/hexanes) afforded 29 mg (31%) of Compound 227. $^1$H NMR (400 MHz, acetone-$d_6$) 7.48 (s, 1H), 6.81 (s, 1H), 6.69 (s, 1H), 5.74 (s, 1H), 2.48 (q, J=7.4, 2H), 1.47 (s, 6H), 1.18 (t, J=7.5, 3H).

EXAMPLE 104

(±)-5,6-Dihydro-6-hydroxymethyl-4-trifluoromethylpyrrolo[3,2-f]quinolin-2(1H)-one (Compound 228, Structure 33a of Scheme VI, where $R_1$=hydroxymethyl, n=0)

Compound 228 was prepared according to a similar procedure described in Example 81: $^1$H NMR (500 MHz, acetone-$d_6$) 11.02 (bs, 1H), 7.39 (d, J=8.8, 1H), 7.10 (d, J=8.8, 1H), 7.01 (s, 1H), 3.94 (m, 2H), 3.86 (m, 1H), 3.55 (m, 1H), 1.42 (d, J=6.1, 2H).

EXAMPLE 105

(±)-5,6-Dihydro-7-ethyl-6-hydroxymethyl-4-trifluoromethylpyrrolo[3,2-f]quinolin-2(1H)-one (Compound 229, Structure 34a of Scheme VI, where $R_1$=hydroxymethyl, $R_2$=ethyl, n=0)

Compound 229 was prepared by ethylation of Compound 228: $^1$H NMR (500 MHz, $CDCl_3$) 11.71 (bs, 1H), 7.21 (d, J=8.5, 1H), 7.15 (s, 1H), 6.80 (d, J=8.5, 1H), 3.74 (m, 1H), 3.48 (m, 1H), 3.32 (m, 1H), 3.19 (m, 1H), 2.78 (m, 1H), 1.34 (d, J=5.9, 2H), 1.11 (t, J=6.5, 3H).

EXAMPLE 106

7,8-Dihydro-6-(2,2,2-trifluoroethyl)-4-trifluoromethylpyrrolo[2,3-g]quinolin-2(1H)-one (Compound 230, Structure 34 of Scheme VI, where $R_1$=H, $R_2$=2,2,2-trifluoroethyl, n=0)

Compound 230 was prepared according to a similar procedure described in Example 81: $^1$H NMR (500 MHz, acetone-$d_6$) 11.10 (bs, 1H), 7.32 (s, 1H), 6.82 (s, 1H), 6.80 (s, 1H), 4.13 (q, J=10.0, 2H), 3.73 (t, J=8.5, 2H), 3.22 (t, J=8.5, 1H).

EXAMPLE 107

6-(2,2,2-Trifluoroethyl)-4-trifluoromethylpyrrolo[2,3-g]quinolin-2(1H)-one (Compound 231, Structure 34b of Scheme VI, where $R_1$=$R_3$=H, $R_2$=2,2,2-trifluoroethyl)

Compound 231 was prepared by oxidation of Compound 230: $^1$H NMR (500 MHz, acetone-$d_6$) 10.93 (bs, 1H), 7.98 (s, 1H), 7.73 (s, 1H), 7.69 (d, J=3.5, 1H), 6.87 (s, 1H), 6.71 (dd, J=3.5 and 1.0, 1H), 5.31 (q, J=9.0, 2H).

EXAMPLE 108

8-Chloro-6-(2,2,2-trifluoroethyl)-4-trifluoromethylpyrrolo[2,3-g]quinolin-2(1H)-one (Compound 232, Structure 34b of Scheme VI, where $R_1$=H, $R_3$=Cl, $R_2$=2,2,2-trifluoroethyl)

Compound 232 was prepared by chloronation of Compound 232: $^1$H NMR (500 MHz, acetone-$d_6$) 11.04 (bs, 1H), 8.06 (s, 1H), 7.85 (s, 1H), 7.70 (s, 1H), 6.95 (s, 1H), 5.36 (q, J=9.0, 2H).

EXAMPLE 109

5-Methyl-7-(2,2,2-trifluoroethyl)-4-trifluoromethylpyrrolo[3,2-f]quinolin-2(1H)-one (Compound 233, Structure 19 of Scheme III, where $R_4$=H, $R_3$=methyl, $R_5$=2,2,2-trifluoroethyl)

This compound was isolated as an over oxidation product of Compound 150 (Structure 18 of Scheme III, where $R_1$=$R_2$=methyl) by the general oxidation procedure described in Example 49: $^1$H NMR (500 MHz, DMSO-$d_6$) 12.2 (bs, 1H), 7.95 (d, J=8.8, 1H), 7.27 (d, J=8.8, 1H), 6.99 (s, 1H), 6.66 (s, 1H), 5.27 (q, $J_{H-F}$=8.8, 2H), 2.53 (s, 3H).

EXAMPLE 110

6-Formyl-5-methyl-7-(2,2,2-trifluoroethyl)-4-trifluoromethyl-7H-pyrrolo[3,2-f]quinolin-2(1H)-one (Compound 234, Structure 19 of Scheme III, where $R_4$=formyl, $R_3$=methyl, $R_5$=2,2,2-trifluoroethyl)

This compound was prepared by the general oxidation procedure described in Example 49 from Compound 150 (Structure 18 of Scheme III, where $R_1$=$R_2$=methyl). $^1$H NMR (500 MHz, DMSO-$d_6$) 11.9 (bs, 1H), 10.18 (s, 1H), 8.06 (d, J=8.8, 1H), 7.52 (d, J=8.8, 1H), 7.07 (s, 1H), 5.65 (q, $J_{H-F}$=8.8, 2H), 2.62 (s, 3H).

EXAMPLE 111

5,6-Dimethyl-7-(2,2-difluorovinyl)-4-trifluoromethyl-7H-pyrrolo[3,2-f]quinolin-2(1H)-one (Compound 235, Structure 19 of Scheme III, where $R_4$=$R_3$=methyl, $R_5$=2,2-difluorovinyl)

This compound was isolated as an over oxidation product of Compound 150 (Structure 18 of Scheme III, where $R_1$=$R_2$=methyl) by the general oxidation procedure described in Example 49: $^1$H NMR (500 MHz, DMSO-$d_6$) 12.4 (bs, 1H), 7.76 (d, J=8.8, 1H), 7.65 (d, J=8.8, 1H), 7.16 (s, 1H), 5.05–5.00 (m, 1H), 2.45 (d, J=0.9, 3H), 1.96 (s, 3H).

EXAMPLE 112

Steroid Receptor Activity

Utilizing the "cis-trans" or "co-transfection" assay described by Evans et al., *Science,* 240:889–95 (May 13, 1988), the disclosure of which is incorporated by reference herein, the compounds of the present invention were tested and found to have strong, specific activity as agonists, partial agonists and antagonists of AR. This assay is described in further detail in U.S. Pat. Nos. 4,981,784 and 5,071,773, the disclosures of which are incorporated herein by reference.

The co-transfection assay provides a method for identifying functional agonists and partial agonists which mimic, or antagonists which inhibit, the effect of native hormones and quantifying their activity for responsive IR proteins. In this regard, the co-transfection assay mimics an in vivo system in the laboratory. Importantly, activity in the co-transfection assay correlates very well with known in vivo activity, such that the co-transfection assay functions as a qualitative and quantitative predictor of a tested compounds in vivo pharmacology. See, e.g., T. Berger et al. 41 *J. Steroid Biochem. Molec. Biol.* 773 (1992), the disclosure of which is herein incorporated by reference.

In the co-transfection assay, a cloned cDNA for an IR (e.g., human PR, AR or GR) under the control of a constitutive promoter (e.g., the SV 40 promoter) is introduced by transfection (a procedure to induce cells to take up foreign genes) into a background cell substantially devoid of endogenous IRs. This introduced gene directs the recipient cells to make the IR protein of interest. A second gene is also introduced (co-transfected) into the same cells in conjunction with the IR gene. This second gene, comprising the cDNA for a reporter protein, such as firefly luciferase (LUC), controlled by an appropriate hormone responsive promoter containing a hormone response element (HRE). This reporter plasmid functions as a reporter for the transcription-modulating activity of the target IR. Thus, the reporter acts as a surrogate for the products (mRNA then protein) normally expressed by a gene under control of the target receptor and its native hormone.

The co-transfection assay can detect small molecule agonists or antagonists of target IRs. Exposing the transfected cells to an agonist ligand compound increases reporter activity in the transfected cells. This activity can be conveniently measured, e.g., by increasing luciferase production, which reflects compound-dependent, IR-mediated increases in reporter transcription. A partial agonist's activity can be detected in a manner similar to that of the full agonist, except that the maximum measured activity, e.g., luciferase production, is less than that of an agonist standard. For example, for AR, a partial agonist can be detected by measuring increased luciferase production, but the maximum effect at high concentration is less than the maximum effect for dihydrotestosterone. To detect antagonists, the co-transfection assay is carried out in the presence of a constant concentration of an agonist to the target IR (e.g., progesterone for PR) known to induce a defined reporter signal. Increasing concentrations of a suspected antagonist will decrease the reporter signal (e.g., luciferase production). The co-transfection assay is therefore useful to detect both agonists and antagonists of specific IRs. Furthermore, it determines not only whether a compound interacts with a particular IR, but whether this interaction mimics (agonizes) or blocks (antagonizes) the effects of the native regulatory molecules on target gene expression, as well as the specificity and strength of this interaction.

The activity of selected steroid receptor modulator compounds of the present invention were evaluated utilizing the co-transfection assay and in standard IR binding assays, according to the following illustrative Examples.

Co-Transfection Assay

CV-1 cells (African green monkey kidney fibroblasts) were cultured in the presence of Dulbecco's Modified Eagle Medium (DMEM) supplemented with 10% charcoal resin-stripped fetal bovine serum then transferred to 96-well microtiter plates one day prior to transfection.

To determine AR agonist and antagonist activity of the compounds of the present invention, the CV-1 cells were transiently transfected by calcium phosphate coprecipitation according to the procedure of Berger et al., 41 *J. Steroid Biochem. Mol. Biol.,* 733 (1992) with the following plasmids: pShAR (5 ng/well), MTV-LUC reporter (100 ng/well), pRS-β-Gal (50 ng/well) and filler DNA (PGEM; 45 ng/well). The receptor plasmid, pRShAR, contains the human AR under constitutive control of the SV-40 promoter, as more fully described in J. A. Simental et al., "Transcriptional activation and nuclear targeting signals of the human androgen receptor", 266 *J. Biol. Chem.,* 510 (1991).

The reporter plasmid, MTV-LUC, contains the cDNA for firefly luciferase (LUC) under control of the mouse mammary tumor virus (MTV) long terminal repeat, a conditional promoter containing an androgen response element. See e.g., Berger et al. supra. In addition, pRS-β-Gal, coding for constitutive expression of *E. coli* β-galactosidase (β-Gal), was included as an internal control for evaluation of transfection efficiency and compound toxicity.

Six hours after transfection, media was removed and the cells were washed with phosphate-buffered saline (PBS). Media containing reference compounds (i.e. progesterone as a PR agonist, mifepristone ((11β, 17β)-11-[4-(dimethylamino)phenyl]-17-hydroxy-17-(1-propynyl)estra-4,9-dien-3-one: RU486; Roussel Uclaf) as a PR antagonist; dihydrotestosterone (DHT; Sigma Chemical) as an AR agonist and 2-OH-flutamide (the active metabolite of 2-methyl-N-[4-nitro-3-(trifluoromethyl)phenyl]pronanamide; Schering-Plough) as an AR antagonist; estradiol (Sigma) as an ER agonist and ICI 164,384 (N-butyl-3,17-dihydroxy-N-methyl-(7-α,17-β)-estra-1,3,5(10)-triene-7-undecanamide; ICI Americas) as an ER antagonist; dexamethasone (Sigma) as a GR agonist and RU486 as a GR antagonist; and aldosterone (Sigma) as a MR agonist and spironolactone ((7-α-[acetylthio]-17-α-hydroxy-3-oxopregn-4-ene-21-carboxylic acid δ-lactone; Sigma) as an MR antagonist) and/or the modulator compounds of the present invention in concentrations ranging from $10^{-12}$ to $10^{-5}$ M were added to the cells. Three to four replicates were used for each sample. Transfections and subsequent procedures were performed on a Biomek 1000 automated laboratory work station.

After 40 hours, the cells were washed with PBS, lysed with a Triton X-100-based buffer and assayed for LUC and β-Gal activities using a luminometer or spectrophotometer, respectively. For each replicate, the normalized response (NR) was calculated as:

LUC response/β-Gal rate where β-Gal rate=β-Gal·1×$10^{-5}$/β-Gal incubation time.

The mean and standard error of the mean (SEM) of the NR were calculated. Data was plotted as the response of the compound compared to the reference compounds over the range of the dose-response curve. For agonist experiments, the effective concentration that produced 50% of the maximum response ($EC_{50}$) was quantified. Agonist efficacy was a function (%) of LUC expression relative to the maximum LUC production by the reference agonist for PR, AR, ER, GR or MR. Antagonist activity was determined by testing the amount of LUC expression in the presence of a fixed amount of DHT as an AR agonist and progesterone as a PR agonist at the $EC_{50}$ concentration. The concentration of test compound that inhibited 50% of LUC expression induced by the reference agonist was quantified ($IC_{50}$). In addition, the efficacy of antagonists was determined as a function (%) of maximal inhibition.

IR Binding Assay

AR Binding: For the whole cell binding assay, COS-1 cells in 96-well microtiter plates containing DMEM-10% FBS were transfected as described above with the following plasmid DNA: pRShAR (2 ng/well), pRS-β-Gal (50 ng/well) and pGEM (48 ng/well). Six hours after transfection, media was removed, the cells were washed with PBS and fresh media was added. The next day, the media was changed to DMEM-serum free to remove any endogenous ligand that might be complexed with the receptor in the cells.

After 24 hours in serum-free media, either a saturation analysis to determine the $K_d$ for tritiated dihydrotestosterone ($^3$H-DHT) on human AR or a competitive binding assay to evaluate the ability of test compounds to compete with $^3$H-DHT for AR was performed. For the saturation analysis, media (DMEM-0.2% CA-FBS) containing $^3$H-DHT (in concentrations ranging from 12 nM to 0.24 nM) in the absence (total binding) or presence (non-specific binding) of a 100-fold molar excess of unlabeled DHT were added to the cells. For the competitive binding assay, media containing 1 nM $^3$H-DHT and test compounds in concentrations ranging from $10^{-10}$ to $10^{-6}$ M were added to the cells. Three replicates were used for each sample. After three hours at 37° C., an aliquot of the total binding media at each concentration of $^3$H-DHT was removed to estimate the amount of free $^3$H-DHT. The remaining media was removed, the cells were washed three times with PBS to remove unbound ligand and cells were lysed with a Triton X-100-based buffer. The lysates were assayed for amount of bound $^3$H-DHT and β-Gal activity using a scintillation counter or spectrophotometer, respectively.

For the saturation analyses, the difference between the total binding and the nonspecific binding, normalized by the β-Gal rate, was defined as specific binding. The specific binding was evaluated by Scatchard analysis to determine the $K_d$ for $^3$H-DHT. See e.g., D. Rodbard, "Mathematics and statistics of ligand assays: an illustrated guide" In: J. Langon and J. J. Clapp, eds., *Ligand Assay*, Masson Publishing U.S.A., Inc., New York, pp. 45–99, (1981), the disclosure of which is herein incorporated by reference. For the competition studies, the data was plotted as the amount of $^3$H-DHT (% of control in the absence of test compound) remaining over the range of the dose-response curve for a given compound. The concentration of test compound that inhibited 50% of the amount of $^3$H-DHT bound in the absence of competing ligand was quantified ($IC_{50}$) after log-logit transformation. The $K_i$ values were determined by application of the Cheng-Prusoff equation to the $IC_{50}$ values, where:

$$K_i = \frac{IC_{50}}{(1+[^3\text{H-DHT}])/K_d \text{ for } ^3\text{H-DHT}}$$

After correcting for non-specific binding, $IC_{50}$ values were determined. The $IC_{50}$ value is defined as the concentration of competing ligand needed to reduce specific binding by 50%. The $IC_{50}$ value was determined graphically from a log-logit plot of the data. The $K_i$ values were determined by application of the Cheng-Prusoff equation to the $IC_{50}$ values, the labeled ligand concentration and the $K_d$ of the labeled ligand.

The antagonist and binding activity assay results of selected androgen receptor modulator compounds of present invention and the standard reference compounds on AR, as well as the cross-reactivity of selected compounds on the PR, ER, MR and GR receptors shown in Tables 1–2 below. Efficacy is reported as the percent maximal response observed for each compound relative to the reference agonist and antagonist compounds indicated above. Also reported in Tables 1–2 for each compound is its antagonist potency or $IC_{50}$ (which is the concentration (nM), required to reduce the maximal response by 50%), its agonist potency or $EC_{50}$ (nM).

TABLE 1

Cotransfection and competitive binding data of selected androgen receptor modulator compounds of present invention and the reference agonist compound, dihydrotestosterone (DHT) and reference antagonists compound, 2-hydroxyflutamide (Flut) and Casodex (Cas), on AR.

| Cmpd No. | AR Agonist CV-1 Cells | | AR Antagonist CV-1 Cells | | AR Binding |
|---|---|---|---|---|---|
| | Efficacy (%) | Potency (nM) | Efficacy (%) | Potency (nM) | $K_i$ (nM) |
| 104 | 78 | 183 | 50 | 1.8 | 15 |
| 105 | 57 | 32 | na | na | 45 |
| 106 | 108 | 12 | na | na | 45 |
| 108 | 66 | 24 | na | na | 6.7 |
| 109 | 97 | 13 | na | na | 1.2 |
| 110 | 106 | 21 | na | na | 21 |
| 112 | na | na | 75 | 10 | 119 |
| 113 | na | na | 65 | 316 | 529 |
| 114 | na | na | 81 | 6.6 | 81 |
| 119 | 94 | 2.5 | na | na | 2.6 |
| 120 | 117 | 4.5 | na | na | 12 |
| 121 | 97 | 43 | na | na | 7.6 |
| 122 | 59 | 34 | na | na | 21 |
| 123 | 104 | 1.4 | na | na | 14 |
| 125 | 121 | 38 | na | na | 1.3 |
| 126 | 53 | 11 | na | na | 2.3 |
| 127 | 66 | 25 | na | na | 6.3 |
| 129 | 79 | 1.6 | na | na | 3.2 |
| 132 | 70 | 4.8 | na | na | 21 |
| 134 | 70 | 4.2 | na | na | 6.8 |
| 137 | 77 | 145 | na | na | 107 |
| 141 | 46 | 86 | 44 | 34 | 97 |
| 144 | na | na | 53 | 23 | 1000 |
| 146 | 38 | 49 | 66 | 1 | 75 |
| 149 | na | na | 81 | 25 | 127 |
| 150 | 95 | 2.1 | na | na | 4.0 |
| 151 | 36 | 120 | 57 | 5.9 | 48 |
| 152 | 74 | 4.9 | na | na | 67 |
| 153 | 76 | 7.6 | na | na | 1.7 |
| 155 | 59 | 9.4 | na | na | 7.4 |
| 158 | 59 | 7.9 | na | na | 7.1 |
| 159 | na | na | 66 | 15 | 989 |
| 161 | 27 | 238 | 66 | 10 | 30 |
| 162 | 71 | 20 | na | na | 113 |
| 163 | na | na | 37 | 8.2 | 1000 |
| 166 | 96 | 24 | na | na | 17 |
| 172 | 89 | 19 | na | na | 12 |
| 173 | 41 | 138 | 56 | 1 | 80 |
| 175 | na | na | 78 | 11 | 239 |
| 177 | na | na | 98 | 790 | 31 |
| 178 | 24 | 21 | 48 | 50 | 900 |
| 179 | 91 | 1.3 | na | na | 4.1 |

TABLE 1-continued

Cotransfection and competitive binding data of selected androgen receptor modulator compounds of present invention and the reference agonist compound, dihydrotestosterone (DHT) and reference antagonists compound, 2-hydroxyflutamide (Flut) and Casodex (Cas), on AR.

| Cmpd No. | AR Agonist CV-1 Cells | | AR Antagonist CV-1 Cells | | AR Binding |
|---|---|---|---|---|---|
| | Efficacy (%) | Potency (nM) | Efficacy (%) | Potency (nM) | $K_i$ (nM) |
| 182 | na | an | 81 | 13 | 1000 |
| 195 | 78 | 11 | na | na | 20 |
| 197 | 66 | 12 | na | na | 79 |
| 198 | 47 | 1.7 | na | na | 58 |
| 199 | 70 | 42 | na | na | 236 |
| 201 | 76 | 11 | na | na | 10 |
| 202 | na | na | 92 | 146 | 1000 |
| 206 | na | na | 90 | 175 | 1000 |
| 215 | 28 | 2070 | 77 | 17 | 47 |
| 216 | 55 | 11 | 28 | 4300 | 8.1 |
| 217 | na | na | 85 | 64 | 1000 |
| 218 | 82 | 10 | na | na | 4.1 |
| 220 | na | na | 67 | 23 | 1000 |
| 221 | na | na | 78 | 311 | 29 |
| 223 | na | na | 66 | 41 | 37 |
| 227 | na | na | 75 | 25 | 33 |
| HO-Flut | na | na | 83 | 25 | 34 |
| Casodex | na | na | 81 | 201 | 117 |
| DHT | 100 | 4.3 | na | na | 1.7 | na = not active (i.e. efficacy of <20 and potency of >10,000);
nd = not determined.

Pharmacological and other Applications

As will be discernible to those skilled in the art, the androgen or progesterone receptor modulator compounds of the present invention can be readily utilized in pharmacological applications where AR or PR antagonist or agonist activity is desired and where it is desired to minimize reactivities with other steroid receptor related IRs. In vivo applications of the invention include administration of the disclosed compounds to mammalian subjects and in particular to humans.

The following Example provides illustrative pharmaceutical composition formulations:

EXAMPLE 113

Hard gelatin capsules are prepared using the following ingredients:

| | Quantity (mg/capsule) |
|---|---|
| COMPOUND 153 | 140 |
| Starch, dried | 100 |
| Magnesium stearate | 10 |
| Total | 250 mg |

The above ingredients are mixed and filled into hard gelatin capsules in 250 mg quantities.

A tablet is prepared using the ingredients below:

| | Quantity (mg/tablet) |
|---|---|
| COMPOUND 153 | 140 |
| Cellulose, microcrystalline | 200 |
| Silicon dioxide, fumed | 10 |
| Stearic acid | 10 |
| Total | 360 mg |

The components are blended and compressed to form tablets each weighing 360 mg.

Tablets, each containing 60 mg of active ingredient, are made as follows:

| | Quantity (mg/tablet) |
|---|---|
| COMPOUND 153 | 60 |
| Starch | 45 |
| Cellulose, microcrystalline | 35 |
| Polyvinylpyrrolidone (PVP) (as 10% solution in water) | 4 |
| Sodium carboxymethyl starch (SCMS) | 4.5 |
| Magnesium stearate | 0.5 |
| Talc | 1.0 |
| Total | 150 mg |

The active ingredient, starch and cellulose are passed through a No. 45 mesh U.S. sieve and mixed thoroughly. The solution of PVP is mixed with the resultant powders, which are then passed through a No. 14 mesh U.S. sieve. The granules so produced are dried at 50° C. and passed through a No. 18 mesh U.S. sieve. The SCMS, magnesium stearate and talc, previously passed through a No. 60 mesh U.S. sieve and then added to the granules which, after mixing, are compressed on a tablet machine to yield tablets each weighing 150 mg.

Suppositories, each containing 225 mg of active ingredient, may be made as follows:

| | Quantity (mg/suppository) |
|---|---|
| COMPOUND 153 | 225 |
| Saturated fatty acid glycerides | 2,000 |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of normal 2 g capacity and allowed to cool.

An intravenous formulation may be prepared as follows:

| | Quantity |
|---|---|
| COMPOUND 153 | 100 mg |
| isotonic saline | 1000 mL |
| glycerol | 100 mL |

The compound is dissolved in the glycerol and then the solution is slowly diluted with isotonic saline. The solution of the above ingredients is then administered intravenously at a rate of 1 mL per minute to a patient.

The present invention includes any combination of the various species and subgeneric groupings falling within the generic disclosure. This invention therefore includes the generic description of the invention with a proviso or negative limitation removing any subject matter from the genus, regardless of whether or not the excised material is specifically recited herein.

While in accordance with the patent statutes, description of the various embodiments and processing conditions have been provided, the scope of the invention is not to be limited thereto or thereby. Modifications and alterations of the present invention will be apparent to those skilled in the art without departing from the scope and spirit of the present invention.

Therefore, it will be appreciated that the scope of this invention is to be defined by the appended claims, rather than by the specific examples which have been presented by way of example.

What is claimed is:

1. A compound of the formula:

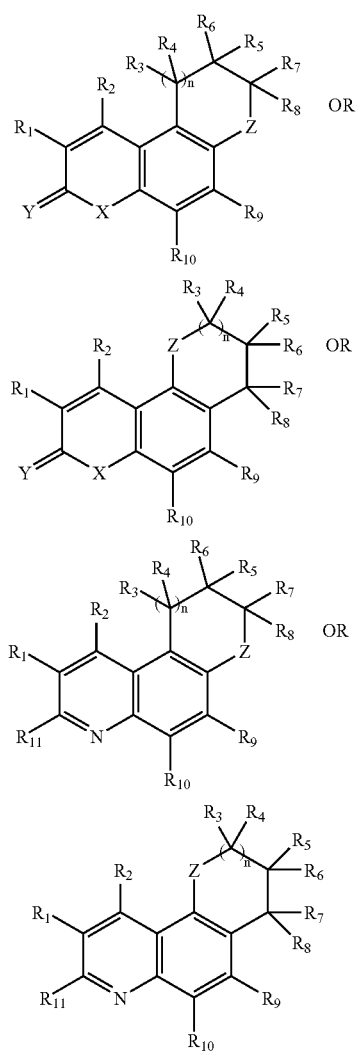

wherein:
$R^1$ is selected from among hydrogen, F, Cl, Br, I, $NO_2$, $OR^{12}$, $SR^{12}$, $SOR^{12}$, $SO_2R^{12}$, $NR^{12}R^{12}$, $C_1$–$C_8$ alkyl, $C_1$–$C_8$ haloalkyl and $C_1$–$C_8$ heteroalkyl, wherein the haloalkyl and heteroalkyl groups are optionally substituted;

$R^2$ is selected from among hydrogen, F, Cl, Br, I, $CF_3$, $CHF_2$, $CH_2F$, $CF_2Cl$, CN, $CF_2OR^{12}$, $CH_2OR$, $OR^{12}$, $SR^{12}$, $SOR^{12}$, $SO_2R^{12}$, $NR^{12}R^{13}$, substituted $C_1$–$C_8$ alkyl, $C_1$–$C_8$ haloalkyl, $C_1$–$C_8$ heteroalkyl, $C_2$–$C_8$ alkenyl and $C_2$–$C_8$ alkynyl, wherein the alkyl, haloalkyl, heteroalkyl, alkenyl and alkynyl groups are optionally substituted;

$R^3$ is selected from among hydrogen, $C_1$–$C_6$ alkyl, $C_1$–$C_6$ haloalkyl and $C_1$–$C_6$ heteroalkyl, wherein the alkyl, haloalkyl and heteroalkyl groups are optionally substituted;

$R^4$ is selected from among hydrogen, F, Cl, Br, I, $OR^{12}$, $NR^{12}R^{13}$, $SR^{12}$, $SOR^{12}$, $SO_2R^{12}$, $C_1$–$C_8$ alkyl, $C_1$–$C_8$ haloalkyl, $C_1$–$C_8$ heteroalkyl, $C_2$–$C_8$ alkynyl, $C_2$–$C_8$ alkenyl, aryl, heteroaryl and arylalkyl, wherein the alkyl, haloalkyl, heteroalkyl, alkynyl, alkenyl, aryl, heteroaryl and arylalkyl groups are optionally substituted;

$R^5$ is selected from among hydrogen, $C_1$–$C_6$ alkyl, $C_1$–$C_6$ haloalkyl and $C_1$–$C_6$ heteroalkyl, wherein the alkyl, haloalkyl and heteroalkyl groups are optionally substituted;

$R^6$ is selected from among hydrogen, F, Cl, Br, I, $OR^{12}$, $NR^{12}R^{13}$, $SR^{12}$, $SOR^{12}$, $SO_2R^{12}$, $C_1$–$C_8$ alkyl, $C_1$–$C_8$ haloalkyl, $C_1$–$C_8$ heteroalkyl, $C_2$–$C_8$ alkynyl, $C_2$–$C_8$ alkenyl, aryl, heteroaryl and arylalkyl, wherein the alkyl, haloalkyl, heteroalkyl, alkynyl, alkenyl, aryl, heteroaryl and arylalkyl groups are optionally substituted;

$R^7$ is selected from among hydrogen, $C_1$–$C_6$ alkyl, $C_1$–$C_6$ haloalkyl and $C_1$–$C_6$ heteroalkyl, wherein the alkyl, haloalkyl and heteroalkyl groups are optionally substituted;

$R^8$ is selected from among hydrogen, F, Cl, Br, I, $OR^{12}$, $NR^{12}R^{13}$, $SR^{12}$, $SOR^{12}$, $SO_2R^{12}$, $C_1$–$C_8$ alkyl, $C_1$–$C_8$ haloalkyl, $C_1$–$C_8$ heteroalkyl, $C_2$–$C_8$ alkynyl, $C_2$–$C_8$ alkenyl, aryl, heteroaryl and arylalkyl, wherein the alkyl, haloalkyl, heteroalkyl, alkynyl, alkenyl, aryl, heteroaryl and arylalkyl groups are optionally substituted; or $R^3$ and $R^5$ taken together form a bond; or $R^5$ and $R^7$ taken together form a bond; or $R^4$ and $R^6$ taken together form a three- to eight-membered saturated or unsaturated carbocyclic ring, wherein the carbocyclic ring is optionally substituted; or $R^6$ and $R^8$ taken together form a three- to eight-membered saturated or unsaturated carbocyclic ring, wherein the carbocyclic ring is optionally substituted;

$R^9$ and $R^{10}$ each independently is selected from among hydrogen, F, Cl, Br, I, CN, $OR^{12}$, $NR^{12}R^{13}$, $C_m(R^{12})_{2m}OR^{13}$, $SR^{12}$, $SOR^{12}$, $SO_2R^{12}$, $NR^{12}C(O)R^{13}$, $C_1$–$C_8$ alkyl, $C_1$–$C_8$ haloalkyl, $C_1$–$C_8$ heteroalkyl and arylalkyl, wherein the alkyl, haloalkyl, heteroalkyl and arylalkyl groups are optionally substituted;

$R^{11}$ is selected from among hydrogen, F, Br, Cl, I, CN, $OR^{14}$, $NR^{14}R^{13}$, and $SR^{14}$;

$R^{12}$ and $R^{13}$ each independently is selected from the group of hydrogen, $C_1$–$C_8$ alkyl, $C_1$–$C_8$ haloalkyl, $C_1$–$C_8$ heteroalkyl, $C_2$–$C_8$ alkenyl, $C_2$–$C_8$ alkynyl, heteroaryl and aryl, wherein the alkyl, haloalkyl, heteroalkyl, alkenyl, alkynyl, heteroaryl and aryl groups are optionally substituted;

$R^{14}$ is selected from among hydrogen, $C_1$–$C_8$ alkyl, $C_1$–$C_8$ haloalkyl, $C_1$–$C_8$ heteroalkyl, aryl, heteroaryl, $C(O)R^{15}$, $CO_2R^{15}$ and $C(O)NR^{15}R^{16}$, wherein the alkyl, haloalkyl, heteroalkyl, aryl and heteroaryl groups are optionally substituted;

$R^{15}$ and $R^{16}$ each independently is selected from among hydrogen, $C_1$–$C_8$ alkyl, $C_1$–$C_8$ haloalkyl, $C_1$–$C_8$ heteroalkyl, wherein the alkyl, haloalkyl and heteroalkyl groups are optionally substituted;

W is O or S;
X is N{$R^{14}$};
Y is selected from among O, S, N{$R^{12}$} and NO{$R^{12}$};
Z is N{$R^{12}$};
n is 0; and
m is 0 or 1;
or a pharmaceutically acceptable salts thereof.

2. A compound according to claim 1, wherein $R^2$ is selected from among F, Cl, Br, $CF_3$, $CF_2Cl$, $CF_2H$, $CFH_2$, substituted $C_1$–$C_6$ alkyl, $C_1$–$C_6$ haloalkyl and $C_1$–$C_6$ heteroalkyl, wherein the haloalkyl and heteroalkyl groups are optionally substituted.

3. A compound according to claim 1, wherein $R^2$ is selected from among $CF_2OR^{12}$, $CH_2OR^{12}$, $OR^{12}$, $SR^{12}$, $SOR^{12}$, $SO_2R^{12}$ and $NR^{12}R^{13}$.

4. A compound according to claim 1, wherein $R^2$ is selected from among hydrogen, F, Cl, Br, $CF_3$, $CF_2Cl$, $CF_2H$, $CFH_2$, substituted $C_1$–$C_4$ alkyl, $C_1$–$C_4$ haloalkyl, $C_1$–$C_4$ heteroalkyl, $C_2$–$C_4$ alkenyl and $C_2$–$C_4$ alkynyl, wherein the haloalkyl, heteroalkyl, alkenyl and alkynyl groups are optionally substituted.

5. A compound according to claim 4, wherein $R^2$ is selected from among F, Cl, $CF_3$, $CF_2Cl$, $CF_2H$, $CFH_2$ and substituted $C_1$–$C_4$ alkyl.

6. A compound according to claim 1, wherein $R^9$ and $R^{10}$ each independently is selected from among hydrogen, F, Cl, Br, $C_1$–$C_6$ alkyl, $C_1$–$C_6$ haloalkyl and $C_1$–$C_6$ heteroalkyl, wherein the alkyl, haloalkyl and heteroalkyl groups are optionally substituted.

7. A compound according to claim 6, wherein $R^9$ and $R^{10}$ each independently is selected from among hydrogen, F, Cl, $C_1$–$C_4$ alkyl, $C_1$–$C_4$ haloalkyl and $C_1$–$C_4$ heteroalkyl, wherein the alkyl, haloalkyl and heteroalkyl groups are optionally substituted.

8. A compound according to claim 7, wherein $R^9$ and $R^{10}$ each independently is selected from among hydrogen, F and $CH_3$.

9. A compound according to claim 1, wherein $R^1$ is selected from among hydrogen, F, Cl, Br, I, substituted $C_1$–$C_6$ alkyl, $C_1$–$C_6$ haloalkyl and $C_1$–$C_6$ heteroalkyl, wherein the haloalkyl and heteroalkyl groups are optionally substituted.

10. A compound according to claim 9, wherein $R^{11}$ is selected from among hydrogen, F, Cl, $C_1$–$C_4$ alkyl, $C_1$–$C_4$ haloalkyl and $C_1$–$C_4$ heteroalkyl, wherein the alkyl, haloalkyl and heteroalkyl groups are optionally substituted.

11. A compound according to claim 9, wherein $R^1$ is hydrogen or F.

12. A compound according to claim 1, wherein Y is O or S.

13. A compound according to claim 12, wherein Y is O.

14. A compound according to claim 1, wherein $R^{11}$ is selected from among F, Cl, CN, $OR^{14}$, $NR^{14}R^{13}$ and $SR^{14}$.

15. A compound according to claim 14, wherein $R^{11}$ is selected from among F, Cl, $OR^{14}$, $SR^{14}$ and $NR^{14}R^{13}$.

16. A compound according to claim 15, wherein $R^{11}$ is selected from among F, Cl, $OR^{14}$ and $SR^{14}$.

17. A compound according to claim 16, wherein $R^{11}$ is $OR^{14}$.

18. A compound according to claim 1, wherein $R^{12}$ is selected from among hydrogen, $C_1$–$C_6$ alkyl, $C_1$–$C_6$ haloalkyl, $C_1$–$C_6$ heteroalkyl, $C_2$–$C_6$ alkenyl, $C_2$–$C_6$ alkynyl, heteroaryl and aryl, wherein the alkyl, haloalkyl, heteroalkyl, alkenyl, alkynyl, heteroaryl and aryl groups are optionally substituted.

19. A compound according to claim 18, wherein $R^{12}$ is selected from among hydrogen, $C_1$–$C_4$ alkyl, $C_1$–$C_4$ haloalkyl and $C_1$–$C_4$ heteroalkyl, wherein the alkyl, haloalkyl and heteroalkyl groups are optionally substituted.

20. A compound according to claim 1, wherein $R^{13}$ is selected from among hydrogen, $C_1$–$C_6$ alkyl, $C_1$–$C_6$ haloalkyl, $C_1$–$C_6$ heteroalkyl, $C_2$–$C_6$ alkenyl, $C_2$–$C_6$ alkynyl, heteroaryl and aryl, wherein the alkyl, haloalkyl, heteroalkyl, alkenyl, alkynyl, heteroaryl and aryl groups are optionally substituted.

21. A compound according to claim 20, wherein $R^{13}$ is selected from among hydrogen, $C_1$–$C_4$ alkyl, $C_1$–$C_4$ haloalkyl and $C_1$–$C_4$ heteroalkyl, wherein the alkyl, haloalkyl and heteroalkyl groups are optionally substituted.

22. A compound according to claim 1, wherein:
$R^3$ and $R^4$ each independently is selected from among hydrogen, $C_1$–$C_6$ alkyl, $C_1$–$C_6$ haloalkyl and $C_1$–$C_6$ heteroalkyl, wherein the alkyl, haloalkyl and heteroalkyl groups are optionally substituted; or
$R^3$ and $R^5$ taken together form a bond; or
$R^4$ and $R^6$ taken together form a four to six membered saturated or unsaturated carbocyclic ring, wherein the carbocyclic ring are optionally substituted.

23. A compound according to claim 22, wherein $R^3$ and $R^4$ each independently is selected from among hydrogen, $C_1$–$C_4$ alkyl, $C_1$–$C_4$ haloalkyl and $C_1$–$C_4$ heteroalkyl, wherein the alkyl, haloalkyl and heteroalkyl groups are optionally substituted.

24. A compound according to claim 1, wherein:
$R^5$ and $R^7$ each independently is selected from among hydrogen, $C_1$–$C_6$ alkyl, $C_1$–$C_6$ haloalkyl and $C_1$–$C_6$ heteroalkyl, wherein the alkyl, haloalkyl and heteroalkyl groups are optionally substituted; or
$R^5$ and $R^7$ taken together form a bond.

25. A compound according to claim 24, wherein $R^5$ and $R^7$ each independently is selected from among hydrogen, $C_1$–$C_4$ alkyl, $C_1$–$C_4$ haloalkyl and $C_1$–$C_4$ heteroalkyl, wherein the alkyl, haloalkyl and heteroalkyl groups are optionally substituted.

26. A compound according to claim 1, wherein:
$R^6$ and $R^8$ each independently is selected from are hydrogen, $C_1$–$C_6$ alkyl, $C_1$–$C_6$ haloalkyl, $C_1$–$C_6$ heteroalkyl, heteroaryl and aryl, wherein the alkyl, haloalkyl, heteroalkyl, heteroaryl and aryl groups are optionally substituted; or
$R^6$ and $R^8$ taken together form a three to eight membered saturated or unsaturated carbocyclic ring, wherein the carbocyclic ring is optionally substituted.

27. A compound according to claim 26, wherein:
$R^6$ and $R^8$ each independently is selected from among hydrogen, $C_1$–$C_4$ alkyl, $C_1$–$C_4$ haloalkyl, $C_1$–$C_4$ heteroalkyl, heteroaryl and aryl, wherein alkyl, haloalkyl, heteroaryl and aryl are optionally substituted; or
$R^6$ and $R^8$ taken together form a four to six membered saturated or unsaturated carbocyclic ring, wherein the carbocyclic ring is optionally substituted.

28. A compound according to claim 1, wherein:
$R^1$ is selected from among hydrogen, F, Cl, Br, I, substituted $C_1$–$C_6$ alkyl, $C_1$–$C_6$ haloalkyl and $C_1$–$C_6$ heteroalkyl, wherein the haloalkyl and heteroalkyl groups are optionally substituted;
$R^2$ is selected from among hydrogen, F, Cl, Br, $CF_3$, $CF_2Cl$, $CF_2H$, $CFH_2$, substituted $C_1$–$C_6$ alkyl; $C_1$–$C_6$ haloalkyl and $C_1$–$C_6$ heteroalkyl, wherein haloalkyl and heteroalkyl groups are optionally substituted; and
$R^3$ and $R^4$ each independently is selected from among hydrogen, $C_1$–$C_6$ alkyl, $C_1$–$C_6$ haloalkyl and $C_1$–$C_6$ heteroalkyl, wherein the alkyl, haloalkyl and heteroalkyl groups are optionally substituted.

29. A compound according to claim 28, wherein:
$R^5$ through $R^8$ each independently is selected from among hydrogen, $C_1$–$C_6$ alkyl, $C_1$–$C_6$ haloalkyl and $C_1$–$C_6$ heteroalkyl, wherein the alkyl, haloalkyl and heteroalkyl groups are optionally substituted; or
$R^6$ and $R^8$ taken together form a four to six membered saturated or unsaturated carbocyclic ring, wherein the carbocyclic ring are optionally substituted.

30. A compound according to claim 29, wherein:
$R^9$ and $R^{10}$ each independently is selected from among hydrogen, F, Cl, Br, $C_1$–$C_6$ alkyl, $C_1$–$C_6$ haloalkyl and $C_1$–$C_6$ heteroalkyl, wherein the alkyl, haloalkyl and heteroalkyl groups are optionally substituted;
$R^{12}$ is selected from among hydrogen, $C_1$–$C_6$ alkyl $C_1$–$C_6$ haloalkyl and $C_1$–$C_6$ heteroalkyl, $C_2$–$C_6$ alkenyl, $C_2$–$C_6$ alkynyl, heteroaryl and aryl, wherein the alkyl, haloalkyl, heteroalkyl, alkenyl, alkynyl, heteroaryl and aryl groups are optionally substituted; and
$R^{14}$ is selected from among hydrogen, $C_1$–$C_6$ alkyl, $C_1$–$C_6$ haloalkyl, $C_1$–$C_6$ heteroalkyl, $C(O)R^{15}$, $CO_2R^{15}$ and $C(O)NR^{15}R^{16}$, wherein the alkyl, haloalkyl and heteroalkyl groups are optionally substituted.

31. A compound according to claim 30, wherein Y is O or S.

32. A compound according to claim 1, wherein said compound is selected from among:
6-Methyl-4-trifluoromethyl-7H-pyrrolo[3,2-f]quinolin-2(1H)-one;
5-Isopropyl-6-methyl-4-trifluoromethyl-7H-pyrrolo[3,2-f]quinolin-2(1H)-one;
5-Allyl-6-methyl-4-trifluoromethyl-7H-pyrrolo[3,2-f]quinolin-2(1H)-one;
5-(4-Methoxyphenyl)-6-methyl-4-trifluoromethyl-7H-pyrrolo[3,2-f]quinolin-2(1H)-one;
5-(3-Trifluoromethylphenyl)-6-methyl-4-trifluoromethyl-7H-pyrrolo[3,2-f]quinolin-2(1H)-one;
4-Trifluoromethyl-5,6,7,8-tetrahydrocyclopentano[g]pyrrolo[3,2-f]quinolin-2(1H)-one;
4-Trifluoromethyl-5,6,7,8,9,10-hexahydrocyeloheptano[g]pyrrolo[3,2-f]quinolin-2(1H)-one;
(±)-4e,5,6,7,7a(cis),8-Hexahydro-8-trifluoroethyl-4-trifluoromethylcyclopentano[g]pyrrolo-[3,2-f]quinolin-2(1H)-one;
(±)-4e,5,6,7,7a(cis),8-Hexahydro-8-ethyl-4-trifluoromethylcyclopentano-[g]pyrrolo-[3,2-f]-quinolin-2(1H)-one;
(±)-5,6-Dihydro-5,6-cis-dimethyl-7-(2,2,2-trifluoroethyl)-4-trifluoromethyl-7H-pyrrolo[3,2-f]-quinolin-2(1H)-one;
(±)-4c,5,6,7,7a(cis),8-Hexahydro-8-propyl-4-trifluoromethylcyclopentano-[g]pyrrolo-[3,2-f]-quinolin-2(1H)-one;
(±)-4c,5,6,7,7a(cis),8-Hexahydro-8-(3-furanylmethyl)-4trifluoromethylcyclopentano[g]-pyrrolo[3,2-f]quinolin-2(1H)-one;
(±)-4c,5,6,7,7a(cis),8-Hexahydro-8-(3-thiophenemethyl)-4-trifluoromethylcyclopentano[g]-pyrrolo[3,2-f]quinolin-2(1H)-one;
(±)-4c,5,6,7,7a(cis),8-Hexahydro-8-(2-methylpropyl)-4-trifluoromethylcyclopentano[g]-pyrrolo[3,2-f]quinolin-2(1H)-one;
(±)-4c,5,6,7,7a(cis),8-Hexahydro-8-(2,2,2-chlorodifluoro-ethyl)-4-trifluoromethylcyclopentano[g]pyrrolo[3,2-f]quinolin-2(1H)-one;
(±)-4c,5,6,7,7a(cis),8-Hexahydro-8-cyclopropylmethyl-4-trifluoromethylcyclopentano[g]-pyrrolo[3,2-f]quinolin-2(1H)-one;
(±)-4c,5,6,7,7a(cis),8-Hexahydro-8-(2,2-dimethoxyethyl)-4-trifluoromethylcyclopentano[g]pyrrolo[3,2-f]quinolin-2(1H)-one;
(±)-4c,5,6,7,8,8a(cis)-Hexahydro-9-(2,2,2-trifluoroethyl)-4-trifluoromethyl-9H-cyclohexano[g]pyrrolo[3,2-f]quinolin-2(1H)-one;
(±)-4c,5,6,7,8,9,9a(cis),10-Octahydro-10-(2,2,2-trifluoroethyl)-4-trifluoromethylcycloheptano[g]pyrrolo[3,2-f]quinolin-2(1H)-one;
(±)-5,6-cis-Dihydro-6-ethyl-5-methyl-7-(2,2,2-trifluoroethyl)-4-trifluoromethyl-7H-pyrrolo[3,2-f]quinolin-2(1H)-one;
(±)-5,6-cis-Dihydro-5-butyl-6-methyl-7-(2,2,2-trifluoroethyl)-4-trifluoromethyl-7H-pyrrolo[3,2-f]quinolin-2(1H)-one;
(±)-5,6-cis-Dihydro-5-(4-nitrophenyl)-6-methyl-7-(2,2,2-trifluoroethyl)-4-trifluoromethyl-7H-pyrrolo[3,2-f]quinolin-2(1H)-one;
(±)-5,6-cis-Dihydro-5-(4-dimethylaminophenyl)-6-methyl-7-(2,2,2-trifluoroethyl)-4-trifluoromethyl-7H-pyrrolo[3,2-f]quinolin-2(1H)-one;
(±)-5,6-cis-Dihydro-5-(4-methoxyphenyl)-6-methyl-7-(2,2,2-trifluoroethyl)-4-trifluoromethyl-7H-pyrrolo[3,2-f]quinolin-2(1H)-one;
(±)-5,6-cis-Dihydro-5-(3-trifluoromethylphenyl)-6-methyl-7-(2,2,2-trifluoroethyl)-4-trifluoromethyl-7H-pyrrolo[3,2-f]quinolin-2(1H)-one;
(±)-5,6-cis-Dihydro-5-(4-fluorophenyl)-6-methyl-7-(2,2,2-trifluoroethyl)-4-trifluoromethyl-7H-pyrrolo[3,2-f]quinolin-2(1H)-one;
(±)-5,6-Dihydro-5-phenyl-7-(2,2,2-trifluoroethyl)-4-trifluoromethyl-7H-pyrrolo[3,2-f]-quinolin-2(1H)-one;
(±)-5,6-cis-Dihydro-5-(4-methoxyphenyl)-6-methyl-4-trifluoromethyl-7H-pyrrolo[3,2-f]-quinolin-2(1H)-one;
(±)-5,6-cis-Dihydro-5-(4-methoxyphenyl)-6-methyl-7-(2,2-dimethoxyethyl)-4-trifluoromethyl-7H-pyrrolo[3,2-f]quinolin-2(1H)-one;
(±)-5,6-cis-Dihydro-5-isopropyl-6-methyl-7-(2,2,2-trifluoroethyl)-4-trifluoromethyl-7H-pyrrolo[3,2-f]quinolin-2(1H)-one;
(±)-5,6-Dihydro-5-ethyl-6-methyl-7-(2,2,2-trifluoroethyl)-4-trifluoromethyl-7H-pyrrolo-[3,2-f]quinolin-2(1H)-one;
(±)-5,6-Dihydro-5-ethyl-6-propyl-7-(2,2,2-trifluoroethyl)-4-trifluoromethyl-7H-pyrrolo-[3,2-f]quinolin-2(1H)-one;
(±)-5,6-Dihydro-5-(2-ethoxycarbonylethyl)-6-methyl-7-(2,2,2-trifluoroethyl)-4-trifluoromethyl-7H-pyrrolo[3,2-f]quinolin-2(1H)-one;
5,6-Dimethyl-7-(2,2,2-trifluoroethyl)-4-trifluoromethyl-7H-pyrrolo[3,2-f]quinolin-2(1H)-one;

6-Methyl-7-(2,2,2-trifluoroethyl)-4-trifluoromethyl-7H-pyrrolo[3,2-f]quinolin-2(1H)-one;
6-Ethyl-5-methyl-7-(2,2,2-trifluoroethyl)-4-trifluoromethyl-7H-pyrrolo[3,2-f]quinolin-2(1H)-one;
5-Ethyl-6-methyl-7-(2,2,2-trifluoroethyl)-4-trifluoromethyl-7H-pyrrolo[3,2-f]quinolin-2(1H)-one;
5-Ethyl-6-propyl-7-(2,2,2-trifluoroethyl)-4-trifluoromethyl-7H-pyrrolo[3,2-f]quinolin-2(1H)one;
5,6,7,8-Tetrahydro-8-(2,2,2-trifluoroethyl)-4-trifluoromethylcyclopentano[g]-pyrrolo[3,2-f]-quinolin-2(1H)-one;
8-Trifluoroethyl-4-trifluoromethyl-6,8-dihydrocyclopentano[g]pyrrolo[3,2-f]quinolin-2(1H)-one;
9-Trifluoroethyl-4-trifluoromethyl-9H-benzo[g]pyrrolo[3,2-f]quinolin-2(1H)-one;
5-(3-Trifluoromethylphenyl)-6-methyl-7-(2,2,2-trifluoroethyl)-4-trifluoromethyl-7H-pyrrolo[3,2-f]quinolin-2(1H)-one;
5-(4-Fluorophenyl)-6-methyl-7-(2,2,2-trifluoroethyl)-4-trifluoromethyl-7H-pyrrolo[3,2-f]-quinolin-2(1H)-one;
5-(2-Ethoxycarbonylethyl)-6-methyl-7-(2,2,2-trifluoroethyl)-4-trifluoromethyl-7H-pyrrolo[3,2-f]quinolin-2(1H)-one;
5-Hydroxymethyl-6-ethyl-7-(2,2,2-trifluoroethyl)-4-trifluoromethyl-7H-pyrrolo[3,2-f]-quinolin-2(1H)-one;
5-Methyl-6-(1-hydroxyethyl)-7-(2,2,2-trifluoroethyl)-4-trifluoromethyl-7H-pyrrolo[3,2-f]-quinolin-2(1H)-one;
5-Methyl-6-acetyl-7-(2,2,2-trifluoroethyl)-4-trifluoromethyl-7H-pyrrolo[3,2-f]quinolin-2(1H)-one;
5-Formyl-6-methyl-7-(2,2,2-trifluoroethyl)-4-trifluoromethyl-7H-pyrrolo[3,2-f]quinolin-2(1H)-one;
5-Acetyloxymethyl-6-ethyl-7-(2,2,2-trifluoroethyl)-4-trifluoromethyl-7H-pyrrolo[3,2-f]-quinolin-2(1H)-one;
2-Acetyloxy-5-hydroxymethyl-6-ethyl-7-(2,2,2-trifluoroethyl)-4-trifluoromethyl-7H-pyrrolo[3,2-f]quinoline;
6-Ethyl-7-(2,2,2-trifluoroethyl)-4-trifluoromethyl-7H-pyrrolo[3,2-f]quinolin-2(1H)-one;
5-Ethoxymethyl-6-ethyl-7-(2,2,2-trifluoroethyl)-4-trifluoromethyl-7H-pyrrolo[3,2-f]quinolin-2(1H)-one;
(+)-6-(1-Methoxyethyl)-5-methyl-7-(2,2,2-trifluoroethyl)-4-trifluoromethyl-7H-pyrrolo[3,2-f]quinolin-2(1H)-one;
7-Allyl-6-methyl-4-trifluoromethyl-5H-pyrrolo[2,3-f]quinolin-2(1H)-one;
6-Ethyl-7-methyl-4-trifluoromethyl-5H-pyrrolo[2,3-f]quinolin-2(1H)-one;
7-(3-Trifluoromethylphenyl)-6-methyl-4-trifluoromethyl-5H-pyrrolo[2,3-f]quinolin-2(1H)-one;
7-(2-Hydroxyethyl)-6-methyl-4-trifluoromethyl-5H-pyrrolo[2,3-f]quinolin-2(1H)-one;
(+)-4c,5,6,7,7a(cis),8-Hexahydro-8-(2,2,2-trifluoroethyl)-4-trifluoromethylcyclopentano-[g]pyrrolo[3,2-f]quinolin-2(1H)-one;
(−)-4c,5,6,7,7a(cis),8-Hexahydro-8-(2,2,2-trifluoroethyl)-4-trifluoromethylcyclopentano-[g]pyrrolo[3,2-f]quinolin-2(1H)-one;
(±)-5,6-Dihydro-6-hydroxymethyl-4-trifluoromethylpyrrolo[3,2-f]quinolin-2(1H)-one;
(±)-5,6-Dihydro-7-ethyl-6-hydroxymethyl-4-trifluoromethylpyrrolo[3,2-f]quinolin-2(1H)-one;
5-Methyl-7-(2,2,2-trifluoroethyl)-4-trifluoromethylpyrrolo[3,2-f]quinolin-2(1H)-one;
6-Formyl-5-methyl-7-(2,2,2-trifluoroethyl)-4-trifluoromethyl-7H-pyrrolo[3,2-f]quinolin-2(1H)-one; and
5,6-Dimethyl-7-(2,2-difluorovinyl)-4-trifluoromethyl-7H-pyrrolo[3,2-f]quinolin-2(1H)-one.

33. A compound according to claim 1, wherein said compound is selected from the group consisting of:
(±)-4c,5,6,7,7a(cis),8-Hexahydro-8-(2,2,2-trifluoroethyl)-4-trifluoromethylcyclopentano-[g]pyrrolo-[3,2-f]quinolin-2(1H)-one;
(±)-4c,5,6,7,7a(cis),8-Hexahydro-8-ethyl-4-trifluoromethylcyclopentano-[g]pyrrolo[3,2-f]-quinolin-2(1H)-one;
(±)-5,6-Dihydro-5,6-cis-dimethyl-7-4-trifluoromethyl-7H-pyrrolo[3,2-f]-quinolin-2(1H)-one;
(±)-4c,5,6,7,7a(cis),8-Hexahydro-8-propyl-4-trifluoromethylcyclopentano-[g]pyrrolo-[3,2-f]quinolin-2(1H)-one;
(±)-4c,5,6,7,7a(cis),8-Hexahydro-8-(2,2,2-chlorodifluoroethyl)-4-trifluoromethylcyclopentano-[g]-pyrrolo[3,2-f]quinolin-2(1H)-one;
(±)-4c,5,6,7,7a(cis),8-Hexahydro-8-cyclopropylmethyl-4-trifluoromethyl-cyclopentano[g]-pyrrolo[3,2-f]quinolin-2(1H)-one;
(±)-4c,5,6,7,8,8a(cis)-Hexahydro-9-(2,2,2-trifluoroethyl)-4-trifluoromethyl-9H-cyclohexano[g]pyrrolo[3,2-f]quinolin-2(1H)-one;
(±)-5,6-cis-Dihydro-6-ethyl-5-methyl-7-(2,2,2-trifluoroethyl)-4-trifluoromethyl-7H-pyrrolo[3,2-f]quinolin-2(1H)-one;
(±)-5,6-cis-Dihydro-5-butyl-6-methyl-7-(2,2,2-trifluoroethyl)-4-trifluoromethyl-7H-pyrrolo[3,2-f]quinolin-2(1H)-one;
(±)-5,6-Dihydro-5-ethyl-6-methyl-7-(2,2,2-trifluoroethyl)-4-trifluoromethyl-7H-pyrrolo[3,2-f]quinolin-2(1H)-one;
(±)-5,6-Dihydro-5-ethyl-6-propyl-7-(2,2,2-trifluoroethyl)-4-trifluoromethyl-7H-pyrrolo[3,2-f]quinolin-2(1H)-one;
(±)-5,6-cis-Dihydro-5-methyl-6-ethyl-7-(2,2,2-trifluoroethyl)-7H-pyrrolo[3,2-f]-quinolin-2(1H)-one;
5,6-Dimethyl-7-(2,2,2-trifluoroethyl)-4-trifluoromethyl-7H-pyrrolo[3,2-f]quinolin-2(1H)-one;
6-Methyl-7-(2,2,2-trifluoroethyl)-4-trifluoromethyl-7H-pyrrolo[3,2-f]quinolin-2(1H)-one;
6-Ethyl-5-methyl-7-(2,2,2-trifluoroethyl)-4-trifluoromethyl-7H-pyrrolo[3,2-f]quinolin-2(1H)-one;
5-Ethyl-6-methyl-7-(2,2,2-trifluoroethyl)-4-trifluoromethyl-7H-pyrrolo[3,2-f]quinolin-2(1H)-one;
5,6,7,8-Tetrahydro-8-trifluoroethyl-4-trifluoromethylcyclopentano[g]pyrrolo[3,2-f]-quinolin-2(1H)-one;
6-Ethyl-7-(2,2,2-trifluoroethyl)-4-trifluoromethyl-7H-pyrrolo[3,2-f]quinolin-2(1H)-one;
(+)-4c,5,6,7,7a(cis),8-Hexahydro-8-(2,2,2-trifluoroethyl)-4-trifluoromethylcyclopentano-[g]-pyrrolo[3,2-f]quinolin-2(1H)-one; and
(−)-4c,5,6,7,7a(cis),8-Hexahydro-8-(2,2,2-trifluoroethyl)-4-trifluoromethylcyclopentano-[g]pyrrolo[3,2-f]quinolin-2(1H)-one.

34. A pharmaceutical composition, comprising:
a pharmaceutically acceptable carrier; and
a compound of formula:

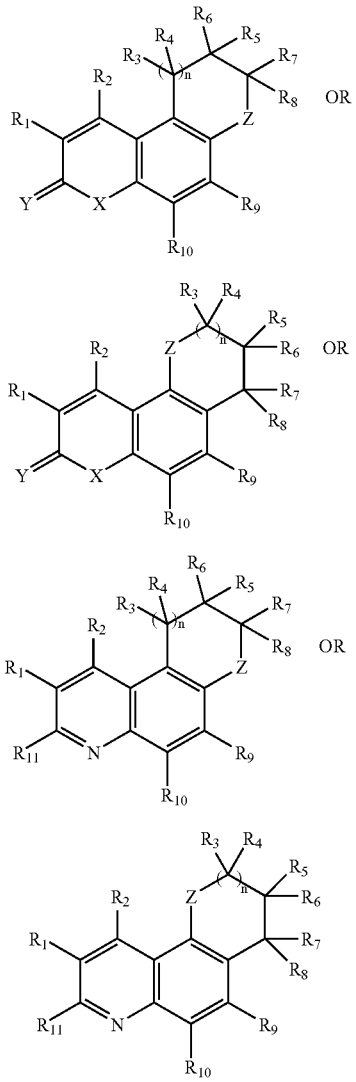

wherein:

R[1] is selected from among hydrogen, F, Cl, Br, I, $NO_2$, $OR^{12}$, $SR^{12}$, $SOR^{12}$, $SO_2R^{12}$, $NR^{12}R^{13}$, $C_1$–$C_8$ alkyl, $C_1$–$C_8$ haloalkyl and $C_1$–$C_8$ heteroalkyl, wherein the alkyl, haloalkyl and heteroalkyl groups are optionally substituted;

R[2] is selected from among F, Cl, Br, I, $CF_3$, $CHF_2$, $CH_2F$, $CF_2Cl$, CN, $CF_2OR^{12}$, $CH_2OR^{12}$, $OR^{12}$, $SR^{12}$, $SOR^{12}$, $SO_2R^{12}$, $NR^{12}R^{13}$, substituted $C_1$–$C_8$ alkyl, $C_1$–$C_8$ haloalkyl, $C_1$–$C_8$ heteroalkyl, $C_2$–$C_8$ alkenyl and $C_2$–$C_8$ alkynyl, wherein the haloalkyl, heteroalkyl, alkenyl and alkynyl groups are optionally substituted;

R[3] is selected from among hydrogen, $C_1$–$C_6$ alkyl, $C_1$–$C_6$ haloalkyl and $C_1$–$C_6$ heteroalkyl, wherein the alkyl, haloalkyl and heteroalkyl groups are optionally substituted;

R[4] is selected from among hydrogen, F, Cl, Br, I, $OR^{12}$, $NR^{12}R^{13}$, $SR^{12}$, $SOR^{12}$, $SO_2R^{12}$, $C_1$–$C_8$ alkyl, $C_1$–$C_8$ haloalkyl, $C_1$–$C_8$ heteroalkyl, $C_2$–$C_8$ alkynyl, $C_2$–$C_8$ alkenyl, aryl, heteroaryl and arylalkyl, wherein the alkyl, haloalkyl, heteroalkyl, alkynyl, alkenyl, aryl, heteroaryl and arylalkyl groups are optionally substituted;

R[5] is selected from among hydrogen, $C_1$–$C_6$ alkyl, $C_1$–$C_6$ haloalkyl and $C_1$–$C_6$ heteroalkyl, wherein the alkyl, haloalkyl and heteroalkyl groups are optionally substituted;

R[6] is selected from among hydrogen, F, Cl, Br, I, $OR^{12}$, $NR^{12}R^{13}$, $SR^{12}$, $SOR^{12}$, $SO_2R^{12}$, $C_1$–$C_8$ alkyl, $C_1$–$C_8$ haloalkyl, $C_1$–$C_8$ heteroalkyl, $C_2$–$C_8$ alkynyl, $C_2$–$C_8$ alkenyl, aryl, heteroaryl and arylalkyl, wherein the alkyl, haloalkyl, heteroalkyl, alkynyl, alkenyl, aryl, heteroaryl and arylalkyl groups are optionally substituted;

R[7] is selected from among hydrogen, $C_1$–$C_6$ alkyl, $C_1$–$C_6$ haloalkyl and $C_1$–$C_6$ heteroalkyl, wherein the alkyl, haloalkyl and heteroalkyl groups are optionally substituted;

R[8] is selected from among hydrogen, F, Cl, Br, I, $OR^{12}$, $NR^{12}R^{13}$, $SR^{12}$, $SOR^{12}$, $SO_2R^{12}$, $C_1$–$C_8$ alkyl, $C_1$–$C_8$ haloalkyl, $C_1$–$C_8$ heteroalkyl, $C_2$–$C_8$ alkynyl, $C_2$–$C_8$ alkenyl, aryl, heteroaryl and arylalkyl, wherein the alkyl, haloalkyl, heteroalkyl, alkynyl, alkenyl, aryl, heteroaryl and arylalkyl groups are optionally substituted; or R[3] and R[5] taken together form a bond; or R[5] and R[7] taken together form a bond; or R[4] and R[6] taken together form a three- to eight-membered saturated or unsaturated carbocyclic ring, wherein the carbocyclic ring is optionally substituted; or R[6] and R[8] taken together form a three- to eight-membered saturated or unsaturated carbocyclic ring, wherein the carbocyclic ring is optionally substituted;

R[9] and R[10] each independently is selected from among hydrogen, F, Cl, Br, I, CN, $OR^{12}$, $NR^{12}R^{13}$, $C_m(R^{12})_{2m}OR^{13}$, $SR^{12}$, $SOR^{12}$, $SO_2R^{12}$, $NR^{12}C(O)R^{13}$, $C_1$–$C_8$ alkyl, $C_1$–$C_8$ haloalkyl, $C_1$–$C_8$ heteroalkyl and arylalkyl, wherein the alkyl, haloalkyl, heteroalkyl and arylalkyl groups are optionally substituted;

R[11] is selected from among hydrogen, F, Br, Cl, I, CN, $OR^{14}$, $NR^{14}R^{13}$ and $SR^{14}$;

R[12] and R[13] each independently is selected from among hydrogen, $C_1$–$C_8$ alkyl, $C_1$–$C_8$ haloalkyl, $C_1$–$C_8$ heteroalkyl, $C_2$–$C_8$ alkenyl, $C_2$–$C_8$ alkynyl, heteroaryl and aryl, wherein the alkyl, haloalkyl, heteroalkyl, alkenyl, alkynyl, heteroaryl and aryl groups are optionally substituted;

R[14] is selected from among hydrogen, $C_1$–$C_8$ alkyl, $C_1$–$C_8$ haloalkyl, $C_1$–$C_8$ heteroalkyl, aryl, heteroaryl, $C(O)R^{15}$, $CO2R^{15}$ and $C(O)NR^{15}R^{16}$, wherein the alkyl, haloalkyl, heteroalkyl, aryl and heteroaryl groups are optionally substituted;

R[15] and R[16] each independently is selected from among hydrogen, $C_1$–$C_8$ alkyl, $C_1$–$C_8$ haloalkyl, $C_1$–$C_8$ heteroalkyl, wherein the alkyl, haloalkyl and heteroalkyl groups are optionally substituted;

W is O or S;

X is $N\{R^{14}\}$;

Y is selected from among O, S, $N\{R^{12}\}$ and $N\{OR^{12}\}$;

Z is $N\{R^{12}\}$;

n is 0; and m is 0 or 1;

or a pharmaceutically acceptable salts thereof.

35. A pharmaceutical composition according to claim 34, wherein the carrier is suitable for enteral, parenteral, suppository, or topical administration.

36. A pharmaceutical composition according to claim 34, wherein $R^1$ is selected from among hydrogen, F, Cl, Br, I, $C_1$–$C_6$ alkyl, $C_1$–$C_6$ haloalkyl and $C_1$–$C_6$ heteroalkyl, wherein the alkyl, haloalkyl and heteroalkyl groups are optionally substituted.

37. A pharmaceutical composition according to claim 36, wherein $R^1$ is selected from among hydrogen, F, Cl, $C_1$–$C_4$ alkyl, $C_1$–$C_4$ haloalkyl and $C_1$–$C_4$ heteroalkyl, wherein the alkyl, haloalkyl and heteroalkyl groups are optionally substituted.

38. A pharmaceutical composition according to claim 34, wherein $R^2$ is selected from among F, Cl, Br, $CF_3$, $CF_2Cl$, $CF_2H$, $CFH_2$, substituted $C_1$–$C_6$ alkyl, $C_1$–$C_6$ haloalkyl and $C_1$–$C_6$ heteroalkyl, wherein the haloalkyl and heteroalkyl groups are optionally substituted.

39. A pharmaceutical composition according to claim 38, wherein $R^2$ is selected from among F, Cl, Br, $CF_3$, $CF_2Cl$, $CF_2H$, $CFH_2$, substituted $C_1$–$C_4$ alkyl, $C_1$–$C_4$ haloalkyl and $C_1$–$C_4$ heteroalkyl, wherein the haloalkyl and heteroalkyl groups are optionally substituted.

40. A pharmaceutical composition according to claim 34, wherein $R^9$ and $R^{10}$ each independently is selected from among hydrogen, F, Cl, Br, $C_1$–$C_6$ alkyl, $C_1$–$C_6$ haloalkyl and $C_1$–$C_6$ heteroalkyl, wherein the alkyl, haloalkyl and heteroalkyl groups are optionally substituted.

41. A pharmaceutical composition according to claim 40, wherein $R^9$ and $R^{10}$ each independently is selected from among hydrogen, F and $CH_3$.

42. A pharmaceutical composition according to claim 34, wherein $R^{11}$ is selected from among hydrogen, F, Cl, CN, $OR^{14}$, $NR^{14}R^{13}$ and $SR^{14}$.

43. A pharmaceutical composition according to claim 42, wherein $R^{11}$ is selected from among hydrogen, F, Cl, $OR^{14}$, SR and $NR^{14}R^{13}$.

44. A pharmaceutical composition according to claim 34, wherein Y is O or S.

45. A pharmaceutical composition according to claim 34, wherein $R^{12}$ is selected from among hydrogen, $C_1$–$C_6$ alkyl, $C_1$–$C_6$ haloalkyl, $C_1$–$C_6$ heteroalkyl, $C_2$–$C_6$ alkenyl, $C_2$–$C_6$ alkynyl, heteroaryl and aryl, wherein the alkyl, haloalkyl, heteroalkyl, alkenyl, alkynyl, heteroaryl and aryl groups are optionally substituted.

46. A pharmaceutical composition according to claim 34, wherein:

$R^3$ and $R^4$ each independently is selected from among hydrogen, $C_1$–$C_6$ alkyl, $C_1$–$C_6$ haloalkyl and $C_1$–$C_6$ heteroalkyl, wherein the alkyl, haloalkyl and heteroalkyl groups are optionally substituted; or $R^3$ and $R^5$ taken together form a bond; or $R^4$ and $R^6$ taken together form a four to six membered carbocyclic ring, wherein the carbocyclic ring is optionally substituted.

47. A pharmaceutical composition according to claim 34, wherein:

$R^5$ and $R^7$ each independently is selected from among hydrogen, $C_1$–$C_6$ alkyl, $C_1$–$C_6$ haloalkyl and $C_1$–$C_6$ heteroalkyl, wherein the alkyl, haloalkyl and heteroalkyl groups are optionally substituted; or $R^5$ and $R^7$ taken together form a bond.

48. A pharmaceutical composition according to claim 34, wherein:

$R^6$ and $R^8$ each independently is selected from among hydrogen, $C_1$–$C_6$ alkyl, $C_1$–$C_6$ haloalkyl, $C_1$–$C_6$ heteroalkyl, heteroaryl and aryl, wherein the alkyl, haloalkyl, heteroalkyl, heteroaryl and aryl groups are optionally substituted; or $R^6$ and $R^8$ taken together form a three to eight membered saturated or unsaturated carbocyclic ring, wherein the carbocyclic ring is optionally substituted.

49. A pharmaceutical composition according to claim 34, wherein:

$R^1$ is selected from among hydrogen, F, Cl, Br, I, $C_1$–$C_6$ alkyl, $C_1$–$C_6$ haloalkyl and $C_1$–$C_6$ heteroalkyl, wherein the alkyl, haloalkyl and heteroalkyl groups are optionally substituted;

$R^2$ is selected from among F, Cl, Br, $CF_3$, $CF_2Cl$, $CF_2H$, $CFH_2$, substituted $C_1$–$C_6$ alkyl; $C_1$–$C_6$ haloalkyl and $C_1$–$C_6$ heteroalkyl, wherein the haloalkyl and heteroalkyl groups are optionally substituted; and $R^3$ and $R^4$ each independently is selected from among hydrogen, $C_1$–$C_6$ alkyl, $C_1$–$C_6$ haloalkyl and $C_1$–$C_6$ heteroalkyl, wherein the alkyl, haloalkyl and heteroalkyl groups are optionally substituted.

50. A pharmaceutical composition according to claim 49, wherein:

$R^5$ through $R^8$ each independently is selected from among hydrogen, $C_1$–$C_6$ alkyl, $C_1$–$C_6$ haloalkyl and $C_1$–$C_6$ heteroalkyl, wherein the alkyl, haloalkyl and heteroalkyl groups are optionally substituted; or $R_6$ and $R^8$ taken together form a four to six membered saturated or unsaturated carbocyclic ring, wherein the carbocyclic ring is optionally substituted.

51. A pharmaceutical composition according to claim 50, wherein:

$R^9$ and $R^{10}$ each independently is selected from among hydrogen, F, Cl, Br, $C_1$–$C_6$ alkyl, $C_1$–$C_6$ haloalkyl and $C_1$–$C_6$ heteroalkyl, wherein the alkyl, haloalkyl and heteroalkyl groups are optionally substituted;

$R^{12}$ is selected from among hydrogen, $C_1$–$C_6$ alkyl, $C_1$–$C_6$ haloalkyl and $C_1$–$C_6$ heteroalkyl, $C_2$–$C_6$ alkenyl, $C_2$–$C_6$ alkynyl, heteroaryl and aryl, wherein the alkyl, haloalkyl, heteroalkyl, alkenyl, alkynyl, heteroaryl and aryl groups are optionally substituted; and $R^{14}$ is selected from among hydrogen, $C_1$–$C_6$ alkyl, $C_1$–$C_6$ haloalkyl, $C_1$–$C_6$ heteroalkyl, $C(O)R^{15}$, $CO_2R^{15}$ and $C(O)NR^{15}R^{16}$, wherein the alkyl, haloalkyl and heteroalkyl groups are optionally substituted.

52. A pharmaceutical composition according to claim 50, wherein Y is O or S.

53. A compound of formula:

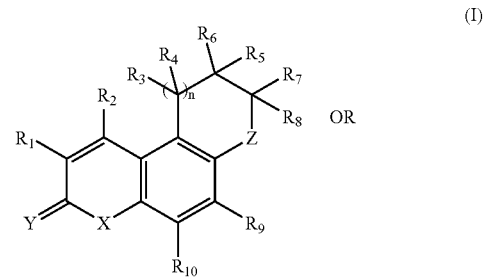

(I)

OR

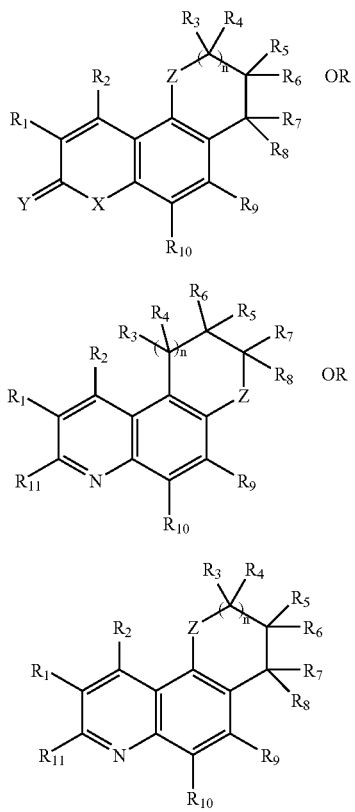

-continued wherein:

R$^1$ is selected from among hydrogen, F, Cl, Br, I, NO$_2$, OR$^{12}$SR$^{12}$, SOR$^{12}$, SO$_2$R$^{12}$, NR$^{12}$ R$^{12}$, C$_1$–C$_8$ alkyl, C$_1$–C$_8$ haloalkyl and C$_1$–C$_8$ heteroalkyl, wherein the alkyl, haloalkyl and heteroalkyl groups are optionally substituted;

R$^2$ is selected from among hydrogen F, Cl, Br, CF$_3$, CHF$_2$, CH$_2$F, CF$_2$Cl, CF$_2$OR$^{12}$, CH$_2$OR, OR$^{12}$, SR$^{12}$, SOR$^{12}$, SO$_2$R$^{12}$, NR$^{12}$R$^{13}$, substituted C$_1$–C$_6$ alkyl C$_1$–C$_6$ haloalkyl, and C$_1$–C$_6$ heteroalkyl, wherein the haloalkyl, and heteroalkyl groups are optionally substituted;

R$^3$ is selected from among hydrogen, C$_1$–C$_6$ alkyl, C$_1$–C$_6$ haloalkyl and C$_1$–C$_6$ heteroalkyl, wherein the alkyl, haloalkyl and heteroalkyl groups are optionally substituted;

R$^4$ is selected from among hydrogen, C$_1$–C$_6$ alkyl, C$_1$–C$_6$ haloalkyl and C$_1$–C$_6$ heteroalkyl, wherein the alkyl, haloalkyl and heteroalkyl groups are optionally substituted;

R$^5$ is selected from among hydrogen, C$_1$–C$_6$ alkyl, C$_1$–C$_6$ haloalkyl and C$_1$–C$_6$ heteroalkyl, wherein the alkyl, haloalkyl and heteroalkyl groups are optionally substituted;

R$^6$ is selected from among hydrogen, C$_1$–C$_6$ alkyl, C$_1$–C$_6$ haloalkyl, C$_1$–C$_6$ heteroaryl and aryl, wherein the alkyl, haloalkyl, heteroalkyl, heteroaryl and aryl groups are optionally substituted;

R$^7$ is selected from among hydrogen, C$_1$–C$_6$ alkyl, C$_1$–C$_6$ haloalkyl and C$_1$–C$_6$ heteroalkyl, wherein the alkyl, haloalkyl and heteroalkyl groups are optionally substituted;

R$^8$ is selected from among hydrogen, C$_1$–C$_6$ alkyl, C$_1$–C$_6$ haloalkyl, C$_1$–C$_6$ heteroalkyl, heteroaryl and aryl, wherein the alkyl, haloalkyl, heteroalkyl, heteroaryl and aryl groups are optionally substituted; or R$^3$ and R$_5$ taken together form a bond; or R$_5$ and R$^7$ taken together form a bond; or R$^4$ and R$^6$ taken together form a three- to eight-membered saturated or unsaturated carbocyclic ring, wherein the carbocyclic ring is optionally substituted; or R$^6$ and R$^8$ taken together form a three- to eight-membered saturated or unsaturated carbocyclic ring, wherein the carbocyclic ring is optionally substituted;

R$^9$ and R$^{10}$ each independently is selected from among hydrogen, F, Cl, Br, I, CN, OR$^{12}$, NR$^{12}$R$^{13}$, C$_m$(R$^{12}$)$_{2m}$OR$^{13}$, SR$^{12}$, SOR$^{12}$, SO$_2$R$^{12}$, NR$^{12}$C(O)R$^{13}$, C$_1$–C$_8$ alkyl, C$_1$–C$_8$ haloalkyl, C$_1$–C$_8$ heteroalkyl and arylalkyl, wherein the alkyl, haloalkyl, heteroalkyl and arylalkyl groups are optionally substituted;

R$^{11}$ is selected from among hydrogen, F, Br, Cl, I, CN, OR$^{14}$, NR$^{14}$R$^{13}$ and SR$^{14}$;

R$^{12}$ and R$^{13}$ each independently is selected from among hydrogen, C$_1$–C$_8$ alkyl, C$_1$–C$_8$ haloalkyl, C$_1$–C$_8$ heteroalkyl, C$_2$–C$_8$ alkenyl, C$_2$–C$_8$ alkynyl, heteroaryl and aryl, wherein the alkyl, haloalkyl, heteroalkyl, alkenyl, alkynyl, heteroaryl and aryl groups are optionally substituted;

R$^{14}$ is selected from among hydrogen, C$_1$–C$_8$ alkyl, C$_1$–C$_8$ haloalkyl, C$_1$–C$_8$ heteroalkyl, aryl, heteroaryl, C(O)R$^{15}$, CO$_2$R$^{15}$ and C(O)NR$^{15}$R$^{16}$, wherein the alkyl, haloalkyl, heteroalkyl, aryl and heteroaryl groups are optionally substituted;

R$^{15}$ and R$^{16}$ each independently is selected from among hydrogen, C$_1$–C$_8$ alkyl, C$_1$–C$_8$ haloalkyl, C$_1$–C$_8$ heteroalkyl, wherein the alkyl, haloalkyl and heteroalkyl groups are optionally substituted;

W is O or S;

X is N{R$^{14}$};

Y is selected from the groups of O, S, N{R$^{12}$} and NO{R$^{12}$};

Z is N{R$^{12}$};

n is 0; and m is 0 or 1;

or a pharmaceutically acceptable salts thereof.

54. A compound according to claim 53, wherein R$^1$ is selected from among hydrogen, F, Cl, Br, I, C$_1$–C$_6$ alkyl, C$_1$–C$_6$ haloalkyl and C$_1$–C$_6$ heteroalkyl, wherein the alkyl, haloalkyl and heteroalkyl groups are optionally substituted.

55. A compound according to claim 53, wherein R$^9$ and R$^{10}$ each independently is selected from among hydrogen, F, Cl, Br, C$_1$–C$_6$ alkyl, C$_1$–C$_6$ haloalkyl and C$_1$–C$_6$ heteroalkyl, wherein the alkyl, haloalkyl and heteroalkyl groups are optionally substituted.

56. A compound according to claim 53, wherein R$^{11}$ is selected from among F, Cl, CN, OR$^{14}$, NR$^{14}$R$^{13}$ and SR$^{14}$.

57. A compound according to claim 53, wherein Y is O or S.

58. A compound according to claim 53, wherein R$^{12}$ is selected from among hydrogen, C$_1$–C$_6$ alkyl, C$_1$–C$_6$ haloalkyl, C$_1$–C$_6$ heteroalkyl, C$_2$–C$_6$ alkenyl, C$_2$–C$_6$ alkynyl, heteroaryl and aryl, wherein the alkyl, haloalkyl, heteroalkyl, alkenyl, alkynyl, heteroaryl and aryl groups are optionally substituted.

59. A compound according to claim 53, wherein:

R$^3$ and R$^4$ each independently is selected from among hydrogen, C$_1$–C$_6$ alkyl, C$_1$–C$_6$ haloalkyl and C$_1$–C$_6$ heteroalkyl, wherein the alkyl, haloalkyl and heteroalkyl groups are optionally substituted; or $R^3$ and $R^5$ taken together form a bond; or $R^4$ and $R^6$ taken together form a four to six membered carbocyclic ring, wherein the carbocyclic ring is optionally substituted.

60. A compound according to claim 34, wherein:

$R^5$ and $R^7$ each independently is selected from among hydrogen, $C_1$–$C_6$ alkyl, $C_1$–$C_6$ haloalkyl, $C_1$–$C_6$ heteroalkyl, wherein the alkyl, haloalkyl and heteroalkyl groups are optionally substituted; or $R^5$ and $R^7$ taken together form a bond.

61. A compound according to claim 34, wherein:

$R^6$ and $R^8$ each independently is selected from among hydrogen, $C_1$–$C_6$ alkyl, $C_1$–$C_6$ haloalkyl, $C_1$–$C_6$ heteroalkyl, heteroaryl and aryl, wherein the alkyl, haloalkyl, heteroalkyl, heteroaryl and aryl groups are optionally substituted; or $R^6$ and $R^8$ taken together form a three to eight membered saturated or unsaturated carbocyclic ring, wherein the carbocyclic ring is optionally substituted.

\* \* \* \* \*

UNITED STATES PATENT AND TRADEMARK OFFICE
CERTIFICATE OF CORRECTION

| | | |
|---|---|---|
| PATENT NO. | : 7,026,484 B2 | Page 1 of 1 |
| APPLICATION NO. | : 10/080926 | |
| DATED | : April 11, 2006 | |
| INVENTOR(S) | : Lin Zhi et al. | |

It is certified that error appears in the above-identified patent and that said Letters Patent is hereby corrected as shown below:

IN THE TITLE PAGES:

Item [56] References Cited, in OTHER PUBLICATIONS:
in Yudin, please replace "Geterotsikicheskikh" with --Geterotsiklicheskikh--
in the first Yamashkin et al., please replace "Chemistry.of" with --Chemistry of--
in Edwards, J., et al., please replace "(1999)" with --(1998)--
in Boyer, M., please replace "http://www.australianprescriber.com/magazines/vol19no1/ap19-1-11.htm(accessed on Jan. 28, 2005." with --http://www.australianprescriber.com/magazines/vol19no1/ap19-1-11.htm (accessed on Jan. 28, 2005).--
in Castillo, P., please replace "o-dihdroxyaromatic" with --o-dihydroxyaromatic--

Signed and Sealed this

Thirty-first Day of October, 2006

JON W. DUDAS
*Director of the United States Patent and Trademark Office*

UNITED STATES PATENT AND TRADEMARK OFFICE
CERTIFICATE OF CORRECTION

PATENT NO.        : 7,026,484 B2
APPLICATION NO. : 10/080926
DATED               : April 11, 2006
INVENTOR(S)      : Lin Zhi et al.

It is certified that error appears in the above-identified patent and that said Letters Patent is hereby corrected as shown below:

IN THE TITLE PAGES:

Item [56] References Cited, in OTHER PUBLICATIONS:
in Yudin, please replace "Geterotsikicheskikh" with --Geterotsiklicheskikh--
in the first Yamashkin et al., please replace "Chemistry.of" with --Chemistry of--
in Edwards, J., et al., please replace "(1999)" with --(1998)--
in Boyer, M., please replace
"http://www.australianprescriber.com/magazines/vol19no1/ap19-1-11.htm(accessed on Jan. 28, 2005." with --http://www.australianprescriber.com/magazines/vol19no1/ap19-1-11.htm (accessed on Jan. 28, 2005).--
in Castillo, P., please replace "o-dihdroxyaromatic" with --o-dihydroxyaromatic--

IN THE SPECIFICATION:
In column 2, beginning at line 7, please replace formulas I-VIII with:

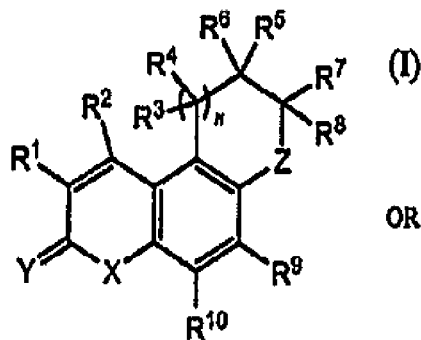   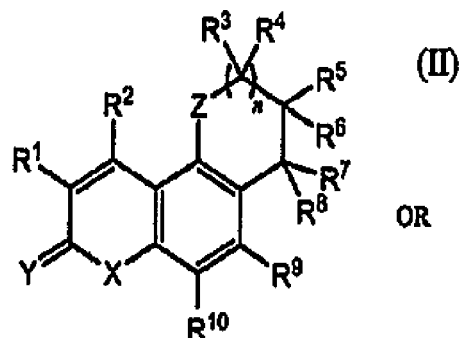

OR

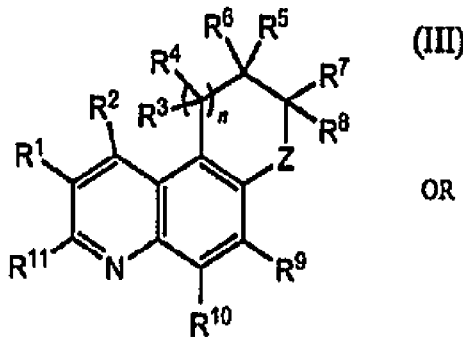   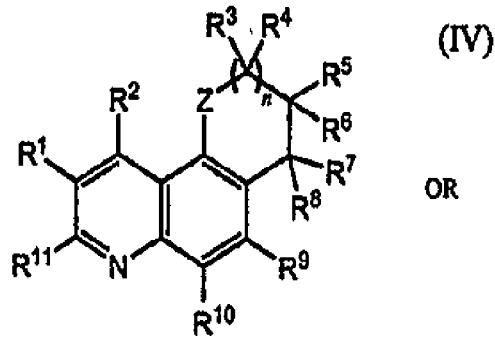

OR

UNITED STATES PATENT AND TRADEMARK OFFICE
CERTIFICATE OF CORRECTION

PATENT NO. : 7,026,484 B2  Page 2 of 16
APPLICATION NO. : 10/080926
DATED : April 11, 2006
INVENTOR(S) : Lin Zhi et al.

It is certified that error appears in the above-identified patent and that said Letters Patent is hereby corrected as shown below:

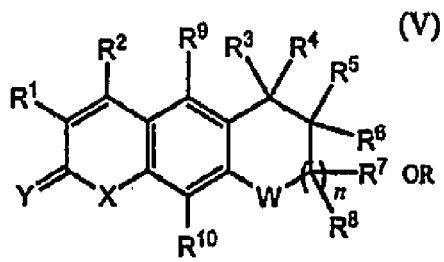 (V)

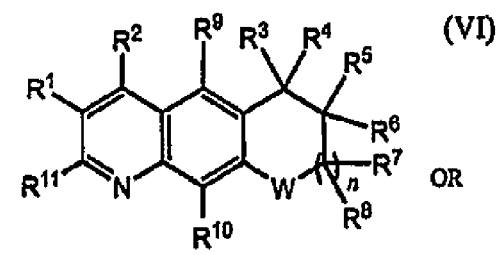 (VI)

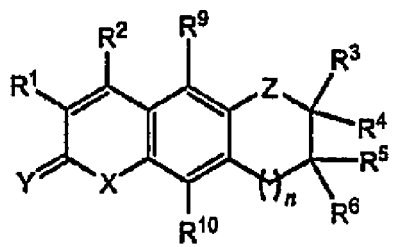 (VII)

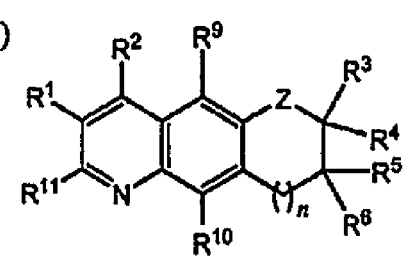 (VIII)

in column 7, beginning at line 15, please replace formulas I-VIII with:

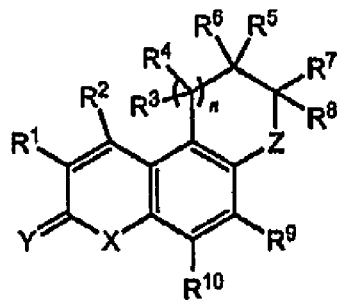 (I) OR

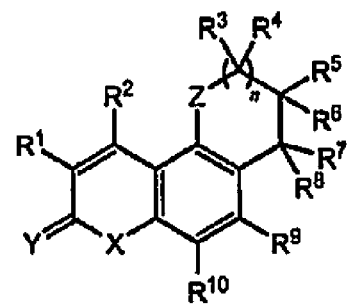 (II) OR

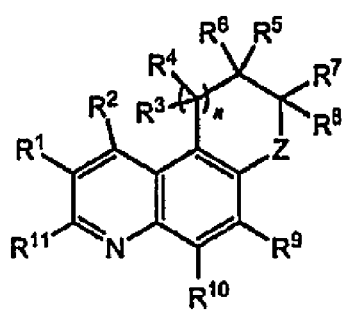 (III) OR

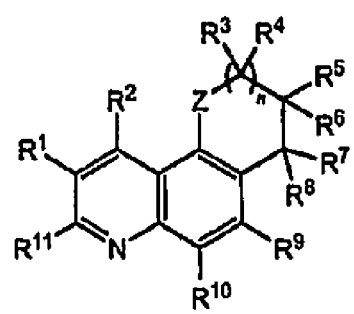 (IV) OR

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

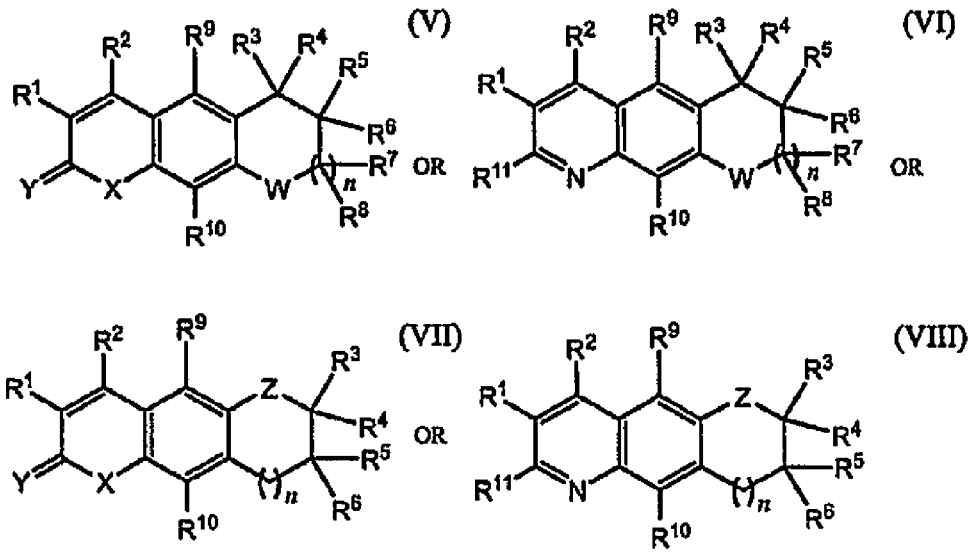

in column 24, lines 53-67, please replace the structures in Scheme II with:

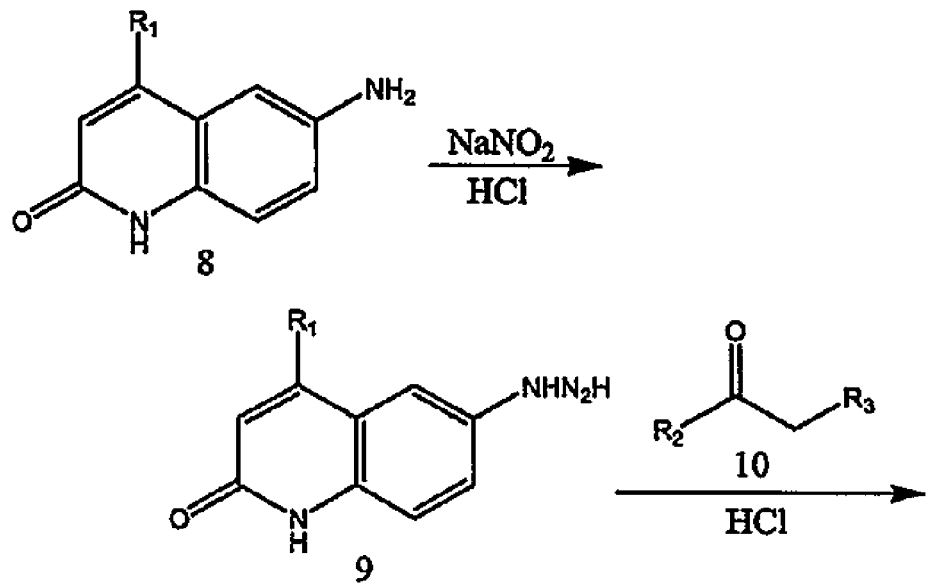

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

in column 57, lines 4-6, please replace
"(Compound 177, Structure 26 of Scheme IV, where $R_2$=methyl. $R_3$=2-hydroxyethyl" with --(Compound 177, Structure 26 of Scheme IV, where $R_2$=methyl, $R_3$=2-hydroxyethyl-- in column 70, line 21, please replace "chloronation" with --chlorination--

IN THE CLAIMS:
Please replace Claims 1, 4, 26, 28, 29, 30, 32, 33, 34, 42, 43, 50, 52, 53, and 60 with the following Claims:

1. A compound of the formula:

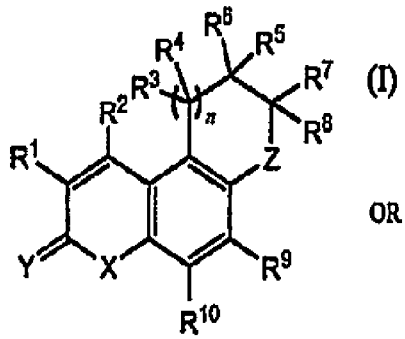 (I)

OR

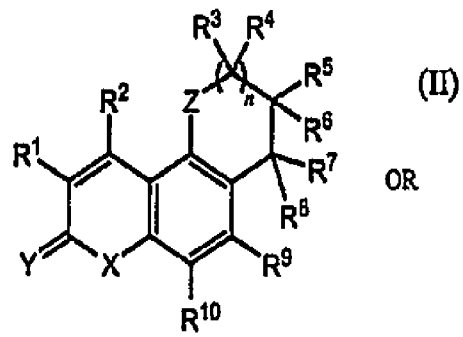 (II)

OR

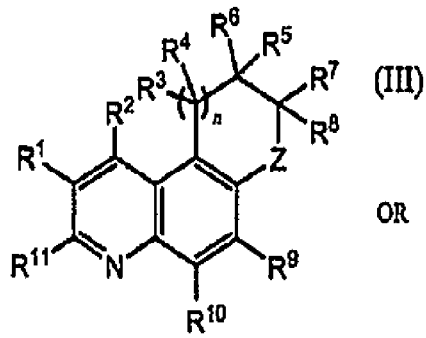 (III)

OR

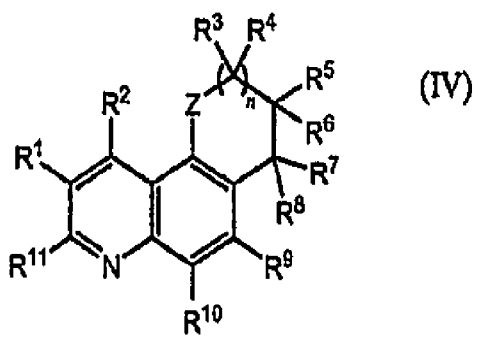 (IV)

UNITED STATES PATENT AND TRADEMARK OFFICE
CERTIFICATE OF CORRECTION

| | |
|---|---|
| PATENT NO. | : 7,026,484 B2 |
| APPLICATION NO. | : 10/080926 |
| DATED | : April 11, 2006 |
| INVENTOR(S) | : Lin Zhi et al. |

It is certified that error appears in the above-identified patent and that said Letters Patent is hereby corrected as shown below:

wherein:

$R^1$ is selected from among hydrogen, F, Cl, Br, I, $NO_2$, $OR^{12}$, $SR^{12}$, $SOR^{12}$, $SO_2R^{12}$, $NR^{12}R^{12}$, substituted $C_1$-$C_8$ alkyl, $C_1$-$C_8$ haloalkyl and $C_1$-$C_8$ heteroalkyl, wherein the haloalkyl and heteroalkyl groups are optionally substituted;

$R^2$ is selected from among F, Cl, Br, I, $CF_3$, $CHF_2$, $CH_2F$, $CF_2Cl$, CN, $CF_2OR^{12}$, $CH_2OR^{12}$, $OR^{12}$, $SR^{12}$, $SOR^{12}$, $SO_2R^{12}$, $NR^{12}R^{13}$, substituted $C_1$-$C_8$ alkyl, $C_1$-$C_8$ haloalkyl, $C_1$-$C_8$ heteroalkyl, $C_2$-$C_8$ alkenyl and $C_2$-$C_8$ alkynyl, wherein the haloalkyl, heteroalkyl, alkenyl and alkynyl groups are optionally substituted;

$R^3$ is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted;

$R^4$ is selected from among hydrogen F, Cl, Br, I, $OR^{12}$, $NR^{12}R^{13}$, $SR^{12}$, $SOR^{12}$, $SO_2R^{12}$, $C_1$-$C_8$ alkyl, $C_1$-$C_8$ haloalkyl, $C_1$-$C_8$ heteroalkyl, $C_2$-$C_8$ alkynyl, $C_2$-$C_8$ alkenyl, aryl, heteroaryl and arylalkyl wherein the alkyl, haloalkyl, heteroalkyl, alkynyl, alkenyl, aryl, heteroaryl and arylalkyl groups are optionally substituted;

$R^5$ is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted;

$R^6$ is selected from among hydrogen F, Cl, Br, I, $OR^{12}$, $NR^{12}R^{13}$, $SR^{12}$, $SOR^{12}$, $SO_2R^{12}$, $C_1$-$C_8$ alkyl, $C_1$-$C_8$ haloalkyl, $C_1$-$C_8$ heteroalkyl, $C_2$-$C_8$ alkynyl, $C_2$-$C_8$ alkenyl, aryl, heteroaryl and arylalkyl, wherein the alkyl, haloalkyl, heteroalkyl, alkynyl, alkenyl, aryl, heteroaryl and arylalkyl groups are optionally substituted;

$R^7$ is selected from among hydrogen, $C_1$-$C_6$ alkyl, $C_1$-$C_6$ haloalkyl and $C_1$-$C_6$ heteroalkyl, wherein the alkyl, haloalkyl, and heteroalkyl groups are optionally substituted;

$R^8$ is selected from among hydrogen F, Cl, Br, I, $OR^{12}$, $NR^{12}R^{13}$, $SR^{12}$, $SOR^{12}$, $SO_2R^{12}$, $C_1$-$C_8$ alkyl, $C_1$-$C_8$ haloalkyl, $C_1$-$C_8$ heteroalkyl, $C_2$-$C_8$ alkynyl, $C_2$-$C_8$ alkenyl, aryl, heteroaryl and arylalkyl, wherein the alkyl, haloalkyl, heteroalkyl, alkynyl, alkenyl, aryl, heteroaryl and arylalkyl groups are optionally substituted; or $R^3$ and $R^5$ taken together form a bond; or $R^5$ and $R^7$ taken together form a bond; or $R^4$ and $R^6$ taken together form a three- to eight-membered saturated or unsaturated carbocyclic ring, wherein the carbocyclic ring is optionally substituted; or $R^6$ and $R^8$ taken together form a three- to eight-membered saturated or unsaturated carbocyclic ring, wherein the carbocyclic ring is optionally substituted;

$R^9$ and $R^{10}$ each independently is selected from among hydrogen, F, Cl, Br, I, CN, $OR^{12}$, $NR^{12}R^{13}$, $C_m(R^{12})_{2m}OR^{13}$, $SR^{12}$, $SOR^{12}$, $SO_2R^{12}$, $NR^{12}C(O)R^{13}$, $C_1$-$C_8$ alkyl, $C_1$-$C_8$ haloalkyl, $C_1$-$C_8$ heteroalkyl and arylalkyl, wherein the alkyl, haloalkyl, heteroalkyl and arylalkyl groups are optionally substituted;

$R^{11}$ is selected from F, Br, Cl, I, CN, $OR^{14}$, $NR^{14}R^{13}$, and $SR^{14}$;

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

$R^{12}$ and $R^{13}$ each independently is selected from the group of hydrogen, $C_1$-$C_8$ alkyl, $C_1$-$C_8$ haloalkyl, $C_1$-$C_8$ heteroalkyl, $C_2$-$C_8$ alkenyl, $C_2$-$C_8$ alkynyl, heteroaryl and aryl wherein the alkyl, haloalkyl, heteroalkyl, alkenyl, alkynyl, heteroaryl and aryl groups are optionally substituted;

$R^{14}$ is selected from among hydrogen, $C_1$-$C_8$ alkyl, $C_1$-$C_8$ haloalkyl, $C_1$-$C_8$ heteroalkyl, aryl, heteroaryl, $C(O)R^{15}$, $CO_2R^{15}$ and $C(O)NR^{15}R^{16}$, wherein the alkyl, haloalkyl, heteroalkyl, aryl and heteroaryl groups are optionally substituted;

$R^{15}$ and $R^{16}$ each independently is selected from among hydrogen, $C_1$-$C_8$ alkyl, $C_1$-$C_8$ haloalkyl, $C_1$-$C_8$ heteroalkyl, wherin the alkyl, haloalkyl and heteroalkyl groups are optionally substituted;

W is O or S;
X is N $\{R^{14}\}$;
Y is seleted from among O, S, N$\{R^{12}\}$ and NO$\{R^{12}\}$;
Z is N$\{R^{12}\}$;
n is 0; and
m is 0 or 1;
or a pharmaceutically acceptable salt thereof.

4. A compound according to claim 1, wherein $R^2$ is selected from among F, Cl, Br, $CF_3$, $CF_2Cl$, $CF_2H$, $CFH_2$, substituted $C_1$-$C_4$ alkyl, $C_1$-$C_4$ haloalkyl, $C_1$-$C_4$ heteroalkyl, $C_2$-$C_4$ alkenyl and $C_2$-$C_4$ alkynyl, wherein the haloalkyl, heteroalkyl, alkenyl and alkynyl groups are optionally substituted.

26. A compound according to claim 1, wherein:
$R^6$ and $R^8$ each indepentently is selected from among hydrogen, $C_1$-$C_6$ alkyl, $C_1$-$C_6$ haloalkyl, $C_1$-$C_6$ heteroalkyl, heteroaryl and aryl, wherein the alkyl, haloalkyl, heteroalkyl, heteroaryl and aryl groups are optionally substituted; or
$R^6$ and $R^8$ taken together form a three to eight membered saturated or unsaturated carbocyclic ring, wherein the carbocyclic ring is optionally substituted.

28. A compound according to claim 1, wherein:
$R^1$ is selected from among hydrogen, F, Cl, Br, I, substituted $C_1$-$C_6$ alkyl, $C_1$-$C_6$ haloalkyl and $C_1$-$C_6$ heteroalkyl, wherein the haloalkyl and heteroalkyl groups are optionally substituted;
$R^2$ is selected from among F, Cl, Br, $CF_3$, $CF_2Cl$, $CF_2H$, $CFH_2$, substituted $C_1$-$C_6$ alkyl, $C_1$-$C_6$ haloalkyl and $C_1$-$C_6$ heteroalkyl, wherein haloalkyl and heteroalkyl groups are optionally substituted; and
$R^3$ and $R^4$ each independently is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted.

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

29. A compound according to claim 28, wherein
$R^5$ through $R^8$ each independently is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted; or
$R^6$ and $R^8$ taken together form a four to six membered saturated or unsaturated carbocyclic ring, wherein the carbocyclic ring is optionally substituted.

30. A compound according to claim 29, wherein:
$R^9$ and $R^{10}$ each independently is selected from among hydrogen, F, Cl, Br, $C_1$-$C_6$ alkyl, $C_1$-$C_6$ haloalkyl and $C_1$-$C_6$ heteroalkyl, wherein the alkyl, haloalkyl and heteroalkyl groups are optionally substituted;
$R^{12}$ is selected from among hydrogen, $C_1$-$C_6$ alkyl, $C_1$-$C_6$ haloalkyl, $C_1$-$C_6$ heteroalkyl, $C_2$-$C_6$ alkenyl, $C_2$-$C_6$ alkynyl, heteroaryl and aryl, wherein the alkyl, haloalkyl, heteroalkyl, alkenyl, alkynyl, heteroaryl and aryl groups are optionally substituted; and
$R^{14}$ is selected from among hydrogen, $C_1$-$C_6$ alkyl, $C_1$-$C_6$ haloalkyl and $C_1$-$C_6$ heteroalkyl, $C(O)R^{15}$, $CO_2R^{15}$ and $C(O)NR^{15}R^{16}$, wherein the alkyl, haloalkyl and heteroalkyl groups are optionally substituted.

32. A compound according to claim 1, wherein said compound is selected from among:
6-Methyl-4-trifluoromethyl-7*H*-pyrrolo[3,2-*f*]quinolin-2(1*H*)-one;
5-Isopropyl-6-methyl-4-trifluoromethyl-7*H*-pyrrolo[3,2-*f*]quinolin-2(1*H*)-one;
5-Allyl-6-methyl-4-trifluoromethyl-7*H*-pyrrolo[3,2-*f*]quinolin-2(1*H*)-one;
5-(4-Methoxyphenyl)-6-methyl-4-trifluoromethyl-7*H*-pyrrolo[3,2-*f*]quinolin-2(1*H*)-one;
5-(3-Trifluoromethylphenyl)-6-methyl-4-trifluoromethyl-7*H*-pyrrolo[3,2-*f*]quinolin-2
 (1*H*)-one;
4-Trifluoromethyl-5,6,7,8-tetrahydrocyclopentano[g]pyrrolo[3,2-*f*]quinolin-2(1*H*)-one;
4-Trifluoromethyl-5,6,7,8,9,10-hexahydrocycloheptano[g]pyrrolo[3,2-*f*]quinolin-2(1*H*)-
 one;
(±)-4c,5,6,7,7a(*cis*),8-Hexahydro-8-trifluoroethyl-4-
 trifluoromethylcyclopentano[g]pyrrolo-[3,2-*f*]quinolin-2(1*H*)-one;
(±)-4c,5,6,7,7a(*cis*),8-Hexahydro-8-ethyl-4-
 trifluoromethylcyclopentano-[g]pyrrolo[3,2-*f*]-quinolin-2(1*H*)-one;
(±)-5,6-Dihydro-5,6-*cis*-dimethyl-7-(2,2,2-trifluoroethyl)-4-
 trifluoromethyl-7*H*-pyrrolo[3,2-*f*]-quinolin-2(1*H*)-one;
(±)-4c,5,6,7,7a(*cis*),8-Hexahydro-8-propyl-4-trifluoromethylcyclopentano-[g]pyrrolo-
 [3,2-*f*]quinolin-2(1*H*)-one;
(±)-4c,5,6,7,7a(*cis*),8-Hexahydro-8-(3-furanylmethyl)-4-trifluoromethylcyclopentano
 [g]-pyrrolo[3,2-*f*]quinolin-2(1*H*)-one;
(±)-4c,5,6,7,7a(*cis*),8-Hexahydro-8-(3-thiophenemethyl)-4-
 trifluoromethylcyclopentano[g]-pyrrolo[3,2-*f*]quinolin-2(1*H*)-one;

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

(±)-4c,5,6,7,7a(*cis*),8-Hexahydro-8-(2-methylpropyl)-4-trifluoromethylcyclopentano[g]-pyrrolo[3,2-*f*]quinolin-2(1*H*)-one;

(±)-4c,5,6,7,7a(*cis*),8-Hexahydro-8-(2,2,2-chlorodifluoro-ethyl)-4-trifluoromethylcyclopentano[g]pyrrolo[3,2-*f*]quinolin-2(1*H*)-one;

(±)-4c,5,6,7,7a(*cis*),8-Hexahydro-8-cyclopropylmethyl-4-trifluoromethylcyclopentano[g]-pyrrolo[3,2-*f*]quinolin-2(1*H*)-one;

(±)-4c,5,6,7,7a(*cis*),8-Hexahydro-8-(2,2-dimethoxyethyl)-4-trifluoromethylcyclopentano[g]pyrrolo[3,2-*f*]quinolin-2(1*H*)-one;

(±)-4c,5,6,7,8,8a(*cis*)-Hexahydro-9-(2,2,2-trifluoroethyl)-4-trifluoromethyl-9*H*-cyclohexano[g]pyrrolo[3,2-*f*]quinolin-2(1*H*)-one;

(±)-4c,5,6,7,8,9,9a(*cis*),10-Octahydro-10-(2,2,2-trifluoroethyl)-4-trifluoromethylcycloheptano[g]pyrrolo[3,2-*f*]quinolin-2(1*H*)-one;

(±)-5,6-*cis*-Dihydro-6-ethyl-5-methyl-7-(2,2,2-trifluoroethyl)-4-trifluoromethyl-7*H*-pyrrolo[3,2-*f*]quinolin-2(1*H*)-one;

(±)-5,6-*cis*-Dihydro-5-butyl-6-methyl-7-(2,2,2-trifluoroethyl)-4-trifluoromethyl-7*H*-pyrrolo[3,2-*f*]quinolin-2(1*H*)-one;

(±)-5,6-*cis*-Dihydro-5-(4-nitrophenyl)-6-methyl-7-(2,2,2-trifluoroethyl)-4-trifluoromethyl-7*H*-pyrrolo[3,2-*f*]quinolin-2(1*H*)-one;

(±)-5,6-*cis*-Dihydro-5-(4-dimethylaminophenyl)-6-methyl-7-(2,2,2-trifluoroethyl)4-trifluoromethyl-7*H*-pyrrolo[3,2-*f*]quinolin-2(1*H*)-one;

(±)-5,6-*cis*-Dihydro-5-(4-methoxyphenyl)-6-methyl-7-(2,2,2-trifluoroethyl)-4-methyl-7*H*-pyrrolo[3,2-*f*]quinolin-2(1*H*)-one;

(±)-5,6-*cis*-Dihydro-5-(3-trifluoromethylphenyl)-6-methyl-7-(2,2,2-trifluoroethyl)-4-trifluoromethyl-7*H*-pyrrolo[3,2-*f*]quinolin-2(1*H*)-one;

(±)-5,6-*cis*-Dihydro-5-(4-fluorophenyl)-6-methyl-7-(2,2,2-trifluoroethyl)-4-trifluoromethyl-7*H*-pyrrolo[3,2-*f*]quinolin-2(1*H*)-one;

(±)-5,6-Dihydro-5-phenyl-7-(2,2,2-trifluoroethyl)-4-trifluoromethyl-7*H*-pyrrolo-3,2-*f*]-quinolin-2(1*H*)-one;

(±)-5,6-*cis*-Dihydro-5-(4-methoxyphenyl)-6-methyl-4-trifluoromethyl-7*H*-pyrrolo [3,2-*f*]-quinolin-2(1*H*)-one;

(±)-5,6-*cis*-Dihydro-5-(4-methoxyphenyl)-6-methyl-7-(2,2-dimethoxyethyl)-4-trifluoromethyl-7*H*-pyrrolo[3,2-*f*]quinolin-2(1*H*)-one;

(±)-5,6-*cis*-Dihydro-5-isopropyl-6-methyl-7-(2,2,2-trifluoroethyl)-4-trifluoromethyl-7*H*-pyrrolo[3,2-*f*]quinolin-2(1*H*)-one;

(±)-5,6-Dihydro-5-ethyl-6-methyl-7-(2,2,2-trifluoroethyl)-4-trifluoromethyl-7*H*-pyrrolo-[3,2-*f*]quinolin-2(1*H*)-one;

(±)-5,6-Dihydro-5-ethyl-6-propyl-7-(2,2,2-trifluoroethyl)-4-trifluoromethyl-7*H*-pyrrolo-[3,2-*f*]quinolin-2(1*H*)-one;

(±)-5,6-Dihydro-5-(2-ethoxycarbonylethyl)-6-methyl-7-(2,2,2-trifluoroethyl)-4-trifluoromethyl-7*H*-pyrrolo[3,2-*f*]quinolin-2(1*H*)-one;

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

5,6-Dimethyl-7-(2,2,2-trifluoroethyl)-4-trifluoromethyl-7*H*-pyrrolo[3,2-*f*]quinolin-2(1*H*)-one;
6-Methyl-7-(2,2,2-trifluoroethyl)-4-trifluoromethyl-7*H*-pyrrolo[3,2-*f*]quinolin-2(1*H*)-one;
6-Ethyl-5-methyl-7-(2,2,2-trifluoroethyl)-4-trifluoromethyl-7*H*-pyrrolo[3,2-*f*]quinolin-2(1*H*)-one;
5-Ethyl-6-methyl-7-(2,2,2-trifluoroethyl)-4-4trifluorometyl-7*H*-pyrrolo[3,2-*f*]quinolin-2(1H)-one;
5-Ethyl-6-propyl-7-(2,2,2-trifluoroethyl)-4-trifluoromethyl-7*H*-pyrrolo[3,2-*f*]quinolin-2(1*H*)-one;
5,6,7,8-Tetrahydro-8-(2,2,2-trifluoroethyl)-4-trifluoromethylcyclopentano[g]-pyrrolo[3,2-*f*]-quinolin-2(1*H*)-one;
8-Trifluoroethyl-4-trifluoromethyl-6,8-dihydrocyclopentano[g]pyrrolo[3,2-*f*]quinolin-2(1*H*)-one;
9-Trifluoroethyl-trifluoromethyl-9*H*-benzo[g]pyrrolo[3,2-*f*]quinolin-2(1*H*)-one;
5-(3-Trifluoromethylphenyl)-6-methyl-7-(2,2,2-trifluoroethyl)-4-trifluoromethyl-7*H*-pyrrolo[3,2-*f*]quinolin-2(1*H*)-one;
5-(4-Fluorophenyl)-6-methyl-7-(2,2,2-trifluoroethyl)-4-trifluoromethyl-7*H*-pyrrolo[3,2-*f*]quinolin-2(1*H*)-one;
5-(2-Ethoxycarbonylethyl)-6-methyl-7-(2,2,2-trifluoroethyl)-4-trifluoromethyl-7*H*-pyrrolo[3,2-*f*]quinolin-2(1*H*)-one;
5-Hydroxymethyl-6-ethyl-7-(2,2,2-trifluoroethyl)-4-trifluoromethyl-7*H*-pyrrolo[3,2-*f*]-quinolin-2(1*H*)-one;
5-Methyl-6-(1-hydroxyethyl)-7-(2,2,2-trifluoroethyl)-4-trifluoromethyl-7*H*-pyrrolo[3,2-*f*]quinolin-2(1*H*)-one;
5-Methyl-6-acetyl-7-(2,2,2-trifluoroethyl)-4-trifluoromethyl-7*H*-pyrrolo[3,2-*f*]quinolin-2(1*H*)-one;
5-Formyl-6-methyl-7-(2,2,2-trifluoroethyl)-4-trifluoromethyl-7*H*-pyrrolo[3,2-*f*]quinolin-2(1*H*)-one;
5-Acetyloxymethyl-6-ethyl-7-(2,2,2-trifluoroethyl)-4-trifluoromethyl-7*H*-pyrrolo[3,2-*f*]quinolin-2(1*H*)-one;
2-Acetyloxy-5-hydroxymethyl-6-ethyl-7-(2,2,2-trifluoroethyl)-4-trifluoromethyl-7*H*-pyrrolo[3,2-*f*]quinoline;
6-Ethyl-7-(2,2,2-trifluoroethyl)-4-trifluoromethyl-7*H*-pyrrolo[3,2-*f*]quinolin-2(1*H*)-one;
5-Ethoxymethyl-6-ethyl-7-(2,2,2-trifluoroethyl)-4-trifluoromethyl-7*H*-pyrrolo[3,2-*f*]-quinolin-2(1*H*)-one;
(+)-6-(1-Methoxyethyl)-5-methyl-7-(2,2,2-trifluoroethyl)-4-trifluoromethyl-7*H*-pyrrolo[3,2-*f*]quinolin-2(1*H*)-one;
7-Allyl-6-methyl-4-trifluoromethyl-5*H*-pyrrolo[2,3-*f*]quinolin-2(1*H*)-one;
6-Ethyl-7-methyl-4-trifluoromethyl-5*H*-pyrrolo[2,3-*f*]quinolin-2(1*H*)-one;

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

7-(3-Trifluoromethylphenyl)-6-methyl-4-trifluoromethyl-5*H*-pyrrolo[2,3-*f*]quinolin-2
 (1*H*)-one;
7-(2-Hydroxyethyl)-6-methyl-4-trifluoromethyl-5*H*-pyrrolo[2,3-*f*]quinolin-2(1*H*)-one;
(+)-4c,5,6,7,7a(*cis*),8-Hexahydro-8-(2,2,2-trifluoroethyl)-4-trifluoromethyl-
 cyclopentano-[g]-pyrrolo[3,2-*f*]quinolin-2(1*H*)-one;
(−)-4c,5,6,7,7a(*cis*),8-Hexahydro-8-(2,2,2-trifluoroethyl)-4-
 trifluoromethylcyclopentano-[g]-pyrrolo[3,2-*f*]quinolin-2(1*H*)-one;
(±)-5,6-Dihydro-6-hydroxymethyl-4-trifluoromethylpyrrolo[3,2-*f*]quinolin-2(1*H*)-one;
(±)-5,6-Dihydro-7-ethyl-6-hydroxymethyl-4-trifluoromethylpyrrolo[3,2-*f*]quinolin-2
 (1*H*)-one;
5-Methyl-7-(2,2,2-trifluoroethyl)-4-trifluoromethylpyrrolo[3,2-*f*]quinolin-2(1*H*)-one;
6-Formyl-5-methyl-7-(2,2,2-trifluoroethyl)-4-trifluoromethyl-7*H*-pyrrolo[3,2-*f*]quinolin-
 2(1*H*)-one; and
5,6-Dimethyl-7-(2,2-difluorovinyl)-4-trifluoromethyl-7*H*-pyrrolo[3,2-*f*]quinolin-2(1*H*)-
 one.

33. A compound according to claim 1, wherein said compound is selected from the group consisting of:
(±)-4c,5,6,7,7a(*cis*),8-Hexahydro-8-(2,2,2-trifluoroethyl)-4-
 trifluoromethylcyclopentano-[g]pyrrolo-[3,2-*f*]quinolin-2(1*H*)-one;
(±)-4c,5,6,7,7a(*cis*),8-Hexahydro-8-ethyl-4-trifluoromethylcyclopentano-[g]pyrrolo
 [3,2-*f*]quinolin-2(1*H*)-one;
(±)-5,6-Dihydro-5,6-*cis*-dimethyl-7-(2,2,2-trifluoroethyl)-4-trifluoromethyl-7*H*-pyrrolo
 [3,2-*f*]-quinolin-2(1*H*)-one;
(±)-4c,5,6,7,7a(*cis*),8-Hexahydro-8-propyl-4-trifluoromethylcyclopentano-[g]pyrrolo-
 [3,2-*f*]quinolin-2(1*H*)-one;
(±)-4c,5,6,7,7a(*cis*),8-Hexahydro-8-(2,2,2-chlorodifluoroethyl)-4-trifluoromethylcyclo-
 pentano-[g]-pyrrolo[3,2-*f*]quinolin-2(1*H*)-one;
(±)-4c,5,6,7,7a(*cis*),8-Hexahydro-8-cyclopropylmethyl-4-trifluoromethylcyclo-
 pentanoo[g]-pyrrolo[3,2-*f*]quinolin-2(1*H*)-one;
(±)-4c,5,6,7,8,8a(*cis*)-Hexahydro-9-(2,2,2-trifluoroethyl)-4-trifluoromethyl-9*H*-
 cyclohexan[g]pyrrolo[3,2-*f*]quinolin-2(1*H*)-one;
(±)-5,6-*cis*-Dihydro-6-ethyl-5-methyl-7-(2,2,2-trifluoroethyl)-4-trifluoromethyl-7*H*-
 pyrrolo[3,2-*f*]quinolin-2(1*H*)-one;
(±)-5,6-*cis*-Dihydro-5-butyl-6-methyl-7-(2,2,2-trifluoroethyl)-4-trifluoromethyl-7*H*-
 pyrrolo[3,2-*f*]quinolin-2(1*H*)-one;
(±)-5,6-Dihydro-5-ethyl-6-methyl-7-(2,2,2-trifluoroethyl)-4-trifluoromethyl-7*H*-pyrrolo
 [3,2-*f*]quinolin-2(1*H*)-one;
(±)-5,6-Dihydro-5-ethyl-6-propyl-7-(2,2,2-trifluoroethyl)-4-trifluoromethyl-7*H*-pyrrolo
 [3,2-*f*]quinolin-2(1*H*)-one;

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

(±)-5,6-*cis*-Dihydro-5-methyl-6-ethyl-7-(2,2,2-trifluoroethyl)-7*H*-pyrrolo[3,2-*f*]-quinolin-2(1*H*)-one;
5,6-Dimethyl-7-(2,2,2-trifluoroethyl)-4-trifluoromethyl-7*H*-pyrrolo[3,2-*f*]quinolin-2(1*H*)-one;
6-Methyl-7-(2,2,2-trifluoroethyl)-4-trifluoromethyl-7*H*-pyrrolo[3,2-*f*]quinolin-2(1*H*)-one;
6-Ethyl-5-methyl-7-(2,2,2-trifluoroethyl)-4-trifluoromethyl-7*H*-pyrrolo[3,2-*f*]quinolin-2(1*H*)-one;
5-Ethyl-6-methyl-7-(2,2,2-trifluoroethyl)-4-trifluoromethyl-7*H*-pyrrolo[3,2-*f*]quinolin-2(1*H*)-one;
5,6,7,8-Tetrahydro-8-trifluoroethyl-4-trifluoromethylcyclopentano[g]pyrrolo[3,2-*f*]-quinolin-2(1*H*)-one;
6-Ethyl-7-(2,2,2-trifluoroethyl)-4-trifluoromethyl-7*H*-pyrrolo[3,2-*f*]quinolin-2(1*H*)-one;
(+)-4c,5,6,7,7a(*cis*),8-Hexahydro-8-(2,2,2-trifluoroethyl)-4-trifluoromethylcyclopentano-g]pyrrolo[3,2-*f*]quinolin-2(1*H*)-one;
(−)-4c,5,6,7,7a(*cis*),8-Hexahydro-8-(2,2,2-trifluoroethyl)-4-trifluoromethylcyclopentano-[g]pyrrolo[3,2-*f*]quinolin-2(1*H*)-one.

34. A pharmaceutical composition, comprising:
a pharmaceutically acceptable carrier; and
a compound of formula:

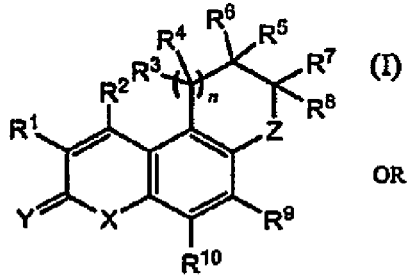 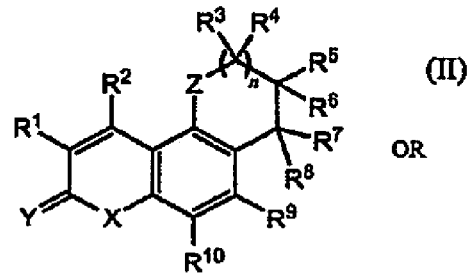

OR

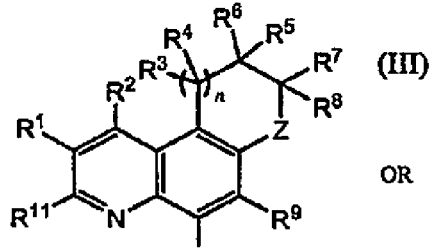 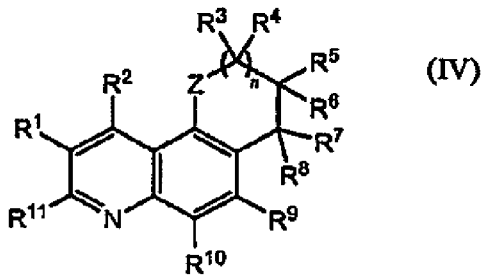

OR

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

wherein:
$R^1$ is selected from among hydrogen, F, Cl, Br, I, $NO_2$, $OR^{12}$, $SR^{12}$, $SOR^{12}$, $SO_2R^{12}$, $NR^{12}R^{13}$, $C_1$-$C_8$ alkyl, $C_1$-$C_8$ haloalkyl and $C_1$-$C_8$ heteroalkyl, wherein the alkyl, haloalkyl and heteroalkyl groups are optionally substituted;

$R^2$ is selected from among F, Cl, Br, I, $CF_3$, $CHF_2$, $CH_2F$, $CF_2Cl$, CN, $CF_2OR^{12}$, $CH_2OR^{12}$, $OR^{12}$, $SR^{12}$, $SOR^{12}$, $SO_2R^{12}$, $NR^{12}R^{13}$, substituted $C_1$-$C_8$ alkyl, $C_1$-$C_8$ haloalkyl, $C_1$-$C_8$ heteroalkyl, $C_2$-$C_8$ alkenyl and $C_2$-$C_8$ alkynyl, wherein the haloalkyl, heteroalkyl, alkenyl and alkynyl groups are optionally substituted;

$R^3$ is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted;

$R^4$ is selected from among hydrogen, F, Cl, Br, I, $OR^{12}$, $NR^{12}R^{13}$, $SR^{12}$, $SOR^{12}$, $SO_2R^{12}$, $C_1$-$C_8$ alkyl, $C_1$-$C_8$ haloalkyl, $C_1$-$C_8$ heteroalkyl, $C_2$-$C_8$ alkynyl, $C_2$-$C_8$ alkenyl, aryl, heteroaryl and arylalkyl, wherein the alkyl, haloalkyl, heteroalkyl, alkynyl, alkenyl, aryl, heteroaryl and arylalkyl groups are optionally substituted;

$R^5$ is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted;

$R^6$ is selected from among hydrogen, F, Cl, Br, I, $OR^{12}$, $NR^{12}R^{13}$, $SR^{12}$, $SOR^{12}$, $SO_2R^{12}$, $C_1$-$C_8$ alkyl, $C_1$-$C_8$ haloalkyl, $C_1$-$C_8$ heteroalkyl, $C_2$-$C_8$ alkynyl, $C_2$-$C_8$ alkenyl, aryl, heteroaryl and arylalkyl, wherein the alkyl, haloalkyl, heteroalkyl, alkynyl, alkenyl, aryl, heteroaryl and arylalkyl groups are optionally substituted;

$R^7$ is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted;

$R^8$ is selected from among hydrogen, F, Cl, Br, I, $OR^{12}$, $NR^{12}R^{13}$, $SR^{12}$, $SOR^{12}$, $SO_2R^{12}$, $C_1$-$C_8$ alkyl, $C_1$-$C_8$ haloalkyl, $C_1$-$C_8$ heteroalkyl, $C_2$-$C_8$ alkynyl, $C_2$-$C_8$ alkenyl, aryl, heteroaryl and arylalkyl, wherein the alkyl, haloalkyl, heteroalkyl, alkynyl alkenyl, aryl, heteroaryl and arylalkyl groups are optionally substituted; or $R^3$ and $R^5$ taken together form a bond; or $R^5$ and $R^7$ taken together form a bond; or $R^4$ and $R^6$ taken together form a three- to eight-membered saturated or unsaturated carbocyclic ring, wherein the carbocyclic ring is optionally substituted; or $R^6$ and $R^8$ taken together form a three- to eight-membered saturated or unsaturated carbocyclic ring, wherein the carbocyclic ring is optionally substituted;

$R^9$ and $R^{10}$ each independently is selected from among hydrogen, F, Cl, Br, I, CN, $OR^{12}$, $NR^{12}R^{13}$, $C_m(R^{12})_{2m}OR^{13}$, $SR^{12}$, $SOR^{12}$, $SO_2R^{12}$, $NR^{12}C(O)R^{13}$, $C_1$-$C_8$ alkyl, $C_1$-$C_8$ haloalkyl, $C_1$-$C_8$ heteroalkyl and arylalkyl, wherein the alkyl, haloalkyl, heteroalkyl and arylalkyl groups are optionally substituted;

$R^{11}$ is selected from among hydrogen, F, Br, Cl, I, CN, $OR^{14}$, $NR^{14}R^{13}$ and $SR^{14}$;

$R^{12}$ and $R^{13}$ each independently is selected from among hydrogen, $C_1$-$C_8$ alkyl, $C_1$-$C_8$ haloalkyl, $C_1$-$C_8$ heteroalkyl, $C_2$-$C_8$ alkenyl, $C_2$-$C_8$ alkynyl, heteroaryl and aryl, wherein the alkyl, haloalkyl, heteroalkyl, alkenyl, alkynyl, heteroaryl and aryl groups are optionally substituted;

UNITED STATES PATENT AND TRADEMARK OFFICE
CERTIFICATE OF CORRECTION

| | |
|---|---|
| PATENT NO. | : 7,026,484 B2 |
| APPLICATION NO. | : 10/080926 |
| DATED | : April 11, 2006 |
| INVENTOR(S) | : Lin Zhi et al. |

It is certified that error appears in the above-identified patent and that said Letters Patent is hereby corrected as shown below:

$R^{14}$ is selected from among hydrogen, $C_1$-$C_8$ alkyl, $C_1$-$C_8$ haloalkyl, $C_1$-$C_8$ heteroalkyl, aryl, heteroaryl, $C(O)R^{15}$, $CO_2R^{15}$ and $C(O)NR^{15}R^{16}$, wherein the alkyl, haloalkyl, heteroalkyl, aryl and heteroaryl groups are optionally substituted;

$R^{15}$ and $R^{16}$ each independently is selected from among hydrogen, $C_1$-$C_8$ alkyl, $C_1$-$C_8$ haloalkyl and $C_1$-$C_8$ heteroalkyl, wherein the alkyl, haloalkyl and heteroalkyl groups are optionally substituted;

W is O or S;
X is N $\{R^{14}\}$;
Y is seleted from among O, S, N$\{R^{12}\}$ and N$\{OR^{12}\}$;
Z is N$\{R^{12}\}$;
n is 0; and
m is 0 or 1;
or a pharmaceutically acceptable salt thereof.

42. A pharmaceutical composition according to claim 34, wherein $R^{11}$ is selected from among F, Cl, CN, $OR^{14}$, $NR^{14}R^{13}$ and $SR^{14}$.

43. A pharmaceutical composition according to claim 42, wherein $R^{11}$ is selected from among F, Cl, $OR^{14}$, $SR^{14}$, $NR^{14}R^{13}$.

50. A pharmaceutical composition according to claim 49, wherein:
$R^5$ through $R^8$ each independently is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted; or
$R^6$ and $R^8$ taken together form a four to six membered saturated or unsaturated carbocyclic ring, wherein the carbocyclic ring is optionally substituted.

52. A pharmaceutical composition according to claim 51 wherein Y is O or S.

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

53. A compound of formula:

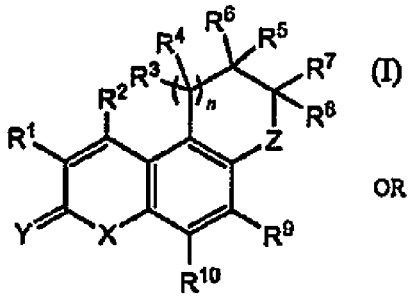 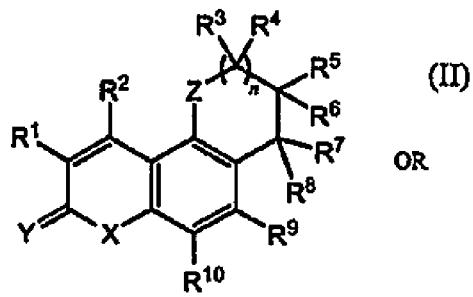

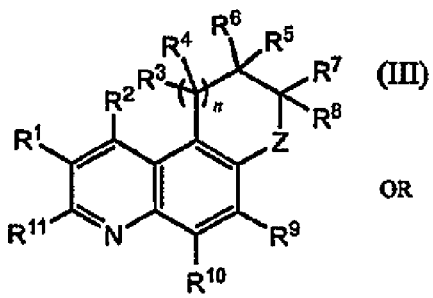 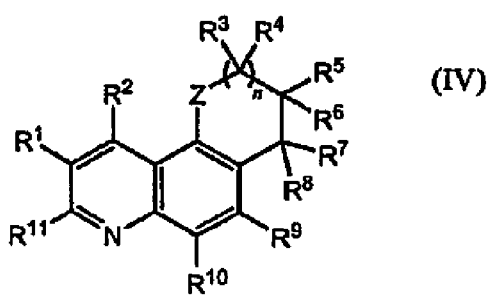

wherein:
$R^1$ is selected from among hydrogen, F, Cl, Br, I, $NO_2$, $OR^{12}$, $SR^{12}$, $SOR^{12}$, $SO_2R^{12}$, $NR^{12}R^{12}$, $C_1$-$C_8$ alkyl, $C_1$-$C_8$ haloalkyl and $C_1$-$C_8$ heteroalkyl, wherein the alkyl, haloalkyl and heteroalkyl groups are optionally substituted;

$R^2$ is selected from among F, Cl, Br, $CF_3$, $CHF_2$, $CH_2F$, $CF_2Cl$, $CF_2OR^{12}$, $CH_2OR^{12}$, $OR^{12}$, $SR^{12}$, $SOR^{12}$, $SO_2R^{12}$, $NR^{12}R^{13}$, substituted $C_1$-$C_6$ alkyl, $C_1$-$C_6$ haloalkyl and $C_1$-$C_6$ heteroalkyl, wherein the haloalkyl, and heteroalkyl groups are optionally substituted;

$R^3$ is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted;

$R^4$ is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted;

$R^5$ is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted;

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

$R^6$ is selected from among hydrogen, $C_1$-$C_6$ alkyl, $C_1$-$C_6$ haloalkyl, $C_1$-$C_6$ heteroalkyl, heteroaryl and aryl, wherein the alkyl, haloalkyl, heteroalkyl, heteroaryl and aryl groups are optionally substituted;

$R^7$ is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted;

$R^8$ is selected from among hydrogen, $C_1$-$C_6$ alkyl, $C_1$-$C_6$ haloalkyl, $C_1$-$C_6$ heteroalkyl, heteroaryl and aryl, wherein the alkyl, haloalkyl, heteroalkyl, heteroaryl and aryl groups are optionally substituted; or $R^3$ and $R^5$ taken together form a bond; or $R^5$ and $R^7$ taken together form a bond; or $R^4$ and $R^6$ taken together form a three- to eight-membered saturated or unsaturated carbocyclic ring, wherein the carbocyclic ring is optionally substituted;

$R^6$ and $R^8$ taken together form a three- to eight-membered saturated or unsaturated carbocyclic ring, wherein the carbocyclic ring is optionally substituted;

$R^9$ and $R^{10}$ each independently is selected from among hydrogen, F, Cl, Br, I, CN, $OR^{12}$, $NR^{12}R^{13}$, $C_m(R^{12})_{2m}OR^{13}$, $SR^{12}$, $SOR^{12}$, $SO_2R^{12}$, $NR^{12}C(O)R^{13}$, $C_1$-$C_8$ alkyl, $C_1$-$C_8$ haloalkyl, $C_1$-$C_8$ heteroalkyl and arylalkyl, wherein the alkyl, haloalkyl, heteroalkyl and arylalkyl groups are optionally substituted;

$R^{11}$ is selected from among F, Br, Cl, I CN, $OR^{14}$, $NR^{14}R^{13}$ and $SR^{14}$;

$R^{12}$ and $R^{13}$ each independently is selected from among hydrogen, $C_1$-$C_8$ alkyl, $C_1$-$C_8$ haloalkyl, $C_1$-$C_8$ heteroalkyl, $C_2$-$C_8$ alkenyl, $C_2$-$C_8$ alkynyl, heteroaryl and aryl, wherein the alkyl, haloalkyl, heteroalkyl, alkenyl, alkynyl, heteroaryl and aryl groups are optionally substituted;

$R^{14}$ is selected from among hydrogen, $C_1$-$C_8$ alkyl, $C_1$-$C_8$ haloalkyl, $C_1$-$C_8$ heteroalkyl, aryl, heteroaryl, $C(O)R^{15}$, $CO_2R^{15}$ and $C(O)NR^{15}R^{16}$, wherein the alkyl, haloalkyl, heteroalkyl, aryl and heteroaryl groups are optionally substituted;

$R^{15}$ and $R^{16}$ each independently is selected from among hydrogen, $C_1$-$C_8$ alkyl, $C_1$-$C_8$ haloalkyl and $C_1$-$C_8$ heteroalkyl, wherein the alkyl, haloalkyl and heteroalkyl groups are optionally substituted;

W is O or S;

X is N $\{R^{14}\}$;

Y is seleted from among O, S, N$\{R^{12}\}$ and NO$\{R^{12}\}$;

Z is N$\{R^{12}\}$;

n is 0; and m is 0 or 1;

or a pharmaceutically acceptable salt thereof.

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

60. A compound according to claim 34, wherein:
  $R^5$ and $R^7$ each independently is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted; or
  $R^5$ and $R^7$ taken together form a bond.

This certificate supersedes Certificate of Correction issued October 31, 2006.

Signed and Sealed this

Twenty-seventh Day of February, 2007

JON W. DUDAS
*Director of the United States Patent and Trademark Office*

UNITED STATES PATENT AND TRADEMARK OFFICE
CERTIFICATE OF CORRECTION

PATENT NO.       : 7,026,484 B2
APPLICATION NO.  : 10/080926
DATED            : April 11, 2006
INVENTOR(S)      : Lin Zhi et al.

It is certified that error appears in the above-identified patent and that said Letters Patent is hereby corrected as shown below:

Col. 82, Line 13 should read
(±)-4c,5,6,7,7a(*cis*),8-Hexahydro-8-(2-methylpropyl)-4-trifluoromethylcyclopentano
 [g]-pyrrolo[3,2-*f*]quinolin-2(1*H*)-one;
(±)-4c,5,6,7,7a(*cis*),8-Hexahydro-8-(2,2,2-chlorodifluoro-ethyl)-4-
 trifluoromethylcyclopentano[g]pyrrolo[3,2-f]quinolin-2(1*H*)-one;
(±}-4c,5,6,7,7a(*cis*),8-Hexahydro-8-cyclopropylmethyl-4-
 trifluoromethylcyclopentano[g]-pyrrolo[3,2-*f*]quinolin-2(1*H*)-one;
(±)-4c,5,6,7,7a(*cis*),8-Hexahydro-8-(2,2-dimethoxyethyl)-4-trifluoromethylcyclo-
 pentano[g]pyrrolo[3,2-*f*]quinolin-2(1*H*)-one;
(±)-4c,5,6,7,8,8a(*cis*)-Hexahydro-9-(2,2,2-trifuoroethyl)-4-trifluoromethyl-9*H*-
 cyclohexano[g]pyrrolo[3,2-*f*]quinolin-2(1*H*)-one;
(±)-4c,5,6,7,8,9,9a(*cis*),10-Octahydro-10-(2,2,2-trifluoroethyl)-4-
 trifluoromethylcycloheptano[g]pyrrolo[3,2-*f*]quinolin-2(1*H*)-one;
(±)-5,6-*cis*-Dihydro-6-ethyl-5-methyl-7-(2,2,2-trifluoroethyl)-4-trifluoromethyl-7*H*-
 pyrrolo[3,2-*f*]quinolin-2(1*H*)-one;
(±)-5,6-*cis*-Dihydro-5-butyl-6-methyl-7-(2,2,2-trifluoroethyl)-4-trifluoromethyl-7*H*-
 pyrrolo[3,2-*f*]quinolin-2(1*H*)-one;
(±)-5,6-*cis*-Dihydro-5-(4-nitrophenyl)-6-methyl-7-(2,2,2-trifluoroethyl)-4-
 trifluoromethyl-7*H*-pyrrolo[3,2-*f*]quinolin-2(1*H*)-one;
(±)-5,6-*cis*-Dihydro-5-(4-dimethylaminophenyl)-6-methyl-7-(2,2,2-trifluoroethyl)4-
 trifluoromethyl-7*H*-pyrrolo[3,2-f]quinolin-2(1*H*)-one;
(±)-5,6-*cis*-Dihydro-5-(4-methoxyphenyl)-6-methyl-7-(2,2,2-trifluoroethyl)4-
 trifluoromethyl-7*H*-pyrrolo[3,2-*f*]quinolin-2(1*H*)-one;
(±)-5,6-*cis*-Dihydro-5-(3-trifluoromethylphenyl)-6-methyl-7-(2,2,2-trifluoroethyl)-4-
 trifluoromethyl-7*H*-pyrrolo[3,2-*f*]quinolin-2(1*H*)-one;
(±)-5,6-*cis*-Dihydro-5-(4-fluorophenyl)-6-methyl-7-(2,2,2-trifluoroethyl)-4-
 trifluoromethyl-7*H*-pyrrolo[3,2-*f*]quinolin-2(1*H)*-one;
(±)-5,6-Dihydro-5-phenyl-7-(2,2,2-trifluoroethyl)-4-trifluoromethyl-7*H*-pyrrolo-3,2-*f*]-
 quinolin-2(1*H*)-one;
(±)-5,6-*cis*-Dihydro-5-(4-methoxyphenyl)-6-methyl-4-trifluoromethyl-7*H*-pyrrolo
 [3,2-*f*]-quinolin-2(1*H*)-one;
(±)-5,6-*cis*-Dihydro-5-(4-methoxyphenyl)-6-methyl-7-(2,2-dimethoxyethyl)-4-
 trifluoromethyl-7*H*-pyrrolo[3,2-f]quinolin-2(1*H*)-one;
(±)-5,6-*cis*-Dihydro-5-isopropyl-6-methyl-7-(2,2,2-trifluoroethyl)-4-trifluoromethyl-
 7*H*-pyrrolo[3,2-*f*]quinolin-2(1*H*)-one;

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

(±)-5,6-Dihydro-5-ethyl-6-methyl-7-(2,2,2-trifluoroethyl)-4-trifluoromethyl-7$H$-pyrrolo-[3,2-$f$]quinolin-2(1$H$)-one;
(±)-5,6-Dihydro-5-ethyl-6-propyl-7-(2,2,2-trifluoroethyl)-4-trifluoromethyl-7$H$-pyrrolo-[3,2-$f$]quinolin-2(1$H$)-one;
(±)-5,6-Dihydro-5-(2-ethoxycarbonylethyl)-6-methyl-7-(2,2,2-trifluoroethyl)-4-trifluoromethyl-7$H$-pyrrolo[3,2-$f$]quinolin-2(1$H$)-one;
5,6-Dimethyl-7-(2,2,2-trifluoroethyl)-4-trifluoromethyl-7$H$-pyrrolo[3,2-$f$]quinolin-2(1$H$)-one;
6-Methyl-7-(2,2,2-trifluoroethyl)-4-trifluoromethyl-7$H$-pyrrolo[3,2-f]quinolin-2(1$H$) one;
6-Ethyl-5-methy-7-(2,2,2-trifluoroethyl)-4-trifluoromethyl-7$H$-pyrrolo[3,2-$f$]quinolin-2(1$H$)-one;
5-Ethyl-6-methyl-7-(2,2,2-trifluoroethyl)-4-trifluoromethyl-7$H$-pyrrolo[3,2-$f$]quinolin-2(1$H$)-one;
5-Ethyl-6-propyl-7-(2,2,2-trifluoroethyl)-4-trifluoromethyl-7$H$-pyrrolo[3,2-$f$]quinolin-2(1$H$)-one;
5,6,7,8-Tetrahydro-8-(2,2,2-trifluoroethyl}-4-trifluoromethylcyclopentano[g]-pyrrolo[3,2-$f$]-quinolin-2(1$H$)-one;
8-Trifluoroethyl-4-trifluoromethyl-6,8-dihydrocyclopentano[g]pyrrolo[3,2-$f$]quinolin-2(1$H$)-one;
9-Trifluoroethyl-trifluoromethyl-9$H$-benzo[g]pyrrolo[3,2-$f$]quinolin-2(1$H$)-one;
5-(3-Trifluoromethylphenyl)-6-methyl-7-(2,2,2-trifluoroethyl)-4-trifluoromethyl-7$H$-pyrrolo[3,2-$f$]quinolin-2(1$H$)-one;
5-(4-Fluorophenyl)-6-methyl-7-(2,2,2-trifluoroethyl)-4-trifluoromethyl-7$H$-pyrrolo[3,2-$f$]quinolin-2(1$H$)-one;
5-(2-Ethoxycarbonylethyl)-6-methyl-7-(2,2,2-trifluoroethyl)-4-trifluoromethyl-7$H$-pyrrolo[3,2-$f$]quinolin-2(1$H$)-one;
5-Hydroxymethyl-6-ethyl-7-(2,2,2-trifluoroethyl)-4-trifluoromethyl-7$H$-pyrrolo[3,2-$f$]-quinolin-2(1$H$)-one;
5-Methyl-6-(1-hydroxyethyl)-7-(2,2,2-trifluoroethyl)-4-trifluoromethyl-7$H$-pyrrolo[3,2-$f$]quinolin-2(1$H$)-one;
5-Methyl-6-acetyl-7-(2,2,2-trifluoroethyl)-4-trifluoromethyl-7$H$-pyrrolo(3,2-$f$]quinolin-2(1$H$)-one;
5-Formyl-6-methyl-7-(2,2,2-trifluoroethyl)-4-trifluoromethyl-7$H$-pyrrolo[3,2-$f$] quinolin-2(1$H$)-one;
5-Acetyloxymethyl-6-ethyl-7-(2,2,2-trifluoroethyl)-4-trifluoromethyl-7$H$-pyrrolo[3,2-$f$] quinolin-2(1$H$)-one;
2-Acetyloxy-5-hydroxymethyl-6-ethyl-7-(2,2,2-trifluoroethyl)-4-trifluoromethyl-7$H$-pyrrolo(3,2-$f$]quinoline;

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

6-Ethyl-7-(2,2,2-trifluoroethyl)-4-trifluoromethyl-7*H*-pyrrolo[3,2-*f*]quinolin-2(1*H*)one;
5-Ethoxymethyl-6-ethyl-7-(2,2,2-trifluoroethyl)-4-trifluoromethyl-7*H*-pyrrolo[3,2-*f*]-
 quinolin-2(1*H*)-one;
(+)-6-(1-Methoxyethyl)-5-methyl-7-(2,2,2-trifluoroethyl)-4-trifluoromethyl-7*H*-pyrrolo
 [3,2-*f*]quinolin-2(1*H*)-one;
7-Allyl-6-methyl-4-trifluoromethyl-5*H*-pyrrolo[2,3-*f*]quinolin-2(1*H*)-one;
6-Ethyl-7-methyl-4-trifluoromethyl-5*H*-pyrrolo[2,3-*f*]quinolin-2(1*H*)-one;
7-(3 Trifluoromethylphenyl)-6-methyl-4-trifluoromethyl-5*H*-pyrrolo[2,3-*f*]quinolin-2
 (1*H*)-one;
7-(2-Hydroxyethyl)-6-methyl-4-trifluoromethyl-5*H*-pyrrolo[2,3-*f*]quinolin-2(1*H*)-one;
(+)-4c,5,6,7,7a(*cis*),8-Hexahydro-8-(2,2,2-trifluoroethyl)-4-trifluoromethyl-
 cyclopentano-[g]-pyrrolo[3,2-*f*]quinolin-2(1*H*)-one;
(–)-4c,5,6,7,7a(*cis*),8-Hexahydro-8-(2,2,2-trifluoroethyl)-4-
trifluoromethylcyclopentano-[g]-pyrrolo[3,2-*f*]quinolin-2(1*H*)-one;
(±)-5,6-Dihydro-6-hydroxymethyl-4-trifuoromethylpyrrolo[3,2-*f*]quinolin-2(1*H*)-one;
(±)-5,6-Dihydro-7-ethyl-6-hydroxymethyl-4-trifluoromethylpyrrolo[3,2-*f*]quinolin-2
 (1*H*)-one;
5-Methyl-7-(2,2,2-trifluoroethyl)-4-trifluoromethylpyrrolo[3,2-*f*]quinolin-2(1*H*)-one;
6-Formyl-5-methyl-7-(2,2,2-trifluoroethyl)-4-trifluoromethyl-7*H*-pyrrolo[3,2-*f*]
 quinolin-2(1*H*)-one; and
5,6-Dimethyl-7-(2,2-difluorovinyl)-4-trifluorolmethyl-7*H*-pyrrolo[3,2-*f*]quinolin-
 2(1*H*)-one.

Col. 84, line 1 should read
33. A compound according to claim 1, wherein said compound is selected from the group consisting of:
(±)-4c,5,6,7,7a(*cis*),8-Hexahydro-8-(2,2,2-trifluoroethyl)-4-
 trifluoromethylcyclopentano-[g]-pyrrolo-[3,2-*f*]quinolin-2(1*H*)-one;
(±)-4c,5,6,7,7a(*cis*),8-Hexahydro-8-ethyl-4-trifluoromethylcyclopentano-[g]pyrrolo
 [3,2-*f*]quinolin-2(1*H*)-one;
(±)-5,6-Dihydro-5,6-*cis*-dimethyl-7-(2,2,2-trifluoroethyl)-4-trifluoromethyl-7*H*-pyrrolo
 [3,2-*f*]-quinolin-2(1*H*)-one;
(±)-4c,5,6,7,7a(*cis*),8-Hexahydro-8-propyl-4-trifluoromethylcyclopentano-[g]pyrrolo-
 [3,2-*f*]quinolin-2(1*H*)-one;
(±)-4c,5,6,7,7a(*cis*),8-Hexahydro-8-(2,2,2-chlorodifluoroethyl)-4-trifuoromethylcyclo-
 pentano-[g]-pyrrolo[3,2-*f*]quinolin-2(1*H*)-one;
(±)-4c,5,6,7,7a(*cis*),8-Hexahydro-8 cyclopropylmethyl-4-trifluoromethylcyclopentano
 [g]pyrrolo[3,2-*f*]quinolin-2(1*H*)-one;

UNITED STATES PATENT AND TRADEMARK OFFICE
CERTIFICATE OF CORRECTION

PATENT NO.       : 7,026,484 B2
APPLICATION NO.  : 10/080926
DATED            : April 11, 2006
INVENTOR(S)      : Lin Zhi et al.

It is certified that error appears in the above-identified patent and that said Letters Patent is hereby corrected as shown below:

(±)4c,5,6,7,8,8a(*cis*)-Hexahydro-9-(2,2,2-trifluoroethyl)-4-trifluoromethyl-9*H*-cyclohexano[g]pyrrolo[3,2-*f*]quinolin-2(1*H*)-one;

(±)-5,6-*cis* -Dihydro-6-ethyl-5-methyl-7-(2,2,2-trifluoroethyl)-4-trifluorometbyl-7*H*-pyrrolo[3,2-*f*]quinolin-2(1*H*)-one;

(±)-5,6-*cis*-Dihydro-5-butyl-6-methyl-7-(2,2,2-trifluoroethyl)-4-trifluoromethyl-7*H*-pyrrolo[3,2-*f*]quinolin-2(1*H*)-one;

(±)-5,6-Dihydro-5-ethyl-6-methyl-7-(2,2,2-trifluoroethyl)-4-trifluoromethyl-7*H*-pyrrolo[3,2-*f*]quinolin-2(1*H*)-one;

(±)-5,6-Dihydro-5-ethyl-6-propyl-7-(2,2,2-trifluoroethyl)-4-trifluoromethyl-7*H*-pyrrolo[3,2-*f*]quinolin-2(1*H*)-one;

(±)-5,6-*cis*-Dihydro-5-methyl-6-ethyl-7-(2,2,2-trifluoroethyl)-7*H*-pyrrolo[3,2-*f*]-quinolin-2(1*H*)-one;

5,6-Dimethyl-7-(2,2,2-trifluoroethyl)-4-trifluoromethyl-7*H*-pyrrolo[3,2-*f*]quinolin-2(1*H*)-one;

6-Methyl-7-(2,2,2-trifluoroethyl)-4-trifluoromethyl-7*H*-pyrrolo[3,2-*f*]quinolin-2(1*H*)-one;

6-Ethyl-5-methyl-7-(2,2,2-trifluoroethyl)-4-trifluoromethyl-7*H*-pyrrolo[3,2-*f*]quinolin-2(1*H*)-one;

5-Ethyl-6-methyl-7-(2,2,2-trifluoroethyl)-4-trifluoromethyl-7*H*-pyrrolo[3,2-*f*]quinolin-2(1*H*)-one;

5,6,7,8-Tetrahydro-8-trifluoroethyl-4-trifluoromethylcyclopentano[g]pyrrolo[3,2-*f*]quinolin-2(1*H*)-one;

6-Ethyl-7-(2,2,2-trifluoroethyl)-4-trifluoromethyl-7*H*-pyrrolo[3,2-*f*]quinolin-2(1*H*)-one;

(+)-4c,5,6,7,7a(*cis*)8-Hexahydro-8-(2,2,2-trifluoroethyl)-trifluoromethylcyclopeatano-[g]pyrrolo[3,2-*f*]quinolin-2(1*H*)-one; and (−)-4c,5,6,7,7a(*cis*),8-Hexahydro-8-(2,2,2-trifluoroethyl)-4-trifluoromethylcyclopentano-[g]pyrrolo[3,2-*f*]quinolin-2(1*H*)-one;

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

Col. 84, line 64 should read
34. A pharmaceutical composition, comprising:
a pharmaceutically acceptable carrier; and
a compound of formula:

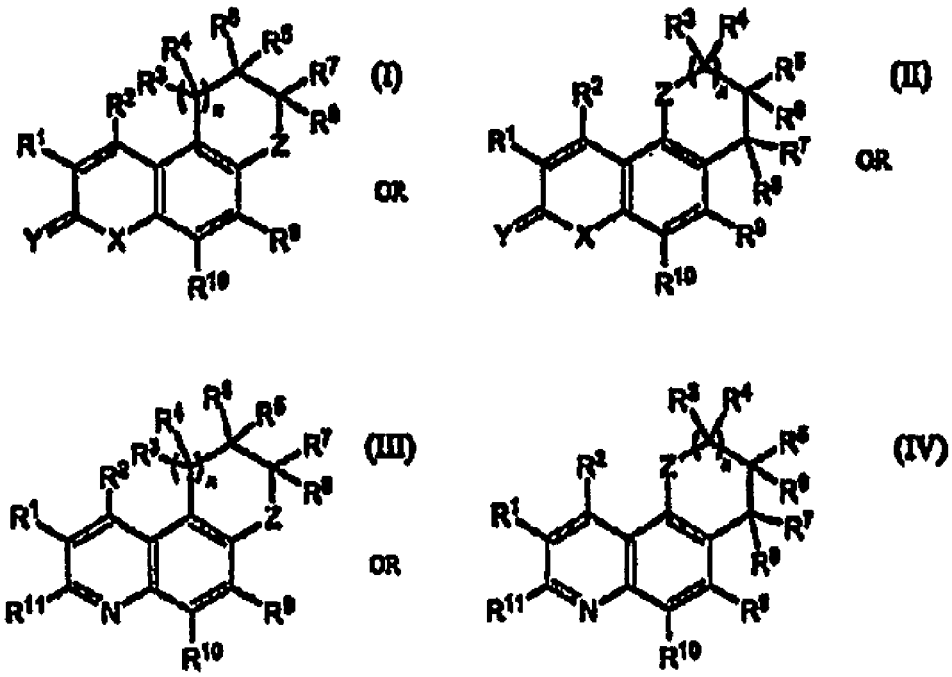

$R^6$ is selected from among hydrogen, $C_1$-$C_6$ alkyl, $C_1$-$C_6$ haloalkyl, $C_1$-$C_6$ heteroalkyl, heteroaryl and aryl, wherein the alkyl, haloalkyl, heteroalkyl, heteroaryl and aryl groups are optionally substituted;

$R^7$ is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted;

$R^8$ is selected from among hydrogen, $C_1$-$C_6$ alkyl, $C_1$-$C_6$ haloalkyl, $C_1$-$C_6$ heteroalkyl, heteroaryl and aryl, wherein the alkyl, haloalkyl, heteroalkyl, heteroaryl and aryl groups are optionally substituted; or $R^3$ and $R^5$ taken together form a bond; or $R^5$ and $R^7$ taken together form a bond; or $R^4$ and $R^6$ taken together form a three- to eight-membered saturated or unsaturated carbocyclic ring, wherein the carbocyclic ring is optionally substituted; or $R^6$ and $R^8$ taken together form a three- to eight-membered saturated or unsaturated carbocyclic ring, wherein the carbocyclic ring is optionally substituted;

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

$R^9$ and $R^{10}$ each independently is selected from among hydrogen, F, Cl, Br, I, CN, $OR^{12}$, $NR^{12}R^{13}$, $C_m(R^{12})_{2m}OR^{13}$, $SR^{12}$, $SOR^{12}$, $SO_2R^{12}$, $NR^{12}C(O)R^{13}$, $C_1$-$C_8$ alkyl, $C_1$-$C_8$ haloalkyl, $C_1$-$C_8$ heteroalkyl and arylalkyl, wherein the alkyl, haloalkyl, heteroalkyl and arylalkyl groups are optionally substituted;

$R^{11}$ is selected from among F, Br, Cl, I CN, $OR^{14}$, $NR^{14}R^{13}$ and $SR^{14}$;

$R^{12}$ and $R^{13}$ each independently is selected from among hydrogen, $C_1$-$C_8$ alkyl, $C_1$-$C_8$ haloalkyl, $C_1$-$C_8$ heteroalkyl, $C_2$-$C_8$ alkenyl, $C_2$-$C_8$ alkynyl, heteroaryl and aryl, wherein the alkyl, haloalkyl, heteroalkyl, alkenyl, alkynyl, heteroaryl and aryl groups are optionally substituted;

$R^{14}$ is selected from among hydrogen, $C_1$-$C_8$ alkyl, $C_1$-$C_8$ haloalkyl, $C_1$-$C_8$ heteroalkyl, aryl, heteroaryl, $C(O)R^{15}$, $CO_2R^{15}$ and $C(O)NR^{15}R^{16}$, wherein the alkyl, haloalkyl, heteroalkyl, aryl and heteroaryl groups are optionally substituted;

$R^{15}$ and $R^{16}$ each independently is selected from among hydrogen, $C_1$-$C_8$ alkyl, $C_1$-$C_8$ haloalkyl and $C_1$-$C_8$ heteroalkyl, wherein the alkyl, haloalkyl and heteroalkyl groups are optionally substituted;

W is O or S;
X is N $\{R^{14}\}$;
Y is selected from among O, S, N$\{R^{12}\}$ and NO$\{R^{12}\}$;
Z is N$\{R^{12}\}$;
n is 0; and
m is 0 or 1;
or a pharmaceutically acceptable salt thereof.

Signed and Sealed this

Twenty-eighth Day of August, 2007

JON W. DUDAS
*Director of the United States Patent and Trademark Office*

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

Col. 82, Line 13 should read
($\pm$)-4c,5,6,7,7a(*cis*),8-Hexahydro-8-(2-methylpropyl)-4-trifluoromethylcyclopentano
 [g]-pyrrolo[3,2-*f*]quinolin-2(1*H*)-one;
($\pm$)-4c,5,6,7,7a(*cis*),8-Hexahydro-8-(2,2,2-chlorodifluoro-ethyl)-4-
 trifluoromethylcyclopentano[g]pyrrolo[3,2-f]quinolin-2(1*H*)-one;
($\pm$)-4c,5,6,7,7a(*cis*),8-Hexahydro-8-cyclopropylmethyl-4-
 trifluoromethylcyclopentano[g]-pyrrolo[3,2-*f*]quinolin-2(1*H*)-one;
($\pm$)-4c,5,6,7,7a(*cis*),8-Hexahydro-8-(2,2-dimethoxyethyl)-4-trifluoromethylcyclo-
 pentano[g]pyrrolo[3,2-*f*]quinolin-2(1*H*)-one;
($\pm$)-4c,5,6,7,8,8a(*cis*)-Hexahydro-9-(2,2,2-trifuoroethyl)-4-trifluoromethyl-9*H*-
 cyclohexano[g]pyrrolo[3,2-*f*]quinolin-2(1*H*)-one;
($\pm$)-4c,5,6,7,8,9,9a(*cis*),10-Octahydro-10-(2,2,2-trifluoroethyl)-4-
 trifluoromethylcycloheptano[g]pyrrolo[3,2-*f*]quinolin-2(1*H*)-one;
($\pm$)-5,6-*cis*-Dihydro-6-ethyl-5-methyl-7-(2,2,2-trifluoroethyl)-4-trifluoromethyl-7*H*-
 pyrrolo[3,2-*f*]quinolin-2(1*H*)-one;
($\pm$)-5,6-*cis*-Dihydro-5-butyl-6-methyl-7-(2,2,2-trifluoroethyl)-4-trifluoromethyl-7*H*-
 pyrrolo[3,2-*f*]quinolin-2(1*H*)-one;
($\pm$)-5,6-*cis*-Dihydro-5-(4-nitrophenyl)-6-methyl-7-(2,2,2-trifluoroethyl)-4-
 trifluoromethyl-7*H*-pyrrolo[3,2-*f*]quinolin-2(1*H*)-one;
($\pm$)-5,6-*cis*-Dihydro-5-(4-dimethylaminophenyl)-6-methyl-7-(2,2,2-trifluoroethyl)4-
 trifluoromethyl-7*H*-pyrrolo[3,2-f]quinolin-2(1*H*)-one;
($\pm$)-5,6-*cis*-Dihydro-5-(4-methoxyphenyl)-6-methyl-7-(2,2,2-trifluoroethyl)4-
 trifluoromethyl-7*H*-pyrrolo[3,2-*f*]quinolin-2(1*H*)-one;
($\pm$)-5,6-*cis*-Dihydro-5-(3-trifluoromethylphenyl)-6-methyl-7-(2,2,2-trifluoroethyl)-4-
 trifluoromethyl-7*H*-pyrrolo[3,2-*f*]quinolin-2(1*H*)-one;
($\pm$)-5,6-*cis*-Dihydro-5-(4-fluorophenyl)-6-methyl-7-(2,2,2-trifluoroethyl)-4-
 trifluoromethyl-7*H*-pyrrolo[3,2-*f*]quinolin-2(1*H)*-one;
($\pm$)-5,6-Dihydro-5-phenyl-7-(2,2,2-trifluoroethyl)-4-trifluoromethyl-7*H*-pyrrolo-3,2-*f*]-
 quinolin-2(1*H*)-one;
($\pm$)-5,6-*cis*-Dihydro-5-(4-methoxyphenyl)-6-methyl-4-trifluoromethyl-7*H*-pyrrolo
 [3,2-*f*]-quinolin-2(1*H*)-one;
($\pm$)-5,6-*cis*-Dihydro-5-(4-methoxyphenyl)-6-methyl-7-(2,2-dimethoxyethyl)-4-
 trifluoromethyl-7*H*-pyrrolo[3,2-f]quinolin-2(1*H*)-one;
($\pm$)-5,6-*cis*-Dihydro-5-isopropyl-6-methyl-7-(2,2,2-trifluoroethyl)-4-trifluoromethyl-
 7*H*-pyrrolo[3,2-*f*]quinolin-2(1*H*)-one;

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

(±)-5,6-Dihydro-5-ethyl-6-methyl-7-(2,2,2-trifluoroethyl)-4-trifluoromethyl-7*H*-pyrrolo-[3,2-*f*]quinolin-2(1*H*)-one;
(±)-5,6-Dihydro-5-ethyl-6-propyl-7-(2,2,2-trifluoroethyl)-4-trifluoromethyl-7*H*-pyrrolo-[3,2-*f*]quinolin-2(1*H*)-one;
(±)-5,6-Dihydro-5-(2-ethoxycarbonylethyl)-6-methyl-7-(2,2,2-trifluoroethyl)-4-trifluoromethyl-7*H*-pyrrolo[3,2-*f*]quinolin-2(1*H*)-one;
5,6-Dimethyl-7-(2,2,2-trifluoroethyl)-4-trifluoromethyl-7*H*-pyrrolo[3,2-*f*]quinolin-2(1*H*)-one;
6-Methyl-7-(2,2,2-trifluoroethyl)-4-trifluoromethyl-7*H*-pyrrolo[3,2-f]quinolin-2(1*H*) one;
6-Ethyl-5-methyl-7-(2,2,2-trifluoroethyl)-4-trifluoromethyl-7*H*-pyrrolo[3,2-*f*]quinolin-2(1*H*)-one;
5-Ethyl-6-methyl-7-(2,2,2-trifluoroethyl)-4-trifluoromethyl-7*H*-pyrrolo[3,2-*f*]quinolin-2(1*H*)-one;
5-Ethyl-6-propyl-7-(2,2,2-trifluoroethyl)-4-trifluoromethyl-7*H*-pyrrolo[3,2-*f*]quinolin-2(1*H*)-one;
5,6,7,8-Tetrahydro-8-(2,2,2-trifluoroethyl)-4-trifluoromethylcyclopentano[g]-pyrrolo[3,2-*f*]-quinolin-2(1*H*)-one;
8-Trifluoroethyl-4-trifluoromethyl-6,8-dihydrocyclopentano[g]pyrrolo[3,2-*f*]quinolin-2(1*H*)-one;
9-Trifluoroethyl-trifluoromethyl-9*H*-benzo[g]pyrrolo[3,2-*f*]quinolin-2(1*H*)-one;
5-(3-Trifluoromethylphenyl)-6-methyl-7-(2,2,2-trifluoroethyl)-4-trifluoromethyl-7*H*-pyrrolo[3,2-*f*]quinolin-2(1*H*)-one;
5-(4-Fluorophenyl)-6-methyl-7-(2,2,2-trifluoroethyl)-4-trifluoromethyl-7*H*-pyrrolo[3,2-*f*]quinolin-2(1*H*)-one;
5-(2-Ethoxycarbonylethyl)-6-methyl-7-(2,2,2-trifluoroethyl)-4-trifluoromethyl-7*H*-pyrrolo[3,2-*f*]quinolin-2(1*H*)-one;
5-Hydroxymethyl-6-ethyl-7-(2,2,2-trifluoroethyl)-4-trifluoromethyl-7*H*-pyrrolo[3,2-*f*]-quinolin-2(1*H*)-one;
5-Methyl-6-(1-hydroxyethyl)-7-(2,2,2-trifluoroethyl)-4-trifluoromethyl-7*H*-pyrrolo[3,2-*f*]quinolin-2(1*H*)-one;
5-Methyl-6-acetyl-7-(2,2,2-trifluoroethyl)-4-trifluoromethyl-7*H*-pyrrolo[3,2-*f*]quinolin-2(1*H*)-one;
5-Formyl-6-methyl-7-(2,2,2-trifluoroethyl)-4-trifluoromethyl-7*H*-pyrrolo[3,2-*f*]quinolin-2(1*H*)-one;
5-Acetyloxymethyl-6-ethyl-7-(2,2,2-trifluoroethyl)-4-trifluoromethyl-7*H*-pyrrolo[3,2-*f*]quinolin-2(1*H*)-one;
2-Acetyloxy-5-hydroxymethyl-6-ethyl-7-(2,2,2-trifluoroethyl)-4-trifluoromethyl-7*H*-pyrrolo(3,2-*f*]quinoline;

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

6-Ethyl-7-(2,2,2-trifluoroethyl)-4-trifluoromethyl-7*H*-pyrrolo[3,2-*f*]quinolin-2(1*H*)one;
5-Ethoxymethyl-6-ethyl-7-(2,2,2-trifluoroethyl)-4-trifluoromethyl-7*H*-pyrrolo[3,2-*f*]-
  quinolin-2(1*H*)-one;
(+)-6-(1-Methoxyethyl)-5-methyl-7-(2,2,2-trifluoroethyl)-4-trifluoromethyl-7*H*-pyrrolo
  [3,2-*f*]quinolin-2(1*H*)-one;
7-Allyl-6-methyl-4-trifluoromethyl-5*H*-pyrrolo[2,3-*f*]quinolin-2(1*H*)-one;
6-Ethyl-7-methyl-4-trifluoromethyl-5*H*-pyrrolo[2,3-*f*]quinolin-2(1*H*)-one;
7-(3-Trifluoromethylphenyl)-6-methyl-4-trifluoromethyl-5*H*-pyrrolo[2,3-*f*]quinolin-2
  (1*H*)-one;
7-(2-Hydroxyethyl)-6-methyl-4-trifluoromethyl-5*H*-pyrrolo[2,3-*f*]quinolin-2(1*H*)-one;
(+)-4c,5,6,7,7a(*cis*),8-Hexahydro-8-(2,2,2-trifluoroethyl)-4-trifluoromethyl-
  cyclopentano-[g]-pyrrolo[3,2-*f*]quinolin-2(1*H*)-one;
(–)-4c,5,6,7,7a(*cis*),8-Hexahydro-8-(2,2,2-trifluoroethyl)-4-
trifluoromethylcyclopentano-[g]-pyrrolo[3,2-*f*]quinolin-2(1*H*)-one;
(±)-5,6-Dihydro-6-hydroxymethyl-4-trifuoromethylpyrrolo[3,2-*f*]quinolin-2(1*H*)-one;

(±)-5,6-Dihydro-7-ethyl-6-hydroxymethyl-4-trifluoromethylpyrrolo[3,2-*f*]quinolin-2
  (1*H*)-one;
5-Methyl-7-(2,2,2-trifluoroethyl)-4-trifluoromethylpyrrolo[3,2-*f*]quinolin-2(1*H*)-one;
6-Formyl-5-methyl-7-(2,2,2-trifluoroethyl)-4-trifluoromethyl-7*H*-pyrrolo[3,2-*f*]
  quinolin-2(1*H*)-one; and
5,6-Dimethyl-7-(2,2-difluorovinyl)-4-trifluorolmethyl-7*H*-pyrrolo[3,2-*f*]quinolin-
  2(1*H*)-one.

Col. 84, line 1 should read
33. A compound according to claim 1, wherein said compound is selected from the
group consisting of:
(±)-4c,5,6,7,7a(*cis*),8-Hexahydro-8-(2,2,2-trifluoroethyl)-4-
  trifluoromethylcyclopentano-[g]-pyrrolo-[3,2-*f*]quinolin-2(1*H*)-one;
(±)-4c,5,6,7,7a(*cis*),8-Hexahydro-8-ethyl-4-trifluoromethylcyclopentano-[g]pyrrolo
  [3,2-*f*]quinolin-2(1*H*)-one;
(±)-5,6-Dihydro-5,6-*cis*-dimethyl-7-(2,2,2-trifluoroethyl)-4-trifluoromethyl-7*H*-pyrrolo
  [3,2-*f*]-quinolin-2(1*H*)-one;
(±)-4c,5,6,7,7a(*cis*),8-Hexahydro-8-propyl-4-trifluoromethylcyclopentano-[g]pyrrolo-
  [3,2-*f*]quinolin-2(1*H*)-one;
(±)-4c,5,6,7,7a(*cis*),8-Hexahydro-8-(2,2,2-chlorodifluoroethyl)-4-trifluoromethylcyclo-
  pentano-[g]-pyrrolo[3,2-*f*]quinolin-2(1*H*)-one;
(±)-4c,5,6,7,7a(*cis*),8-Hexahydro-8 cyclopropylmethyl-4-trifluoromethylcyclopentano
  [g]pyrrolo[3,2-*f*]quinolin-2(1*H*)-one;

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

($\pm$)4c,5,6,7,8,8a(*cis*)-Hexahydro-9-(2,2,2-trifluoroethyl)-4-trifluoromethyl-9*H*-cyclohexano[g]pyrrolo[3,2-*f*]quinolin-2(1*H*)-one;

($\pm$)-5,6-*cis* -Dihydro-6-ethyl-5-methyl-7-(2,2,2-trifluoroethyl)-4-trifluoromethyl-7*H*-pyrrolo[3,2-*f*]quinolin-2(1*H*)-one;

($\pm$)-5,6-*cis*-Dihydro-5-butyl-6-methyl-7-(2,2,2-trifluoroethyl)-4-trifluoromethyl-7*H*-pyrrolo[3,2-*f*]quinolin-2(1*H*)-one;

($\pm$)-5,6-Dihydro-5-ethyl-6-methyl-7-(2,2,2-trifluoroethyl)-4-trifluoromethyl-7*H*-pyrrolo[3,2-*f*]quinolin-2(1*H*)-one;

($\pm$)-5,6-Dihydro-5-ethyl-6-propyl-7-(2,2,2-trifluoroethyl)-4-trifluoromethyl-7*H*-pyrrolo[3,2-*f*]quinolin-2(1*H*)-one;

($\pm$)-5,6-*cis*-Dihydro-5-methyl-6-ethyl-7-(2,2,2-trifluoroethyl)-7*H*-pyrrolo[3,2-*f*]-quinolin-2(1*H*)-one;

5,6-Dimethyl-7-(2,2,2-trifluoroethyl)-4-trifluoromethyl-7*H*-pyrrolo[3,2-*f*]quinolin-2(1*H*)-one;

6-Methyl-7-(2,2,2-trifluoroethyl)-4-trifluoromethyl-7*H*-pyrrolo[3,2-*f*]quinolin-2(1*H*)-one;

6-Ethyl-5-methyl-7-(2,2,2-trifluoroethyl)-4-trifluoromethyl-7*H*-pyrrolo[3,2-*f*]quinolin-2(1*H*)-one;

5-Ethyl-6-methyl-7-(2,2,2-trifluoroethyl)-4-trifluoromethyl-7*H*-pyrrolo[3,2-*f*]quinolin-2(1*H*)-one;

5,6,7,8-Tetrahydro-8-trifluoroethyl-4-trifluoromethylcyclopentano[g]pyrrolo[3,2-*f*]quinolin-2(1*H*)-one;

6-Ethyl-7-(2,2,2-trifluoroethyl)-4-trifluoromethyl-7*H*-pyrrolo[3,2-*f*]quinolin-2(1*H*)-one;

(+)-4c,5,6,7,7a(*cis*)8-Hexahydro-8-(2,2,2-trifluoroethyl)-4-trifluoromethylcyclopentano-[g]pyrrolo[3,2-*f*]quinolin-2(1*H*)-one; and (−)-4c,5,6,7,7a(*cis*),8-Hexahydro-8-(2,2,2-trifluoroethyl)-4-trifluoromethylcyclopentano-[g]pyrrolo[3,2-*f*]quinolin-2(1*H*)-one.

UNITED STATES PATENT AND TRADEMARK OFFICE
CERTIFICATE OF CORRECTION

PATENT NO.        : 7,026,484 B2
APPLICATION NO. : 10/080926
DATED              : April 11, 2006
INVENTOR(S)      : Lin Zhi et al.

It is certified that error appears in the above-identified patent and that said Letters Patent is hereby corrected as shown below:

Col. 84, line 64 should read
34. A pharmaceutical composition, comprising:
a pharmaceutically acceptable carrier; and
a compound of formula:

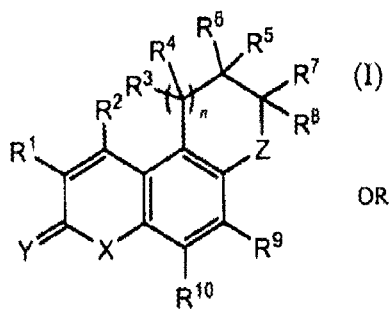

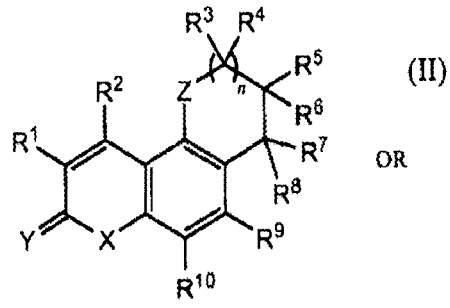

OR

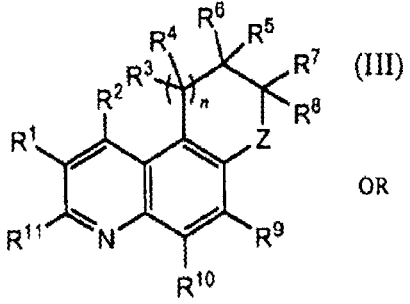

OR

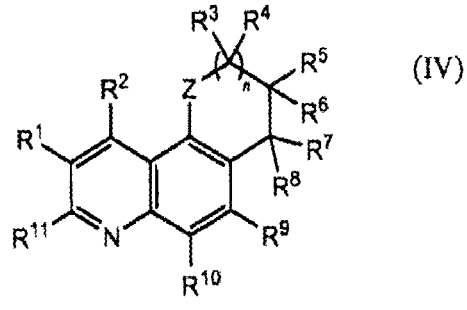

wherein:
$R^1$ is selected from among hydrogen, F, Cl, Br, I, $NO_2$, $OR^{12}$, $SR^{12}$, $SOR^{12}$, $SO_2R^{12}$, $NR^{12}R^{13}$, $C_1$-$C_8$ alkyl, $C_1$-$C_8$ haloalkyl and $C_1$-$C_8$ heteroalkyl, wherein the alkyl, haloalkyl and heteroalkyl groups are optionally substituted;
$R^2$ is selected from among F, Cl, Br, I, $CF_3$, $CHF_2$, $CH_2F$, $CH_2Cl$, CN, $CF_2OR^{12}$, $CH_2OR^{12}$, $OR^{12}$, $SR^{12}$, $SOR^{12}$, $SO_2R^{12}$, $NR^{12}R^{13}$, substituted $C_1$-$C_8$ alkyl, $C_1$-$C_8$ haloalkyl, $C_1$-$C_8$ heteroalkyl, $C_2$-$C_8$ alkenyl and $C_2$-$C_8$ alkynyl, wherein the haloalkyl, heteroalkyl, alkenyl and alkynyl groups are optionally substituted;

UNITED STATES PATENT AND TRADEMARK OFFICE
CERTIFICATE OF CORRECTION

| | |
|---|---|
| PATENT NO. | : 7,026,484 B2 |
| APPLICATION NO. | : 10/080926 |
| DATED | : April 11, 2006 |
| INVENTOR(S) | : Lin Zhi et al. |

It is certified that error appears in the above-identified patent and that said Letters Patent is hereby corrected as shown below:

$R^3$ is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted;

$R^4$ is selected from among hydrogen, F, Cl, Br, I, $OR^{12}$, $NR^{12}R^{13}$, $SR^{12}$, $SOR^{12}$, $SO_2R^{12}$, $C_1$-$C_8$ alkyl, $C_1$-$C_8$ haloalkyl, $C_1$-$C_8$ heteroalkyl, $C_2$-$C_8$ alkynyl, $C_2$-$C_8$ alkenyl, aryl, heteroaryl and arylalkyl, wherein the alkyl, haloalkyl, heteroalkyl, alkynyl, alkenyl, aryl, heteroaryl and arylalkyl groups are optionally substituted;

$R^5$ is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted;

$R^6$ is selected from among hydrogen, F, Cl, Br, I, $OR^{12}$, $NR^{12}R^{13}$, $SR^{12}$, $SOR^{12}$, $SO_2R^{12}$, $C_1$-$C_8$ alkyl, $C_1$-$C_8$ haloalkyl, $C_1$-$C_8$ heteroalkyl, $C_2$-$C_8$ alkynyl, $C_2$-$C_8$ alkenyl, aryl, heteroaryl and arylalkyl, wherein the alkyl, haloalkyl, heteroalkyl, alkynyl, alkenyl, aryl, heteroaryl and arylalkyl groups are optionally substituted;

$R^7$ is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted;

$R^8$ is selected from among hydrogen, F, Cl, Br, I, $OR^{12}$, $NR^{12}R^{13}$, $SR^{12}$, $SOR^{12}$, $SO_2R^{12}$, $C_1$-$C_8$ alkyl, $C_1$-$C_8$ haloalkyl, $C_1$-$C_8$ heteroalkyl, $C_2$-$C_8$ alkynyl, $C_2$-$C_8$ alkenyl, aryl, heteroaryl and arylalkyl, wherein the alkyl, haloalkyl, heteroalkyl, alkynyl, alkenyl, aryl, heteroaryl and arylalkyl groups are optionally substituted; or $R^3$ and $R^5$ taken together form a bond; or $R^5$ and $R^7$ taken together form a bond; or $R^4$ and $R^6$ taken together form a three- to eight-membered saturated or unsaturated carbocyclic ring, wherein the carbocyclic ring is optionally substituted; or $R^6$ and $R^8$ taken together form a three- to eight-membered saturated or unsaturated carbocyclic ring, wherein the carbocyclic ring is optionally substituted;

$R^9$ and $R^{10}$ each independently is selected from among hydrogen, F, Cl, Br, I, CN, $OR^{12}$, $NR^{12}R^{13}$, $C_m(R^{12})_{2m}OR^{13}$, $SR^{12}$, $SOR^{12}$, $SO_2R^{12}$, $NR^{12}C(O)R^{13}$, $C_1$-$C_8$ alkyl, $C_1$-$C_8$ haloalkyl, $C_1$-$C_8$ heteroalkyl and arylalkyl, wherein the alkyl, haloalkyl, heteroalkyl and arylalkyl groups are optionally substituted;

$R^{11}$ is selected from among F, Br, Cl, I CN, $OR^{14}$, $NR^{14}R^{13}$ and $SR^{14}$;

$R^{12}$ and $R^{13}$ each independently is selected from among hydrogen, $C_1$-$C_8$ alkyl, $C_1$-$C_8$ haloalkyl, $C_1$-$C_8$ heteroalkyl, $C_2$-$C_8$ alkenyl, $C_2$-$C_8$ alkynyl, heteroaryl and aryl, wherein the alkyl, haloalkyl, heteroalkyl, alkenyl, alkynyl, heteroaryl and aryl groups are optionally substituted;

UNITED STATES PATENT AND TRADEMARK OFFICE
CERTIFICATE OF CORRECTION

PATENT NO.       : 7,026,484 B2
APPLICATION NO.  : 10/080926
DATED            : April 11, 2006
INVENTOR(S)      : Lin Zhi et al.

It is certified that error appears in the above-identified patent and that said Letters Patent is hereby corrected as shown below:

$R^{14}$ is selected from among hydrogen, $C_1$-$C_8$ alkyl, $C_1$-$C_8$ haloalkyl, $C_1$-$C_8$ heteroalkyl, aryl, heteroaryl, $C(O)R^{15}$, $CO_2R^{15}$ and $C(O)NR^{15}R^{16}$, wherein the alkyl, haloalkyl, heteroalkyl, aryl and heteroaryl groups are optionally substituted;

$R^{15}$ and $R^{16}$ each independently is selected from among hydrogen, $C_1$-$C_8$ alkyl, $C_1$-$C_8$ haloalkyl and $C_1$-$C_8$ heteroalkyl, wherein the alkyl, haloalkyl and heteroalkyl groups are optionally substituted;

W is O or S;
X is N $\{R^{14}\}$;
Y is selected from among O, S, $N\{R^{12}\}$ and $NO\{R^{12}\}$;
Z is $N\{R^{12}\}$;
n is 0; and
m is 0 or 1;
or a pharmaceutically acceptable salt thereof.

This certificate supersedes the Certificate of Correction issued August 28, 2007.

Signed and Sealed this

Sixth Day of January, 2009

JON W. DUDAS
*Director of the United States Patent and Trademark Office*

UNITED STATES PATENT AND TRADEMARK OFFICE
CERTIFICATE OF CORRECTION

PATENT NO. : 7,026,484 B2  
APPLICATION NO. : 10/080926  
DATED : April 11, 2006  
INVENTOR(S) : Lin Zhi et al.

It is certified that error appears in the above-identified patent and that said Letters Patent is hereby corrected as shown below:

IN THE TITLE PAGES:

Item [56] References Cited, in OTHER PUBLICATIONS:  
in Yudin, please replace "Geterotsikicheskikh" with --Geterotsiklicheskikh--  
in the first Yamashkin et al., please replace "Chemistry.of" with --Chemistry of--  
in Edwards, J., et al., please replace "(1999)" with --(1998)--  
in Boyer, M., please replace "http://www.australianprescriber.com/magazines/vol19no1/ap19-1-11.htm(accessed on Jan. 28, 2005." with --http://www.australianprescriber.com/magazines/vol19no1/ap19-1-11.htm (accessed on Jan. 28, 2005).--  
in Castillo, P., please replace "o-dihdroxyaromatic" with --o-dihydroxyaromatic--

IN THE SPECIFICATION:

In column 2, beginning at line 7, please replace formulas I-VIII with:

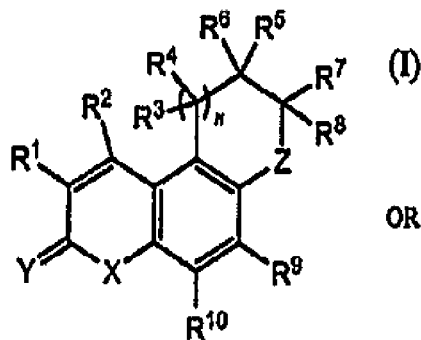
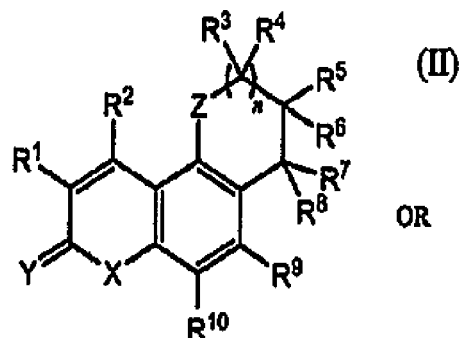
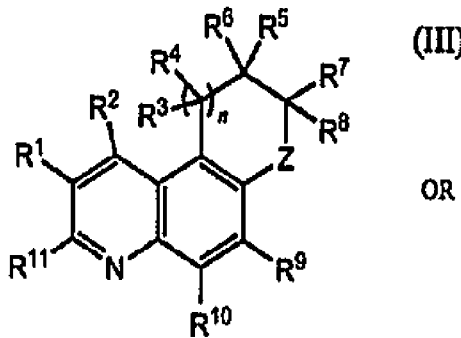
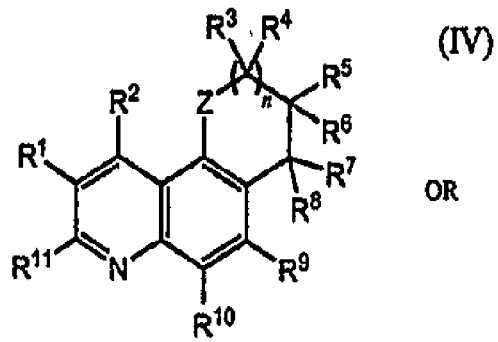

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

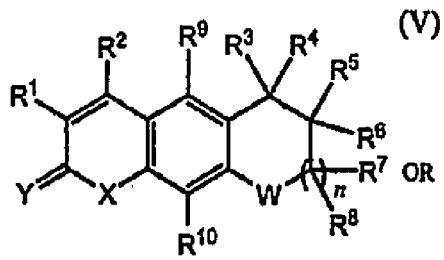
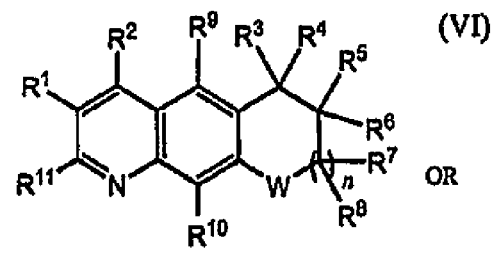
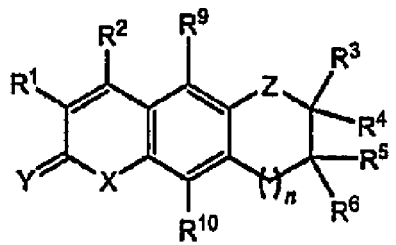
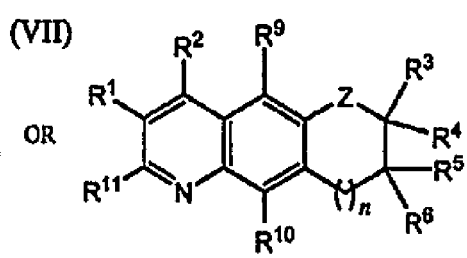

in column 7, beginning at line 15, please replace formulas I-VIII with:

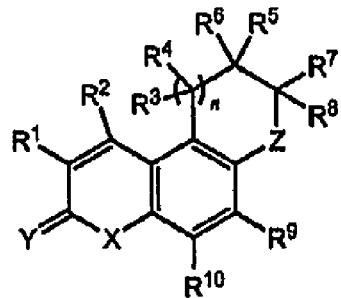
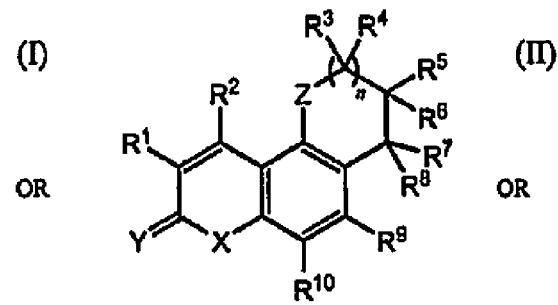
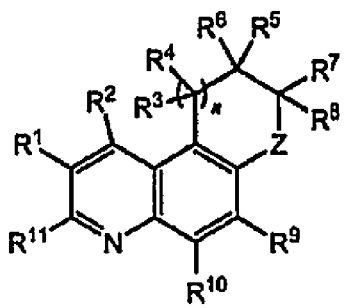
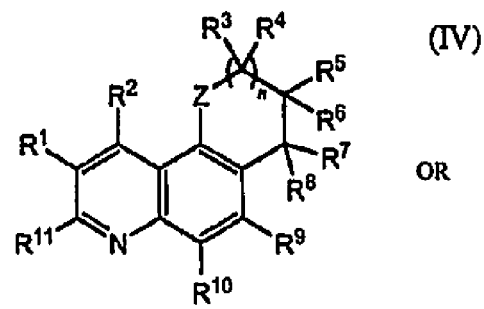

UNITED STATES PATENT AND TRADEMARK OFFICE
CERTIFICATE OF CORRECTION

PATENT NO. : 7,026,484 B2  Page 3 of 17
APPLICATION NO. : 10/080926
DATED : April 11, 2006
INVENTOR(S) : Lin Zhi et al.

It is certified that error appears in the above-identified patent and that said Letters Patent is hereby corrected as shown below:

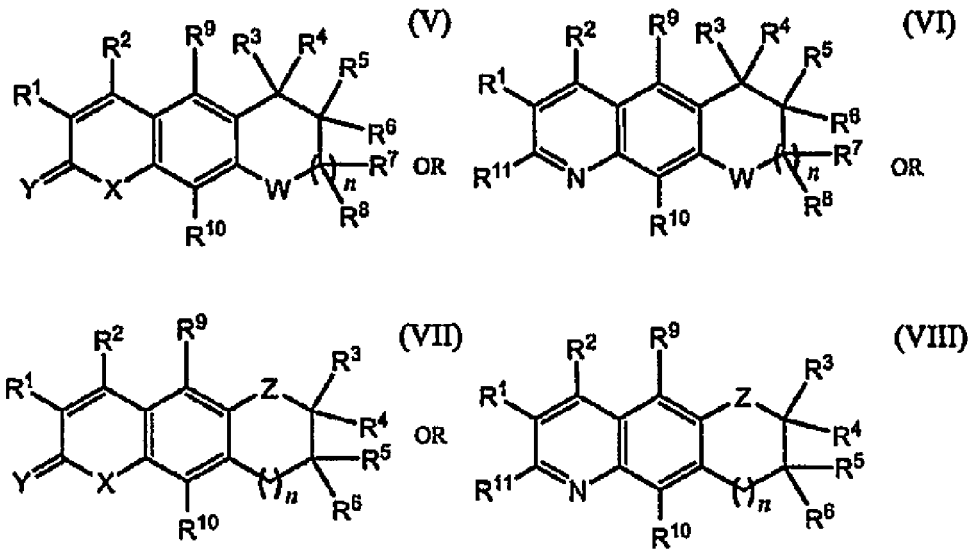

in column 24, lines 53-67, please replace the structures in Scheme II with:

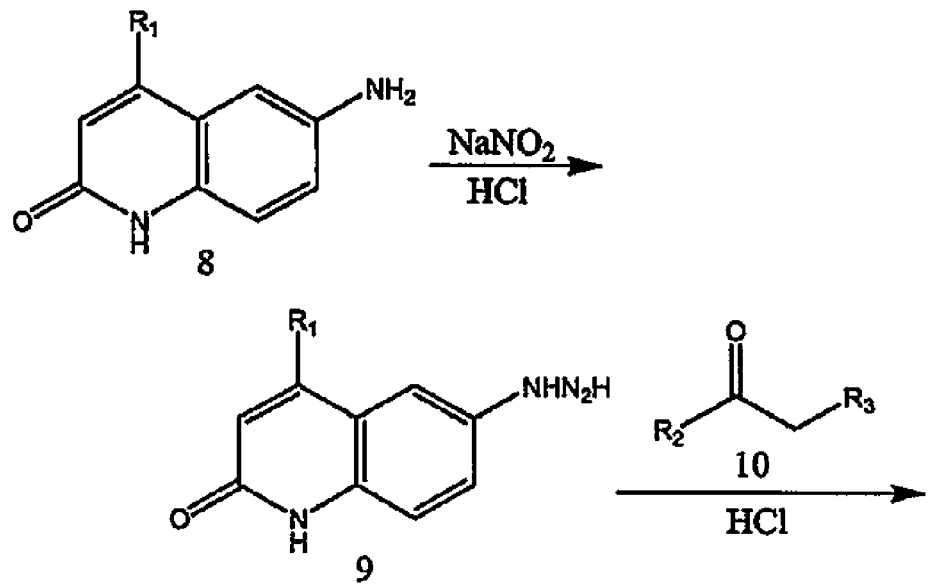

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

in column 57, lines 4-6, please replace
"(Compound 177, Structure 26 of Scheme IV, where $R_2$=methyl. $R_3$=2-hydroxyethyl" with --(Compound 177, Structure 26 of Scheme IV, where $R_2$=methyl, $R_3$=2-hydroxyethyl-- in column 70, line 21, please replace "chloronation" with --chlorination--

IN THE CLAIMS:
Please replace Claims 1, 4, 26, 28, 29, 30, 32, 33, 34, 42, 43, 50, 52, 53, and 60 with the following Claims:

1. A compound of the formula:

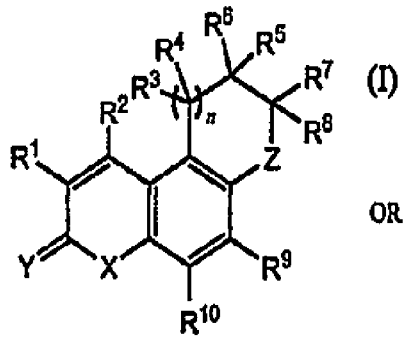
(I)

OR

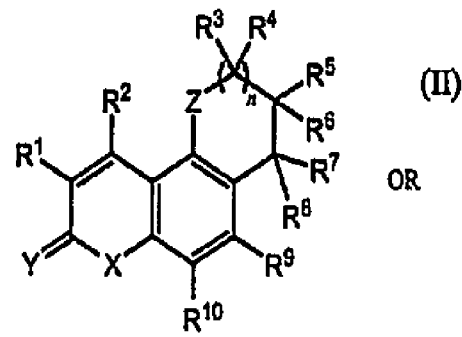
(II)

OR

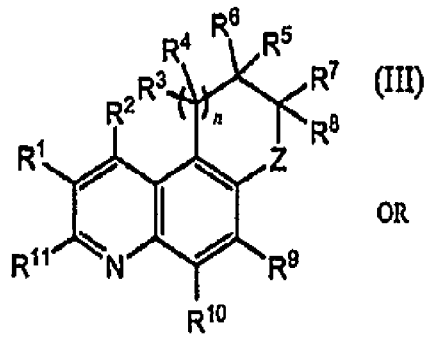
(III)

OR

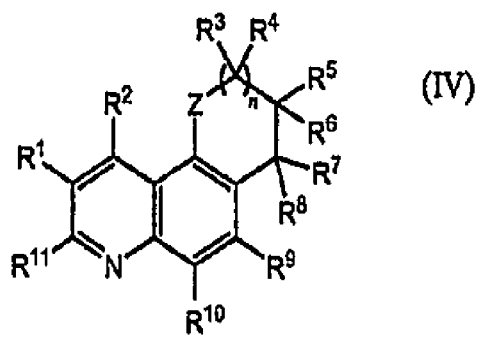
(IV)

UNITED STATES PATENT AND TRADEMARK OFFICE
CERTIFICATE OF CORRECTION

| | |
|---|---|
| PATENT NO. | : 7,026,484 B2 |
| APPLICATION NO. | : 10/080926 |
| DATED | : April 11, 2006 |
| INVENTOR(S) | : Lin Zhi et al. |

It is certified that error appears in the above-identified patent and that said Letters Patent is hereby corrected as shown below:

wherein:

$R^1$ is selected from among hydrogen, F, Cl, Br, I, $NO_2$, $OR^{12}$, $SR^{12}$, $SOR^{12}$, $SO_2R^{12}$, $NR^{12}R^{12}$, substituted $C_1$-$C_8$ alkyl, $C_1$-$C_8$ haloalkyl and $C_1$-$C_8$ heteroalkyl, wherein the haloalkyl and heteroalkyl groups are optionally substituted;

$R^2$ is selected from among F, Cl, Br, I, $CF_3$, $CHF_2$, $CH_2F$, $CF_2Cl$, CN, $CF_2OR^{12}$, $CH_2OR^{12}$, $OR^{12}$, $SR^{12}$, $SOR^{12}$, $SO_2R^{12}$, $NR^{12}R^{13}$, substituted $C_1$-$C_8$ alkyl, $C_1$-$C_8$ haloalkyl, $C_1$-$C_8$ heteroalkyl, $C_2$-$C_8$ alkenyl and $C_2$-$C_8$ alkynyl, wherein the haloalkyl, heteroalkyl, alkenyl and alkynyl groups are optionally substituted;

$R^3$ is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted;

$R^4$ is selected from among hydrogen F, Cl, Br, I, $OR^{12}$, $NR^{12}R^{13}$, $SR^{12}$, $SOR^{12}$, $SO_2R^{12}$, $C_1$-$C_8$ alkyl, $C_1$-$C_8$ haloalkyl, $C_1$-$C_8$ heteroalkyl, $C_2$-$C_8$ alkynyl, $C_2$-$C_8$ alkenyl, aryl, heteroaryl and arylalkyl wherein the alkyl, haloalkyl, heteroalkyl, alkynyl, alkenyl, aryl, heteroaryl and arylalkyl groups are optionally substituted;

$R^5$ is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted;

$R^6$ is selected from among hydrogen F, Cl, Br, I, $OR^{12}$, $NR^{12}R^{13}$, $SR^{12}$, $SOR^{12}$, $SO_2R^{12}$, $C_1$-$C_8$ alkyl, $C_1$-$C_8$ haloalkyl, $C_1$-$C_8$ heteroalkyl, $C_2$-$C_8$ alkynyl, $C_2$-$C_8$ alkenyl, aryl, heteroaryl and arylalkyl, wherein the alkyl, haloalkyl, heteroalkyl, alkynyl, alkenyl, aryl, heteroaryl and arylalkyl groups are optionally substituted;

$R^7$ is selected from among hydrogen, $C_1$-$C_6$ alkyl, $C_1$-$C_6$ haloalkyl and $C_1$-$C_6$ heteroalkyl, wherein the alkyl, haloalkyl, and heteroalkyl groups are optionally substituted;

$R^8$ is selected from among hydrogen F, Cl, Br, I, $OR^{12}$, $NR^{12}R^{13}$, $SR^{12}$, $SOR^{12}$, $SO_2R^{12}$, $C_1$-$C_8$ alkyl, $C_1$-$C_8$ haloalkyl, $C_1$-$C_8$ heteroalkyl, $C_2$-$C_8$ alkynyl, $C_2$-$C_8$ alkenyl, aryl, heteroaryl and arylalkyl, wherein the alkyl, haloalkyl, heteroalkyl, alkynyl, alkenyl, aryl, heteroaryl and arylalkyl groups are optionally substituted; or $R^3$ and $R^5$ taken together form a bond; or $R^5$ and $R^7$ taken together form a bond; or $R^4$ and $R^6$ taken together form a three- to eight-membered saturated or unsaturated carbocyclic ring, wherein the carbocyclic ring is optionally substituted; or $R^6$ and $R^8$ taken together form a three- to eight-membered saturated or unsaturated carbocyclic ring, wherein the carbocyclic ring is optionally substituted;

$R^9$ and $R^{10}$ each independently is selected from among hydrogen, F, Cl, Br, I, CN, $OR^{12}$, $NR^{12}R^{13}$, $C_m(R^{12})_{2m}OR^{13}$, $SR^{12}$, $SOR^{12}$, $SO_2R^{12}$, $NR^{12}C(O)R^{13}$, $C_1$-$C_8$ alkyl, $C_1$-$C_8$ haloalkyl, $C_1$-$C_8$ heteroalkyl and arylalkyl, wherein the alkyl, haloalkyl, heteroalkyl and arylalkyl groups are optionally substituted;

$R^{11}$ is selected from F, Br, Cl, I, CN, $OR^{14}$, $NR^{14}R^{13}$, and $SR^{14}$;

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

$R^{12}$ and $R^{13}$ each independently is selected from the group of hydrogen, $C_1$-$C_8$ alkyl, $C_1$-$C_8$ haloalkyl, $C_1$-$C_8$ heteroalkyl, $C_2$-$C_8$ alkenyl, $C_2$-$C_8$ alkynyl, heteroaryl and aryl wherein the alkyl, haloalkyl, heteroalkyl, alkenyl, alkynyl, heteroaryl and aryl groups are optionally substituted;

$R^{14}$ is selected from among hydrogen, $C_1$-$C_8$ alkyl, $C_1$-$C_8$ haloalkyl, $C_1$-$C_8$ heteroalkyl, aryl, heteroaryl, $C(O)R^{15}$, $CO_2R^{15}$ and $C(O)NR^{15}R^{16}$, wherein the alkyl, haloalkyl, heteroalkyl, aryl and heteroaryl groups are optionally substituted;

$R^{15}$ and $R^{16}$ each independently is selected from among hydrogen, $C_1$-$C_8$ alkyl, $C_1$-$C_8$ haloalkyl, $C_1$-$C_8$ heteroalkyl, wherin the alkyl, haloalkyl and heteroalkyl groups are optionally substituted;

W is O or S;
X is N $\{R^{14}\}$;
Y is seleted from among O, S, N$\{R^{12}\}$ and NO$\{R^{12}\}$;
Z is N$\{R^{12}\}$;
n is 0; and
m is 0 or 1;
or a pharmaceutically acceptable salt thereof.

4. A compound according to claim 1, wherein $R^2$ is selected from among F, Cl, Br, $CF_3$, $CF_2Cl$, $CF_2H$, $CFH_2$, substituted $C_1$-$C_4$ alkyl, $C_1$-$C_4$ haloalkyl, $C_1$-$C_4$ heteroalkyl, $C_2$-$C_4$ alkenyl and $C_2$-$C_4$ alkynyl, wherein the haloalkyl, heteroalkyl, alkenyl and alkynyl groups are optionally substituted.

26. A compound according to claim 1, wherein:
$R^6$ and $R^8$ each indepentently is selected from among hydrogen, $C_1$-$C_6$ alkyl, $C_1$-$C_6$ haloalkyl, $C_1$-$C_6$ heteroalkyl, heteroaryl and aryl, wherein the alkyl, haloalkyl, heteroalkyl, heteroaryl and aryl groups are optionally substituted; or
$R^6$ and $R^8$ taken together form a three to eight membered saturated or unsaturated carbocyclic ring, wherein the carbocyclic ring is optionally substituted.

28. A compound according to claim 1, wherein:
$R^1$ is selected from among hydrogen, F, Cl, Br, I, substituted $C_1$-$C_6$ alkyl, $C_1$-$C_6$ haloalkyl and $C_1$-$C_6$ heteroalkyl, wherein the haloalkyl and heteroalkyl groups are optionally substituted;
$R^2$ is selected from among F, Cl, Br, $CF_3$, $CF_2Cl$, $CF_2H$, $CFH_2$, substituted $C_1$-$C_6$ alkyl, $C_1$-$C_6$ haloalkyl and $C_1$-$C_6$ heteroalkyl, wherein haloalkyl and heteroalkyl groups are optionally substituted; and
$R^3$ and $R^4$ each independently is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted.

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

29. A compound according to claim 28, wherein
$R^5$ through $R^8$ each independently is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted; or
$R^6$ and $R^8$ taken together form a four to six membered saturated or unsaturated carbocyclic ring, wherein the carbocyclic ring is optionally substituted.

30. A compound according to claim 29, wherein:
$R^9$ and $R^{10}$ each independently is selected from among hydrogen, F, Cl, Br, $C_1$-$C_6$ alkyl, $C_1$-$C_6$ haloalkyl and $C_1$-$C_6$ heteroalkyl, wherein the alkyl, haloalkyl and heteroalkyl groups are optionally substituted;
$R^{12}$ is selected from among hydrogen, $C_1$-$C_6$ alkyl, $C_1$-$C_6$ haloalkyl, $C_1$-$C_6$ heteroalkyl, $C_2$-$C_6$ alkenyl, $C_2$-$C_6$ alkynyl, heteroaryl and aryl, wherein the alkyl, haloalkyl, heteroalkyl, alkenyl, alkynyl, heteroaryl and aryl groups are optionally substituted; and
$R^{14}$ is selected from among hydrogen, $C_1$-$C_6$ alkyl, $C_1$-$C_6$ haloalkyl and $C_1$-$C_6$ heteroalkyl, $C(O)R^{15}$, $CO_2R^{15}$ and $C(O)NR^{15}R^{16}$, wherein the alkyl, haloalkyl and heteroalkyl groups are optionally substituted.

32. A compound according to claim 1, wherein said compound is selected from among:
6-Methyl-4-trifluoromethyl-7*H*-pyrrolo[3,2-*f*]quinolin-2(1*H*)-one;
5-Isopropyl-6-methyl-4-trifluoromethyl-7*H*-pyrrolo[3,2-*f*]quinolin-2(1*H*)-one;
5-Allyl-6-methyl-4-trifluoromethyl-7*H*-pyrrolo[3,2-*f*]quinolin-2(1*H*)-one;
5-(4-Methoxyphenyl)-6-methyl-4-trifluoromethyl-7*H*-pyrrolo[3,2-*f*]quinolin-2(1*H*)-one;
5-(3-Trifluoromethylphenyl)-6-methyl-4-trifluoromethyl-7*H*-pyrrolo[3,2-*f*]quinolin-2
    (1*H*)-one;
4-Trifluoromethyl-5,6,7,8-tetrahydrocyclopentano[g]pyrrolo[3,2-*f*]quinolin-2(1*H*)-one;
4-Trifluoromethyl-5,6,7,8,9,10-hexahydrocycloheptano[g]pyrrolo[3,2-*f*]quinolin-2(1*H*)-
    one;
(±)-4c,5,6,7,7a(*cis*),8-Hexahydro-8-trifluoroethyl-4-
    trifluoromethylcyclopentano[g]pyrrolo-[3,2-*f*]quinolin-2(1*H*)-one;
(±)-4c,5,6,7,7a(*cis*),8-Hexahydro-8-ethyl-4-
    trifluoromethylcyclopentano-[g]pyrrolo[3,2-*f*]-quinolin-2(1*H*)-one;
(±)-5,6-Dihydro-5,6-*cis*-dimethyl-7-(2,2,2-trifluoroethyl)-4-
    trifluoromethyl-7*H*-pyrrolo[3,2-*f*]-quinolin-2(1*H*)-one;
(±)-4c,5,6,7,7a(*cis*),8-Hexahydro-8-propyl-4-trifluoromethylcyclopentano-[g]pyrrolo-
    [3,2-*f*]quinolin-2(1*H*)-one;
(±)-4c,5,6,7,7a(*cis*),8-Hexahydro-8-(3-furanylmethyl)-4-trifluoromethylcyclopentano
    [g]-pyrrolo[3,2-*f*]quinolin-2(1*H*)-one;
(±)-4c,5,6,7,7a(*cis*),8-Hexahydro-8-(3-thiophenemethyl)-4-
    trifluoromethylcyclopentano[g]-pyrrolo[3,2-*f*]quinolin-2(1*H*)-one;

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

Col. 82, Line 13 should read
(±)-4c,5,6,7,7a(*cis*),8-Hexahydro-8-(2-methylpropyl)-4-trifluoromethylcyclopentano
 [g]-pyrrolo[3,2-*f*]quinolin-2(1*H*)-one;
(±)-4c,5,6,7,7a(*cis*),8-Hexahydro-8-(2,2,2-chlorodifluoro-ethyl)-4-
 trifluoromethylcyclopentano[g]pyrrolo[3,2-f]quinolin-2(1*H*)-one;
(±)-4c,5,6,7,7a(*cis*),8-Hexahydro-8-cyclopropylmethyl-4-
 trifluoromethylcyclopentano[g]-pyrrolo[3,2-*f*]quinolin-2(1*H*)-one;
(±)-4c,5,6,7,7a(*cis*),8-Hexahydro-8-(2,2-dimethoxyethyl)-4-trifluoromethylcyclo-
 pentano[g]pyrrolo[3,2-*f*]quinolin-2(1*H*)-one;
(±)-4c,5,6,7,8,8a(*cis*)-Hexahydro-9-(2,2,2-trifuoroethyl)-4-trifluoromethyl-9*H*-
 cyclohexano[g]pyrrolo[3,2-*f*]quinolin-2(1*H*)-one;
(±)-4c,5,6,7,8,9,9a(*cis*),10-Octahydro-10-(2,2,2-trifluoroethyl)-4-
 trifluoromethylcycloheptano[g]pyrrolo[3,2-*f*]quinolin-2(1*H*)-one;
(±)-5,6-*cis*-Dihydro-6-ethyl-5-methyl-7-(2,2,2-trifluoroethyl)-4-trifluoromethyl-7*H*-
 pyrrolo[3,2-*f*]quinolin-2(1*H*)-one;
(±)-5,6-*cis*-Dihydro-5-butyl-6-methyl-7-(2,2,2-trifluoroethyl)-4-trifluoromethyl-7*H*-
 pyrrolo[3,2-*f*]quinolin-2(1*H*)-one;
(±)-5,6-*cis*-Dihydro-5-(4-nitrophenyl)-6-methyl-7-(2,2,2-trifluoroethyl)-4-
 trifluoromethyl-7*H*-pyrrolo[3,2-*f*]quinolin-2(1*H*)-one;
(±)-5,6-*cis*-Dihydro-5-(4-dimethylaminophenyl)-6-methyl-7-(2,2,2-trifluoroethyl)4-
 trifluoromethyl-7*H*-pyrrolo[3,2-f]quinolin-2(1*H*)-one;
(±)-5,6-*cis*-Dihydro-5-(4-methoxyphenyl)-6-methyl-7-(2,2,2-trifluoroethyl)4-
 trifluoromethyl-7*H*-pyrrolo[3,2-*f*]quinolin-2(1*H*)-one;
(±)-5,6-*cis*-Dihydro-5-(3-trifluoromethylphenyl)-6-methyl-7-(2,2,2-trifluoroethyl)-4-
 trifluoromethyl-7*H*-pyrrolo[3,2-*f*]quinolin-2(1*H*)-one;
(±)-5,6-*cis*-Dihydro-5-(4-fluorophenyl)-6-methyl-7-(2,2,2-trifluoroethyl)-4-
 trifluoromethyl-7*H*-pyrrolo[3,2-*f*]quinolin-2(1*H)*-one;
(±)-5,6-Dihydro-5-phenyl-7-(2,2,2-trifluoroethyl)-4-trifluoromethyl-7*H*-pyrrolo-3,2-*f*]-
 quinolin-2(1*H*)-one;
(±)-5,6-*cis*-Dihydro-5-(4-methoxyphenyl)-6-methyl-4-trifluoromethyl-7*H*-pyrrolo
 [3,2-*f*]-quinolin-2(1*H*)-one;
(±)-5,6-*cis*-Dihydro-5-(4-methoxyphenyl)-6-methyl-7-(2,2-dimethoxyethyl)-4-
 trifluoromethyl-7*H*-pyrrolo[3,2-f]quinolin-2(1*H*)-one;
(±)-5,6-*cis*-Dihydro-5-isopropyl-6-methyl-7-(2,2,2-trifluoroethyl)-4-trifluoromethyl-
 7*H*-pyrrolo[3,2-*f*]quinolin-2(1*H*)-one;

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

(±)-5,6-Dihydro-5-ethyl-6-methyl-7-(2,2,2-trifluoroethyl)-4-trifluoromethyl-7*H*-pyrrolo-[3,2-*f*]quinolin-2(1*H*)-one;
(±)-5,6-Dihydro-5-ethyl-6-propyl-7-(2,2,2-trifluoroethyl)-4-trifluoromethyl-7*H*-pyrrolo-[3,2-*f*]quinolin-2(1*H*)-one;
(±)-5,6-Dihydro-5-(2-ethoxycarbonylethyl)-6-methyl-7-(2,2,2-trifluoroethyl)-4-trifluoromethyl-7*H*-pyrrolo[3,2-*f*]quinolin-2(1*H*)-one;
5,6-Dimethyl-7-(2,2,2-trifluoroethyl)-4-trifluoromethyl-7*H*-pyrrolo[3,2-*f*]quinolin-2(1*H*)-one;
6-Methyl-7-(2,2,2-trifluoroethyl)-4-trifluoromethyl-7*H*-pyrrolo[3,2-f]quinolin-2(1*H*) one;
6-Ethyl-5-methyl-7-(2,2,2-trifluoroethyl)-4-trifluoromethyl-7*H*-pyrrolo[3,2-*f*]quinolin-2 (1*H*)-one;
5-Ethyl-6-methyl-7-(2,2,2-trifluoroethyl)-4-trifluoromethyl-7*H*-pyrrolo[3,2-*f*]quinolin-2 (1*H*)-one;
5-Ethyl-6-propyl-7-(2,2,2-trifluoroethyl)-4-trifluoromethyl-7*H*-pyrrolo[3,2-*f*]quinolin-2 (1*H*)-one;
5,6,7,8-Tetrahydro-8-(2,2,2-trifluoroethyl)-4-trifluoromethylcyclopentano[g]-pyrrolo [3,2-*f*]-quinolin-2(1*H*)-one;
8-Trifluoroethyl-4-trifluoromethyl-6,8-dihydrocyclopentano[g]pyrrolo[3,2-*f*]quinolin-2 (1*H*)-one;
9-Trifluoroethyl-trifluoromethyl-9*H*-benzo[g]pyrrolo[3,2-*f*]quinolin-2(1*H*)-one;
5-(3-Trifluoromethylphenyl)-6-methyl-7-(2,2,2-trifluoroethyl)-4-trifluoromethyl-7*H*-pyrrolo[3,2-*f*]quinolin-2(1*H*)-one;
5-(4-Fluorophenyl)-6-methyl-7-(2,2,2-trifluoroethyl)-4-trifluoromethyl-7*H*-pyrrolo[3,2-*f*]quinolin-2(1*H*)-one;
5-(2-Ethoxycarbonylethyl)-6-methyl-7-(2,2,2-trifluoroethyl)-4-trifluoromethyl-7*H*-pyrrolo[3,2-*f*]quinolin-2(1*H*)-one;
5-Hydroxymethyl-6-ethyl-7-(2,2,2-trifluoroethyl)-4-trifluoromethyl-7*H*-pyrrolo[3,2-*f*]-quinolin-2(1*H*)-one;
5-Methyl-6-(1-hydroxyethyl)-7-(2,2,2-trifluoroethyl)-4-trifluoromethyl-7*H*-pyrrolo[3,2-*f*]quinolin-2(1*H*)-one;
5-Methyl-6-acetyl-7-(2,2,2-trifluoroethyl)-4-trifluoromethyl-7*H*-pyrrolo[3,2-*f*]quinolin-2(1*H*)-one;
5-Formyl-6-methyl-7-(2,2,2-trifluoroethyl)-4-trifluoromethyl-7*H*-pyrrolo[3,2-*f*] quinolin-2(1*H*)-one;
5-Acetyloxymethyl-6-ethyl-7-(2,2,2-trifluoroethyl)-4-trifluoromethyl-7*H*-pyrrolo[3,2-*f*] quinolin-2(1*H*)-one;
2-Acetyloxy-5-hydroxymethyl-6-ethyl-7-(2,2,2-trifluoroethyl)-4-trifluoromethyl-7*H*-pyrrolo(3,2-*f*]quinoline;

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

6-Ethyl-7-(2,2,2-trifluoroethyl)-4-trifluoromethyl-7*H*-pyrrolo[3,2-*f*]quinolin-2(1*H*)one;
5-Ethoxymethyl-6-ethyl-7-(2,2,2-trifluoroethyl)-4-trifluoromethyl-7*H*-pyrrolo[3,2-*f*]-
    quinolin-2(1*H*)-one;
(+)-6-(1-Methoxyethyl)-5-methyl-7-(2,2,2-trifluoroethyl)-4-trifluoromethyl-7*H*-pyrrolo
    [3,2-*f*]quinolin-2(1*H*)-one;
7-Allyl-6-methyl-4-trifluoromethyl-5*H*-pyrrolo[2,3-*f*]quinolin-2(1*H*)-one;
6-Ethyl-7-methyl-4-trifluoromethyl-5*H*-pyrrolo[2,3-*f*]quinolin-2(1*H*)-one;
7-(3-Trifluoromethylphenyl)-6-methyl-4-trifluoromethyl-5*H*-pyrrolo[2,3-*f*]quinolin-2
    (1*H*)-one;
7-(2-Hydroxyethyl)-6-methyl-4-trifluoromethyl-5*H*-pyrrolo[2,3-*f*]quinolin-2(1*H*)-one;
(+)-4c,5,6,7,7a(*cis*),8-Hexahydro-8-(2,2,2-trifluoroethyl)-4-trifluoromethyl-
    cyclopentano-[g]-pyrrolo[3,2-*f*]quinolin-2(1*H*)-one;
(−)-4c,5,6,7,7a(*cis*),8-Hexahydro-8-(2,2,2-trifluoroethyl)-4-
trifluoromethylcyclopentano-[g]-pyrrolo[3,2-*f*]quinolin-2(1*H*)-one;
(±)-5,6-Dihydro-6-hydroxymethyl-4-trifuoromethylpyrrolo[3,2-*f*]quinolin-2(1*H*)-one;
(±)-5,6-Dihydro-7-ethyl-6-hydroxymethyl-4-trifluoromethylpyrrolo[3,2-*f*]quinolin-2
    (1*H*)-one;
5-Methyl-7-(2,2,2-trifluoroethyl)-4-trifluoromethylpyrrolo[3,2-*f*]quinolin-2(1*H*)-one;
6-Formyl-5-methyl-7-(2,2,2-trifluoroethyl)-4-trifluoromethyl-7*H*-pyrrolo[3,2-*f*]
    quinolin-2(1*H*)-one; and
5,6-Dimethyl-7-(2,2-difluorovinyl)-4-trifluorolmethyl-7*H*-pyrrolo[3,2-*f*]quinolin-
    2(1*H*)-one.

Col. 84, line 1 should read
33. A compound according to claim 1, wherein said compound is selected from the group consisting of:
(±)-4c,5,6,7,7a(*cis*),8-Hexahydro-8-(2,2,2-trifluoroethyl)-4-
    trifluoromethylcyclopentano-[g]-pyrrolo-[3,2-*f*]quinolin-2(1*H*)-one;
(±)-4c,5,6,7,7a(*cis*),8-Hexahydro-8-ethyl-4-trifluoromethylcyclopentano-[g]pyrrolo
    [3,2-*f*]quinolin-2(1*H*)-one;
(±)-5,6-Dihydro-5,6-*cis*-dimethyl-7-(2,2,2-trifluoroethyl)-4-trifluoromethyl-7*H*-pyrrolo
    [3,2-*f*]-quinolin-2(1*H*)-one;
(±)-4c,5,6,7,7a(*cis*),8-Hexahydro-8-propyl-4-trifluoromethylcyclopentano-[g]pyrrolo-
    [3,2-*f*]quinolin-2(1*H*)-one;
(±)-4c,5,6,7,7a(*cis*),8-Hexahydro-8-(2,2,2-chlorodifluoroethyl)-4-trifluoromethylcyclo-
    pentano-[g]-pyrrolo[3,2-*f*]quinolin-2(1*H*)-one;
(±)-4c,5,6,7,7a(*cis*),8-Hexahydro-8 cyclopropylmethyl-4-trifluoromethylcyclopentano
    [g]pyrrolo[3,2-*f*]quinolin-2(1*H*)-one;

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

(±)4c,5,6,7,8,8a(*cis*)-Hexahydro-9-(2,2,2-trifluoroethyl)-4-trifluoromethyl-9*H*-cyclohexano[g]pyrrolo[3,2-*f*]quinolin-2(1*H*)-one;

(±)-5,6-*cis* -Dihydro-6-ethyl-5-methyl-7-(2,2,2-trifluoroethyl)-4-trifluoromethyl-7*H*-pyrrolo[3,2-*f*]quinolin-2(1*H*)-one;

(±)-5,6-*cis*-Dihydro-5-butyl-6-methyl-7-(2,2,2-trifluoroethyl)-4-trifluoromethyl-7*H*-pyrrolo[3,2-*f*]quinolin-2(1*H*)-one;

(±)-5,6-Dihydro-5-ethyl-6-methyl-7-(2,2,2-trifluoroethyl)-4-trifluoromethyl-7*H*-pyrrolo[3,2-*f*]quinolin-2(1*H*)-one;

(±)-5,6-Dihydro-5-ethyl-6-propyl-7-(2,2,2-trifluoroethyl)-4-trifluoromethyl-7*H*-pyrrolo[3,2-*f*]quinolin-2(1*H*)-one;

(±)-5,6-*cis*-Dihydro-5-methyl-6-ethyl-7-(2,2,2-trifluoroethyl)-7*H*-pyrrolo[3,2-*f*]-quinolin-2(1*H*)-one;

5,6-Dimethyl-7-(2,2,2-trifluoroethyl)-4-trifluoromethyl-7*H*-pyrrolo[3,2-*f*]quinolin-2(1*H*)-one;

6-Methyl-7-(2,2,2-trifluoroethyl)-4-trifluoromethyl-7*H*-pyrrolo[3,2-*f*]quinolin-2(1*H*)-one;

6-Ethyl-5-methyl-7-(2,2,2-trifluoroethyl)-4-trifluoromethyl-7*H*-pyrrolo[3,2-*f*]quinolin-2(1*H*)-one;

5-Ethyl-6-methyl-7-(2,2,2-trifluoroethyl)-4-trifluoromethyl-7*H*-pyrrolo[3,2-*f*]quinolin-2(1*H*)-one;

5,6,7,8-Tetrahydro-8-trifluoroethyl-4-trifluoromethylcyclopentano[g]pyrrolo[3,2-*f*]quinolin-2(1*H*)-one;

6-Ethyl-7-(2,2,2-trifluoroethyl)-4-trifluoromethyl-7*H*-pyrrolo[3,2-*f*]quinolin-2(1*H*)-one;

(+)-4c,5,6,7,7a(*cis*)8-Hexahydro-8-(2,2,2-trifluoroethyl)-4-trifluoromethylcyclopentano-[g]pyrrolo[3,2-*f*]quinolin-2(1*H*)-one; and (−)-4c,5,6,7,7a(*cis*),8-Hexahydro-8-(2,2,2-trifluoroethyl)-4-trifluoromethylcyclopentano-[g]pyrrolo[3,2-*f*]quinolin-2(1*H*)-one.

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

Col. 84, line 64 should read
34. A pharmaceutical composition, comprising:
a pharmaceutically acceptable carrier; and
a compound of formula:

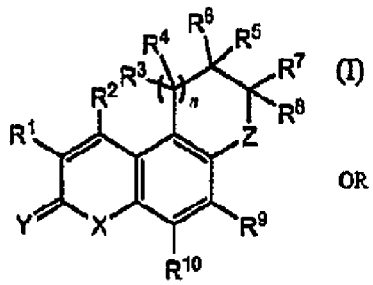 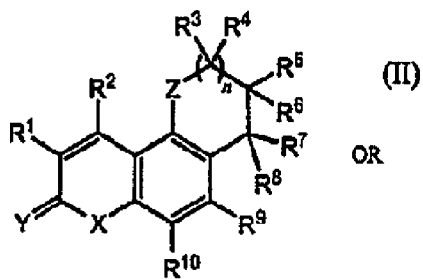

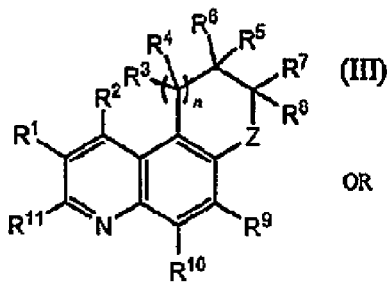 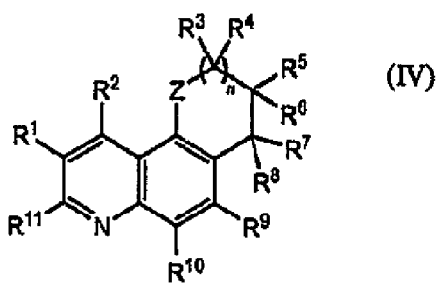

wherein:
$R^1$ is selected from among hydrogen, F, Cl, Br, I, $NO_2$, $OR^{12}$, $SR^{12}$, $SOR^{12}$, $SO_2R^{12}$, $NR^{12}R^{13}$, $C_1$-$C_8$ alkyl, $C_1$-$C_8$ haloalkyl and $C_1$-$C_8$ heteroalkyl, wherein the alkyl, haloalkyl and heteroalkyl groups are optionally substituted;

$R^2$ is selected from among F, Cl, Br, I, $CF_3$, $CHF_2$, $CH_2F$, $CH_2Cl$, CN, $CF_2OR^{12}$, $CH_2OR^{12}$, $OR^{12}$, $SR^{12}$, $SOR^{12}$, $SO_2R^{12}$, $NR^{12}R^{13}$, substituted $C_1$-$C_8$ alkyl, $C_1$-$C_8$ haloalkyl, $C_1$-$C_8$ heteroalkyl, $C_2$-$C_8$ alkenyl and $C_2$-$C_8$ alkynyl, wherein the haloalkyl, heteroalkyl, alkenyl and alkynyl groups are optionally substituted;

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

$R^3$ is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted;

$R^4$ is selected from among hydrogen, F, Cl, Br, I, $OR^{12}$, $NR^{12}R^{13}$, $SR^{12}$, $SOR^{12}$, $SO_2R^{12}$, $C_1$-$C_8$ alkyl, $C_1$-$C_8$ haloalkyl, $C_1$-$C_8$ heteroalkyl, $C_2$-$C_8$ alkynyl, $C_2$-$C_8$ alkenyl, aryl, heteroaryl and arylalkyl, wherein the alkyl, haloalkyl, heteroalkyl, alkynyl, alkenyl, aryl, heteroaryl and arylalkyl groups are optionally substituted;

$R^5$ is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted;

$R^6$ is selected from among hydrogen, F, Cl, Br, I, $OR^{12}$, $NR^{12}R^{13}$, $SR^{12}$, $SOR^{12}$, $SO_2R^{12}$, $C_1$-$C_8$ alkyl, $C_1$-$C_8$ haloalkyl, $C_1$-$C_8$ heteroalkyl, $C_2$-$C_8$ alkynyl, $C_2$-$C_8$ alkenyl, aryl, heteroaryl and arylalkyl, wherein the alkyl, haloalkyl, heteroalkyl, alkynyl, alkenyl, aryl, heteroaryl and arylalkyl groups are optionally substituted;

$R^7$ is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted;

$R^8$ is selected from among hydrogen, F, Cl, Br, I, $OR^{12}$, $NR^{12}R^{13}$, $SR^{12}$, $SOR^{12}$, $SO_2R^{12}$, $C_1$-$C_8$ alkyl, $C_1$-$C_8$ haloalkyl, $C_1$-$C_8$ heteroalkyl, $C_2$-$C_8$ alkynyl, $C_2$-$C_8$ alkenyl, aryl, heteroaryl and arylalkyl, wherein the alkyl, haloalkyl, heteroalkyl, alkynyl, alkenyl, aryl, heteroaryl and arylalkyl groups are optionally substituted; or $R^3$ and $R^5$ taken together form a bond; or $R^5$ and $R^7$ taken together form a bond; or $R^4$ and $R^6$ taken together form a three- to eight-membered saturated or unsaturated carbocyclic ring, wherein the carbocyclic ring is optionally substituted; or $R^6$ and $R^8$ taken together form a three- to eight-membered saturated or unsaturated carbocyclic ring, wherein the carbocyclic ring is optionally substituted;

$R^9$ and $R^{10}$ each independently is selected from among hydrogen, F, Cl, Br, I, CN, $OR^{12}$, $NR^{12}R^{13}$, $C_m(R^{12})_{2m}OR^{13}$, $SR^{12}$, $SOR^{12}$, $SO_2R^{12}$, $NR^{12}C(O)R^{13}$, $C_1$-$C_8$ alkyl, $C_1$-$C_8$ haloalkyl, $C_1$-$C_8$ heteroalkyl and arylalkyl, wherein the alkyl, haloalkyl, heteroalkyl and arylalkyl groups are optionally substituted;

$R^{11}$ is selected from among hydrogen, F, Br, Cl, I, CN, $OR^{14}$, $NR^{14}R^{13}$ and $SR^{14}$;

$R^{12}$ and $R^{13}$ each independently is selected from among hydrogen, $C_1$-$C_8$ alkyl, $C_1$-$C_8$ haloalkyl, $C_1$-$C_8$ heteroalkyl, $C_2$-$C_8$ alkenyl, $C_2$-$C_8$ alkynyl, heteroaryl and aryl, wherein the alkyl, haloalkyl, heteroalkyl, alkenyl, alkynyl, heteroaryl and aryl groups are optionally substituted;

UNITED STATES PATENT AND TRADEMARK OFFICE
CERTIFICATE OF CORRECTION

| | | |
|---|---|---|
| PATENT NO. | : 7,026,484 B2 | |
| APPLICATION NO. | : 10/080926 | |
| DATED | : April 11, 2006 | |
| INVENTOR(S) | : Lin Zhi et al. | |

It is certified that error appears in the above-identified patent and that said Letters Patent is hereby corrected as shown below:

$R^{14}$ is selected from among hydrogen, $C_1$-$C_8$ alkyl, $C_1$-$C_8$ haloalkyl, $C_1$-$C_8$ heteroalkyl, aryl, heteroaryl, $C(O)R^{15}$, $CO_2R^{15}$ and $C(O)NR^{15}R^{16}$, wherein the alkyl, haloalkyl, heteroalkyl, aryl and heteroaryl groups are optionally substituted;

$R^{15}$ and $R^{16}$ each independently is selected from among hydrogen, $C_1$-$C_8$ alkyl, $C_1$-$C_8$ haloalkyl and $C_1$-$C_8$ heteroalkyl, wherein the alkyl, haloalkyl and heteroalkyl groups are optionally substituted;

W is O or S;

X is N $\{R^{14}\}$;

Y is seleted from among O, S, N$\{R^{12}\}$ and N$\{OR^{12}\}$;

Z is N$\{R^{12}\}$;

n is 0; and m is 0 or 1;

or a pharmaceutically acceptable salt thereof.

42. A pharmaceutical composition according to claim 34, wherein $R^{11}$ is selected from among F, Cl, CN, $OR^{14}$, $NR^{14}R^{13}$ and $SR^{14}$.

43. A pharmaceutical composition according to claim 42, wherein $R^{11}$ is selected from among F, Cl, $OR^{14}$, $SR^{14}$, $NR^{14}R^{13}$.

50. A pharmaceutical composition according to claim 49, wherein:

$R^5$ through $R^8$ each independently is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted; or $R^6$ and $R^8$ taken together form a four to six membered saturated or unsaturated carbocyclic ring, wherein the carbocyclic ring is optionally substituted.

52. A pharmaceutical composition according to claim 51 wherein Y is O or S.

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

53. A compound of formula:

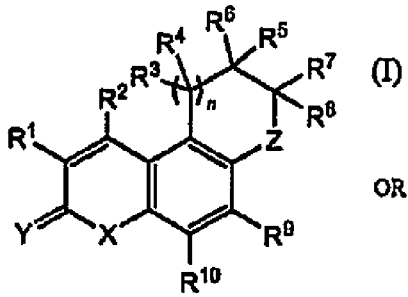 (I)

OR

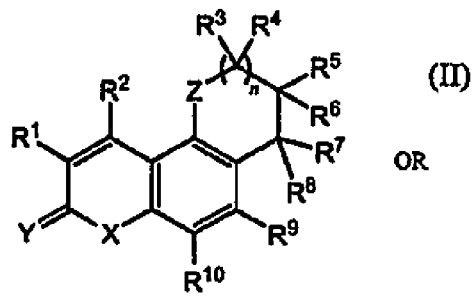 (II)

OR

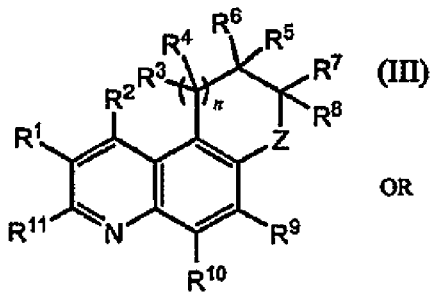 (III)

OR

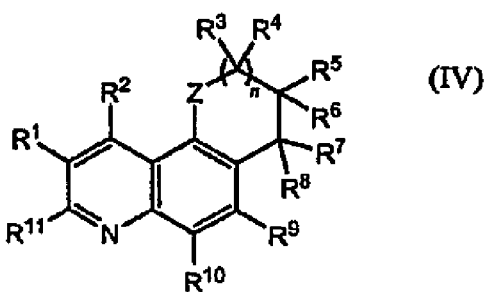 (IV)

wherein:

$R^1$ is selected from among hydrogen, F, Cl, Br, I, $NO_2$, $OR^{12}$, $SR^{12}$, $SOR^{12}$, $SO_2R^{12}$, $NR^{12}R^{12}$, $C_1$-$C_8$ alkyl, $C_1$-$C_8$ haloalkyl and $C_1$-$C_8$ heteroalkyl, wherein the alkyl, haloalkyl and heteroalkyl groups are optionally substituted;

$R^2$ is selected from among F, Cl, Br, $CF_3$, $CHF_2$, $CH_2F$, $CF_2Cl$, $CF_2OR^{12}$, $CH_2OR^{12}$, $OR^{12}$, $SR^{12}$, $SOR^{12}$, $SO_2R^{12}$, $NR^{12}R^{13}$, substituted $C_1$-$C_6$ alkyl, $C_1$-$C_6$ haloalkyl and $C_1$-$C_6$ heteroalkyl, wherein the haloalkyl, and heteroalkyl groups are optionally substituted;

$R^3$ is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted;

$R^4$ is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted;

$R^5$ is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted;

UNITED STATES PATENT AND TRADEMARK OFFICE
CERTIFICATE OF CORRECTION

| | |
|---|---|
| PATENT NO. | : 7,026,484 B2 |
| APPLICATION NO. | : 10/080926 |
| DATED | : April 11, 2006 |
| INVENTOR(S) | : Lin Zhi et al. |

It is certified that error appears in the above-identified patent and that said Letters Patent is hereby corrected as shown below:

$R^6$ is selected from among hydrogen, $C_1$-$C_6$ alkyl, $C_1$-$C_6$ haloalkyl, $C_1$-$C_6$ heteroalkyl, heteroaryl and aryl, wherein the alkyl, haloalkyl, heteroalkyl, heteroaryl and aryl groups are optionally substituted;

$R^7$ is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted;

$R^8$ is selected from among hydrogen, $C_1$-$C_6$ alkyl, $C_1$-$C_6$ haloalkyl, $C_1$-$C_6$ heteroalkyl, heteroaryl and aryl, wherein the alkyl, haloalkyl, heteroalkyl, heteroaryl and aryl groups are optionally substituted; or $R^3$ and $R^5$ taken together form a bond; or $R^5$ and $R^7$ taken together form a bond; or $R^4$ and $R^6$ taken together form a three- to eight-membered saturated or unsaturated carbocyclic ring, wherein the carbocyclic ring is optionally substituted;

$R^6$ and $R^8$ taken together form a three- to eight-membered saturated or unsaturated carbocyclic ring, wherein the carbocyclic ring is optionally substituted;

$R^9$ and $R^{10}$ each independently is selected from among hydrogen, F, Cl, Br, I, CN, $OR^{12}$, $NR^{12}R^{13}$, $C_m(R^{12})_{2m}OR^{13}$, $SR^{12}$, $SOR^{12}$, $SO_2R^{12}$, $NR^{12}C(O)R^{13}$, $C_1$-$C_8$ alkyl, $C_1$-$C_8$ haloalkyl, $C_1$-$C_8$ heteroalkyl and arylalkyl, wherein the alkyl, haloalkyl, heteroalkyl and arylalkyl groups are optionally substituted;

$R^{11}$ is selected from among F, Br, Cl, I CN, $OR^{14}$, $NR^{14}R^{13}$ and $SR^{14}$;

$R^{12}$ and $R^{13}$ each independently is selected from among hydrogen, $C_1$-$C_8$ alkyl, $C_1$-$C_8$ haloalkyl, $C_1$-$C_8$ heteroalkyl, $C_2$-$C_8$ alkenyl, $C_2$-$C_8$ alkynyl, heteroaryl and aryl, wherein the alkyl, haloalkyl, heteroalkyl, alkenyl, alkynyl, heteroaryl and aryl groups are optionally substituted;

$R^{14}$ is selected from among hydrogen, $C_1$-$C_8$ alkyl, $C_1$-$C_8$ haloalkyl, $C_1$-$C_8$ heteroalkyl, aryl, heteroaryl, $C(O)R^{15}$, $CO_2R^{15}$ and $C(O)NR^{15}R^{16}$, wherein the alkyl, haloalkyl, heteroalkyl, aryl and heteroaryl groups are optionally substituted;

$R^{15}$ and $R^{16}$ each independently is selected from among hydrogen, $C_1$-$C_8$ alkyl, $C_1$-$C_8$ haloalkyl and $C_1$-$C_8$ heteroalkyl, wherein the alkyl, haloalkyl and heteroalkyl groups are optionally substituted;

W is O or S;

X is N $\{R^{14}\}$;

Y is seleted from among O, S, $N\{R^{12}\}$ and $NO\{R^{12}\}$;

Z is $N\{R^{12}\}$;

n is 0; and m is 0 or 1;

or a pharmaceutically acceptable salt thereof.

UNITED STATES PATENT AND TRADEMARK OFFICE
CERTIFICATE OF CORRECTION

PATENT NO. : 7,026,484 B2
APPLICATION NO. : 10/080926
DATED : April 11, 2006
INVENTOR(S) : Lin Zhi et al.

It is certified that error appears in the above-identified patent and that said Letters Patent is hereby corrected as shown below:

60. A compound according to claim 34, wherein:
 $R^5$ and $R^7$ each independently is selected from among hydrogen, $C_1$-$C_6$ alkyl, $C_1$-$C_6$ haloalkyl and $C_1$-$C_6$ heteroalkyl, wherein the alkyl, haloalkyl and heteroalkyl groups are optionally substituted; or
 $R^5$ and $R^7$ taken together form a bond.

This certificate supersedes all previously issued the Certificates of Correction.

Signed and Sealed this

Thirtieth Day of June, 2009

JOHN DOLL
*Acting Director of the United States Patent and Trademark Office*

UNITED STATES PATENT AND TRADEMARK OFFICE
Certificate

Patent No. 7,026,484 B2                          Patented: April 11, 2006

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Lin Zhi, San Diego, CA (US); and Cornelis Arjan Van Oeveren, San Diego, CA (US).

Signed and Sealed this Twenty-Ninth Day of September 2009.

*JANET L. ANDRES*
*Supervisory Patent Examiner*
*Art Unit 1625*